(12) United States Patent
Altenbach et al.

(10) Patent No.: US 9,777,020 B2
(45) Date of Patent: Oct. 3, 2017

(54) FURO-3-CARBOXAMIDE DERIVATIVES AND METHODS OF USE

(71) Applicant: AbbVie Inc., North Chicago, IL (US)

(72) Inventors: Robert J. Altenbach, Chicago, IL (US); Huaqing Liu, Buffalo Grove, IL (US); Bruce Clapham, Lindenhurst, IL (US); Ana L. Aguirre, Chicago, IL (US); Marlon Cowart, Round Lake Beach, IL (US); John R. Koenig, Chicago, IL (US); Kathy Sarris, Mundelein, IL (US); Marc J. Scanio, Lindenhurst, IL (US); Kerren K. Swinger, Lexington, MA (US); Anil Vasudevan, Union Grove, WI (US); Clara I. Villamil, Glenview, IL (US); Kevin R. Woller, Antioch, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/603,043

(22) Filed: Jan. 22, 2015

(65) Prior Publication Data

US 2015/0210720 A1    Jul. 30, 2015

Related U.S. Application Data

(60) Provisional application No. 61/931,232, filed on Jan. 24, 2014.

(51) Int. Cl.
| C07D 407/12 | (2006.01) |
| C07D 491/048 | (2006.01) |
| C07D 491/20 | (2006.01) |
| C07D 519/00 | (2006.01) |
| C07D 307/83 | (2006.01) |
| C07D 405/12 | (2006.01) |
| C07D 491/107 | (2006.01) |
| C07D 493/10 | (2006.01) |

(52) U.S. Cl.
CPC ......... *C07D 519/00* (2013.01); *C07D 307/83* (2013.01); *C07D 405/12* (2013.01); *C07D 407/12* (2013.01); *C07D 491/048* (2013.01); *C07D 491/107* (2013.01); *C07D 491/20* (2013.01); *C07D 493/10* (2013.01)

(58) Field of Classification Search
CPC . C07D 407/12; C07D 491/048; C07D 491/20
See application file for complete search history.

(56) References Cited

U.S. PATENT DOCUMENTS

| 6,262,272 | B1 * | 7/2001 | Ragan et al. ............... 546/278.1 |
| 2005/0101602 | A1 | 5/2005 | Basha | |

OTHER PUBLICATIONS

Albaugh P., et al., "Discovery of GNF-5837, a Selective TRK Inhibitor with Efficacy in Rodent Cancer Tumor Models," ACS Medicinal Chemistry Letters, 2012, vol. 3 (2), pp. 140-145.

Coleman R.S., et al., "A Direct and Efficient Total Synthesis of the Tubulin-Binding Agents Ceratamine a and B; Use of IBX for a Remarkable Heterocycle Dehydrogenation," Organic Letters, 2009, vol. 11 (10), pp. 2133-2136.

Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.

Deising S., et al., "Ngf-Evoked Sensitization of Muscle Fascia Nociceptors in Humans," Pain, 2012, vol. 153 (8), pp. 1673-1679.

Dyck P.J., et al, "Ntradermal Recombinant Human Nerve Growth Factor Induces Pressure Allodynia and Lowered Heat-Pain Threshold in Humans," Neurology, 1997, vol. 48 (2), pp. 501-505.

Eliel E. L. et al., Stereochemistry of Organic Compounds, 1994, John Wiley & Sons, Inc. New York, pp. 119-120, 1206.

Evans R.J., et al., "Proof of Concept Trial of Tanezumab for the Treatment of Symptoms Associated with Interstitial Cystitis," The Journal of Urology, 2011, vol. 185 (5), pp. 1716-1721.

Fragiadaki M., et al., "Hyperglycemia Causes Renal Cell Damage via Ccn2-Induced Activation of the Trka Receptor: Implications for Diabetic Nephropathy," Diabetes, 2012, vol. 61 (9), pp. 2280-2288.

Ghilardi J.R., et al., "Administration of a Tropomyosin Receptor Kinase Inhibitor Attenuates Sarcoma-Induced Nerve Sprouting, Neuroma Formation and Bone Cancer Pain," Molecular Pain, 2010, vol. 6, p. 87.

Ghilardi J.R., et al., "Sustained Blockade of Neurotrophin Receptors TRKA, TRKB and TRKC Reduces Non-Malignant Skeletal Pain But Not the Maintenance of Sensory and Sympathetic Nerve Fibers," Bone, 2011, vol. 48 (2), pp. 389-398.

Hayashi K., et al., "Involvement of NGF in the Rat Model of Persistent Muscle Pain Associated with Taut Band," The Journal of Pain : Official Journal of the American Pain Society, 2011, vol. 12 (10), pp. 1059-1068.

Joshi S.K., et al., "Animal Models of Pain for Drug Discovery," Expert Opinion on Drug Discovery, 2006, vol. 1 (4), pp. 341-352.

Katz N., et al., "Efficacy and Safety of Tanezumab in the Treatment of Chronic Low Back," Pain, 2011, vol. 152 (10), pp. 2248-2258.

(Continued)

*Primary Examiner* — Bruck Kifle
(74) *Attorney, Agent, or Firm* — Michael J. Ward

(57) ABSTRACT

Compounds of formula (I)

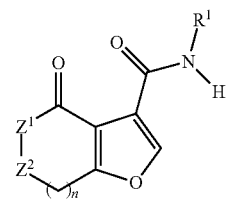

and pharmaceutically acceptable salts, esters, amides, or radiolabelled forms thereof, wherein $R^1$, $Z^1$, $Z^2$, and n are as defined in the specification, are useful in treating conditions or disorders prevented by or ameliorated by Tropomysin receptor kinases (Trk). Methods for making the compounds are disclosed. Also disclosed are pharmaceutical compositions of compounds of formula (I), and methods for using such compounds and compositions.

23 Claims, No Drawings

(56) References Cited

OTHER PUBLICATIONS

Lane N.E., et al., "Tanezumab for the Treatment of Pain From Osteoarthritis of the Knee," The New England Journal of Medicine, 2010, vol. 363 (16), pp. 1521-1531.
Mantyh P.W., et al., "Antagonism of Nerve Growth Factor-TRKA Signaling and the Relief of Pain," Anesthesiology, 2011, vol. 115 (1), pp. 189-204.
Mantyh W.G., et al., "Blockade of Nerve Sprouting and Neuroma Formation Markedly Attenuates the Development of Late Stage Cancer Pain," Neuroscience, 2010, vol. 171 (2), pp. 588-598.
Patapoutian A., et al., "TRK Receptors: Mediators of Neurotrophin Action," Current Opinion in Neurobiology, 2001, vol. 11 (3), pp. 272-280.
Pezet S., et al., "Neurotrophins: Mediators and Modulators of Pain," Annual Review of Neuroscience, 2006, vol. 29, pp. 507-538.
Prescott, Ed., Methods in Cell Biology, vol. XIV, Academic Press, New York, 1976, pp. 33.
Ro L.S., et al., "Effect of NGF and Anti-NGF on Neuropathic Pain in Rats Following Chronic Constriction Injury of the Sciatic Nerve," Pain, 1999, vol. 79 (2-3), pp. 265-274.
Schnitzer T.J., et al., "Long-Term Open-Label Study of Tanezumab for Moderate to Severe Osteoarthritic Knee Pain," Osteoarthritis and Cartilage / Oars, Osteoarthritis Research Society, 2011, vol. 19 (6), pp. 639-646.
Shelton D.L., et al., "Nerve Growth Factor Mediates Hyperalgesia and Cachexia in auto-immune arthritis," Pain, 2005, vol. 116 (1-2), pp. 8-16.
Thress K., et al., "Identification and Preclinical Characterization of Az-23, a Novel, Selective, and Orally Bioavailable Inhibitor of the TRK Kinase Pathway," Molecular Cancer Therapeutics, 2009, vol. 8 (7), pp. 1818-1827.
Truzzi F., et al., "Neurotrophins and their Receptors Stimulate Melanoma Cell Proliferation and Migration," The Journal of Investigative Dermatology, 2008, vol. 128 (8), pp. 2031-2040.
Ugolini G., et al., "The Function Neutralizing Anti-Trka Antibody Mnac13 Reduces Inflammatory and Neuropathic Pain," Proceedings of the National Academy of Sciences of the United States of America, 2007, vol. 104 (8), pp. 2985-2990.
Vogel H.G., ed., Drug Discovery and Evaluation: Pharmacological Assays, 2nd Edition, Springer-Verlag Berlin Heidelberg, 2002, pp. 702-706.
Wang T., et al., "Discovery of Disubstituted Imidazo[4,5-B]Pyridines and Purines as Potent TRKA Inhibitors," ACS Medicinal Chemistry Letters, 2012, vol. 3 (9), pp. 705-709.
Wang T., et al., "TRK Kinase Inhibitors as New Treatments for Cancer and Pain," Expert Opinion on Therapeutic Patents, 2009, vol. 19 (3), pp. 305-319.

\* cited by examiner

FURO-3-CARBOXAMIDE DERIVATIVES AND METHODS OF USE

CROSS-REFERENCE TO RELATED APPLICATIONS

This claims priority to U.S. Patent Application No. 61/931,232, filed on Jan. 24, 2014, the entire contents of which is fully incorporated herein by reference.

BACKGROUND OF THE INVENTION

Technical Field

The invention relates to furo-3-carboxamides that are inhibitors of TrkA (Tropomyosin receptor kinase isoform A), useful in treating diseases and conditions mediated and modulated by TrkA. Additionally, the invention relates to compositions containing compounds of the invention and processes of their preparation.

Description of Related Technology

TrkA is member of the Trk (Tropomyosin receptor) receptor family. Currently this family is known to include three highly homologous isoforms, called TrkA, TrkB, and TrkC. Trk receptors (Trks) are high affinity receptor tyrosine kinases. Trks bind adenosine triphosphate (ATP) and modulate intracellular signaling through their kinase enzymatic activity which is able to phosphorylate specific tyrosine residues of target proteins and peptides. Each Trk receptor isoform can be activated by endogenous peptidic factors known as neurotrophins (NT), which act as agonists of the Trk receptor. NGF (nerve growth factor) is a high affinity activator of TrkA. BDNF (brain-derived neurotrophic factor) and NT-4/5 are high affinity activators of TrkB (Tropomyosin receptor kinase isoform B). NT3 is a high affinity activator of TrkC (Tropomyosin receptor kinase isoform C). Trks are expressed in neurons, and have been implicated in the development and function of the nervous system, as well as other physiological processes.

Neurotrophins and their Trk receptors have been implicated in pain sensation and in inflammation. Pezet S, et al. Ann Rev Neuroscience 2006; 29:507-538; Mantyh P W, et al. Anesthesiology 2011; 115:189-204; and Patapoutian A, et al. Current Opinion in Neurobiology 2001; 11:272-280. Studies have shown that NGF, the agonist of TrkA, modulates pain in adult mammals. Dyck P J, et al. Neurology 1997; 48; 501-505; and Deising S, et al. Pain 2012; 153: 1673-1679. Studies have also shown that inhibitors of the NGF/TrkA pathway are effective in blocking pain. Lane N E, et al. New England J Med 2010; 363:1521-1531; Schnitzer T J, et al. Osteoarthritis Cartilage 2011; 19:639-646; Katz N, et al. Pain 2011; 152:2248-2258; Evans R J, et al. J. Urology 2011; 185:1716-1721; Shelton D L, et al. Pain 2005; 116:8-16; Ro L S, et al. Pain 1999; 79:265-274; and Ugolini G, et al. Proceedings of the National Academy of Sciences of the USA 2007; 104:2985-2990. TrkA inhibitors block NGF signaling through its receptor (TrkA) and have been found effective in reducing pain in animal models. Ghilardi J R, et al. Bone 2011; 48:389-298; Ghilardi J R, et al. Molecular Pain 2010; 6:87; Mantyh, W G, et al, Neuroscience 2010; 17:588-598; and Hayashi K, et al. Journal of Pain 2011; 12:1059-1068. The TrkA, TrkB, and TrkC isoforms have high structural homology. Of the potent Trk inhibitor structural classes described, testing of isoform selectivity has revealed a lack of selectivity for any particular Trk isoform, hence they have been termed 'pan-Trk' inhibitors (Albaugh P, et al. ACS Medicinal Chemistry Letters 2012; 3:140-145), able to inhibit TrkA, TrkB, and TrkC. Wang T, et al. Expert Opinion on Therapeutic Patents 2009; 19:305-319.

Although compounds and mechanisms exist that are used clinically to treat pain, there is need for new compounds that can effectively treat different types of pain. Pain of various types (e.g., inflammatory pain, post-surgical pain, osteoarthritis pain, neuropathic pain) afflicts virtually all humans and animals at one time or another, and a substantial number of medical disorders and conditions produce some sort of pain as a prominent concern requiring treatment. As such, it would be particularly beneficial to identify new compounds for treating the various types of pain.

SUMMARY

The invention is directed to faro-3-carboxamides having a structure of Formula (I):

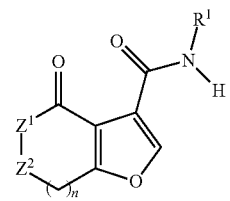

(I)

or a pharmaceutically acceptable salt, ester, amide, or radiolabelled form thereof, wherein:

n is 1 or 2;

$R^1$ is phenyl or monocyclic heteroaryl, wherein the monocyclic heteroaryl contains one or two ring nitrogens and optionally one ring oxygen or one ring sulfur, wherein the phenyl or monocyclic heteroaryl isoptionally substituted with 1, 2, or 3 substituents selected from the group consisting of $C_1$-$C_6$-alkyl; $C_1$-$C_6$-alkylcarbonylamino; hydroxy$C_1$-$C_6$-alkylcarbonylamino; $C_1$-$C_6$-alkoxy$C_1$-$C_6$alkylcarbonylamino; $C_1$-$C_6$-alkoxy; $C_1$-$C_6$-alkoxy$C_1$-$C_6$-alkoxy; $C_1$-$C_6$-alkoxy$C_1$-$C_6$-alkyl; $C_1$-$C_6$-alkoxycarbonyl; $C_1$-$C_6$-alkoxycarbonyl$C_1$-$C_6$-alkyl; aminocarbonyl; $C_1$-$C_6$-alkylaminocarbonyl; hydroxy$C_1$-$C_6$-alkylaminocarbonyl; $C_1$-$C_6$-alkoxy$C_1$-$C_6$-alkylaminocarbonyl; cyano; carboxy; hydroxy; hydroxy$C_1$-$C_6$-alkoxy; hydroxy$C_1$-$C_6$-alkyl; di(hydroxy)$C_1$-$C_6$-alkyl; di($C_1$-$C_6$alkyl)amino; di(hydroxy$C_1$-$C_6$-alkyl)amino; di($C_1$-$C_6$-alkoxy$C_1$-$C_6$alkyl)amino; ($C_1$-$C_6$-alkoxy$C_1$-$C_6$-alkyl)(hydroxy$C_1$-$C_6$-alkyl)amino; halo$C_1$-$C_6$-alkyl; and halogen; wherein only 1 substituent can be present on the two atoms adjacent to the atom connected to the amide nitrogen pendant on the furan ring; or $R^1$ is fused-bicyclic heteroaryl, wherein the fused-bicyclic heteroaryl contains 1, 2, 3 or 4 ring nitrogens and optionally one ring oxygen or one ring sulfur, wherein the fused-bicyclic heteroaryl isoptionally substituted with 1, 2, 3, or 4 substituents selected from the group consisting of $C_1$-$C_6$-alkyl; $C_1$-$C_6$-alkylcarbonylamino; hydroxy$C_1$-$C_6$-alkylcarbonylamino; $C_1$-$C_6$-alkoxy$C_1$-$C_6$-alkylcarbonylamino; $C_1$-$C_6$-alkoxy; $C_1$-$C_6$-alkoxy$C_1$-$C_6$-alkoxy; $C_1$-$C_6$alkoxy-$C_1$-$C_6$alkyl; $C_1$-$C_6$-alkoxycarbonyl; $C_1$-$C_6$-alkoxycarbonyl$C_1$-$C_6$-alkyl; $C_3$-$C_7$-cycloalkyloxy; $M_4$-$M_7$-heterocycleoxy, wherein the heterocycle of $M_4$-$M_7$-heterocycleoxy isoptionally substituted with $C_1$-$C_6$-alkyl; aminocarbonyl; $C_1$-$C_6$-alkylaminocarbonyl; hydroxy$C_1$-$C_6$-alkylaminocarbonyl; $C_1$-$C_6$-alkoxy$C_1$-$C_6$-alkylamincarbonyl; cyano;

hydroxy; hydroxyC$_1$-C$_6$-alkoxy; hydroxyC$_1$-C$_6$-alkyl; di(C$_1$-C$_6$alkyl)amino; di(hydroxyC$_1$-C$_6$-alkyl)amino; di(C$_1$-C$_6$-alkoxyC$_1$-C$_6$-alkyl)amino; (C$_1$-C$_6$-alkoxyC$_1$-C$_6$-alkyl)(hydroxyC$_1$-C$_6$-alkyl)amino; haloC$_1$-C$_6$-alkyl; halogen; C$_1$-C$_6$-alkylsulfonylaminoC$_2$-C$_6$-alkyl; and (i),

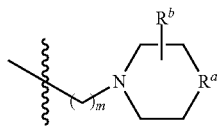

(i)

wherein R$^a$ is selected from the group consisting of a bond, CH$_2$, CHR$^b$, O, S, and N—R$^c$; wherein only 1 substituent can be present on the two atoms adjacent to the atom connected to the amide nitrogen pendant on the furan ring;

m is 2, 3 or 4 when (i) is attached to a ring nitrogen atom of the bicyclic heteroaryl; or m is 0, 1, 2, 3 or 4 when (i) is attached to a ring carbon atom of the bicyclic heteroaryl;

R$^b$, at each occurrence, is independently selected from the group consisting of hydrogen, C$_1$-C$_6$-alkyl, haloC$_1$-C$_6$-alkyl, C$_1$-C$_6$-alkoxyC$_1$-C$_6$-alkyl, and hydroxyC$_1$-C$_6$-alkyl;

R$^c$ is selected from the group consisting of hydrogen, C$_1$-C$_6$-alkyl, C$_1$-C$_6$-alkoxycarbonyl, C$_1$-C$_6$-alkycarbonyl, C$_1$-C$_6$-alkysulfonyl, di(C$_1$-C$_6$-alkyl)aminosulfonyl, heterocyclecarbonyl, C$_3$-C$_7$-cycloalkylcarbonyl, —C(O)NH$_2$, —C(O)NH(alkyl), —C(O)N(alkyl)$_2$ and —C(=NCN)NHCH$_3$; or R$^1$ is (ii), (iii), or (iv);

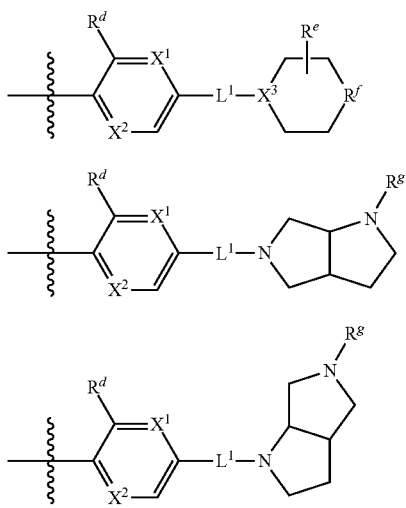

(ii)

(iii)

(iv)

wherein both X$^1$ and X$^2$ are CH, or one of X$^1$ and X$^2$ is N and the other is CH;

X$^3$ is CH or N;

L$^1$ is a bond, C(O), or —NHC(O)—;

R$^d$ is selected form the group consisting of hydrogen; C$_1$-C$_6$alkoxy; fluoroC$_1$-C$_6$-alkoxy; C$_1$-C$_6$-alkoxyC$_1$-C$_6$-alkoxy; C$_3$-C$_7$-cycloalkyloxy; C$_3$-C$_7$-cycloalkylC$_1$-C$_6$-alkoxy; hydroxyC$_1$-C$_6$-alkoxy; phenylC$_1$-C$_6$-alkoxyC$_1$-C$_6$-alkoxy; M$_4$-M$_7$-heterocycleoxy, wherein the heterocycle of heterocycleoxy isoptionally substituted with C$_1$-C$_6$-alkyl or oxo; and phenoxy, wherein the phenyl of phenoxy isoptionally substituted with hydroxyC$_1$-C$_6$-alkyl, C$_1$-C$_6$-alkoxy, C$_1$-C$_6$-alkoxyC$_1$-C$_6$-alkoxy, or C$_1$-C$_6$-alkoxycarbonyl;

R$^e$ at each occurrence is independently selected from the group consisting of hydrogen, C$_1$-C$_6$-alkyl, di(C$_1$-C$_6$-alkyl)amino, haloC$_1$-C$_6$-alkyl, C$_1$-C$_6$-alkoxyC$_1$-C$_6$alkyl, and hydroxyC$_1$-C$_6$-alkyl;

R$^f$ is selected from the group consisting of a bond, CH$_2$, CHR$^e$, CH$_2$CH$_2$, O, NR$^g$, and CH$_2$NR$^g$;

R$^g$ is selected from the group consisting of hydrogen; C$_1$-C$_6$-alkyl; C$_1$-C$_6$-alkoxycarbonyl; C$_1$-C$_6$-alkycarbonyl; C$_1$-C$_6$-alkysulfonyl; di(C$_1$-C$_6$-alkyl)aminosulfonyl; C$_3$-C$_7$-cycloalkylcarbonyl; C$_1$-C$_6$-alkoxyC$_1$-C$_6$-alkylcarbony; hydroxyC$_2$-C$_6$-alkyl; hydroxyC$_1$-C$_6$-alkylcarbonyl; formyl; —C(O)NH$_2$; —C(O)NH(alkyl); —C(O)N(alkyl)$_2$; —C(=NCN)NHCH$_3$; and M$_4$-M$_7$-heterocyclecarbonyl, wherein the heterocycle of heterocyclecarbonyl isoptionally substituted with C$_1$-C$_6$-alkyl;

Z$^1$ is NR$^2$ or CR$^3$R$^4$;

R$^2$ is selected from the group consisting of hydrogen, C$_1$-C$_6$-alkyl, hydroxyC$_2$-C$_6$-alkyl, di(hydroxy)C$_2$-C$_6$-alkyl, C$_1$-C$_6$-alkoxyC$_2$-C$_6$alkyl, hydroxyC$_2$-C$_6$-alkoxyC$_2$-C$_6$-alkyl, C$_1$-C$_6$-alkylcarbonyloxyC$_2$-C$_6$-alkyl, C$_1$-C$_6$-alkoxycarbonylC$_1$-C$_6$-alkyl, C$_1$-C$_6$-alkylcarbonylC$_1$-C$_6$-alkyl and phenylC$_1$-C$_6$-alkoxyC$_2$-C$_6$alkyl;

R$^3$ and R$^4$ are each independently selected from the group consisting of hydrogen, C$_1$-C$_6$-alkyl, hydroxyC$_1$-C$_6$-alkyl, aminoC$_1$-C$_6$-alkyl, and phenyl, wherein phenyl is optionally substituted with 1, 2, 3 or 4 substituents selected from halogen, C$_1$-C$_6$-alkyl, and cyano; or R$^3$ and R$^4$ taken together with the carbon atom to which they are attached form a M$_4$-M$_7$-heterocycle optionally substituted with 1, 2 or 3 halogen, C$_1$-C$_6$-alkyl, cyano or oxo;

Z$^2$ is O, NR$^5$, or CR$^6$R$^7$;

R$^5$ is selected from the group consisting of hydrogen, C$_1$-C$_6$-alkyl, C$_1$-C$_6$-alkylsulfonyl, C$_1$-C$_6$-alkylcarbonyl, and C$_1$-C$_6$-alkoxycarbonyl; and R$^6$ and R$^7$ are each independently selected from the group consisting of hydrogen, C$_1$-C$_6$-alkyl, C$_1$-C$_6$-alkoxyC$_1$-C$_6$-alkyl, hydroxyC$_1$-C$_6$-alkyl, aminoC$_1$-C$_6$-alkyl, aminocarbonyl, and C$_1$-C$_6$-alkoxycarbonyl;

wherein one or more of R$^3$, R$^4$, R$^6$ and R$^7$ is other than hydrogen; or

R$^6$ and R$^7$ taken together with the carbon atom to which they are attached form a C$_3$-C$_6$-cycloalkyl or M$_4$-M$_7$-heterocycle, wherein the C$_3$-C$_6$-cycloalkyl or M$_4$-M$_7$-heterocycle are optionally substituted with 1, 2, or 3 substituents selected from C$_1$-C$_6$-alkyl, cyano, aminocarbonyl, halogen, oxo and C$_1$-C$_6$-alkylcarbonyl.

Another aspect of the invention relates to pharmaceutical compositions comprising compounds of the invention. Such compositions can be administered in accordance with a method of the invention, typically as part of a therapeutic regimen for treatment or prevention of conditions and disorders related to Trk receptor kinases (and particularly TrkA kinase) activity.

Yet another aspect of the invention relates to a method of selectively modulating TrkA receptor kinase activity. The method is useful for treating, or preventing conditions and disorders related to TrkA modulation in mammals. More particularly, the method is useful for treating or preventing conditions and disorders related to pain, neuropathy, inflammation, auto-immune disease, fibrosis, chronic kidney disease, and cancer. Accordingly, the compounds and compositions of the invention are useful as a medicament for treating or preventing TrkA receptor kinases modulated disease.

The compounds, compositions comprising the compounds, methods for making the compounds, and methods for treating or preventing conditions and disorders by administering the compounds are further described herein.

These and other objects of the invention are described in the following paragraphs. These objects should not be deemed to narrow the scope of the invention.

DETAILED DESCRIPTION OF THE INVENTION

Compounds of formula (I) are disclosed in this invention

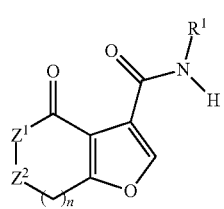

(I)

wherein $R^1$, $Z^1$, $Z^2$, and n are as defined above in the Summary. Compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds which can be isolated from a reaction mixture.

Definition of Terms

Certain terms as used in the specification are intended to refer to the following definitions, as detailed below.

The term "alkenyl" as used herein, means a straight or branched hydrocarbon chain containing from 2 to 10 carbons and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxyalkylamino" as used herein means an alkoxyalkyl group, as defined herein, appended to the parent molecular moiety through an amino group, as defined herein. Representative examples of alkoxyalkylamino include, but are not limited to, ethoxyethylamino, methoxyethylamino, and methoxypropylamino.

The term "alkoxyalkylaminocarbonyl" as used herein means an alkoxyalkylamino group, as defined herein, appended to the parent molecular moiety through a carbonyl group, as defined herein. Representative examples of alkoxyalkylaminocarbonyl include, but are not limited to, ethoxyethylaminocarbonyl, methoxyethylaminocarbonyl, and methoxypropylaminocarbonyl.

The term "alkoxyalkylcarbonyl" as used herein means an alkoxyalkyl group, as defined herein, appended to the parent molecular moiety through a carbonyl group, as defined herein. Representative examples of alkoxyalkylcarbonyl include, but are not limited to, ethoxyethylcarbonyl, methoxyethylcarbonyl, and methoxypropylcarbonyl.

The term "alkoxyalkylcarbonylamino" as used herein means an alkoxycarbonyl group, as defined herein, appended to the parent molecular moiety through a carbonyl group, as defined herein. Representative examples of alkoxyalkylcarbonylamino include, but are not limited to, ethoxyethylcarbonylamino, methoxyethylcarbonylamino, and methoxypropylcarbonylamino.

The term "(alkoxyalkyl)(hydroxyalkyl)amino," as used herein, refers to one alkoxyalkyl group and one hydroxyalkyl group, as defined herein, appended to the parent molecular moiety through an amino group, as defined herein. Representative examples of (alkoxyalkyl)(hydroxyalkyl)amino include, but are not limited to, (methoxyethyl)(hydroxyethyl)amino, (ethoxyethyl)(hydroxyethyl)amino, and (methoxyethyl)(hydroxypropyl)amino, and the like.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, isopropoxycarbonyl, and tert-butoxycarbonyl.

The term "alkoxycarbonylalkyl" as used herein, means an alkoxycarbonyl group, as defined herein, appended to the parent molecular moiety through an alkylene group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkyl" as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylamino" means an alkyl group appended to the parent molecular moiety through an amino group, as defined herein. Representative examples of alkylamino include, but are not limited to, methylamino, ethylamino, and sec-butylamino.

The term "alkylaminocarbonyl" means an alkylamino group appended to the parent molecular moiety through a carbonyl group, as defined herein. Representative examples of alkylaminocarbonyl include, but are not limited to, methylaminocarbonyl, ethylaminocarbonyl, and isopropylaminocarbonyl, and the like.

The term "alkylcarbonyl" as used herein means an alkyl group, as defined herein, appended to the parent molecular moiety through a carbonyl group, as defined herein. Representative examples of alkylcarbonyl include, but are not limited to, methylcarbonyl (acetyl), ethylcarbonyl, isopropylcarbonyl, n-propylcarbonyl, and the like.

The term "alkylcarbonylamino" means —N(H)—C(O)-alkyl.

The term "alkylcarbonylalkyl" refers to an alkylcarbonyl group appended to the parent molecular moiety through an alkylene moiety. Representative examples of alkylcarbonylalkyl include, but are not limited to, propan-2-onyl, and 3-methyl-butan-2-onyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylcarbonyloxyalkyl" refers to an alkylcarbonyloxy group appended to the parent molecular moiety through an alkylene moiety. Representative examples of alkylcarbonyloxyalkyl include, but are not limited to, 2-(acetyloxy)ethyl, 3-(acetyloxy)propyl, and 3-(propionyloxy)propyl.

The term "alkylene" denotes a divalent group derived from a straight or branched chain hydrocarbon containing from 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylsulfonyl," as used herein, refers to an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylamino," as used herein, refers to an alkylsulfonyl group, as defined herein, appended to the parent molecular moiety through an amino group, as defined herein. Representative examples of alkylsulfonylamino include, but are not limited to, methylsulfonylamino, ethylsulfonylamino, and n-butylsulfonylamino, and the like.

The term "alkylsulfonylaminoalkyl," as used herein, refers to an alkylsulfonylamino group, as defined herein, appended to the parent molecular moiety through an alkylene group, as defined herein. Representative examples of alkylsulfonylaminoalkyl include, but are not limited to, methylsulfonylaminoethyl, ethylsulfonylaminoethyl, and isopropylsulfonylaminoethyl, and the like.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amino" as used herein means an —NH$_2$ group.

The term "aminocarbonyl" (alone or in combination with another term(s)) means —C(O)—NH$_2$.

The term "aminoalkyl" as used herein, means at least one amino group, as defined herein, is appended to the parent molecular moiety through an alkylene group, as defined herein. Representative examples of aminoalkyl include, but are not limited to, aminomethyl, 2-aminoethyl, 3-aminopropyl, and 4-amino-2-ethylheptyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "arylalkyl" as used herein, means an aryl group, as defined herein, appended to the parent molecular moiety through an alkylene group, as defined herein. Representative examples of arylalkyl include, but are not limited to, benzyl, 1-phenylethyl, 2-phenylethyl, 3-phenylpropyl, and 2-naphth-2-ylethyl.

The term "aryloxy," as used herein, refers to an aryl group, as defined herein, appended to the parent molecular moiety through an oxy moiety, as defined herein.

Representative examples of aryloxy include, but are not limited to, phenoxy, naphthyloxy, 3-bromophenoxy, 4-chlorophenoxy, 4-methylphenoxy, 3,5-dimethoxyphenoxy, and the like.

The term "carbonyl" as used herein means a —C(=O)— group.

The term "carboxy," as used herein, refers to a —CO$_2$H group.

The term "cyano" as used herein, means a —CN group.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group, or a bridged monocyclic ring system in which two non-adjacent carbon atoms of the monocyclic ring are linked by an alkylene bridge containing one, two, three, or four carbon atoms. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "cycloalkenylalkyl," as used herein, refers to a cycloalkenyl group attached to the parent molecular moiety through an alkyl group.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$] nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "cycloalkylalkyl" as used herein, means a cycloalkyl group appended to the parent molecular moiety through an alkyl group, as defined herein.

The term "cycloalkylalkoxy" as used herein, means cycloalkyl group, as defined herein, appended to the parent molecular moiety through an alkoxy group, as defined herein. Representative examples of cycloalkylalkoxy include, but are not limited to, cyclopropylmethoxy, cyclobutylmethoxy, and cyclopentylethoxy, and the like.

The term "cycloalkylcarbonyl" as used herein, means cycloalkyl group, as defined herein, appended to the parent molecular moiety through a carbonyl group, as defined herein. Representative examples of cycloalkylcarbonyl include, but are not limited to, cyclopropylcarbonyl, 2-cyclobutylcarbonyl, and cyclohexylcarbonyl.

The term "cycloalkyloxy" as used herein, means cycloalkyl group, as defined herein, appended to the parent molecular moiety through an oxygen atom, as defined herein. Representative examples of cycloalkyloxy include, but are not limited to, cyclopropyloxy, cyclobutyloxy, cyclopentyloxy, cyclohexyloxy, cycloheptyloxy, and cyclooctyloxy.

The term "di(alkoxyalkyl)amino," as used herein, refers to two independent alkoxyalkyl groups, as defined herein, appended to the parent molecular moiety through an amino group, as defined herein. Representative examples of di(alkoxyalkyl)amino include, but are not limited to, di(methoxyethyl)amino, di(ethoxypropyl)amino, and (methoxyethyl)(ethoxyethyl)amino, and the like.

The term "di(alkyl)amino," as used herein, refers to two independent alkyl groups, as defined herein, appended to the parent molecular moiety through an amino group, as defined herein. Representative examples of di(alkyl)amino include, but are not limited to, dimethylamino, diethylamino, ethylmethylamino, butylmethylamino, ethylhexylamino, and the like.

The term "di(alkyl)aminosulfonyl," as used herein, refers to a di(alkyl)amino group, as defined herein, appended to the parent molecular moiety through a sulfonyl group, as defined herein. Representative examples of di(alkyl)aminosulfonyl include, but are not limited to, di(methyl)aminosulfonyl, di(ethyl)aminosulfonyl, and (methyl)(ethyl)aminosulfonyl, and the like.

The term "di(hydroxy)alkyl" as used herein, means two hydroxy groups, as defined herein, are appended to the parent molecular moiety through an alkylene group, as defined herein. Representative examples of di(hydroxy) alkyl include, but are not limited to, propane-1,2-diol and butane-1,3-diol.

The term "di(hydroxyalkyl)amino," as used herein, refers to two independent hydroxyalkyl groups, as defined herein, appended to the parent molecular moiety through an amino group, as defined herein. Representative examples of di(hydroxyalkyl)amino include, but are not limited to, di(2-hydroxyethyl)aminosulfonyl, di(3-hydroxyethyl)aminosulfonyl, and (2-hydroxyethyl)(2-hydroxypropyl) aminosulfonyl, and the like.

The term "fluoroalkoxy" as used herein, means an alkoxy group, as defined herein, in which one, two, three, four, five, six, seven or eight hydrogen atoms are replaced by fluorine. Representative examples of haloalkoxy include, but are not limited to, fluoromethoxy, 2-fluoroethoxy, 2,2-difluoroethoxy, 2,2,2-trifluoroethoxy, trifluoromethoxy, difluoromethoxy, pentafluoroethoxy, 1,1,2-trifluoroisopropoxy, and trifluoropropyl such as 3,3,3-trifluoropropoxy.

The term "fluoroalkyl" as used herein, means an alkyl group, as defined herein, in which one, two, three, four, five, six, seven or eight hydrogen atoms are replaced by fluorine. Representative examples of haloalkyl include, but are not limited to, fluoromethyl, 2-fluoroethyl, 2,2-difluoroethyl, 2,2,2-trifluoroethyl, trifluoromethyl, difluoromethyl, pentafluoroethyl, 1,1,2-trifluoroisopropyl, and trifluoropropyl such as 3,3,3-trifluoropropyl.

The term "formyl," as used herein, refers to a —C(O)H group.

The term "halo" or "halogen" as used herein, means Cl, Br, I, or F.

The term "haloalkyl" as used herein, means an alkyl group, as defined herein, in which one, two, three, four, five, six, seven or eight hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heteroaryl" as used herein, means a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo [1,2-a]pyridinyl, indazolyl, indolyl, isoindolyl, isoquinolinyl, naphthyridinyl, pyridoimidazolyl, quinolinyl, thiazolo [5,4-b]pyridin-2-yl, thiazolo[5,4-d]pyrimidin-2-yl, and 5,6, 7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroarylalkyl" as used herein, means a heteroaryl, as defined herein, appended to the parent molecular moiety through an alkyl group, as defined herein.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$] decane), and oxa-adamantane (2-oxatricyclo[3.3.1.1$^{3,7}$] decane). The monocyclic, bicyclic, and tricyclic heterocycles are connected to the parent molecular moiety through any carbon atom or any nitrogen atom contained within the rings, and can be unsubstituted or substituted.

The term "heterocyclealkyl", as used herein, refers to refers to a heterocycle group attached to the parent molecular moiety through an alkyl group.

The term "heterocyclecarbonyl," as used herein, refers to a heterocycle, as defined herein, appended to the parent molecular moiety through a carbonyl group, as defined herein.

The term "heterocycleoxy," as used herein, refers to a heterocycle, as defined herein, appended to the parent molecular moiety through an oxy group, as defined herein.

The term "heteroatom" as used herein, means a nitrogen, oxygen, or sulfur atom.

The term "hydroxyl" or "hydroxy" as used herein, means an —OH group.

The term "hydroxyalkoxy" as used herein, means at least one hydroxy group, as defined herein, is appended to the parent molecular moiety through an alkoxy group, as defined herein. Representative examples of hydroxyalkoxy include, but are not limited to, 2-hydroxyethoxy, 2-hydroxypropoxy, and 3-hydroxypropoxy, and the like.

The term "hydroxyalkyl" as used herein, means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 3-hydroxypropyl, and 2-ethyl-4-hydroxyheptyl.

The term "hydroxyalkylamino" as used herein, means at least one hydroxyalkyl group, as defined herein, is appended to the parent molecular moiety through an amino group, as defined herein. Representative examples of hydroxyalkylamino include, but are not limited to, 2-hydroxyethylamino, 2-hydroxypropylamino, and 3-hydroxybutylamino, and the like.

The term "hydroxyalkylaminocarbonyl" as used herein, means a hydroxyalkylamino group, as defined herein, is appended to the parent molecular moiety through a carbonyl group, as defined herein. Representative examples of hydroxyalkylaminocarbonyl include, but are not limited to, 2-hydroxyethylaminocarbonyl, 2-hydroxypropylaminocarbonylo, and 3-hydroxybutylaminocarbonyl, and the like.

The term "hydroxyalkoxyalkyl" as used herein, means a hydroxyalkoxy group, as defined herein, appended to the parent molecular moiety through an alkylene group, as defined herein. Representative examples of hydroxyalkoxyalkyl include, but are not limited to, (2-hydroxy-ethoxy)-ethyl, and (3-hydroxyl-propoxyl)-ethyl.

The term "hydroxyalkylcarbonyl" as used herein, means a hydroxyalkyl group, as defined herein, as appended to the parent molecular moiety through a carbonyl group, as defined herein. Representative examples include, but are not limited to, 2-hydroxyacetyl, and 4-hydroxybutanoyl.

The term "hydroxyalkylcarbonylamino" as used herein, means a hydroxyalkylcarbonyl group, as defined herein, as appended to the parent molecular moiety through an amino group, as defined herein. Representative examples include, but are not limited to, hydroxymethylcarbonylamino, 1-hydroxyethylcarbonylamino, and 2-hydroxyethylcarbonylamino.

The term "oxo" as used herein means (=O).

The term "oxy," as used herein, refers to a —O— group.

The term "phenyloxy" or "phenoxy," as used herein, refers to a phenyl group, optionally substituted, appended to the parent molecular moiety through an oxy moiety, as defined herein. Representative examples of phenyloxy or phenoxy include, but are not limited to, phenoxy, 3-bromophenoxy, 4-chlorophenoxy, 4-methylphenoxy, 3,5-dimethoxyphenoxy, and the like.

The term "phenylalkoxyalkoxy," as used herein, refers to a phenyl group, optionally substituted, appended to the parent molecular moiety through an alkoxyalkoxy moiety, as defined herein. Representative examples of phenylalkoxyalkoxy include, but are not limited to, 2-(benzyloxy)ethoxy, 2-(1-phenylethoxyl)ethoxy, and the like.

The term "phenylalkoxyalkyl," as used herein, refers to a phenyl group, optionally substituted, appended to the parent molecular moiety through an alkoxyalkyl moiety, as defined herein. Representative examples of phenylalkoxyalkyl include, but are not limited to, 2-(benzyloxy)ethyl, 2-(1-phenylethoxyl)ethyl, and the like.

The term "sulfonyl," as used herein, refers to a —S(O)$_2$— group.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

As used herein, the number of ring atoms in a heterocyclic moiety can be identified by the prefix "$M_x$-$M_y$," where x is the minimum and y is the maximum number of ring atoms in the heterocyclic moiety.

As used herein, the term "radiolabel" refers to a compound of the invention in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^3$H (tritium), $^{14}$C, $^{11}$C, $^{15}$O, $^{18}$F, $^{35}$S, $^{123}$I, and $^{125}$I.

Compounds of the Invention

Compounds of the invention can have the Formula (I) as described in the Summary.

Particular values of variable groups in compounds of Formula (I) are as follows. Such values can be used where appropriate with any of the other values, definitions, claims or embodiments defined hereinbefore or hereinafter.

In one embodiment, n is 1 or 2.

In another embodiment, n is 1.

In another embodiment, n is 2.

In one embodiment, R$^1$ is phenyl or monocyclic heteroaryl, wherein the monocyclic heteroaryl contains one or two ring nitrogens and optionally one ring oxygen or one ring sulfur, wherein the phenyl or monocyclic heteroaryl isoptionally substituted with 1, 2, or 3 substituents selected from the group consisting of $C_1$-$C_6$-alkyl; $C_1$-$C_6$-alkylcarbonylamino; hydroxy$C_1$-$C_6$-alkylcarbonylamino; $C_1$-$C_6$-alkoxy$C_1$-$C_6$alkylcarbonylamino; $C_1$-$C_6$-alkoxy; $C_1$-$C_6$-alkoxy$C_1$-$C_6$-alkoxy; $C_1$-$C_6$-alkoxy$C_1$-$C_6$-alkyl; $C_1$-$C_6$-alkoxycarbonyl; $C_1$-$C_6$-alkoxycarbonyl$C_1$-$C_6$-alkyl; aminocarbonyl; $C_1$-$C_6$-alkylaminocarbonyl; hydroxy$C_1$-$C_6$-alkylaminocarbonyl; $C_1$-$C_6$-alkoxy$C_1$-$C_6$-alkylaminocarbonyl; cyano; carboxy; hydroxy; hydroxy$C_1$-$C_6$-alkoxy; hydroxy$C_1$-$C_6$-alkyl; di(hydroxy)$C_1$-$C_6$-alkyl; di($C_1$-$C_6$alkyl)amino; di(hydroxy$C_1$-$C_6$-alkyl)amino; di($C_1$-$C_6$-alkoxy$C_1$-$C_6$alkyl)amino; ($C_1$-$C_6$-alkoxy$C_1$-$C_6$-alkyl)(hydroxy$C_1$-$C_6$-alkyl)amino; halo$C_1$-$C_6$-alkyl; and halogen; wherein only 1 substituent can be present on the two atoms adjacent to the atom connected to the amide nitrogen pendant on the furan ring.

In another embodiment, R$^1$ is phenyl or monocyclic heteroaryl, wherein the monocyclic heteroaryl contains one or two ring nitrogens and optionally one ring oxygen or one ring sulfur, wherein the phenyl or monocyclic heteroaryl isoptionally substituted with 1 or 2 substituents selected from the group consisting of $C_1$-$C_6$-alkyl; $C_1$-$C_6$-alkylcarbonylamino; $C_1$-$C_6$-alkoxy; $C_1$-$C_6$-alkoxy$C_1$-$C_6$-alkoxy; $C_1$-$C_6$-alkoxycarbonyl$C_1$-$C_6$-alkyl; aminocarbonyl; cyano; carboxy; hydroxy; hydroxy$C_1$-$C_6$-alkyl; di($C_1$-$C_6$alkyl)amino; di(hydroxy$C_1$-$C_6$-alkyl)amino; halo$C_1$-$C_6$-alkyl; and halogen; wherein only 1 substituent can be present on the two atoms adjacent to the atom connected to the amide nitrogen pendant on the furan ring.

In one embodiment, R$^1$ is fused-bicyclic heteroaryl, wherein the fused-bicyclic heteroaryl contains 1, 2, 3 or 4 ring nitrogens and optionally one ring oxygen or one ring sulfur, wherein the fused-bicyclic heteroaryl isoptionally substituted with 1, 2, 3, or 4 substituents selected from the group consisting of $C_1$-$C_6$-alkyl; $C_1$-$C_6$-alkylcarbonylamino; hydroxy$C_1$-$C_6$-alkylcarbonylamino; $C_1$-$C_6$-alkoxy$C_1$-$C_6$-alkylcarbonylamino; $C_1$-$C_6$-alkoxy; $C_1$-$C_6$-alkoxy$C_1$-$C_6$-alkoxy; $C_1$-$C_6$alkoxy-$C_1$-$C_6$alkyl; $C_1$-$C_6$-alkoxycarbonyl; $C_1$-$C_6$-alkoxycarbonyl$C_1$-$C_6$-alkyl; $C_3$-$C_7$-cycloalkyloxy; $M_4$-$M_7$-heterocycleoxy, wherein the heterocycle of $M_4$-$M_7$-heterocycleoxy isoptionally substituted with $C_1$-$C_6$-alkyl; aminocarbonyl; $C_1$-$C_6$-alkylaminocarbonyl; hydroxy$C_1$-$C_6$-alkylaminocarbonyl; $C_1$-$C_6$-alkoxy$C_1$-$C_6$-alkylamincarbonyl; cyano; hydroxy; hydroxy$C_1$-$C_6$-alkoxy; hydroxy$C_1$-$C_6$-alkyl; di($C_1$-$C_6$alkyl)amino; di(hydroxy$C_1$-$C_6$-alkyl)amino; di($C_1$-$C_6$-alkoxy$C_1$-$C_6$-alkyl)amino; ($C_1$-$C_6$-alkoxy$C_1$-$C_6$-alkyl)(hydroxy$C_1$-$C_6$-alkyl)amino; halo$C_1$-$C_6$-alkyl; halogen; $C_1$-$C_6$-alkylsulfonylamino$C_2$-$C_6$-alkyl; and (i),

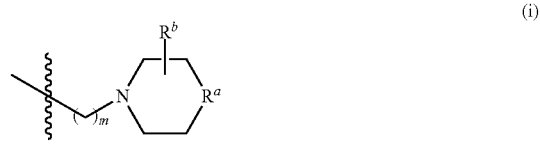

(i)

wherein R$^a$ is selected from the group consisting of a bond, CH$_2$, CHR$^b$, O, S, and N—R$^c$; wherein only 1 substituent can be present on the two atoms adjacent to the atom connected to the amide nitrogen pendant on the furan ring; m is 2, 3 or 4 when (i) is attached to a ring nitrogen atom of the bicyclic heteroaryl; or m is 0, 1, 2, 3 or 4 when (i) is attached to a ring carbon atom of the bicyclic heteroaryl; R$^b$, at each occurrence, is independently selected from the group consisting of hydrogen, $C_1$-$C_6$-alkyl, halo$C_1$-$C_6$-alkyl, $C_1$-$C_6$-alkoxy$C_1$-$C_6$-alkyl, and hydroxy$C_1$-$C_6$-alkyl; and R$^c$ is selected from the group consisting of hydrogen, $C_1$-$C_6$-alkyl, $C_1$-$C_6$-alkoxycarbonyl, $C_1$-$C_6$-alkycarbonyl, $C_1$-$C_6$-alkysulfonyl, di($C_1$-$C_6$-alkyl)aminosulfonyl, heterocyclecarbonyl, $C_3$-$C_7$-cycloalkylcarbonyl, —C(O)NH$_2$, —C(O)NH(alkyl), —C(O)N(alkyl)$_2$ and —C(=NCN)NHCH$_3$.

In another embodiment, R$^1$ is fused-bicyclic heteroaryl, wherein the fused-bicyclic heteroaryl contains 1 or 2 ring nitrogens and optionally one ring oxygen or one ring sulfur, wherein the fused-bicyclic heteroaryl isoptionally substituted with 1, 2, 3, or 4 substituents selected from the group consisting of $C_1$-$C_6$-alkyl; $C_1$-$C_6$-alkoxycarbonyl; hydroxy$C_1$-$C_6$-alkyl; halogen; $C_1$-$C_6$-alkylsulfonylamino$C_2$-$C_6$-alkyl; and (i),

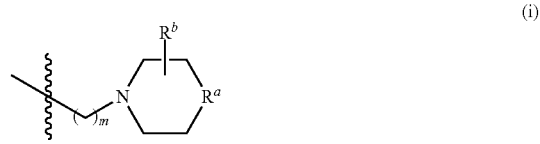

(i)

wherein $R^a$ is selected from the group consisting of a bond, O, S, and N—$R^c$; wherein only 1 substituent can be present on the two atoms adjacent to the atom connected to the amide nitrogen pendant on the furan ring; m is 2 when (i) is attached to a ring nitrogen atom of the bicyclic heteroaryl; $R^b$ is hydrogen; and $R^c$ is $C_1$-$C_6$-alkyl.

In one embodiment, $R^1$ is (ii), (iii), or (iv);

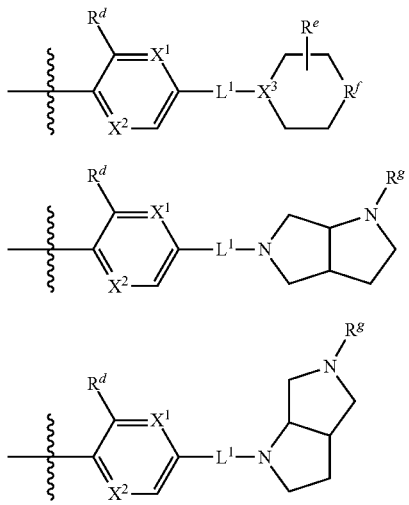

wherein both $X^1$ and $X^2$ are CH, or one of $X^1$ and $X^2$ is N and the other is CH; $X^3$ is CH or N; $L^1$ is a bond, C(O), or —NHC(O)—; $R^d$ is selected form the group consisting of hydrogen; $C_1$-$C_6$alkoxy; fluoro$C_1$-$C_6$-alkoxy; $C_1$-$C_6$-alkoxy$C_1$-$C_6$-alkoxy; $C_3$-$C_7$-cycloalkyloxy; $C_3$-$C_7$-cycloalkyl$C_1$-$C_6$-alkoxy; hydroxy$C_1$-$C_6$-alkoxy; phenyl$C_1$-$C_6$-alkoxy$C_1$-$C_6$-alkoxy; $M_4$-$M_7$-heterocycleoxy, wherein the heterocycle of heterocycleoxy isoptionally substituted with $C_1$-$C_6$-alkyl or oxo; and phenoxy, wherein the phenyl of phenoxy isoptionally substituted with hydroxy$C_1$-$C_6$-alkyl, $C_1$-$C_6$-alkoxy, $C_1$-$C_6$-alkoxy$C_1$-$C_6$-alkoxy, or $C_1$-$C_6$-alkoxycarbonyl; $R^e$ at each occurrence is independently selected from the group consisting of hydrogen, $C_1$-$C_6$-alkyl, di($C_1$-$C_6$-alkyl)amino, halo$C_1$-$C_6$-alkyl, $C_1$-$C_6$-alkoxy$C_1$-$C_6$alkyl, and hydroxy$C_1$-$C_6$-alkyl; $R^f$ is selected from the group consisting of a bond, $CH_2$, $CHR^e$, $CH_2CH_2$, O, $NR^g$, and $CH_2NR^g$; and $R^g$ is selected from the group consisting of hydrogen; $C_1$-$C_6$-alkyl; $C_1$-$C_6$-alkoxycarbonyl; $C_1$-$C_6$-alkycarbonyl; $C_1$-$C_6$-alkysulfonyl; di($C_1$-$C_6$-alkyl)aminosulfonyl; $C_3$-$C_7$-cycloalkylcarbonyl; $C_1$-$C_6$-alkoxy$C_1$-$C_6$-alkylcarbony; hydroxy$C_2$-$C_6$-alkyl; hydroxy$C_1$-$C_6$-alkylcarbonyl; formyl; —C(O)NH$_2$; —C(O)NH(alkyl); —C(O)N(alkyl)$_2$; —C(=NCN)NHCH$_3$; and $M_4$-$M_7$-heterocyclecarbonyl, wherein the heterocycle of heterocyclecarbonyl isoptionally substituted with $C_1$-$C_6$-alkyl.

In another embodiment, $R^1$ is (ii), (iii), or (iv);

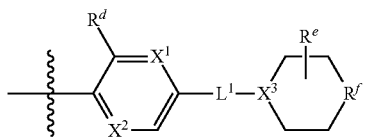

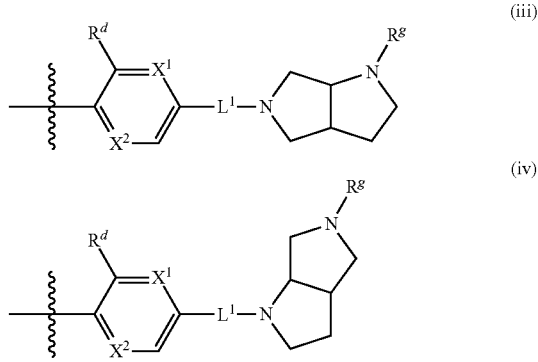

wherein both $X^1$ and $X^2$ are CH, or one of $X^1$ and $X^2$ is N and the other is CH; $X^3$ is CH or N; $L^1$ is a bond; $R^d$ is selected form the group consisting of hydrogen; $C_1$-$C_6$alkoxy; fluoro$C_1$-$C_6$-alkoxy; $C_1$-$C_6$-alkoxy$C_1$-$C_6$-alkoxy; hydroxy$C_1$-$C_6$-alkoxy; phenyl$C_1$-$C_6$-alkoxy$C_1$-$C_6$-alkoxy; $M_4$-$M_7$-heterocycleoxy, wherein the heterocycle of heterocycleoxy isoptionally substituted with oxo; and phenoxy, wherein the phenyl of phenoxy isoptionally substituted with hydroxy$C_1$-$C_6$-alkyl, or $C_1$-$C_6$-alkoxycarbonyl; $R^e$ at each occurrence is independently selected from the group consisting of hydrogen, di($C_1$-$C_6$-alkyl)amino, $C_1$-$C_6$-alkoxy$C_1$-$C_6$alkyl, and hydroxy$C_1$-$C_6$-alkyl; $R^f$ is selected from the group consisting of a bond, $CH_2$, O, and $NR^g$; and $R^g$ is selected from the group consisting of hydrogen; $C_1$-$C_6$-alkyl; $C_1$-$C_6$-alkoxycarbonyl; $C_1$-$C_6$-alkycarbonyl; $C_1$-$C_6$-alkysulfonyl; di($C_1$-$C_6$-alkyl)aminosulfonyl; hydroxy$C_2$-$C_6$-alkyl; formyl; —C(=NCN)NHCH$_3$; and $M_4$-$M_7$-heterocyclecarbonyl, wherein the heterocycle of heterocyclecarbonyl isoptionally substituted with $C_1$-$C_6$-alkyl.

In one embodiment, $Z^1$ is $NR^2$ or $CR^3R^4$.

In another embodiment, $Z^1$ is $NR^2$.

In another embodiment, $Z^1$ is $CR^3R^4$.

In one embodiment, $R^2$ is selected from the group consisting of hydrogen, $C_1$-$C_6$-alkyl, hydroxy$C_2$-$C_6$-alkyl, di(hydroxy)$C_2$-$C_6$-alkyl, $C_1$-$C_6$-alkoxy$C_2$-$C_6$alkyl, hydroxy$C_2$-$C_6$-alkoxy$C_2$-$C_6$-alkyl, $C_1$-$C_6$-alkylcarbonyloxy$C_2$-$C_6$-alkyl, $C_1$-$C_6$-alkoxycarbonyl$C_1$-$C_6$-alkyl, $C_1$-$C_6$-alkylcarbonyl$C_1$-$C_6$-alkyl and phenyl$C_1$-$C_6$-alkoxy$C_2$-$C_6$alkyl.

In another embodiment, $R^2$ is selected from the group consisting of hydrogen, $C_1$-$C_6$-alkyl, hydroxy$C_2$-$C_6$-alkyl, di(hydroxy)$C_2$-$C_6$-alkyl, $C_1$-$C_6$-alkoxy$C_2$-$C_6$alkyl, hydroxy$C_2$-$C_6$-alkoxy$C_2$-$C_6$-alkyl, $C_1$-$C_6$-alkylcarbonyloxy$C_2$-$C_6$-alkyl, and phenyl$C_1$-$C_6$-alkoxy$C_2$-$C_6$alkyl.

In one embodiment, $R^3$ and $R^4$ are each independently selected from the group consisting of hydrogen, $C_1$-$C_6$-alkyl, hydroxy$C_1$-$C_6$-alkyl, amino$C_1$-$C_6$-alkyl, and phenyl, wherein phenyl isoptionally substituted with 1, 2, 3 or 4 substituents selected from halogen, $C_1$-$C_6$-alkyl, and cyano.

In another embodiment, $R^3$ and $R^4$ are each independently selected from the group consisting of hydrogen, $C_1$-$C_6$-alkyl, hydroxy$C_1$-$C_6$-alkyl, amino$C_1$-$C_6$-alkyl, and phenyl, wherein phenyl isoptionally substituted with 1 or 2 halogen.

In one embodiment, $R^3$ and $R^4$ taken together with the carbon atom to which they are attached form a $M_4$-$M_7$-heterocycle optionally substituted with 1, 2 or 3 halogen, $C_1$-$C_6$-alkyl, cyano or oxo.

In another embodiment, $R^3$ and $R^4$ taken together with the carbon atom to which they are attached form a $M_4$-$M_7$-heterocycle.

In one embodiment, $Z^2$ is O, $NR^5$, or $CR^6R^7$.
In another embodiment, $Z^2$ is O.
In another embodiment, $Z^2$ is $NR^5$.
In another embodiment, $Z^2$ is $CR^6R^7$.

In one embodiment, $R^5$ is selected from the group consisting of hydrogen, $C_1$-$C_6$-alkyl, $C_1$-$C_6$-alkylsulfonyl, $C_1$-$C_6$-alkylcarbonyl, and $C_1$-$C_6$-alkoxycarbonyl.

In another embodiment, $R^5$ is selected from the group consisting of hydrogen and $C_1$-$C_6$-alkylsulfonyl.

In one embodiment, $R^6$ and $R^7$ are each independently selected from the group consisting of hydrogen, $C_1$-$C_6$-alkyl, $C_1$-$C_6$-alkoxyC$_1$-$C_6$-alkyl, hydroxyC$_1$-$C_6$-alkyl, aminoC$_1$-$C_6$-alkyl, aminocarbonyl, and $C_1$-$C_6$-alkoxycarbonyl.

In another embodiment, $R^6$ and $R^7$ are each independently selected from the group consisting of hydrogen, $C_1$-$C_6$-alkyl, $C_1$-$C_6$-alkoxyC$_1$-$C_6$-alkyl, hydroxyC$_1$-$C_6$-alkyl, aminocarbonyl, and $C_1$-$C_6$-alkoxycarbonyl.

In one embodiment, $R^6$ and $R^7$ taken together with the carbon atom to which they are attached form a $C_3$-$C_6$-cycloalkyl or $M_4$-$M_7$-heterocycle, wherein the $C_3$-$C_6$-cycloalkyl or $M_4$-$M_7$-heterocycle are optionally substituted with 1, 2, or 3 substituents selected from $C_1$-$C_6$-alkyl, cyano, aminocarbonyl, halogen, oxo and $C_1$-$C_6$-alkylcarbonyl.

In another embodiment, $R^6$ and $R^7$ taken together with the carbon atom to which they are attached form a $C_3$-$C_6$-cycloalkyl or $M_4$-$M_7$-heterocycle, wherein the $C_3$-$C_6$-cycloalkyl or $M_4$-$M_7$-heterocycle are optionally substituted with 1 $C_1$-$C_6$-alkylcarbonyl.

In one embodiment, n is 1 or 2; $Z^1$ is $NR^2$; $Z^2$ is $CR^6R^7$; and $R^2$, $R^6$ and $R^7$ are as defined in the Summary. In another embodiment, n is 1 or 2; $Z^1$ is $NR^2$; $Z^2$ is $CR^6R^7$; $R^1$ is phenyl or monocyclic heteroaryl, wherein the monocyclic heteroaryl contains one or two ring nitrogens and optionally one ring oxygen or one ring sulfur, wherein the phenyl or monocyclic heteroaryl isoptionally substituted with 1, 2, or 3 substituents selected from the group consisting of $C_1$-$C_6$-alkyl; $C_1$-$C_6$-alkylcarbonylamino; hydroxyC$_1$-$C_6$-alkylcarbonylamino; $C_1$-$C_6$-alkoxyC$_1$-$C_6$alkylcarbonylamino; $C_1$-$C_6$-alkoxy; $C_1$-$C_6$-alkoxyC$_1$-$C_6$-alkoxy; $C_1$-$C_6$-alkoxyC$_1$-$C_6$-alkyl; $C_1$-$C_6$-alkoxycarbonyl; $C_1$-$C_6$-alkoxycarbonylC$_1$-$C_6$-alkyl; aminocarbonyl; $C_1$-$C_6$-alkylaminocarbonyl; hydroxyC$_1$-$C_6$-alkylaminocarbonyl; $C_1$-$C_6$-alkoxyC$_1$-$C_6$-alkylaminocarbonyl; cyano; carboxy; hydroxy; hydroxyC$_1$-$C_6$-alkoxy; hydroxyC$_1$-$C_6$-alkyl; di(hydroxy)C$_1$-$C_6$-alkyl; di(C$_1$-$C_6$alkyl)amino; di(hydroxyC$_1$-$C_6$-alkyl)amino; di(C$_1$-$C_6$-alkoxyC$_1$-$C_6$-alkyl)amino; (C$_1$-$C_6$-alkoxyC$_1$-$C_6$-alkyl)(hydroxyC$_1$-$C_6$-alkyl)amino; haloC$_1$-$C_6$-alkyl; and halogen; wherein only 1 substituent can be present on the two atoms adjacent to the atom connected to the amide nitrogen pendant on the furan ring; and $R^2$, $R^6$ and $R^7$ are as defined in the Summary.

In one embodiment, n is 1; $Z^1$ is $NR^2$; $Z^2$ is $CR^6R^7$; $R^1$ is phenyl optionally substituted with 1 or 2 substituents selected from the group consisting of $C_1$-$C_6$-alkyl; $C_1$-$C_6$-alkylcarbonylamino; aminocarbonyl; cyano; hydroxy; and di(C$_1$-$C_6$alkyl)amino; wherein only 1 substituent can be present on the two atoms adjacent to the atom connected to the amide nitrogen pendant on the furan ring; or $R^1$ is monocyclic heteroaryl, wherein the monocyclic heteroaryl is pyridyl, pyrazinyl or isoxazolyl, wherein the monocyclic heteroaryl isoptionally substituted with 1, 2, or 3 substituents selected from the group consisting of $C_1$-$C_6$-alkyl; $C_1$-$C_6$-alkoxy; $C_1$-$C_6$-alkoxycarbonylC$_1$-$C_6$-alkyl; hydroxyC$_1$-$C_6$-alkyl; haloC$_1$-$C_6$-alkyl; and halogen; wherein only 1 substituent can be present on the two atoms adjacent to the atom connected to the amide nitrogen pendant on the furan ring; $R^2$ is hydrogen or $C_1$-$C_6$-alkyl; and $R^6$ and $R^7$ are each hydrogen.

In one embodiment, n is 1; $Z^1$ is $NR^2$; $Z^2$ is $CR^6R^7$; $R^1$ is monocyclic heteroaryl, wherein the monocyclic heteroaryl is pyridyl, wherein the monocyclic heteroaryl isoptionally substituted with 1, 2, or 3 substituents selected from the group consisting of $C_1$-$C_6$-alkoxy; $C_1$-$C_6$-alkoxyC$_1$-$C_6$-alkoxy; carboxy; hydroxyC$_1$-$C_6$-alkyl; and di(hydroxyC$_1$-$C_6$-alkyl)amino; wherein only 1 substituent can be present on the two atoms adjacent to the atom connected to the amide nitrogen pendant on the furan ring; $R^2$ is hydrogen or $C_1$-$C_6$-alkoxyC$_2$-$C_6$alkyl; and $R^6$ and $R^7$ are each independently $C_1$-$C_6$-alkyl.

In one embodiment, n is 1 or 2; $Z^1$ is $NR^2$; $Z^2$ is $CR^6R^7$; $R^1$ is fused-bicyclic heteroaryl, wherein the fused-bicyclic heteroaryl contains 1, 2, 3 or 4 ring nitrogens and optionally one ring oxygen or one ring sulfur, wherein the fused-bicyclic heteroaryl is optionally substituted with 1, 2, 3, or 4 substituents selected from the group consisting of $C_1$-$C_6$-alkyl; $C_1$-$C_6$-alkylcarbonylamino; hydroxyC$_1$-$C_6$-alkylcarbonylamino; $C_1$-$C_6$-alkoxyC$_1$-$C_6$-alkylcarbonylamino; $C_1$-$C_6$-alkoxy; $C_1$-$C_6$-alkoxyC$_1$-$C_6$-alkoxy; $C_1$-$C_6$alkoxy-$C_1$-$C_6$alkyl; $C_1$-$C_6$-alkoxycarbonyl; $C_1$-$C_6$-alkoxycarbonylC$_1$-$C_6$-alkyl; $C_3$-$C_7$-cycloalkyloxy; $M_4$-$M_7$-heterocycleoxy, wherein the heterocycle of $M_4$-$M_7$-heterocycleoxy isoptionally substituted with $C_1$-$C_6$-alkyl; aminocarbonyl; $C_1$-$C_6$-alkylaminocarbonyl; hydroxyC$_1$-$C_6$-alkylaminocarbonyl; $C_1$-$C_6$-alkoxyC$_1$-$C_6$-alkylamincarbonyl; cyano; hydroxy; hydroxyC$_1$-$C_6$-alkoxy; hydroxyC$_1$-$C_6$-alkyl; di(C$_1$-$C_6$alkyl)amino; di(hydroxyC$_1$-$C_6$-alkyl)amino; di(C$_1$-$C_6$-alkoxyC$_1$-$C_6$-alkyl)amino; (C$_1$-$C_6$-alkoxyC$_1$-$C_6$-alkyl)(hydroxyC$_1$-$C_6$-alkyl)amino; haloC$_1$-$C_6$-alkyl; halogen; $C_1$-$C_6$-alkylsulfonylaminoC$_2$-$C_6$-alkyl; and (i),

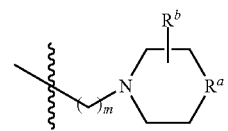

(i)

wherein $R^a$ is selected from the group consisting of a bond, $CH_2$, $CHR^b$, O, S, and N—$R^c$; wherein only 1 substituent can be present on the two atoms adjacent to the atom connected to the amide nitrogen pendant on the furan ring; m is 2, 3 or 4 when (i) is attached to a ring nitrogen atom of the bicyclic heteroaryl; or m is 0, 1, 2, 3 or 4 when (i) is attached to a ring carbon atom of the bicyclic heteroaryl; $R^b$, at each occurrence, is independently selected from the group consisting of hydrogen, $C_1$-$C_6$-alkyl, haloC$_1$-$C_6$-alkyl, $C_1$-$C_6$-alkoxyC$_1$-$C_6$-alkyl, and hydroxyC$_1$-$C_6$-alkyl; and $R^c$ is selected from the group consisting of hydrogen, $C_1$-$C_6$-alkyl, $C_1$-$C_6$-alkoxycarbonyl, $C_1$-$C_6$-alkycarbonyl, $C_1$-$C_6$-alkysulfonyl, di(C$_1$-$C_6$-alkyl)aminosulfonyl, heterocyclecarbonyl, $C_3$-$C_7$-cycloalkylcarbonyl, —C(O)NH$_2$, —C(O)NH(alkyl), —C(O)N(alkyl)$_2$ and —C(=NCN)NHCH$_3$; and $R^2$, $R^6$ and $R^7$ are as defined in the Summary.

In one embodiment, n is 1; $Z^1$ is $NR^2$; $Z^2$ is $CR^6R^7$; $R^1$ is fused-bicyclic heteroaryl, wherein the fused-bicyclic heteroaryl is 2H-indazol-5-yl, 1H-indazol-5-yl, 1H-benzimidazol-5-yl, 1,3-benzothiazol-6-yl, quinolin-6-yl, 1H-indazol-6-yl, 1,3-benzothiazol-2-yl, wherein the fused-bicyclic heteroaryl isoptionally substituted with 1, 2, or 3, substituents selected from the group consisting of $C_1$-$C_6$-alkyl;

$C_1$-$C_6$-alkoxycarbonyl; hydroxy$C_1$-$C_6$-alkyl; halogen; $C_1$-$C_6$-alkylsulfonylamino$C_2$-$C_6$-alkyl; and (i),

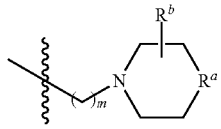
(i)

wherein $R^a$ is selected from the group consisting of a bond, O, and N—$R^c$; wherein only 1 substituent can be present on the two atoms adjacent to the atom connected to the amide nitrogen pendant on the furan ring; m is 2; $R^b$ is hydrogen; $R^c$ is $C_1$-$C_6$-alkyl; $R^2$ is hydrogen or $C_1$-$C_6$-alkyl; and $R^6$ and $R^7$ are each hydrogen.

In one embodiment, n is 1 or 2; $Z^1$ is $NR^2$; $Z^2$ is $CR^6R^7$; $R^1$ is (ii), (iii), or (iv);

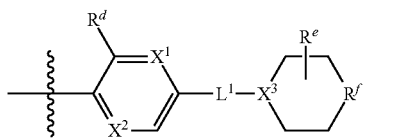
(ii)

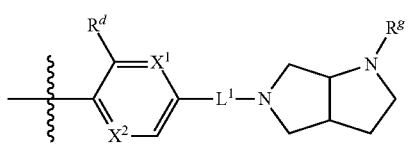
(iii)

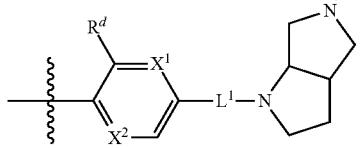
(iv)

wherein both $X^1$ and $X^2$ are CH, or one of $X^1$ and $X^2$ is N and the other is CH; $X^3$ is CH or N; $L^1$ is a bond, C(O), or —NHC(O)—; $R^d$ is selected form the group consisting of hydrogen; $C_1$-$C_6$alkoxy; fluoro$C_1$-$C_6$-alkoxy; $C_1$-$C_6$-alkoxy$C_1$-$C_6$-alkoxy; $C_3$-$C_7$-cycloalkyloxy; $C_3$-$C_7$-cycloalkyl$C_1$-$C_6$-alkoxy; $M_4$-$M_7$-heterocycleoxy, wherein the heterocycle of heterocycleoxy isoptionally substituted with $C_1$-$C_6$-alkyl or oxo; hydroxy$C_1$-$C_6$-alkoxy; phenyl$C_1$-$C_6$-alkoxy$C_1$-$C_6$-alkoxy; and phenoxy, wherein the phenyl of phenoxy isoptionally substituted with hydroxy$C_1$-$C_6$-alkyl, $C_1$-$C_6$-alkoxy, $C_1$-$C_6$-alkoxy$C_1$-$C_6$-alkoxy, or $C_1$-$C_6$-alkoxycarbonyl; $R^e$ at each occurrence is independently selected from the group consisting of hydrogen, $C_1$-$C_6$-alkyl, di($C_1$-$C_6$-alkyl)amino, halo$C_1$-$C_6$-alkyl, $C_1$-$C_6$-alkoxy$C_1$-$C_6$alkyl, and hydroxy$C_1$-$C_6$-alkyl; $R^f$ is selected from the group consisting of a bond, $CH_2$, $CHR^e$, $CH_2CH_2$, O, $NR^g$, and $CH_2NR^g$; and $R^g$ is selected from the group consisting of hydrogen; $C_1$-$C_6$-alkyl; $C_1$-$C_6$-alkoxycarbonyl; $C_1$-$C_6$-alkycarbonyl; $C_1$-$C_6$-alkysulfonyl; di($C_1$-$C_6$-alkyl)aminosulfonyl; $C_3$-$C_7$-cycloalkylcarbonyl; $C_1$-$C_6$-alkoxy$C_1$-$C_6$-alkylcarbonyl; hydroxy$C_2$-$C_6$-alkyl; hydroxy$C_1$-$C_6$-alkylcarbonyl; formyl; —C(O)NH$_2$; —C(O)NH(alkyl); —C(O)N(alkyl)$_2$; —C(=NCN)NHCH$_3$; and $M_4$-$M_7$-heterocyclecarbonyl, wherein the heterocycle of heterocyclecarbonyl isoptionally substituted with $C_1$-$C_6$-alkyl; and $R^2$, $R^6$ and $R^7$ are as defined in the Summary.

In one embodiment, n is 1 or 2; $Z^1$ is $NR^2$; $Z^2$ is $CR^6R^7$; $R^1$ is (ii);

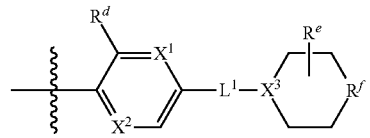
(ii)

wherein both $X^1$ and $X^2$ are CH, or one of $X^1$ and $X^2$ is N and the other is CH; $X^3$ is N; $L^1$ is a bond; $R^d$ is selected form the group consisting of hydrogen; $C_1$-$C_6$alkoxy; $C_1$-$C_6$-alkoxy$C_1$-$C_6$-alkoxy; hydroxy$C_1$-$C_6$-alkoxy; phenyl$C_1$-$C_6$-alkoxy$C_1$-$C_6$-alkoxy; $M_4$-$M_7$-heterocycleoxy, wherein the heterocycle of heterocycleoxy isoptionally substituted with $C_1$-$C_6$-alkyl or oxo; and phenoxy, wherein the phenyl of phenoxy isoptionally substituted with hydroxy$C_1$-$C_6$-alkyl or $C_1$-$C_6$-alkoxycarbonyl; $R^e$ at each occurrence is hydrogen; $R^f$ is selected from the group consisting of a $CH_2$, O, and $NR^g$; $R^g$ is selected from the group consisting of hydrogen; $C_1$-$C_6$-alkyl; $C_1$-$C_6$-alkoxycarbonyl; $C_1$-$C_6$-alkycarbonyl; di($C_1$-$C_6$-alkyl)aminosulfonyl; —C(=NCN)NHCH$_3$; and $M_4$-$M_7$-heterocyclecarbonyl, wherein the heterocycle of heterocyclecarbonyl isoptionally substituted with $C_1$-$C_6$-alkyl; $R^2$ is hydrogen, $C_1$-$C_6$-alkyl, hydroxy$C_2$-$C_6$-alkyl, $C_1$-$C_6$-alkoxy$C_2$-$C_6$alkyl, hydroxy$C_2$-$C_6$-alkoxy$C_2$-$C_6$-alkyl, $C_1$-$C_6$-alkylcarbonyloxy$C_2$-$C_6$-alkyl, and phenyl$C_1$-$C_6$-alkoxy$C_2$-$C_6$alkyl; and $R^6$ and $R^7$ are each hydrogen.

In one embodiment, n is 1; $Z^1$ is $NR^2$; $Z^2$ is $CR^6R^7$; $R^1$ is $R^1$ is (ii), (iii), or (iv);

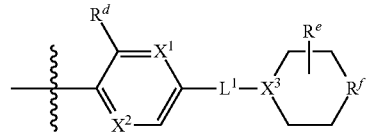
(ii)

(iii)

(iv)

wherein both $X^1$ and $X^2$ are CH, or one of $X^1$ and $X^2$ is N and the other is CH; $X^3$ is CH or N; $L^1$ is a bond; $R^d$ is selected form the group consisting of $C_1$-$C_6$alkoxy; fluoro$C_1$-$C_6$-alkoxy; $C_1$-$C_6$-alkoxy$C_1$-$C_6$-alkoxy; and $M_4$-$M_7$-heterocycleoxy, wherein the heterocycle of heterocycleoxy isoptionally substituted with oxo; $R^e$ at each occurrence is independently selected from the group consisting of hydrogen, di($C_1$-$C_6$-alkyl)amino, $C_1$-$C_6$-alkoxy$C_1$-$C_6$alkyl, and hydroxyC$_1$-C$_6$-alkyl; R$^f$ is selected from the group consisting of a bond, CH$_2$, and NR$^g$; R$^g$ is selected from the group consisting of hydrogen; C$_1$-C$_6$-alkyl; C$_1$-C$_6$-alkycarbonyl; C$_1$-C$_6$-alkysulfonyl; hydroxyC$_2$-C$_6$-alkyl; formyl; —C(=NCN)NHCH$_3$; and M$_4$-M$_7$-heterocyclecarbonyl, wherein the heterocycle of heterocyclecarbonyl is optionally substituted with C$_1$-C$_6$-alkyl; R$^2$ is selected from the group consisting of hydrogen, C$_1$-C$_6$-alkyl, hydroxyC$_2$-C$_6$-alkyl, di(hydroxy)C$_2$-C$_6$-alkyl, C$_1$-C$_6$-alkoxyC$_2$-C$_6$alkyl, and hydroxyC$_2$-C$_6$-alkoxyC$_2$-C$_6$-alkyl; R$^6$ is selected from the group consisting of hydrogen and C$_1$-C$_6$-alkyl; and R$^7$ is selected from the group consisting of C$_1$-C$_6$-alkyl and hydroxyC$_1$-C$_6$-alkyl; or R$^6$ and R$^7$ taken together with the carbon atom to which they are attached form a C$_3$-C$_6$-cycloalkyl or M$_4$-M$_7$-heterocycle, wherein the M$_4$-M$_7$-heterocycle is optionally substituted with 1 or 2 substituents selected from C$_1$-C$_6$-alkyl, oxo and C$_1$-C$_6$-alkylcarbonyl.

In one embodiment, n is 1 or 2; Z$^1$ is CR$^3$R$^4$; Z$^2$ is NR$^5$; and R$^3$, R$^4$ and R$^5$ are as defined in the Summary.

In one embodiment, n is 1 or 2; Z$^1$ is CR$^3$R$^4$; Z$^2$ is NR$^5$; R$^1$ is phenyl or monocyclic heteroaryl, wherein the monocyclic heteroaryl contains one or two ring nitrogens and optionally one ring oxygen or one ring sulfur, wherein the phenyl or monocyclic heteroaryl is optionally substituted with 1, 2, or 3 substituents selected from the group consisting of C$_1$-C$_6$-alkyl; C$_1$-C$_6$-alkylcarbonylamino; hydroxyC$_1$-C$_6$-alkylcarbonylamino; C$_1$-C$_6$-alkoxyC$_1$-C$_6$alkylcarbonylamino; C$_1$-C$_6$-alkoxy; C$_1$-C$_6$-alkoxyC$_1$-C$_6$-alkoxy; C$_1$-C$_6$-alkoxyC$_1$-C$_6$-alkyl; C$_1$-C$_6$-alkoxycarbonyl; C$_1$-C$_6$-alkoxycarbonylC$_1$-C$_6$-alkyl; aminocarbonyl; C$_1$-C$_6$-alkylaminocarbonyl; hydroxyC$_1$-C$_6$-alkylaminocarbonyl; C$_1$-C$_6$-alkoxyC$_1$-C$_6$-alkylaminocarbonyl; cyano; carboxy; hydroxy; hydroxyC$_1$-C$_6$-alkoxy; hydroxyC$_1$-C$_6$-alkyl; di(hydroxy)C$_1$-C$_6$-alkyl; di(C$_1$-C$_6$alkyl)amino; di(hydroxyC$_1$-C$_6$-alkyl)amino; di(C$_1$-C$_6$-alkoxyC$_1$-C$_6$-alkyl)amino; (C$_1$-C$_6$-alkoxyC$_1$-C$_6$-alkyl)(hydroxyC$_1$-C$_6$-alkyl)amino; haloC$_1$-C$_6$-alkyl; and halogen; wherein only 1 substituent can be present on the two atoms adjacent to the atom connected to the amide nitrogen pendant on the furan ring; and R$^3$, R$^4$ and R$^5$ are as defined in the Summary.

In one embodiment, n is 1 or 2; Z$^1$ is CR$^3$R$^4$; Z$^2$ is NR$^5$; R$^1$ is fused-bicyclic heteroaryl, wherein the fused-bicyclic heteroaryl contains 1, 2, 3 or 4 ring nitrogens and optionally one ring oxygen or one ring sulfur, wherein the fused-bicyclic heteroaryl isoptionally substituted with 1, 2, 3, or 4 substituents selected from the group consisting of C$_1$-C$_6$-alkyl; C$_1$-C$_6$-alkylcarbonylamino; hydroxyC$_1$-C$_6$-alkylcarbonylamino; C$_1$-C$_6$-alkoxyC$_1$-C$_6$-alkylcarbonylamino; C$_1$-C$_6$-alkoxy; C$_1$-C$_6$-alkoxyC$_1$-C$_6$-alkoxy; C$_1$-C$_6$alkoxy-C$_1$-C$_6$alkyl; C$_1$-C$_6$-alkoxycarbonyl; C$_1$-C$_6$-alkoxycarbonylC$_1$-C$_6$-alkyl; C$_3$-C$_7$-cycloalkyloxy; M$_4$-M$_7$-heterocycleoxy, wherein the heterocycle of M$_4$-M$_7$-heterocycleoxy isoptionally substituted with C$_1$-C$_6$-alkyl; aminocarbonyl; C$_1$-C$_6$-alkylaminocarbonyl; hydroxyC$_1$-C$_6$-alkylaminocarbonyl; C$_1$-C$_6$-alkoxyC$_1$-C$_6$-alkylamincarbonyl; cyano; hydroxy; hydroxyC$_1$-C$_6$-alkoxy; hydroxyC$_1$-C$_6$-alkyl; di(C$_1$-C$_6$alkyl)amino; di(hydroxyC$_1$-C$_6$-alkyl)amino; di(C$_1$-C$_6$-alkoxyC$_1$-C$_6$-alkyl)amino; (C$_1$-C$_6$-alkoxyC$_1$-C$_6$-alkyl)(hydroxyC$_1$-C$_6$-alkyl)amino; haloC$_1$-C$_6$-alkyl; halogen; C$_1$-C$_6$-alkylsulfonylaminoC$_2$-C$_6$-alkyl; and (i),

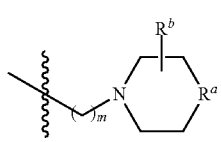

(i)

wherein R$^a$ is selected from the group consisting of a bond, CH$_2$, CHR$^b$, O, S, and N—R$^c$; wherein only 1 substituent can be present on the two atoms adjacent to the atom connected to the amide nitrogen pendant on the furan ring; m is 2, 3 or 4 when (i) is attached to a ring nitrogen atom of the bicyclic heteroaryl; or m is 0, 1, 2, 3 or 4 when (i) is attached to a ring carbon atom of the bicyclic heteroaryl; R$^b$, at each occurrence, is independently selected from the group consisting of hydrogen, C$_1$-C$_6$-alkyl, haloC$_1$-C$_6$-alkyl, C$_1$-C$_6$-alkoxyC$_1$-C$_6$-alkyl, and hydroxyC$_1$-C$_6$-alkyl; and R$^c$ is selected from the group consisting of hydrogen, C$_1$-C$_6$-alkyl, C$_1$-C$_6$-alkoxycarbonyl, C$_1$-C$_6$-alkycarbonyl, C$_1$-C$_6$-alkysulfonyl, di(C$_1$-C$_6$-alkyl)aminosulfonyl, heterocyclecarbonyl, C$_3$-C$_7$-cycloalkylcarbonyl, —C(O)NH$_2$, —C(O)NH(alkyl), —C(O)N(alkyl)$_2$ and —C(=NCN)NHCH$_3$; and R$^3$, R$^4$ and R$^5$ are as defined in the Summary.

In one embodiment, n is 1; Z$^1$ is CR$^3$R$^4$; Z$^2$ is NR$^5$; R$^1$ is fused-bicyclic heteroaryl, wherein the fused-bicyclic heteroaryl is 2H-indazol-5-yl, wherein the fused-bicyclic heteroaryl isoptionally substituted with 1 or 2 C$_1$-C$_6$-alkyl; wherein only 1 substituent can be present on the two atoms adjacent to the atom connected to the amide nitrogen pendant on the furan ring; R$^3$ and R$^4$ are both hydrogen; and R$^5$ is hydrogen or C$_1$-C$_6$-alkylsulfonyl.

In one embodiment, n is 1 or 2; Z$^1$ is CR$^3$R$^4$; Z$^2$ is NR$^5$; R$^1$ is (ii), (iii), or (iv);

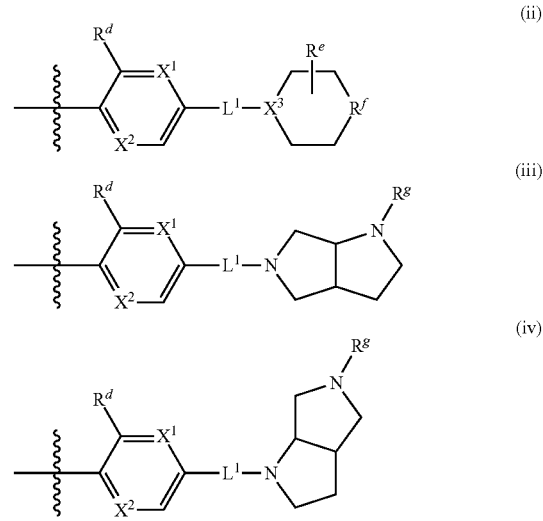

wherein both X$^1$ and X$^2$ are CH, or one of X$^1$ and X$^2$ is N and the other is CH; X$^3$ is CH or N; L$^1$ is a bond, C(O), or —NHC(O)—; R$^d$ is selected form the group consisting of hydrogen; C$_1$-C$_6$alkoxy; fluoroC$_1$-C$_6$-alkoxy; C$_1$-C$_6$-alkoxyC$_1$-C$_6$-alkoxy; C$_3$-C$_7$-cycloalkyloxy; C$_3$-C$_7$-cycloalkylC$_1$-C$_6$-alkoxy; hydroxyC$_1$-C$_6$-alkoxy; phenylC$_1$-C$_6$-alkoxyC$_1$-C$_6$-alkoxy; M$_4$-M$_7$-heterocycleoxy, wherein the heterocycle of heterocycleoxy isoptionally substituted with C$_1$-C$_6$-alkyl or oxo; and phenoxy, wherein the phenyl of phenoxy isoptionally substituted with hydroxyC$_1$-C$_6$-alkyl, C$_1$-C$_6$-alkoxy, C$_1$-C$_6$-alkoxyC$_1$-C$_6$-alkoxy, or C$_1$-C$_6$-alkoxycarbonyl; R$^e$ at each occurrence is independently selected from the group consisting of hydrogen, C$_1$-C$_6$-alkyl, di(C$_1$-C$_6$-alkyl)amino, haloC$_1$-C$_6$-alkyl, C$_1$-C$_6$-alkoxyC$_1$-C$_6$alkyl, and hydroxyC$_1$-C$_6$-alkyl; R$^f$ is selected from the group consisting of a bond, CH$_2$, CHR$^e$, CH$_2$CH$_2$, O, NR$^g$, and CH$_2$NR$^g$; R$^g$ is selected from the group consisting of hydrogen; $C_1$-$C_6$-alkyl; $C_1$-$C_6$-alkoxycarbonyl; $C_1$-$C_6$-alkycarbonyl; $C_1$-$C_6$-alkysulfonyl; di($C_1$-$C_6$-alkyl)aminosulfonyl; $C_3$-$C_7$-cycloalkylcarbonyl; $C_1$-$C_6$-alkoxy$C_1$-$C_6$-alkylcarbonyl; hydroxy$C_2$-$C_6$-alkyl; hydroxy$C_1$-$C_6$-alkylcarbonyl; formyl; —C(O)NH$_2$; —C(O)NH(alkyl); —C(O)N(alkyl)$_2$; —C(=NCN)NHCH$_3$; and $M_4$-$M_7$-heterocyclecarbonyl, wherein the heterocycle of heterocyclecarbonyl isoptionally substituted with $C_1$-$C_6$-alkyl; and $R^3$, $R^4$ and $R^5$ are as defined in the Summary.

In one embodiment, n is 1 or 2; $Z^1$ is $CR^3R^4$; $Z^2$ is $CR^6R^7$; and $R^3$, $R^4$, $R^6$ and $R^7$ are as defined in the Summary.

In one embodiment, n is 1 or 2; $Z^1$ is $CR^3R^4$; $Z^2$ is $CR^6R^7$; $R^1$ is phenyl or monocyclic heteroaryl, wherein the monocyclic heteroaryl contains one or two ring nitrogens and optionally one ring oxygen or one ring sulfur, wherein the phenyl or monocyclic heteroaryl is optionally substituted with 1, 2, or 3 substituents selected from the group consisting of $C_1$-$C_6$-alkyl; $C_1$-$C_6$-alkylcarbonylamino; hydroxy$C_1$-$C_6$-alkylcarbonylamino; $C_1$-$C_6$-alkoxy$C_1$-$C_6$alkylcarbonylamino; $C_1$-$C_6$-alkoxy; $C_1$-$C_6$-alkoxy$C_1$-$C_6$-alkoxy; $C_1$-$C_6$-alkoxy$C_1$-$C_6$-alkyl; $C_1$-$C_6$-alkoxycarbonyl; $C_1$-$C_6$-alkoxycarbonyl$C_1$-$C_6$-alkyl; aminocarbonyl; $C_1$-$C_6$-alkylaminocarbonyl; hydroxy$C_1$-$C_6$-alkylaminocarbonyl; $C_1$-$C_6$-alkoxy$C_1$-$C_6$-alkylaminocarbonyl; cyano; carboxy; hydroxy; hydroxy$C_1$-$C_6$-alkoxy; hydroxy$C_1$-$C_6$-alkyl; di(hydroxy)$C_1$-$C_6$-alkyl; di($C_1$-$C_6$alkyl)amino; di(hydroxy$C_1$-$C_6$-alkyl)amino; di($C_1$-$C_6$-alkoxy$C_1$-$C_6$alkyl)amino; ($C_1$-$C_6$-alkoxy$C_1$-$C_6$-alkyl)(hydroxy$C_1$-$C_6$-alkyl)amino; halo$C_1$-$C_6$-alkyl; and halogen; wherein only 1 substituent can be present on the two atoms adjacent to the atom connected to the amide nitrogen pendant on the furan ring; and $R^3$, $R^4$, $R^6$ and $R^7$ are as defined in the Summary.

In one embodiment, n is 1 or 2; $Z^1$ is $CR^3R^4$; $Z^2$ is $CR^6R^7$; $R^1$ is fused-bicyclic heteroaryl, wherein the fused-bicyclic heteroaryl contains 1, 2, 3 or 4 ring nitrogens and optionally one ring oxygen or one ring sulfur, wherein the fused-bicyclic heteroaryl is optionally substituted with 1, 2, 3, or 4 substituents selected from the group consisting of $C_1$-$C_6$-alkyl; $C_1$-$C_6$-alkylcarbonylamino; hydroxy$C_1$-$C_6$-alkylcarbonylamino; $C_1$-$C_6$-alkoxy$C_1$-$C_6$-alkylcarbonylamino; $C_1$-$C_6$-alkoxy; $C_1$-$C_6$-alkoxy$C_1$-$C_6$-alkoxy; $C_1$-$C_6$alkoxy-$C_1$-$C_6$alkyl; $C_1$-$C_6$-alkoxycarbonyl; $C_1$-$C_6$-alkoxycarbonyl$C_1$-$C_6$-alkyl; $C_3$-$C_7$-cycloalkyloxy; $M_4$-$M_7$-heterocycleoxy, wherein the heterocycle of $M_4$-$M_7$-heterocycleoxy isoptionally substituted with $C_1$-$C_6$-alkyl; aminocarbonyl; $C_1$-$C_6$-alkylaminocarbonyl; hydroxy$C_1$-$C_6$-alkylaminocarbonyl; $C_1$-$C_6$-alkoxy$C_1$-$C_6$-alkylamincarbonyl; cyano; hydroxy; hydroxy$C_1$-$C_6$-alkoxy; hydroxy$C_1$-$C_6$-alkyl; di($C_1$-$C_6$alkyl)amino; di(hydroxy$C_1$-$C_6$-alkyl)amino; di($C_1$-$C_6$-alkoxy$C_1$-$C_6$-alkyl)amino; ($C_1$-$C_6$-alkoxy$C_1$-$C_6$-alkyl)(hydroxy$C_1$-$C_6$-alkyl)amino; halo$C_1$-$C_6$-alkyl; halogen; $C_1$-$C_6$-alkylsulfonylamino$C_2$-$C_6$-alkyl; and (i),

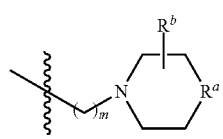

(i)

wherein $R^a$ is selected from the group consisting of a bond, CH$_2$, CHR$^b$, O, S, and N—R$^c$; wherein only 1 substituent can be present on the two atoms adjacent to the atom connected to the amide nitrogen pendant on the furan ring; m is 2, 3 or 4 when (i) is attached to a ring nitrogen atom of the bicyclic heteroaryl; or m is 0, 1, 2, 3 or 4 when (i) is attached to a ring carbon atom of the bicyclic heteroaryl; R$^b$, at each occurrence, is independently selected from the group consisting of hydrogen, $C_1$-$C_6$-alkyl, halo$C_1$-$C_6$-alkyl, $C_1$-$C_6$-alkoxy$C_1$-$C_6$-alkyl, and hydroxy$C_1$-$C_6$-alkyl; R$^c$ is selected from the group consisting of hydrogen, $C_1$-$C_6$-alkyl, $C_1$-$C_6$-alkoxycarbonyl, $C_1$-$C_6$-alkycarbonyl, $C_1$-$C_6$-alkysulfonyl, di($C_1$-$C_6$-alkyl)aminosulfonyl, heterocyclecarbonyl, $C_3$-$C_7$-cycloalkylcarbonyl, —C(O)NH$_2$, —C(O)NH(alkyl), —C(O)N(alkyl)$_2$ and —C(=NCN)NHCH$_3$; and $R^3$, $R^4$, $R^6$ and $R^7$ are as defined in the Summary.

In one embodiment, n is 1; $Z^1$ is $CR^3R^4$; $Z^2$ is $CR^6R^7$; $R^1$ is fused-bicyclic heteroaryl, wherein the fused-bicyclic heteroaryl is 1H-indazol-5-yl, 2H-indazol-5-yl, or 1H-benzimidazol-5-yl, wherein the fused-bicyclic heteroaryl isoptionally substituted with 1 or 2 $C_1$-$C_6$-alkyl or hydroxy$C_1$-$C_6$-alkyl; wherein only 1 substituent can be present on the two atoms adjacent to the atom connected to the amide nitrogen pendant on the furan ring; $R^3$ is hydrogen or $C_1$-$C_6$-alkyl; $R^4$ is hydrogen, $C_1$-$C_6$-alkyl, or hydroxy$C_1$-$C_6$-alkyl; $R^6$ is selected from the group consisting of hydrogen and $C_1$-$C_6$-alkyl; and $R^7$ is selected from the group consisting of hydrogen, $C_1$-$C_6$-alkyl, hydroxy$C_1$-$C_6$-alkyl, aminocarbonyl, and $C_1$-$C_6$-alkoxycarbonyl; or $R^6$ and $R^7$ taken together with the carbon atom to which they are attached form a $C_3$-$C_6$-cycloalkyl.

In one embodiment, n is 1 or 2; $Z^1$ is $CR^3R^4$; $Z^2$ is $CR^6R^7$; $R^1$ is (ii), (iii), or (iv);

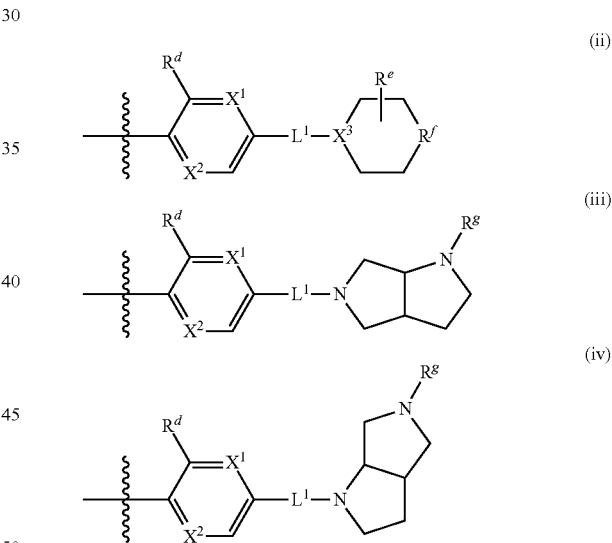

wherein both $X^1$ and $X^2$ are CH, or one of $X^1$ and $X^2$ is N and the other is CH; $X^3$ is CH or N; $L^1$ is a bond, C(O), or —NHC(O)—; R$^d$ is selected form the group consisting of hydrogen; $C_1$-$C_6$alkoxy; fluoro$C_1$-$C_6$-alkoxy; $C_1$-$C_6$-alkoxy$C_1$-$C_6$-alkoxy; $C_3$-$C_7$-cycloalkyloxy; $C_3$-$C_7$-cycloalkyl$C_1$-$C_6$-alkoxy; hydroxy$C_1$-$C_6$-alkoxy; phenyl$C_1$-$C_6$-alkoxy$C_1$-$C_6$-alkoxy; $M_4$-$M_7$-heterocycleoxy, wherein the heterocycle of heterocycleoxy isoptionally substituted with $C_1$-$C_6$-alkyl or oxo; and phenoxy, wherein the phenyl of phenoxy isoptionally substituted with hydroxy$C_1$-$C_6$-alkyl, $C_1$-$C_6$-alkoxy, $C_1$-$C_6$-alkoxy$C_1$-$C_6$-alkoxy, or $C_1$-$C_6$-alkoxycarbonyl; R$^e$ at each occurrence is independently selected from the group consisting of hydrogen, $C_1$-$C_6$-alkyl, di($C_1$-$C_6$-alkyl)amino, halo$C_1$-$C_6$-alkyl, $C_1$-$C_6$-alkoxy$C_1$-$C_6$alkyl, and hydroxy$C_1$-$C_6$-alkyl; R$^f$ is selected from the group consisting of a bond, CH$_2$, CHR$^e$, CH$_2$CH$_2$, O, NR$^g$, and CH$_2$NR$^g$; R$^g$ is selected from the group consisting of hydrogen; C$_1$-C$_6$-alkyl; C$_1$-C$_6$-alkoxycarbonyl; C$_1$-C$_6$-alkycarbonyl; C$_1$-C$_6$-alkysulfonyl; di(C$_1$-C$_6$-alkyl)aminosulfonyl; C$_3$-C$_7$-cycloalkylcarbonyl; C$_1$-C$_6$-alkoxyC$_1$-C$_6$-alkylcarbonyl; hydroxyC$_2$-C$_6$-alkyl; hydroxyC$_1$-C$_6$-alkylcarbonyl; formyl; —C(O)NH$_2$; —C(O)NH(alkyl); —C(O)N(alkyl)$_2$; —C(=NCN)NHCH$_3$; and M$_4$-M$_7$-heterocyclecarbonyl, wherein the heterocycle of heterocyclecarbonyl isoptionally substituted with C$_1$-C$_6$-alkyl; and R$^3$, R$^4$, R$^6$ and R$^2$ are as defined in the Summary.

In one embodiment, n is 1; Z$^1$ is CR$^3$R$^4$; Z$^2$ is CR$^6$R$^7$; R$^1$ is (ii);

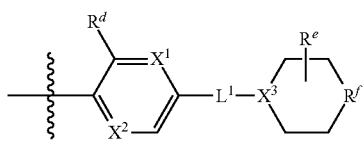

(ii)

wherein both X$^1$ and X$^2$ are CH, or one of X$^1$ and X$^2$ is N and the other is CH; X$^3$ is N; L$^1$ is a bond; R$^d$ is selected form the group consisting of hydrogen and C$_1$-C$_6$alkyl; R$^e$ at each occurrence is hydrogen; R$^f$ is NR$^g$; R$^g$ is selected from the group consisting of hydrogen, C$_1$-C$_6$-alkoxycarbonyl, C$_1$-C$_6$-alkycarbonyl, and C$_1$-C$_6$-alkysulfonyl; R$^3$ is selected from the group consisting of hydrogen or C$_1$-C$_6$-alkyl; R$^4$ is selected from the group consisting of hydrogen, aminoC$_1$-C$_6$-alkyl, and phenyl, wherein phenyl isoptionally substituted with 1, 2 or 3 halogen; R$^6$ is selected from the group consisting of hydrogen and C$_1$-C$_6$-alkyl; and R$^7$ are is selected from the group consisting of hydrogen, C$_1$-C$_6$-alkyl, C$_1$-C$_6$-alkoxyC$_1$-C$_6$-alkyl, and hydroxyC$_1$-C$_6$-alkyl; or R$^6$ and R$^7$ taken together with the carbon atom to which they are attached form a M$_4$-M$_7$-heterocycle.

In one embodiment, n is 1 or 2; Z$^1$ is CR$^3$R$^4$; Z$^2$ is O; and R$^3$ and R$^4$ are as defined in the Summary.

In one embodiment, n is 1 or 2; Z$^1$ is CR$^3$R$^4$; Z$^2$ is O; R$^1$ is phenyl or monocyclic heteroaryl, wherein the monocyclic heteroaryl contains one or two ring nitrogens and optionally one ring oxygen or one ring sulfur, wherein the phenyl or monocyclic heteroaryl is optionally substituted with 1, 2, or 3 substituents selected from the group consisting of C$_1$-C$_6$-alkyl; C$_1$-C$_6$-alkylcarbonylamino; hydroxyC$_1$-C$_6$-alkylcarbonylamino; C$_1$-C$_6$-alkoxyC$_1$-C$_6$alkylcarbonylamino; C$_1$-C$_6$-alkoxy; C$_1$-C$_6$-alkoxyC$_1$-C$_6$-alkoxy; C$_1$-C$_6$-alkoxyC$_1$-C$_6$-alkyl; C$_1$-C$_6$-alkoxycarbonyl; C$_1$-C$_6$-alkoxycarbonylC$_1$-C$_6$-alkyl; aminocarbonyl; C$_1$-C$_6$-alkylaminocarbonyl; hydroxyC$_1$-C$_6$-alkylaminocarbonyl; C$_1$-C$_6$-alkoxyC$_1$-C$_6$-alkylaminocarbonyl; cyano; carboxy; hydroxy; hydroxyC$_1$-C$_6$-alkoxy; hydroxyC$_1$-C$_6$-alkyl; di(hydroxy)C$_1$-C$_6$-alkyl; di(C$_1$-C$_6$alkyl)amino; di(hydroxyC$_1$-C$_6$-alkyl)amino; di(C$_1$-C$_6$-alkoxyC$_1$-C$_6$alkyl)amino; (C$_1$-C$_6$-alkoxyC$_1$-C$_6$-alkyl)(hydroxyC$_1$-C$_6$-alkyl)amino; haloC$_1$-C$_6$-alkyl; and halogen; wherein only 1 substituent can be present on the two atoms adjacent to the atom connected to the amide nitrogen pendant on the furan ring; and R$^3$ and R$^4$ are as defined in the Summary.

In one embodiment, n is 1 or 2; Z$^1$ is CR$^3$R$^4$; Z$^2$ is O; R$^1$ is fused-bicyclic heteroaryl, wherein the fused-bicyclic heteroaryl contains 1, 2, 3 or 4 ring nitrogens and optionally one ring oxygen or one ring sulfur, wherein the fused-bicyclic heteroaryl isoptionally substituted with 1, 2, 3, or 4 substituents selected from the group consisting of C$_1$-C$_6$-alkyl; C$_1$-C$_6$-alkylcarbonylamino; hydroxyC$_1$-C$_6$-alkylcarbonylamino; C$_1$-C$_6$-alkoxyC$_1$-C$_6$-alkylcarbonylamino; C$_1$-C$_6$-alkoxy; C$_1$-C$_6$-alkoxyC$_1$-C$_6$-alkoxy; C$_1$-C$_6$alkoxy-C$_1$-C$_6$alkyl; C$_1$-C$_6$-alkoxycarbonyl; C$_1$-C$_6$-alkoxycarbonylC$_1$-C$_6$-alkyl; C$_3$-C$_7$-cycloalkyloxy; M$_4$-M$_7$-heterocycleoxy, wherein the heterocycle of M$_4$-M$_7$-heterocycleoxy isoptionally substituted with C$_1$-C$_6$-alkyl; aminocarbonyl; C$_1$-C$_6$-alkylaminocarbonyl; hydroxyC$_1$-C$_6$-alkylaminocarbonyl; C$_1$-C$_6$-alkoxyC$_1$-C$_6$-alkylamincarbonyl; cyano; hydroxy; hydroxyC$_1$-C$_6$-alkoxy; hydroxyC$_1$-C$_6$-alkyl; di(C$_1$-C$_6$alkyl)amino; di(hydroxyC$_1$-C$_6$-alkyl)amino; di(C$_1$-C$_6$-alkoxyC$_1$-C$_6$-alkyl)amino; (C$_1$-C$_6$-alkoxyC$_1$-C$_6$-alkyl)(hydroxyC$_1$-C$_6$-alkyl)amino; haloC$_1$-C$_6$-alkyl; halogen; C$_1$-C$_6$-alkylsulfonylaminoC$_2$-C$_6$-alkyl; and (i),

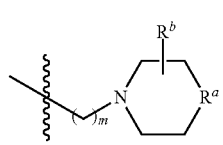

(i)

wherein R$^a$ is selected from the group consisting of a bond, CH$_2$, CHR$^b$, O, S, and N—R$^e$; wherein only 1 substituent can be present on the two atoms adjacent to the atom connected to the amide nitrogen pendant on the furan ring; m is 2, 3 or 4 when (i) is attached to a ring nitrogen atom of the bicyclic heteroaryl; or m is 0, 1, 2, 3 or 4 when (i) is attached to a ring carbon atom of the bicyclic heteroaryl; R$^b$, at each occurrence, is independently selected from the group consisting of hydrogen, C$_1$-C$_6$-alkyl, haloC$_1$-C$_6$-alkyl, C$_1$-C$_6$-alkoxyC$_1$-C$_6$-alkyl, and hydroxyC$_1$-C$_6$-alkyl; R$^e$ is selected from the group consisting of hydrogen, C$_1$-C$_6$-alkyl, C$_1$-C$_6$-alkoxycarbonyl, C$_1$-C$_6$-alkycarbonyl, C$_1$-C$_6$-alkysulfonyl, di(C$_1$-C$_6$-alkyl)aminosulfonyl, heterocyclecarbonyl, C$_3$-C$_7$-cycloalkylcarbonyl, —C(O)NH$_2$, —C(O)NH(alkyl), —C(O)N(alkyl)$_2$ and —C(=NCN)NHCH$_3$; and R$^3$ and R$^4$ are as defined in the Summary.

In one embodiment, n is 1 or 2; Z$^1$ is CR$^3$R$^4$; Z$^2$ is O; R$^1$ is (ii), (iii), or (iv);

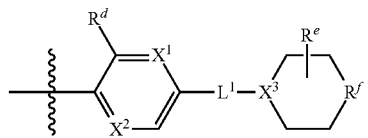

(ii)

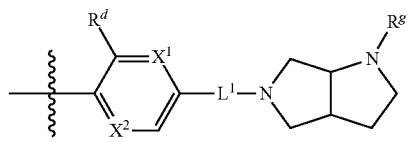

(iii)

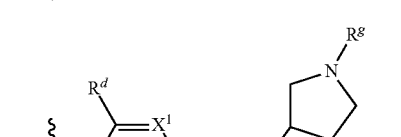

(iv)

wherein both X$^1$ and X$^2$ are CH, or one of X$^1$ and X$^2$ is N and the other is CH; X$^3$ is CH or N; L$^1$ is a bond, C(O), or —NHC(O)—; R$^d$ is selected form the group consisting of hydrogen; C$_1$-C$_6$alkoxy; fluoroC$_1$-C$_6$-alkoxy; C$_1$-C$_6$- alkoxyC$_1$-C$_6$-alkoxy; C$_3$-C$_7$-cycloalkyloxy; C$_3$-C$_7$-cycloalkylC$_1$-C$_6$-alkoxy; hydroxyC$_1$-C$_6$-alkoxy; phenylC$_1$-C$_6$-alkoxyC$_1$-C$_6$-alkoxy; M$_4$-M$_7$-heterocycleoxy, wherein the heterocycle of heterocycleoxy isoptionally substituted with C$_1$-C$_6$-alkyl or oxo; and phenoxy, wherein the phenyl of phenoxy isoptionally substituted with hydroxyC$_1$-C$_6$-alkyl, C$_1$-C$_6$-alkoxy, C$_1$-C$_6$-alkoxyC$_1$-C$_6$-alkoxy, or C$_1$-C$_6$-alkoxycarbonyl; R$^e$ at each occurrence is independently selected from the group consisting of hydrogen, C$_1$-C$_6$-alkyl, di(C$_1$-C$_6$-alkyl)amino, haloC$_1$-C$_6$-alkyl, C$_1$-C$_6$-alkoxyC$_1$-C$_6$alkyl, and hydroxyC$_1$-C$_6$-alkyl; R$^f$ is selected from the group consisting of a bond, CH$_2$, CHR$^e$, CH$_2$CH$_2$, O, NR$^g$, and CH$_2$NR$^g$; R$^g$ is selected from the group consisting of hydrogen; C$_1$-C$_6$-alkyl; C$_1$-C$_6$-alkoxycarbonyl; C$_1$-C$_6$-alkycarbonyl; C$_1$-C$_6$-alkysulfonyl; di(C$_1$-C$_6$-alkyl)aminosulfonyl; C$_3$-C$_7$-cycloalkylcarbonyl; C$_1$-C$_6$-alkoxyC$_1$-C$_6$-alkylcarbonyl; hydroxyC$_2$-C$_6$-alkyl; hydroxyC$_1$-C$_6$-alkylcarbonyl; formyl; —C(O)NH$_2$; —C(O)NH(alkyl); —C(O)N(alkyl)$_2$; —C(=NCN)NHCH$_3$; and M$_4$-M$_7$-heterocyclecarbonyl, wherein the heterocycle of heterocyclecarbonyl isoptionally substituted with C$_1$-C$_6$-alkyl; and R$^3$ and R$^4$ are as defined in the Summary.

In one embodiment, n is 1; Z$^1$ is CR$^3$R$^4$; Z$^2$ is O; R$^1$ is (ii);

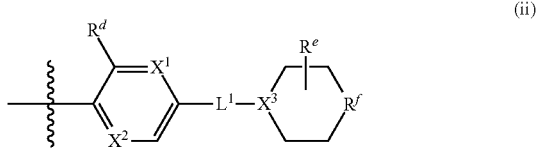

(ii)

wherein both X$^1$ and X$^2$ are CH, or one of X$^1$ and X$^2$ is N and the other is CH; X$^3$ is N; L$^1$ is a bond; R$^d$ is C$_1$-C$_6$alkyl; R$^e$ at each occurrence is hydrogen; R$^f$ is NR$^g$; R$^g$ is C$_1$-C$_6$-alkycarbonyl; and R$^3$ and R$^4$ are each independently C$_1$-C$_6$-alkyl; or R$^3$ and R$^4$ taken together with the carbon atom to which they are attached form a M$_4$-M$_7$-heterocycle.

Specific embodiments contemplated as part of the invention also include, but are not limited to, compounds of Formula (I), as defined, for example:

N-(2-methyl-2H-indazol-5-yl)-4-oxo-4,5,6,7-tetrahydrofuro[3,2-c]pyridine-3-carboxamide;
5-methyl-N-(2-methyl-2H-indazol-5-yl)-4-oxo-4,5,6,7-tetrahydrofuro[3,2-c]pyridine-3-carboxamide;
N-[4-(morpholin-4-yl)phenyl]-4-oxo-4,5,6,7-tetrahydrofuro[3,2-c]pyridine-3-carboxamide;
5-methyl-N-(4-methylphenyl)-4-oxo-4,5,6,7-tetrahydrofuro[3,2-c]pyridine-3-carboxamide;
tert-butyl 4-(3-methoxy-4-{[(4-oxo-4,5,6,7-tetrahydrofuro[3,2-c]pyridin-3-yl)carbonyl]amino}phenyl)piperazine-1-carboxylate;
N-[2-methoxy-4-(piperazin-1-yl)phenyl]-4-oxo-4,5,6,7-tetrahydrofuro[3,2-c]pyridine-3-carboxamide;
N-[2-methoxy-6-(4-methylpiperazin-1-yl)pyridin-3-yl]-4-oxo-5,6,7,8-tetrahydro-4H-furo[3,2-c]azepine-3-carboxamide;
N-[6-(4-acetylpiperazin-1-yl)-2-ethoxypyridin-3-yl]-5-[2-(benzyloxy)ethyl]-4-oxo-4,5,6,7-tetrahydrofuro[3,2-c]pyridine-3-carboxamide;
N-[6-(4-acetylpiperazin-1-yl)-2-ethoxypyridin-3-yl]-5-(2-hydroxyethyl)-4-oxo-4,5,6,7-tetrahydrofuro[3,2-c]pyridine-3-carboxamide;
N-[4-(4-acetylpiperazin-1-yl)phenyl]-4-oxo-4,5,6,7-tetrahydrofuro[3,2-c]pyridine-3-carboxamide;
N-(1-methyl-1H-indazol-5-yl)-4-oxo-4,5,6,7-tetrahydrofuro[3,2-c]pyridine-3-carboxamide;
N-(1H-benzimidazol-5-yl)-4-oxo-4,5,6,7-tetrahydrofuro[3,2-c]pyridine-3-carboxamide;
N-(4-carbamoylphenyl)-4-oxo-4,5,6,7-tetrahydrofuro[3,2-c]pyridine-3-carboxamide;
N-(1H-indazol-5-yl)-4-oxo-4,5,6,7-tetrahydrofuro[3,2-c]pyridine-3-carboxamide;
N-(2-methyl-1,3-benzothiazol-6-yl)-4-oxo-4,5,6,7-tetrahydrofuro[3,2-c]pyridine-3-carboxamide;
N-[5-(4-methylpiperazin-1-yl)pyridin-2-yl]-4-oxo-4,5,6,7-tetrahydrofuro[3,2-c]pyridine-3-carboxamide;
N-[4-(4-methylpiperazin-1-yl)phenyl]-4-oxo-4,5,6,7-tetrahydrofuro[3,2-c]pyridine-3-carboxamide;
N-[4-(4-acetylpiperazin-1-yl)-2-methoxyphenyl]-4-oxo-4,5,6,7-tetrahydrofuro[3,2-c]pyridine-3-carboxamide;
N-[6-(4-acetylpiperazin-1-yl)-2-ethoxypyridin-3-yl]-4-oxo-4,5,6,7-tetrahydrofuro[3,2-c]pyridine-3-carboxamide;
N-[6-(4-acetylpiperazin-1-yl)-2-(2-methoxyethoxyl)pyridin-3-yl]-4-oxo-4,5,6,7-tetrahydrofuro[3,2-c]pyridine-3-carboxamide;
N-[6-(4-acetylpiperazin-1-yl)-2-(oxetan-3-yloxy)pyridin-3-yl]-4-oxo-4,5,6,7-tetrahydrofuro[3,2-c]pyridine-3-carboxamide;
5-methyl-N-[4-(4-methylpiperazin-1-yl)phenyl]-4-oxo-4,5,6,7-tetrahydrofuro[3,2-c]pyridine-3-carboxamide;
N-(1H-indazol-5-yl)-5-methyl-4-oxo-4,5,6,7-tetrahydrofuro[3,2-c]pyridine-3-carboxamide;
5-methyl-N-(1-methyl-1H-indazol-5-yl)-4-oxo-4,5,6,7-tetrahydrofuro[3,2-c]pyridine-3-carboxamide;
5-methyl-N-[4-(morpholin-4-yl)phenyl]-4-oxo-4,5,6,7-tetrahydrofuro[3,2-c]pyridine-3-carboxamide;
N-(4-carbamoylphenyl)-5-methyl-4-oxo-4,5,6,7-tetrahydrofuro[3,2-c]pyridine-3-carboxamide;
N-(1H-benzimidazol-5-yl)-5-methyl-4-oxo-4,5,6,7-tetrahydrofuro[3,2-c]pyridine-3-carboxamide;
N-[4-(4-acetylpiperazin-1-yl)phenyl]-5-methyl-4-oxo-4,5,6,7-tetrahydrofuro[3,2-c]pyridine-3-carboxamide;
5-methyl-N-(2-methyl-1,3-benzothiazol-6-yl)-4-oxo-4,5,6,7-tetrahydrofuro[3,2-c]pyridine-3-carboxamide;
N-(4-methylphenyl)-4-oxo-4,5,6,7-tetrahydrofuro[3,2-c]pyridine-3-carboxamide;
N-(4-hydroxyphenyl)-4-oxo-4,5,6,7-tetrahydrofuro[3,2-c]pyridine-3-carboxamide;
N-(4-acetamidophenyl)-4-oxo-4,5,6,7-tetrahydrofuro[3,2-c]pyridine-3-carboxamide;
4-oxo-N-(quinolin-6-yl)-4,5,6,7-tetrahydrofuro[3,2-c]pyridine-3-carboxamide;
N-(1H-indazol-6-yl)-4-oxo-4,5,6,7-tetrahydrofuro[3,2-c]pyridine-3-carboxamide;
N-(2,6-dimethoxypyridin-3-yl)-4-oxo-4,5,6,7-tetrahydrofuro[3,2-c]pyridine-3-carboxamide;
N-(1,2-oxazol-3-yl)-4-oxo-4,5,6,7-tetrahydrofuro[3,2-c]pyridine-3-carboxamide;
4-oxo-N-(pyrazin-2-yl)-4,5,6,7-tetrahydrofuro[3,2-c]pyridine-3-carboxamide;
N-(5-methyl-1,2-oxazol-3-yl)-4-oxo-4,5,6,7-tetrahydrofuro[3,2-c]pyridine-3-carboxamide;
N-(4-cyanophenyl)-4-oxo-4,5,6,7-tetrahydrofuro[3,2-c]pyridine-3-carboxamide;
N-(5-fluoropyridin-2-yl)-4-oxo-4,5,6,7-tetrahydrofuro[3,2-c]pyridine-3-carboxamide;
N-(6-methoxypyridin-3-yl)-4-oxo-4,5,6,7-tetrahydrofuro[3,2-c]pyridine-3-carboxamide;
N-(5-chloropyridin-2-yl)-4-oxo-4,5,6,7-tetrahydrofuro[3,2-c]pyridine-3-carboxamide;

N-(3-cyanophenyl)-4-oxo-4,5,6,7-tetrahydrofuro[3,2-c]pyridine-3-carboxamide;
N-(6-ethoxypyridin-3-yl)-4-oxo-4,5,6,7-tetrahydrofuro[3,2-c]pyridine-3-carboxamide;
N-(3-methyl-1H-indazol-5-yl)-4-oxo-4,5,6,7-tetrahydrofuro[3,2-c]pyridine-3-carboxamide;
N-(6-methyl-1H-indazol-5-yl)-4-oxo-4,5,6,7-tetrahydrofuro[3,2-c]pyridine-3-carboxamide;
N-(1,3-benzothiazol-2-yl)-4-oxo-4,5,6,7-tetrahydrofuro[3,2-c]pyridine-3-carboxamide;
methyl 5-{[(4-oxo-4,5,6,7-tetrahydrofuro[3,2-c]pyridin-3-yl)carbonyl]amino}-1H-indazole-3-carboxylate;
N-[4-(diethylamino)phenyl]-4-oxo-4,5,6,7-tetrahydrofuro[3,2-c]pyridine-3-carboxamide;
N-[1-(2-hydroxypropyl)-1H-indazol-5-yl]-4-oxo-4,5,6,7-tetrahydrofuro[3,2-c]pyridine-3-carboxamide;
N-(2-{2-[(methylsulfonyl)amino]ethyl}-2H-indazol-5-yl)-4-oxo-4,5,6,7-tetrahydrofuro[3,2-c]pyridine-3-carboxamide;
N-{2-[2-(4-methylpiperazin-1-yl)ethyl]-2H-indazol-5-yl}-4-oxo-4,5,6,7-tetrahydrofuro[3,2-c]pyridine-3-carboxamide;
N-[1-(2-hydroxyethyl)-1H-indazol-5-yl]-4-oxo-4,5,6,7-tetrahydrofuro[3,2-c]pyridine-3-carboxamide;
4-oxo-N-{1-[2-(pyrrolidin-1-yl)ethyl]-1H-indazol-5-yl}-4,5,6,7-tetrahydrofuro[3,2-c]pyridine-3-carboxamide;
N-[2-(2-hydroxypropyl)-2H-indazol-5-yl]-4-oxo-4,5,6,7-tetrahydrofuro[3,2-c]pyridine-3-carboxamide;
N-{1-[2-(morpholin-4-yl)ethyl]-1H-indazol-5-yl}-4-oxo-4,5,6,7-tetrahydrofuro[3,2-c]pyridine-3-carboxamide;
N-{1-[2-(4-methylpiperazin-1-yl)ethyl]-1H-indazol-5-yl}-4-oxo-4,5,6,7-tetrahydrofuro[3,2-c]pyridine-3-carboxamide;
N-(1-{2-[(methylsulfonyl)amino]ethyl}-1H-indazol-5-yl)-4-oxo-4,5,6,7-tetrahydrofuro[3,2-c]pyridine-3-carboxamide;
N-(4-hydroxyphenyl)-5-methyl-4-oxo-4,5,6,7-tetrahydrofuro[3,2-c]pyridine-3-carboxamide;
N-(4-acetamidophenyl)-5-methyl-4-oxo-4,5,6,7-tetrahydrofuro[3,2-c]pyridine-3-carboxamide;
5-methyl-4-oxo-N-[4-(piperidin-1-yl)phenyl]-4,5,6,7-tetrahydrofuro[3,2-c]pyridine-3-carboxamide;
5-methyl-4-oxo-N-(quinolin-3-yl)-4,5,6,7-tetrahydrofuro[3,2-c]pyridine-3-carboxamide;
5-methyl-4-oxo-N-(quinolin-6-yl)-4,5,6,7-tetrahydrofuro[3,2-c]pyridine-3-carboxamide;
N-(1H-indazol-6-yl)-5-methyl-4-oxo-4,5,6,7-tetrahydrofuro[3,2-c]pyridine-3-carboxamide;
N-(2,6-dimethoxypyridin-3-yl)-5-methyl-4-oxo-4,5,6,7-tetrahydrofuro[3,2-c]pyridine-3-carboxamide;
5-methyl-N-(5-methyl-1,2-oxazol-3-yl)-4-oxo-4,5,6,7-tetrahydrofuro[3,2-c]pyridine-3-carboxamide;
N-(4-cyanophenyl)-5-methyl-4-oxo-4,5,6,7-tetrahydrofuro[3,2-c]pyridine-3-carboxamide;
N-(5-fluoropyridin-2-yl)-5-methyl-4-oxo-4,5,6,7-tetrahydrofuro[3,2-c]pyridine-3-carboxamide;
N-(6-methoxypyridin-3-yl)-5-methyl-4-oxo-4,5,6,7-tetrahydrofuro[3,2-c]pyridine-3-carboxamide;
N-(5-chloropyridin-2-yl)-5-methyl-4-oxo-4,5,6,7-tetrahydrofuro[3,2-c]pyridine-3-carboxamide;
N-(3-cyanophenyl)-5-methyl-4-oxo-4,5,6,7-tetrahydrofuro[3,2-c]pyridine-3-carboxamide;
N-(6-ethoxypyridin-3-yl)-5-methyl-4-oxo-4,5,6,7-tetrahydrofuro[3,2-c]pyridine-3-carboxamide;
5-methyl-N-(3-methyl-1H-indazol-5-yl)-4-oxo-4,5,6,7-tetrahydrofuro[3,2-c]pyridine-3-carboxamide;
5-methyl-N-(6-methyl-1H-indazol-5-yl)-4-oxo-4,5,6,7-tetrahydrofuro[3,2-c]pyridine-3-carboxamide;
N-(1,3-benzothiazol-2-yl)-5-methyl-4-oxo-4,5,6,7-tetrahydrofuro[3,2-c]pyridine-3-carboxamide;
5-methyl-4-oxo-N-[5-(trifluoromethyl)pyridin-2-yl]-4,5,6,7-tetrahydrofuro[3,2-c]pyridine-3-carboxamide;
N-(6-chloro-1H-indazol-5-yl)-5-methyl-4-oxo-4,5,6,7-tetrahydrofuro[3,2-c]pyridine-3-carboxamide;
5-methyl-N-(2-methyl-1H-benzimidazol-5-yl)-4-oxo-4,5,6,7-tetrahydrofuro[3,2-c]pyridine-3-carboxamide;
N-{4-[4-(3,3-dimethylbutanoyl)piperazin-1-yl]-2-methoxyphenyl}-4-oxo-4,5,6,7-tetrahydrofuro[3,2-c]pyridine-3-carboxamide;
N-{2-methoxy-4-[4-(pyrrolidin-1-ylcarbonyl)piperazin-1-yl]phenyl}-4-oxo-4,5,6,7-tetrahydrofuro[3,2-c]pyridine-3-carboxamide;
N-{4-[4-(dimethylsulfamoyl)piperazin-1-yl]-2-methoxyphenyl}-4-oxo-4,5,6,7-tetrahydrofuro[3,2-c]pyridine-3-carboxamide;
methyl 4-{[6-(4-methylpiperazin-1-yl)-3-{[(4-oxo-5,6,7,8-tetrahydro-4H-furo[3,2-c]azepin-3-yl)carbonyl]amino}pyridin-2-yl]oxy}benzoate;
N-{2-[4-(hydroxymethyl)phenoxy]-6-(4-methylpiperazin-1-yl)pyridin-3-yl}-4-oxo-5,6,7,8-tetrahydro-4H-furo[3,2-c]azepine-3-carboxamide;
N-[6-(4-acetylpiperazin-1-yl)-2-ethoxypyridin-3-yl]-5-(2-methoxyethyl)-4-oxo-4,5,6,7-tetrahydrofuro[3,2-c]pyridine-3-carboxamide;
N-[6-(4-acetylpiperazin-1-yl)-2-(2-methoxyethoxy)pyridin-3-yl]-5-[2-(benzyloxy)ethyl]-4-oxo-4,5,6,7-tetrahydrofuro[3,2-c]pyridine-3-carboxamide;
N-{6-(4-acetylpiperazin-1-yl)-2-[2-(benzyloxy)ethoxy]pyridin-3-yl}-5-[2-(benzyloxy)ethyl]-4-oxo-4,5,6,7-tetrahydrofuro[3,2-c]pyridine-3-carboxamide;
N-[6-(4-acetylpiperazin-1-yl)-2-(2-methoxyethoxyl)pyridin-3-yl]-5-(2-hydroxyethyl)-4-oxo-4,5,6,7-tetrahydrofuro[3,2-c]pyridine-3-carboxamide;
N-[6-(4-acetylpiperazin-1-yl)-2-(2-hydroxyethoxyl)pyridin-3-yl]-5-(2-hydroxyethyl)-4-oxo-4,5,6,7-tetrahydrofuro[3,2-c]pyridine-3-carboxamide;
N-[6-(4-acetylpiperazin-1-yl)-2-ethoxypyridin-3-yl]-5-(3-hydroxypropyl)-4-oxo-4,5,6,7-tetrahydrofuro[3,2-c]pyridine-3-carboxamide;
N-[6-(4-acetylpiperazin-1-yl)-2-ethoxypyridin-3-yl]-5-(4-hydroxybutyl)-4-oxo-4,5,6,7-tetrahydrofuro[3,2-c]pyridine-3-carboxamide;
N-[6-(4-acetylpiperazin-1-yl)-2-ethoxypyridin-3-yl]-5-[2-(2-hydroxyethoxyl)ethyl]-4-oxo-4,5,6,7-tetrahydrofuro[3,2-c]pyridine-3-carboxamide;
tert-butyl 4-(6-ethoxy-5-{[(4-oxo-4,5,6,7-tetrahydrofuro[3,2-c]pyridin-3-yl)carbonyl]amino}pyridin-2-yl)piperazine-1-carboxylate;
N-{6-[4-(N-cyano-N-methylcarbamimidoyl)piperazin-1-yl]-2-ethoxypyridin-3-yl}-4-oxo-4,5,6,7-tetrahydrofuro[3,2-c]pyridine-3-carboxamide;
(2R)-1-[3-{[6-(4-acetylpiperazin-1-yl)-2-ethoxypyridin-3-yl]carbamoyl}-4-oxo-6,7-dihydrofuro[3,2-c]pyridin-5(4H)-yl]propan-2-yl acetate;
N-[6-(4-acetylpiperazin-1-yl)-2-ethoxypyridin-3-yl]-5-[(2R)-2-hydroxypropyl]-4-oxo-4,5,6,7-tetrahydrofuro[3,2-c]pyridine-3-carboxamide;
(2S)-1-[3-{[6-(4-acetylpiperazin-1-yl)-2-ethoxypyridin-3-yl]carbamoyl}-4-oxo-6,7-dihydrofuro[3,2-c]pyridin-5(4H)-yl]propan-2-yl acetate;
N-[6-(4-acetylpiperazin-1-yl)-2-ethoxypyridin-3-yl]-5-[(2S)-2-hydroxypropyl]-4-oxo-4,5,6,7-tetrahydrofuro[3,2-c]pyridine-3-carboxamide;

(2R)-2-[3-{[6-(4-acetylpiperazin-1-yl)-2-ethoxypyridin-3-yl]carbamoyl}-4-oxo-6,7-dihydrofuro[3,2-c]pyridin-5(4H)-yl]propyl acetate;

N-[6-(4-acetylpiperazin-1-yl)-2-ethoxypyridin-3-yl]-5-[(2R)-1-hydroxypropan-2-yl]-4-oxo-4,5,6,7-tetrahydrofuro[3,2-c]pyridine-3-carboxamide;

(2S)-2-[3-{[6-(4-acetylpiperazin-1-yl)-2-ethoxypyridin-3-yl]carbamoyl}-4-oxo-6,7-dihydrofuro[3,2-c]pyridin-5(4H)-yl]propyl acetate;

N-[6-(4-acetylpiperazin-1-yl)-2-ethoxypyridin-3-yl]-5-[(2S)-1-hydroxypropan-2-yl]-4-oxo-4,5,6,7-tetrahydrofuro[3,2-c]pyridine-3-carboxamide;

N-[6-(4-acetylpiperazin-1-yl)-2-ethoxypyridin-3-yl]-5-(1-hydroxy-2-methylpropan-2-yl)-4-oxo-4,5,6,7-tetrahydrofuro[3,2-c]pyridine-3-carboxamide;

1-[3-{[6-(4-acetylpiperazin-1-yl)-2-ethoxypyridin-3-yl]carbamoyl}-4-oxo-6,7-dihydrofuro[3,2-c]pyridin-5(4H)-yl]-2-methylpropan-2-yl acetate;

N-[6-(4-acetylpiperazin-1-yl)-2-ethoxypyridin-3-yl]-5-(2-hydroxy-2-methylpropyl)-4-oxo-4,5,6,7-tetrahydrofuro[3,2-c]pyridine-3-carboxamide;

N-{6-(4-acetylpiperazin-1-yl)-2-[(3S)-tetrahydrofuran-3-yloxy]pyridin-3-yl}-4-oxo-4,5,6,7-tetrahydrofuro[3,2-c]pyridine-3-carboxamide;

N-[2-ethoxy-6-(morpholin-4-yl)pyridin-3-yl]-4-oxo-4,5,6,7-tetrahydrofuro[3,2-c]pyridine-3-carboxamide;

N-[2-(2-hydroxy-2-methylpropoxy)-6-(morpholin-4-yl)pyridin-3-yl]-4-oxo-4,5,6,7-tetrahydrofuro[3,2-c]pyridine-3-carboxamide;

methyl(6-ethoxy-5-{[(4-oxo-4,5,6,7-tetrahydrofuro[3,2-c]pyridin-3-yl)carbonyl]amino}pyridin-2-yl)acetate;

N-[2-ethoxy-6-(2-hydroxyethyl)pyridin-3-yl]-4-oxo-4,5,6,7-tetrahydrofuro[3,2-c]pyridine-3-carboxamide;

N-[6-(4-acetylpiperazin-1-yl)-2-methoxypyridin-3-yl]-4-oxo-2',3',4',5',6',7-hexahydro-5H-spiro[1-benzofuran-6,4'-pyran]-3-carboxamide;

N-[6-(4-acetylpiperazin-1-yl)-2-ethoxypyridin-3-yl]-4'-oxo-4',7'-dihydro-5'H-spiro[cyclobutane-1,6'-furo[3,2-c]pyridine]-3'-carboxamide;

N-[6-(4-acetylpiperazin-1-yl)-2-ethoxypyridin-3-yl]-4'-oxo-4',7'-dihydro-5'H-spiro[cyclohexane-1,6'-furo[3,2-c]pyridine]-3'-carboxamide;

1-acetyl-N-[6-(4-acetylpiperazin-1-yl)-2-ethoxypyridin-3-yl]-4'-oxo-4',7'-dihydro-5'H-spiro[azetidine-3,6'-furo[3,2-c]pyridine]-3'-carboxamide;

N-[6-(4-acetylpiperazin-1-yl)-2-ethoxypyridin-3-yl]-4-oxo-4,7-dihydro-5H-spiro[furo[3,2-c]pyridine-6,3'-oxetane]-3-carboxamide;

(6R)—N-[6-(4-acetylpiperazin-1-yl)-2-ethoxypyridin-3-yl]-6-[(1R)-1-hydroxyethyl]-4-oxo-4,5,6,7-tetrahydrofuro[3,2-c]pyridine-3-carboxamide;

N-[6-(4-acetylpiperazin-1-yl)-2-ethoxypyridin-3-yl]-5'-(2-hydroxyethyl)-4'-oxo-4',7'-dihydro-5'H-spiro[cyclobutane-1,6'-furo[3,2-c]pyridine]-3'-carboxamide;

N-[6-(4-acetylpiperazin-1-yl)-2-ethoxypyridin-3-yl]-4'-oxo-4',7'-dihydro-5'H-spiro[cyclopropane-1,6'-furo[3,2-c]pyridine]-3'-carboxamide;

N-{6-[4-(N'-cyano-N-methylcarbamimidoyl)piperazin-1-yl]-2-ethoxypyridin-3-yl}-4'-oxo-4',7'-dihydro-5'H-spiro[cyclobutane-1,6'-furo[3,2-c]pyridine]-3'-carboxamide;

N-[6-(4-acetylpiperazin-1-yl)-2-ethoxypyridin-3-yl]-5-(2,3-dihydroxypropyl)-6,6-dimethyl-4-oxo-4,5,6,7-tetrahydrofuro[3,2-c]pyridine-3-carboxamide;

N-[2-methoxy-4-(piperazin-1-yl)phenyl]-6,6-dimethyl-4-oxo-4,5,6,7-tetrahydrofuro[3,2-c]pyridine-3-carboxamide;

N-{2-methoxy-6-[4-(morpholin-4-ylcarbonyl)piperazin-1-yl]pyridin-3-yl}-6,6-dimethyl-4-oxo-4,5,6,7-tetrahydrofuro[3,2-c]pyridine-3-carboxamide;

N-[6-(4-acetylpiperazin-1-yl)-2-methoxypyridin-3-yl]-6,6-dimethyl-4-oxo-4,5,6,7-tetrahydrofuro[3,2-c]pyridine-3-carboxamide;

N-{2-methoxy-6-[4-(pyrrolidin-1-ylcarbonyl)piperazin-1-yl]pyridin-3-yl}-6,6-dimethyl-4-oxo-4,5,6,7-tetrahydrofuro[3,2-c]pyridine-3-carboxamide;

N-[2-methoxy-4-(piperazin-1-yl)phenyl]-6-methyl-4-oxo-4,5,6,7-tetrahydrofuro[3,2-c]pyridine-3-carboxamide;

N-{2-methoxy-4-[4-(methylsulfonyl)piperazin-1-yl]phenyl}-6,6-dimethyl-4-oxo-4,5,6,7-tetrahydrofuro[3,2-c]pyridine-3-carboxamide;

N-[4-(4-acetylpiperazin-1-yl)-2-methoxyphenyl]-6,6-dimethyl-4-oxo-4,5,6,7-tetrahydrofuro[3,2-c]pyridine-3-carboxamide;

N-[2-ethoxy-6-(piperazin-1-yl)pyridin-3-yl]-6,6-dimethyl-4-oxo-4,5,6,7-tetrahydrofuro[3,2-c]pyridine-3-carboxamide;

N-[6-(4-acetylpiperazin-1-yl)-2-ethoxypyridin-3-yl]-6,6-dimethyl-4-oxo-4,5,6,7-tetrahydrofuro[3,2-c]pyridine-3-carboxamide;

N-{6-[(3aR,6aR)-hexahydropyrrolo[3,4-b]pyrrol-5(1H)-yl]-2-isopropoxypyridin-3-yl}-6,6-dimethyl-4-oxo-4,5,6,7-tetrahydrofuro[3,2-c]pyridine-3-carboxamide;

N-{2-methoxy-6-[(3aR,6aR)-5-methylhexahydropyrrolo[3,4-b]pyrrol-1(2H)-yl]pyridin-3-yl}-6,6-dimethyl-4-oxo-4,5,6,7-tetrahydrofuro[3,2-c]pyridine-3-carboxamide;

N-{6-[(3aS,6aS)-1-(2-hydroxyethyl)hexahydropyrrolo[3,4-b]pyrrol-5(1H)-yl]-2-isopropoxypyridin-3-yl}-6,6-dimethyl-4-oxo-4,5,6,7-tetrahydrofuro[3,2-c]pyridine-3-carboxamide;

N-{2-isopropoxy-6-[(3aR,6aR)-1-[(4-methylpiperazin-1-yl)carbonyl]hexahydropyrrolo[3,4-b]pyrrol-5(1H)-yl]pyridin-3-yl}-6,6-dimethyl-4-oxo-4,5,6,7-tetrahydrofuro[3,2-c]pyridine-3-carboxamide;

N-{6-[(3S)-4-acetyl-3-(hydroxymethyl)piperazin-1-yl]-2-isopropoxypyridin-3-yl}-6,6-dimethyl-4-oxo-4,5,6,7-tetrahydrofuro[3,2-c]pyridine-3-carboxamide;

N-{6-[(2S)-4-acetyl-2-(hydroxymethyl)piperazin-1-yl]-2-isopropoxypyridin-3-yl}-6,6-dimethyl-4-oxo-4,5,6,7-tetrahydrofuro[3,2-c]pyridine-3-carboxamide;

N-{6-[(2S)-2-(hydroxymethyl)-4-(morpholin-4-ylcarbonyl)piperazin-1-yl]-2-isopropoxypyridin-3-yl}-6,6-dimethyl-4-oxo-4,5,6,7-tetrahydrofuro[3,2-c]pyridine-3-carboxamide;

N-{6-[(3S)-3-(dimethylamino)pyrrolidin-1-yl]-2-isopropoxypyridin-3-yl}-6,6-dimethyl-4-oxo-4,5,6,7-tetrahydrofuro[3,2-c]pyridine-3-carboxamide;

N-{6-[(3S)-3-(hydroxymethyl)piperidin-1-yl]-2-isopropoxypyridin-3-yl}-6,6-dimethyl-4-oxo-4,5,6,7-tetrahydrofuro[3,2-c]pyridine-3-carboxamide;

N-{6-[(3R)-4-acetyl-3-(hydroxymethyl)piperazin-1-yl]-2-isopropoxypyridin-3-yl}-6,6-dimethyl-4-oxo-4,5,6,7-tetrahydrofuro[3,2-c]pyridine-3-carboxamide;

N-{6-[(2R)-4-acetyl-2-(hydroxymethyl)piperazin-1-yl]-2-isopropoxypyridin-3-yl}-6,6-dimethyl-4-oxo-4,5,6,7-tetrahydrofuro[3,2-c]pyridine-3-carboxamide;

N-{6-[bis(2-hydroxyethyl)amino]-2-isopropoxypyridin-3-yl}-6,6-dimethyl-4-oxo-4,5,6,7-tetrahydrofuro[3,2-c]pyridine-3-carboxamide;

N-[2,6-bis(2-methoxyethoxy)pyridin-3-yl]-6,6-dimethyl-4-oxo-4,5,6,7-tetrahydrofuro[3,2-c]pyridine-3-carboxamide;

N-{6-[(3S)-4-acetyl-3-(methoxymethyl)piperazin-1-yl]-2-(2-hydroxy-2-methylpropoxy)pyridin-3-yl}-6,6-dimethyl-4-oxo-4,5,6,7-tetrahydrofuro[3,2-c]pyridine-3-carboxamide;

N-[2-ethoxy-6-(2-hydroxyethyl)pyridin-3-yl]-6,6-dimethyl-4-oxo-4,5,6,7-tetrahydrofuro[3,2-c]pyridine-3-carboxamide;

N-[2-ethoxy-6-(hydroxymethyl)pyridin-3-yl]-6,6-dimethyl-4-oxo-4,5,6,7-tetrahydrofuro[3,2-c]pyridine-3-carboxamide;

6-ethoxy-5-({[5-(2-methoxyethyl)-6,6-dimethyl-4-oxo-4,5,6,7-tetrahydrofuro[3,2-c]pyridin-3-yl]carbonyl}amino)pyridine-2-carboxylic acid;

6,6-dimethyl-N-(1-methyl-1H-indazol-5-yl)-4-oxo-4,5,6,7-tetrahydro-1-benzofuran-3-carboxamide;

6,6-dimethyl-N-(2-methyl-2H-indazol-5-yl)-4-oxo-4,5,6,7-tetrahydro-1-benzofuran-3-carboxamide;

N-[4-(4-acetylpiperazin-1-yl)phenyl]-6,6-dimethyl-4-oxo-4,5,6,7-tetrahydro-1-benzofuran-3-carboxamide;

6,6-dimethyl-4-oxo-N-[6-(piperazin-1-yl)pyridin-3-yl]-4,5,6,7-tetrahydro-1-benzofuran-3-carboxamide;

N-(2-methyl-2H-indazol-5-yl)-4-oxo-4,7-dihydro-5H-spiro[1-benzofuran-6,1'-cyclobutane]-3-carboxamide;

6,6-dimethyl-4-oxo-N-[5-(piperazin-1-yl)pyridin-2-yl]-4,5,6,7-tetrahydro-1-benzofuran-3-carboxamide;

6,6-dimethyl-N-{4-[4-(methylsulfonyl)piperazin-1-yl]phenyl}-4-oxo-4,5,6,7-tetrahydro-1-benzofuran-3-carboxamide;

N-[2-(2-hydroxyethyl)-2H-indazol-5-yl]-6,6-dimethyl-4-oxo-4,5,6,7-tetrahydro-1-benzofuran-3-carboxamide;

N-[2-(hydroxymethyl)-1H-benzimidazol-5-yl]-6,6-dimethyl-4-oxo-4,5,6,7-tetrahydro-1-benzofuran-3-carboxamide;

6,6-dimethyl-N-{5-[4-(methylsulfonyl)piperazin-1-yl]pyridin-2-yl}-4-oxo-4,5,6,7-tetrahydro-1-benzofuran-3-carboxamide;

N-[5-(4-acetylpiperazin-1-yl)pyridin-2-yl]-6,6-dimethyl-4-oxo-4,5,6,7-tetrahydro-1-benzofuran-3-carboxamide;

N-[2-methoxy-4-(piperazin-1-yl)phenyl]-6,6-dimethyl-4-oxo-4,5,6,7-tetrahydro-1-benzofuran-3-carboxamide;

N-[4-(4-acetylpiperazin-1-yl)-2-methoxyphenyl]-6,6-dimethyl-4-oxo-4,5,6,7-tetrahydro-1-benzofuran-3-carboxamide;

N-(2-methyl-2H-indazol-5-yl)-4-oxo-4,7-dihydro-5H-spiro[1-benzofuran-6,1'-cyclopropane]-3-carboxamide;

N-(2-methyl-2H-indazol-5-yl)-4-oxo-4,5,6,7-tetrahydrofuro[2,3-c]pyridine-3-carboxamide;

N-(2-methyl-2H-indazol-5-yl)-6-(methylsulfonyl)-4-oxo-4,5,6,7-tetrahydrofuro[2,3-c]pyridine-3-carboxamide;

6-methyl-$N^3$-(2-methyl-2H-indazol-5-yl)-4-oxo-4,5,6,7-tetrahydro-1-benzofuran-3,6-dicarboxamide;

methyl 6-methyl-3-[(2-methyl-2H-indazol-5-yl)carbamoyl]-4-oxo-4,5,6,7-tetrahydro-1-benzofuran-6-carboxylate;

6-(hydroxymethyl)-6-methyl-N-(2-methyl-2H-indazol-5-yl)-4-oxo-4,5,6,7-tetrahydro-1-benzofuran-3-carboxamide;

tert-butyl 4-[4-({[6-(hydroxymethyl)-6-methyl-4-oxo-4,5,6,7-tetrahydro-1-benzofuran-3-yl]carbonyl}amino)-3-methoxyphenyl]piperazine-1-carboxylate;

6-(methoxymethyl)-N-[2-methoxy-4-(piperazin-1-yl)phenyl]-6-methyl-4-oxo-4,5,6,7-tetrahydro-1-benzofuran-3-carboxamide;

5-(hydroxymethyl)-5-methyl-N-(2-methyl-2H-indazol-5-yl)-4-oxo-4,5,6,7-tetrahydro-1-benzofuran-3-carboxamide;

5,5-dimethyl-N-(2-methyl-2H-indazol-5-yl)-4-oxo-4,5,6,7-tetrahydro-1-benzofuran-3-carboxamide;

N-[4-(4-acetylpiperazin-1-yl)-2-methoxyphenyl]-5-(aminomethyl)-5-methyl-4-oxo-4,5,6,7-tetrahydro-1-benzofuran-3-carboxamide;

N-[4-(4-acetylpiperazin-1-yl)-2-methoxyphenyl]-4-oxo-4,7-dihydrospiro[furo[2,3-c]pyran-5,4'-piperidine]-3-carboxamide;

N-[6-(4-acetylpiperazin-1-yl)-2-methoxypyridin-3-yl]-5,5-dimethyl-4-oxo-4,7-dihydro-5H-furo[2,3-c]pyran-3-carboxamide;

N-[4-(4-acetylpiperazin-1-yl)-2-methoxyphenyl]-4-oxo-4,7-dihydrospiro[furo[2,3-c]pyran-5,3'-oxetane]-3-carboxamide;

N-[6-(4-acetylpiperazin-1-yl)-2-ethoxypyridin-3-yl]-5,6,6-trimethyl-4-oxo-4,5,6,7-tetrahydrofuro[3,2-c]pyridine-3-carboxamide;

N-[6-(4-acetylpiperazin-1-yl)-2-ethoxypyridin-3-yl]-5-(2-hydroxyethyl)-6,6-dimethyl-4-oxo-4,5,6,7-tetrahydrofuro[3,2-c]pyridine-3-carboxamide;

N-[6-(4-acetylpiperazin-1-yl)-2-ethoxypyridin-3-yl]-5-(2-methoxyethyl)-6,6-dimethyl-4-oxo-4,5,6,7-tetrahydrofuro[3,2-c]pyridine-3-carboxamide;

N-[6-(4-acetylpiperazin-1-yl)-2-ethoxypyridin-3-yl]-5-[2-(2-hydroxyethoxyl)ethyl]-6,6-dimethyl-4-oxo-4,5,6,7-tetrahydrofuro[3,2-c]pyridine-3-carboxamide;

N-[6-(4-acetylpiperazin-1-yl)-2-(2-methoxyethoxyl)pyridin-3-yl]-6,6-dimethyl-4-oxo-4,5,6,7-tetrahydrofuro[3,2-c]pyridine-3-carboxamide;

N-[6-(4-acetylpiperazin-1-yl)-2-(2,2,2-trifluoroethoxyl)pyridin-3-yl]-6,6-dimethyl-4-oxo-4,5,6,7-tetrahydrofuro[3,2-c]pyridine-3-carboxamide;

N-[6-(4-acetylpiperazin-1-yl)-2-(oxetan-3-yloxy)pyridin-3-yl]-6,6-dimethyl-4-oxo-4,5,6,7-tetrahydrofuro[3,2-c]pyridine-3-carboxamide;

N-[6-(4-acetylpiperazin-1-yl)-2-(tetrahydro-2H-pyran-4-yloxy)pyridin-3-yl]-6,6-dimethyl-4-oxo-4,5,6,7-tetrahydrofuro[3,2-c]pyridine-3-carboxamide;

N-{6-(4-acetylpiperazin-1-yl)-2-[(3S)-tetrahydrofuran-3-yloxy]pyridin-3-yl}-6,6-dimethyl-4-oxo-4,5,6,7-tetrahydrofuro[3,2-c]pyridine-3-carboxamide;

N-[6-(4-formylpiperazin-1-yl)-2-(2-methoxyethoxyl)pyridin-3-yl]-6,6-dimethyl-4-oxo-4,5,6,7-tetrahydrofuro[3,2-c]pyridine-3-carboxamide;

N-{6-(4-acetylpiperazin-1-yl)-2-[(1-oxidothietan-3-yl)oxy]pyridin-3-yl}-6,6-dimethyl-4-oxo-4,5,6,7-tetrahydrofuro[3,2-c]pyridine-3-carboxamide;

N-[6-(1-acetylpiperidin-4-yl)-2-ethoxypyridin-3-yl]-6,6-dimethyl-4-oxo-4,5,6,7-tetrahydrofuro[3,2-c]pyridine-3-carboxamide; and N-[6-(4-acetylpiperazin-1-yl)-2-ethoxypyridin-3-yl]-5-(2,5-difluorophenyl)-4-oxo-4,5,6,7-tetrahydro-1-benzofuran-3-carboxamide.

Compound names are assigned by using Name Release 12.00 v. 12.5 naming algorithm by Advanced Chemical Development or Struct=Name naming algorithm as part of CHEMDRAW® ULTRA v. 12.0.2.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

On occasion, the relative stereochemistry of an enantiomeric pair is known, however, the absolute configuration is not known. In that circumstance, the relative stereochemistry descriptor terms "R*" and "S*" are used. The terms "R*" and "S*" used herein are defined in Eliel, E. L.; Wilen, S. H. Stereochemistry of Organic Compounds; John Wiley & Sons, Inc.: New York, 1994; pp 119-120 and 1206.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention.

The present invention also includes isotopically-labeled compounds, which are identical to those recited in formula (I) or formula (II), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Compounds incorporating positron-emitting isotopes are useful in medical imaging and positron-emitting tomography (PET) studies for determining the distribution of receptors. Suitable positron-emitting isotopes that can be incorporated in compounds of formula (I) or formula (II) are $^{11}C$, $^{13}N$, $^{15}O$, and $^{18}F$. Isotopically-labeled compounds of formula (I) or formula (II) can generally be prepared by conventional techniques known to those skilled in the art or by processes analogous to those described in the accompanying Examples using appropriate isotopically-labeled reagent in place of non-isotopically-labeled reagent.

Methods for Preparing Compounds of the Invention

The compounds of the invention can be better understood in connection with the following synthetic schemes and methods which illustrate a means by which the compounds can be prepared.

The compounds of this invention can be prepared by a variety of synthetic procedures. Representative procedures are shown in, but are not limited to, Schemes 1-10.

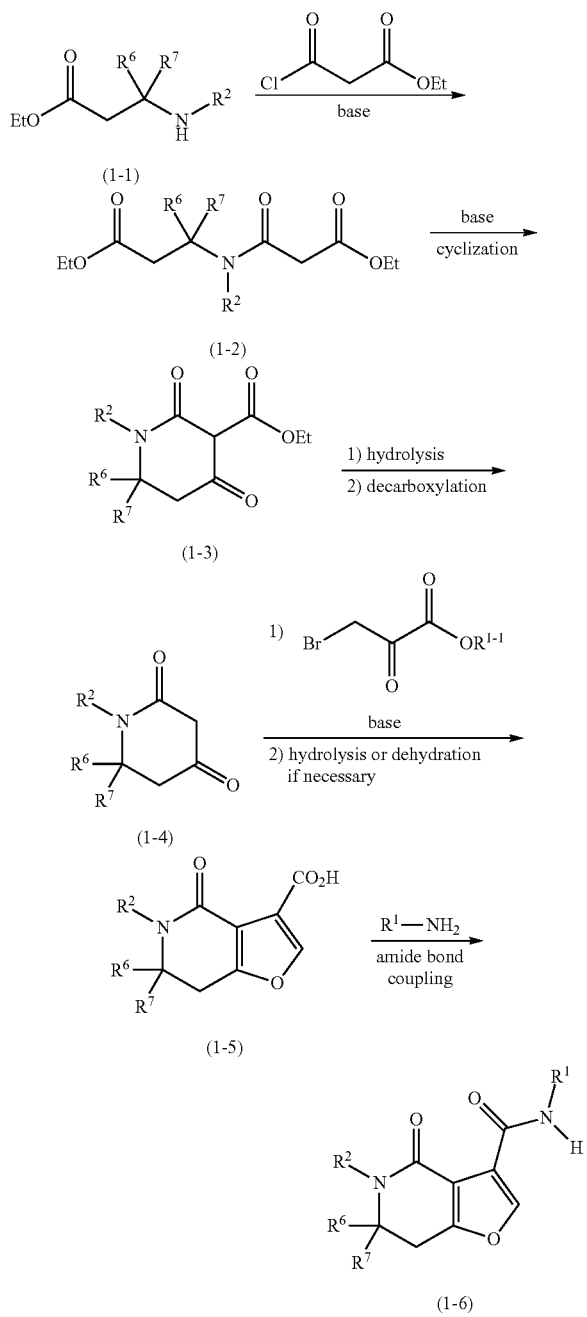

As shown in Scheme 1, compounds of Formula (1-6) can be prepared from compounds of Formula (1-1), wherein $R^1$, $R^2$, $R^6$ and $R^7$ are as defined in the Summary. Compounds of Formula (1-1) can be purchased commercially, or wherein $R^2$ is other than hydrogen prepared by reductive alkylation of the corresponding amino ester, or prepared by Michael reaction between an amine, $R^2NH_2$, and ethyl acrylate. Compounds of Formula (1-1) can be reacted with a malonyl chloride (illustrated with ethyl malonyl chloride) in the presence of a base such as triethylamine or diisopropylethylamine in a solvent such as dichloromethane initially at or near 0° C. with subsequent warming to ambient temperature over a total reaction time of 1-24 hours to give compounds of Formula (1-2). Treatment of compounds of Formula (1-2) with a base such as sodium ethoxide or potassium tert-butoxide in ethanol or sodium methoxide in methanol or potassium hydroxide in a mixture of methanol and water with optionally added tetrahydrofuran at room temperature to refluxing over 2-24 hours provides compounds of Formula (1-3). Compounds of Formula (1-3) can be transformed to compounds of Formula (1-4) in water or a mixture of water and acetonitrile at reflux over 30 minutes to 8 hours. Compounds of Formula (1-4) can be reacted with a bromopyruvate or bromopyruvic acid ($BrCH_2C(O)CO_2R^{1-1}$, wherein $R^{1-1}$ is hydrogen or $C_1$-$C_6$-alkyl) in the presence of a base such as potassium hydroxide, sodium bicarbonate, sodium ethoxide, or potassium tert-butoxide in solvents such as methanol or ethanol optionally mixed with water at ambient temperature over 1-24 hours to give compounds of Formula (1-5). Dehydration can be required to complete aromatization of the furan ring. This can be achieved by treatment in heated (70-100° C.) aqueous hydrochloric acid, aqueous hydrochloric acid in tetrahydrofuran, or hydrochloric acid in dioxane for 1-24 hours, or with treatment with acetic acid and acetic anhydride heated to 100-110° C. for 30 minutes to 24 hours, or with methanesulfonyl chloride and triethylamine in dichloromethane at room temperature from 30 minutes to 24 hours to give compounds of Formula (1-5). When $R^{1-1}$ is $C_1$-$C_6$-alkyl, hydrolysis of the intermediate furanyl ester may be required. This can be achieved under acidic conditions described above, or under basic conditions such as treatment with lithium hydroxide or sodium hydroxide in methanol or a mixture of methanol and tetrahydrofuran at room temperature for 15 minutes to overnight to give compounds of Formula (1-5). Compounds of Formula (1-5) can be coupled with an amine, $R^1$—$NH_2$, to give compounds of Formula (1-6). Examples of conditions known to generate amides from a mixture of a carboxylic acid and an amine include but are not limited to adding a coupling reagent such as but not limited to N-(3-dimethylaminopropyl)-N'-ethylcarbodiimide or 1-(3-dimethylaminopropyl)-3-ethylcarbodiimide (EDC, EDAC or EDCI), 1,3-dicyclohexylcarbodiimide (DCC), bis(2-oxo-3-oxazolidinyl)phosphinic chloride (BOPCl), 2-(7-azabenzotriazol-1-yl)-N,N,N',N'-tetramethyluronium hexafluorophosphate or O-(7-azabenzotriazol-1-yl)-N,N,N', N'-tetramethyluronium hexafluorophosphate (HATU), O-benzotriazol-1-yl-N,N,N',N'-tetramethyluronium tetrafluoroborate (TBTU), and 2-(1H-benzo[d][1,2,3]triazol-1-yl)-1,1,3,3-tetramethylisouronium hexafluorophosphate(V) (HBTU). The coupling reagents may be added as a solid, a solution, or as the reagent bound to a solid support resin. In addition to the coupling reagents, auxiliary-coupling reagents may facilitate the coupling reaction. Auxiliary coupling reagents that are often used in the coupling reactions include but are not limited to (dimethylamino)pyridine (DMAP), 1-hydroxy-7-azabenzotriazole (HOAT) and 1-hydroxybenzotriazole (HOBT). The reaction may be carried out optionally in the presence of a base such as triethylamine or diisopropylethylamine. The coupling reaction may be carried out in solvents such as but not limited to tetrahydrofuran, N,N-dimethylformamide, N,N-dimethylacetamide, dichloromethane, and ethyl acetate. The reaction may be conducted at ambient or elevated temperatures. Alternatively, compounds of Formula (1-5) can be reacted with a chloroformate such as ethyl chloroformate in the presence of a base such as triethylamine in solvents such as acetonitrile or tetrahydrofuran at ambient temperature and then treated with an amine, $R^1$—$NH_2$, and further reacted over 4-24 hours to give compounds of Formula (1-6). Compounds of Formula (1-6) are representative of compounds of Formula (I).

Scheme 2

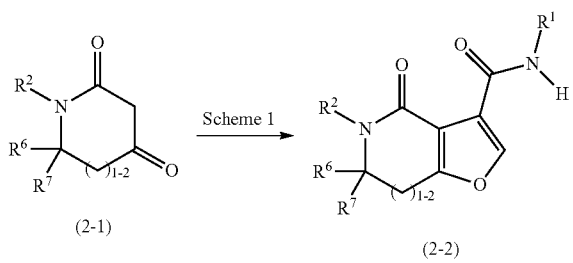

(2-1)          (2-2)

As shown in Scheme 2, compounds of Formula (2-2) can be prepared from compounds of Formula (2-1), wherein $R^1$, $R^2$, $R^6$ and $R^7$ are as defined in the Summary. Specifically, $R^6$ and $R^7$ are each independently selected from the group consisting of hydrogen. $C_1$-$C_6$-alkyl, and hydroxy$C_1$-$C_6$-alkyl or $R^6$ and $R^7$ taken together with the carbon atom to which they are attached form a $C_3$-$C_6$-cycloalkyl or $M_4$-$M_7$-heterocycle, wherein the $C_3$-$C_6$-cycloalkyl or $M_4$-$M_7$-heterocycle are optionally substituted with 1, 2, or 3 substituents selected from $C_1$-$C_6$-alkyl, cyano, aminocarbonyl, halogen, oxo and $C_1$-$C_6$-alkylcarbonyl. Compounds of Formula (2-1) can be either piperidine-2,4-diones or azepane-2,4-diones. The sequences described in Scheme 1 can be used to convert compounds of Formula (2-1) to compounds of Formula (2-2). Compounds of Formula (2-2) are representative of compounds of Formula (I).

Scheme 3

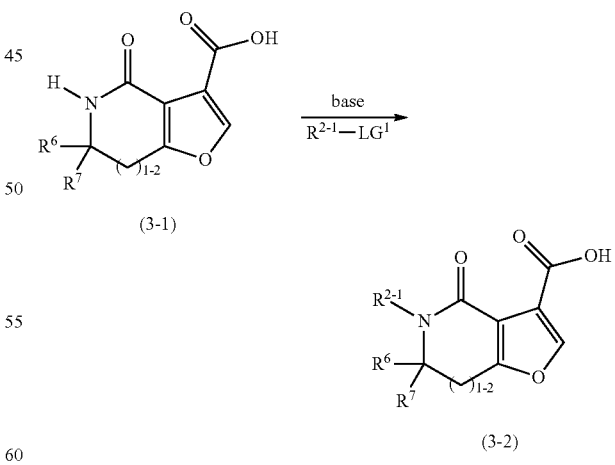

As shown in Scheme 3, compounds of Formula (3-1), wherein $R^6$ and $R^7$ are as defined in the Summary, can be alkylated to give compounds of Formula (3-2). Compounds of Formula (3-1) can be reacted with an alkylating agent, $R^{2-1}$ $LG^1$ (wherein $R^{2-1}$ is $C_1$-$C_6$-alkyl, $C_1$-$C_6$-alkoxy$C_2$-$C_6$alkyl, $C_1$-$C_6$-alkylcarbonyloxy$C_2$-$C_6$-alkyl, $C_1$-$C_6$-alkoxycarbonyl$C_1$-$C_6$-alkyl, $C_1$-$C_6$-alkylcarbonyl$C_1$-$C_6$- alkyl and phenylC$_1$-C$_6$-alkoxyC$_2$-C$_6$alkyl and LG$^1$ is chloro, bromo, iodo, or a sulfonate) in the presence of a base such as sodium hydride in a solvent such as N,N-dimethylformamide at 0° C. to room temperature over 4-24 hours to give compounds of Formula (3-2). In some instances the carboxylic acid will also react under these reaction conditions resulting in formation of an ester. The ester can be hydrolyzed using the conditions described in Scheme 1 to give compounds of Formula (3-2). Compounds of Formula (3-2) are representative of compounds of Formula (I).

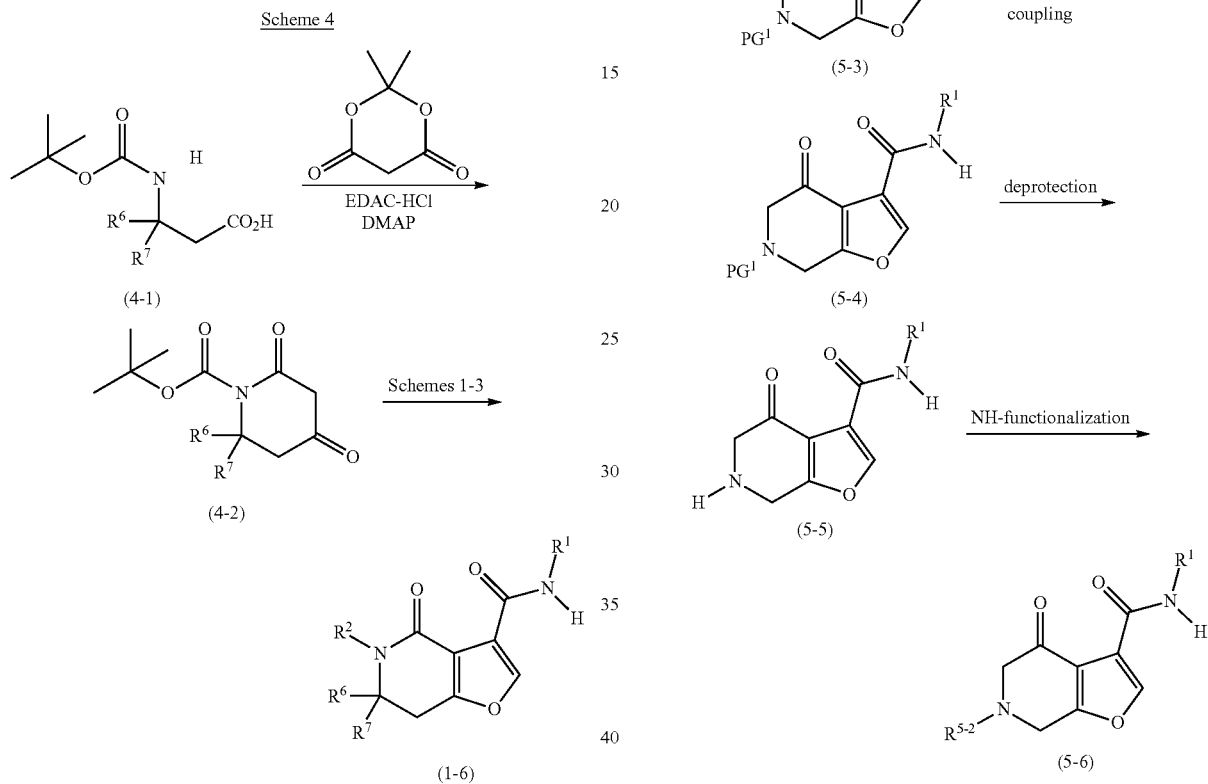

As shown in Scheme 4, compounds of Formula (4-1), wherein R$^6$ and R$^7$ are as defined in the Summary, can be converted to compounds of Formula (4-2). Compounds of Formula (4-1) can be reacted with 2,2-dimethyl-1,3-dioxane-4,6-dione (Meldrum's acid) in the presence of 1-(3-dimethylaminopropyl)-3-ethylcarbodiimide hydrochloride (EDAC-HCl) and dimethylaminopyridine (DMAP) in a solvent such as dichloromethane initially at 0° C. followed by warming to ambient temperature for 4-24 hours to give compounds of Formula (4-2). Compounds of Formula (4-2) can be converted to compounds of Formula (1-6) using the chemical sequences described in Schemes 1-3. The tert-butoxycarbonyl protecting group is removed in the course of these sequences.

As shown in Scheme 5, compounds of Formulas (5-4), (5-5), and (5-6), wherein R$^1$ is as defined in the Summary, can be prepared from compounds of Formula (5-1). Compounds of Formula (5-1), wherein R$^{5-1}$ is a C$_1$-C$_6$-alkyl and PG$^1$ is a nitrogen protecting group, can be reacted with a base such as potassium tert-butoxide in a solvent such as ether initially at 0° C. followed by warming to ambient temperature for 4-24 hours to give compounds of Formula (5-2). Compounds of Formula (5-2) can be converted to compounds of Formula (5-3) and Formula (5-4) using the chemical methodologies described in Scheme 1. Compounds of Formula (5-4), wherein PG$^1$ is C$_1$-C$_6$-alkoxycarbonyl, are representative of compounds of Formula (I). Compounds of Formula (5-4) can be deprotected using conditions dependent on the nitrogen protection group to give compounds of Formula (5-5) which are representative of compounds of Formula (I). Compounds of Formula (5-5) can be further functionalized by alkylation, sulfonamidation, amidation, and carbamoylation reactions to give compounds of Formula (5-6), wherein R$^{5-2}$ is C$_1$-C$_6$-alkyl, C$_1$-C$_6$-alkylsulfonyl, C$_1$-C$_6$-alkylcarbonyl, and C$_1$-C$_6$-alkoxycarbonyl. Compounds of Formula (5-6) are representative of compounds of Formula (I).

Scheme-6

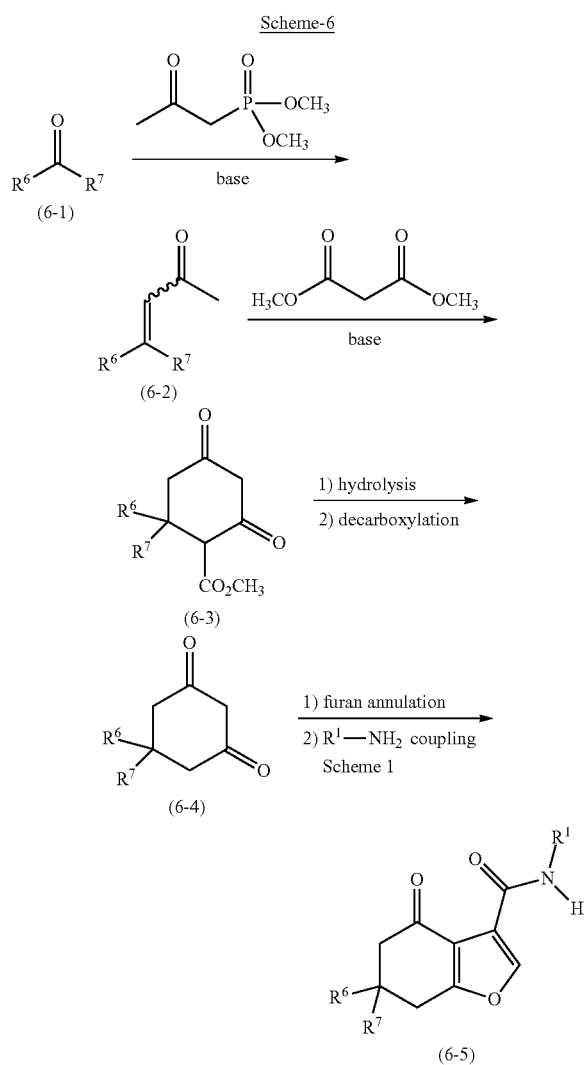

As shown in Scheme 6, compounds of Formula (6-5), wherein $R^1$, $R^6$ and $R^7$ are as defined in the Summary, can be prepared from compounds of Formula (6-1). Compounds of Formula (6-1) can be reacted with dimethyl 2-oxopropylphosphonate in the presence of a base such as potassium hydroxide in a mixture of ethanol and water initially at 0° C. followed by warming to ambient temperature for 4-24 hours to give compounds of Formula (6-2). Compounds of Formula (6-2) can be reacted with dimethyl malonate in the presence of a base such as sodium methoxide in methanol at reflux for 1-12 hours to give compounds of Formula (6-3). Compounds of Formula (6-3) are converted to compounds of Formula (6-4) in a two-step process. The initial step is hydrolysis achieved with refluxing in aqueous sodium hydroxide over 1-6 hours. The subsequent step is decarboxylation accomplished in aqueous sulfuric acid heated to reflux for 1-6 hours and then at ambient temperature for 2-24 hours. Some compounds of Formula (6-4) are commercially available or are obtained from acid hydrolysis of the corresponding substituted 1,5-dimethoxycyclohexa-1,4-dienes. Compounds of Formula (6-4) are converted to compounds of Formula (6-5) following the furan annulation and amide bond formation sequences described in Scheme 1. Compounds of Formula (6-5) are representative of compounds of Formula (I).

Scheme-7

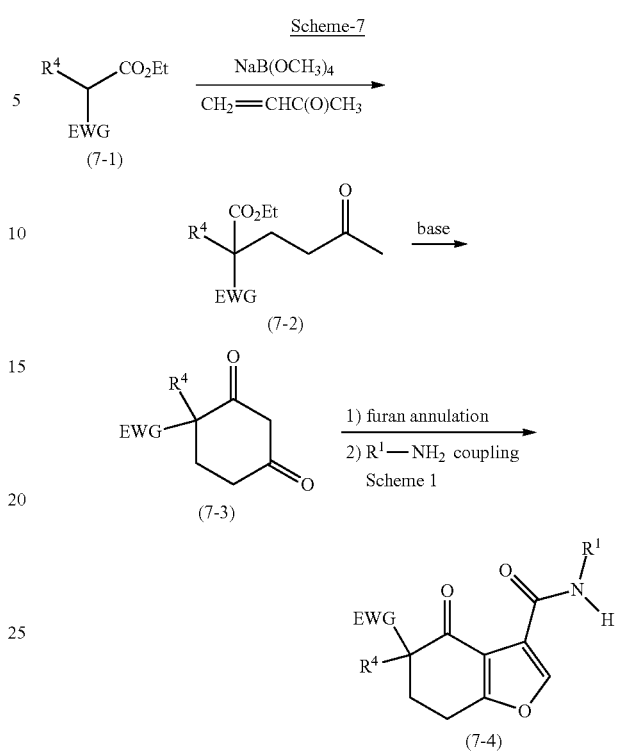

As shown in Scheme 7, compounds of Formula (7-4), wherein $R^1$ and $R^4$ are as described in the Summary and EWG represents an electron withdrawing group such as cyano, $C_1$-$C_6$-alkoxycarbonyl, or aminocarbonyl can be prepared from compounds of Formula (7-1). Compounds of Formula (7-1) can be treated with methyl vinyl ketone in the presence of sodium tetramethoxyborate at room temperature in a solvent such as acetonitrile for 3-7 days to deliver compounds of Formula (7-2). Compounds of Formula (7-2) can be treated with a base such as potassium tert-butoxide in a solvent such as a mixture of ethanol and tetrahydrofuran at 0° C. Compounds of Formula (7-3) are converted to compounds of Formula (7-4) following the furan annulation and amide bond formation sequences described in Scheme 1. The electron withdrawing group of compounds of Formula (7-4) can be further transformed.

Scheme 8

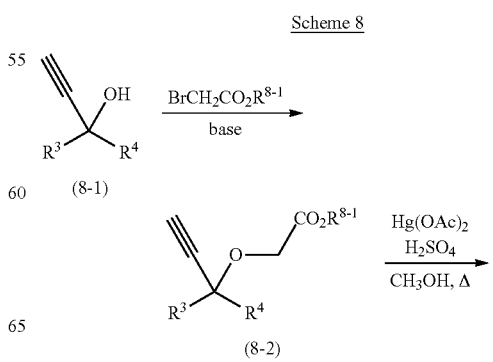

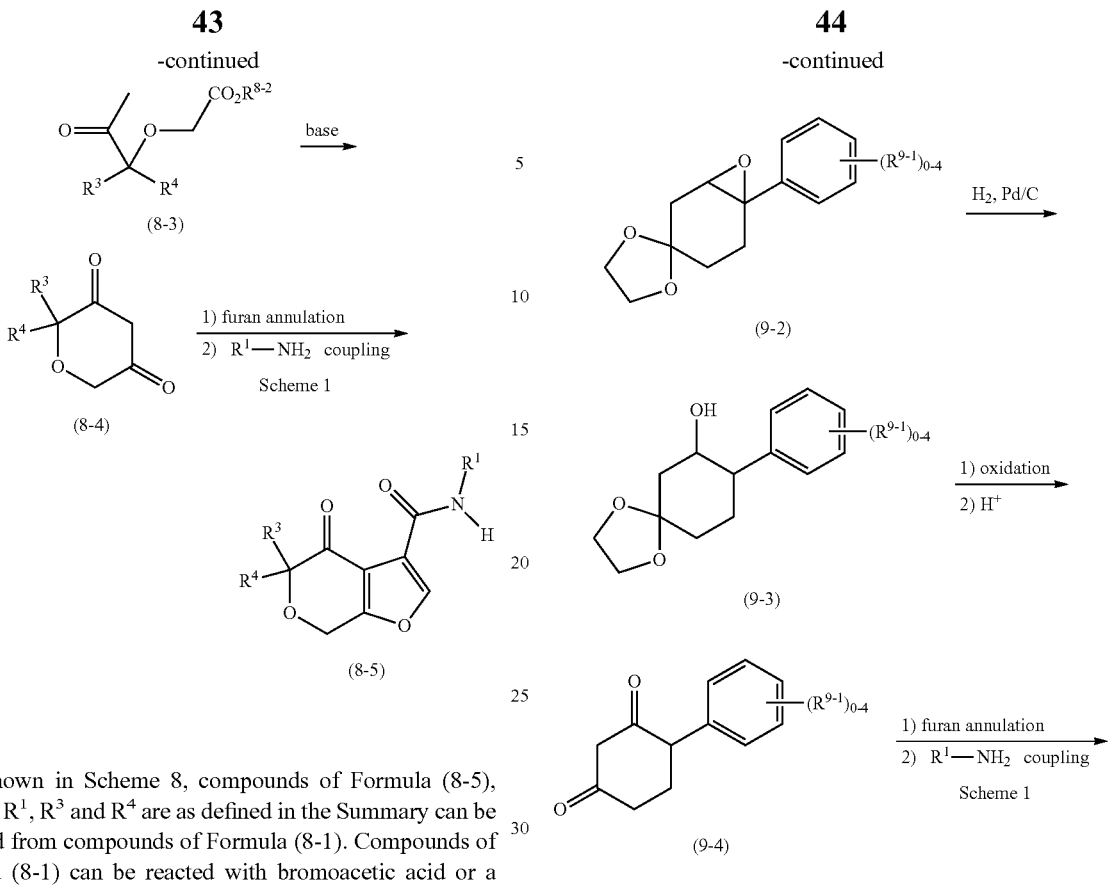

As shown in Scheme 8, compounds of Formula (8-5), wherein $R^1$, $R^3$ and $R^4$ are as defined in the Summary can be prepared from compounds of Formula (8-1). Compounds of Formula (8-1) can be reacted with bromoacetic acid or a bromoacetate, such as ethyl bromoacetate, wherein $R^{8-1}$ is hydrogen or $C_1$-$C_6$-alkyl, in the presence of a base such as sodium hydride in tetrahydrofuran at ambient temperature over 6-24 hours to give compounds of Formula (8-2). Compounds of Formula (8-2) can be reacted with mercury (II) acetate and sulfuric acid in methanol heated to approximately 60° C. for 30 minutes to 4 hours to give compounds of Formula (8-3), wherein $R^{8-2}$ is $C_1$-$C_6$-alkyl. When compounds of Formula (8-2) represent a carboxylic acid, compounds of Formula (8-2) are converted to the corresponding methyl esters of Formula (8-3). Compounds of Formula (8-3) can be treated with a base such as potassium tert-butoxide in ethanol or t-butanol and tetrahydrofuran at 0° C. for 30 minutes to 2 hours to give compounds of Formula (8-4). Compounds of Formula (8-4) are converted to compounds of Formula (8-5) following the furan annulation and amide bond formation sequences described in Scheme 1. Compounds of Formula (8-5) are representative of compounds of Formula (I).

Scheme 9

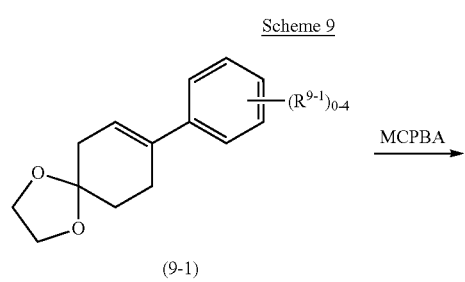

As shown in Scheme 9, compounds of Formula (9-1) can be transformed to compounds of Formula (9-5), wherein $R^1$ is as defined in the Summary and $R^{9-1}$ are 0-4 independently selected substituents on the phenyl ring selected from halogen, $C_1$-$C_6$-alkyl and cyano. Compounds of Formula (9-1) can be epoxidized with 3-chloroperoxybenzoic acid (MCPBA) in dichloromethane at ambient temperature over 4-24 hours to give compounds of Formula (9-2). Compounds of Formula (9-2) can be hydrogenated in the presence of palladium on carbon in methanol at ambient temperature over 4-24 hours to give compounds of Formula (9-3). The hydroxy group of compounds of Formula (9-3) can be first oxidized with a reagent such as Dess-Martin periodinane in dichloromethane at room temperature over 6-24 hours, and then the ketal can be hydrolyzed with hydrochloric acid in acetone heated in an 80° C. bath for 1-8 hours to give compounds of Formula (9-4). Compounds of Formula (9-4) are converted to compounds of Formula (9-5) following the furan annulation and amide bond formation sequences described in Scheme 1. Compounds of Formula (9-5) are representative of compounds of Formula (I).

Scheme 10

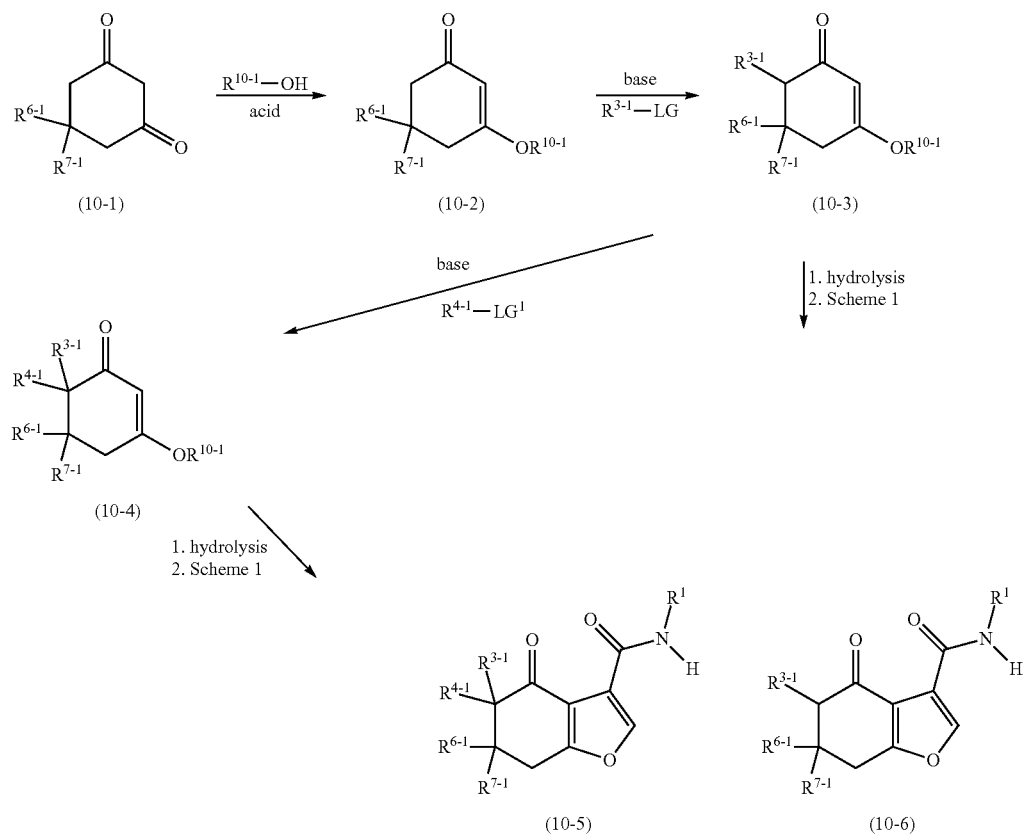

As shown in Scheme 10, compounds of Formula (10-5) and Formula (10-6) can be prepared from compounds of Formula (10-1). Compounds of Formula (10-1) (wherein $R^{6-1}$ and $R^{7-1}$ are $C_1$-$C_6$-alkyl or $C_1$-$C_6$-alkoxy$C_1$-$C_6$-alkyl, or wherein $R^{6-1}$ and $R^{7-1}$ taken together with the carbon atom to which they are attached form a $C_3$-$C_6$-cycloalkyl or $M_4$-$M_7$-heterocycle, wherein the $C_3$-$C_6$-cycloalkyl or $M_4$-$M_7$-heterocycle are optionally substituted with 1, 2, or 3 substituents selected from $C_1$-$C_6$-alkyl, cyano, halogen, oxo and $C_1$-$C_6$-alkylcarbonyl, and wherein the $M_4$-$M_7$-heterocycle does not contain N—H) can be reacted with an alcohol, $R^{10-1}$—OH (wherein $R^{10-1}$ is $C_1$-$C_6$-alkyl) in the presence of an acid such as sulfuric acid or p-toluenesulfonic acid at ambient temperature to reflux to provide compounds of Formula (10-2). Compounds of Formula (10-2) can be reacted with a base, such as lithium diisopropylamide, and an alkylating reagent, $R^{3-1}$-$LG^1$ (wherein $R^{3-1}$ is $C_1$-$C_6$-alkyl and $LG^1$ is chloro, bromo, iodo, or a sulfonate), in a solvent such as tetrahydrofuran at −20° C. to −78° C. to give compounds of Formula (10-3). Compounds of Formula (10-3) can be reacted with a base, such as lithium diisopropylamide, and an alkylating reagent, $R^{4-1}$-$LG^1$ (wherein $R^{4-1}$ is $C_1$-$C_6$-alkyl and $LG^1$ is chloro, bromo, iodo, or a sulfonate) in a solvent such as tetrahydrofuran at −20° C. to −78° C. to give compounds of Formula (10-4). Compounds of Formula (10-4) can be hydrolyzed in the presence of an acid, such as hydrochloric acid, in water, methanol, or acetone, or mixtures thereof. Subsequently, using the chemical sequences described in Scheme 1 to introduce the fused furan and amide groups give compounds of Formula (10-5), wherein $R^1$ is as described in the Summary. Similarly, compounds of Formula (10-3) can be converted to compounds of Formula (10-6). Compounds of Formula (10-5) and Formula (10-6) are representative of compounds of Formula (I).

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

Many of the compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis (4$^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Compositions of the Invention

The invention also provides pharmaceutical compositions comprising a therapeutically effective amount of a compound of Formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally", as used herein, refers to modes of administration which include intravenous, intramuscular, intraperitoneal, intrasternal, subcutaneous, intraarticular injection and infusion.

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Ophthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts or esters, or amides derived from inorganic or organic acids. The term "pharmaceutically acceptable salts and esters and amides", as used herein, refer to carboxylate salts, amino acid addition salts, zwitterions, and esters and amides of compounds of Formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid. An example of a suitable salt is a hydrochloride salt.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Preferred salts of the compounds of the invention are the tartrate and hydrochloride salts.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulfuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, and piperazine.

The term "pharmaceutically acceptable ester", as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$-alkyl esters and $C_5$-to-$C_7$-cycloalkyl esters, although $C_1$-to-$C_4$-alkyl esters are preferred. Esters of the compounds of Formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also may be prepared by reaction of the compound with an acid such as hydrochloric acid and an alcohol such as methanol or ethanol.

The term "pharmaceutically acceptable amide", as used herein, refers to non-toxic amides of the invention derived from ammonia, primary $C_1$-to-$C_6$-alkyl amines and secondary $C_1$-to-$C_6$-dialkyl amines. In the case of secondary amines, the amine may also be in the form of a 5- or 6-membered heterocycle containing one nitrogen atom. Amides derived from ammonia, $C_1$-to-$C_3$-alkyl primary amides and $C_1$-to-$C_2$-dialkyl secondary amides are preferred. Amides of the compounds of Formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The invention contemplates pharmaceutically active compounds either chemically synthesized or formed by in vivo biotransformation to compounds of Formula (I)

Methods of the Invention

The compounds and compositions of the invention are useful for treating and preventing certain diseases and disorders in humans and animals. As an important consequence of the ability of the compounds of the invention to modulate the effects of Trk's in cells, the compounds described in the invention can affect physiological processes in humans and animals. In this way, the compounds and compositions described in the invention are useful for treating and preventing diseases and disorders modulated by Trk. Typically, treatment or prevention of such diseases and disorders can be effected by selectively modulating Trk's in a mammal, by administering a compound or composition of the invention, either alone or in combination with another active agent as part of a therapeutic regimen.

The compounds of the invention, including but not limited to those specified in the examples, possess an affinity for Trk and therefore, the compounds of the invention may be useful for the treatment and prevention of diseases or conditions such as pain, including osteoarthritis pain, joint pain, neuropathic pain, post-surgical pain, low back pain, and diabetic neuropathy, pain during surgery, cancer pain, chemotherapy induced pain, headaches, including cluster headache, tension headache, migraine pain, trigeminal neuralgia, shingles pain, post-herpetic neuralgia, carpal tunnel syndrome, inflammatory pain, pain from rheumatoid arthritis, colitis, pain of interstitial cystitis, visceral pain, pain from kidney stone, pain from gallstone, angina, fibromyalgia, chronic pain syndrome, thalamic pain syndrome, pain from stroke, phantom limb pain, sunburn, radiculopathy, complex regional pain syndrome, HIV sensory neuropathy, central neuropathic pain syndromes, multiple sclerosis pain, Parkinson disease pain, spinal cord injury pain, menstrual pain, toothache, pain from bone metastasis, pain from endometriosis, pain from uterine fibroids, nociceptive pain, hyperalgesias, and temporomandibular joint pain, inflammation, auto-immune disease, rheumatoid arthritis, psoriasis, psoriatic arthritis, asthma, Crohn's disease, inflammatory bladder cystitis, inflammatory bowel disease, joint swelling, diabetic nephropathy, kidney fibrosis, chronic kidney disease, cancer, neuroblastoma, melanoma, myeloma, cancers of the pancreas, prostate, ovary, colon, thyroid, lung, brain, esophagus, kidney, of bone, and blood.

Compounds of the invention are particularly useful for treating and preventing a condition or disorder affecting pain.

The ability of the compounds of the invention, including, but not limited to, those specified in the examples, to treat the pain of osteoarthritis may be demonstrated by Lane N E, et al. New England J Med 2010; 363:1521-1531; Schnitzer T J, et al. Osteoarthritis Cartilage 2011; 19:639-646.

The ability of the compounds of the invention, including, but not limited to, those specified in the examples, to treat lower back pain may be demonstrated by Katz N, et al. Pain 2011; 152:2248-2258.

The ability of the compounds of the invention, including, but not limited to, those specified in the examples, to treat the pain of cystitis may be demonstrated by Evans R J, et al. J. Urology 2011; 185:1716-1721.

The ability of the compounds of the invention, including, but not limited to, those specified in the examples, to treat the pain of auto-immune arthritis may be demonstrated by Shelton D L, et al. Pain 2005; 116:8-16.

The ability of the compounds of the invention, including, but not limited to, those specified in the examples, to treat neuropathic pain or inflammatory pain may be demonstrated by Ro L S, et al. Pain 1999; 79:265-274; Ugolini G, et al. Proceedings of the National Academy of Sciences of the USA 2007; 104:2985-2990.

The ability of the compounds of the invention, including, but not limited to, those specified in the examples, to treat the pain of bone fracture may be demonstrated by Ghilardi J R, et al. Bone 2011; 48:389-298.

The ability of the compounds of the invention, including, but not limited to, those specified in the examples, to treat myofascial pain syndrome may be demonstrated by Hayashi K, et al. Journal of Pain 2011; 12:1059-1068.

The ability of the compounds of the invention, including, but not limited to, those specified in the examples, to treat diabetic nephropathy and pathological kidney fibrosis may be demonstrated by Fragiadaki M, et al. Diabetes 2012; 61:2280-2289.

The ability of the compounds of the invention, including, but not limited to, those specified in the examples, to treat cancer may be demonstrated by Albaugh P, et al. ACS Medicinal Chemistry Letters (2012; 3:140-145.

The ability of the compounds of the invention, including, but not limited to, those specified in the examples, to treat neuroblastoma may be demonstrated by Wang T, et al. ACS Medicinal Chemistry Letters 2012; 3:705-709; Thress K. et al. Molecular Cancer Therapeutics 2009; 8:1818-1827.

The ability of the compounds of the invention, including, but not limited to, those specified in the examples, to treat melanoma may be demonstrated by Truzzi F, et al. Journal of Investigative Dermatology 2008; 128:2031-2040.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt or ester, or amide form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed;

the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

For treatment or prevention of disease, the total daily dose of the compounds of this invention administered to a human or lower animal may range from about 0.0003 to about 100 mg/kg/day. For purposes of oral administration, more preferable doses can be in the range of from about 0.0003 to about 30 mg/kg/day. If desired, the effective daily dose can be divided into multiple doses for purposes of administration; consequently, single dose compositions may contain such amounts or submultiples thereof to make up the daily dose.

The compounds and processes of the invention will be better understood by reference to the following examples, which are intended as an illustration of and not a limitation upon the scope of the invention.

EXAMPLES

Abbreviations: APCI for atmospheric pressure chemical ionization; CAS for Chemical Abstracts Service; CI or chemical ionization; DCI for desorption chemical ionization; DMSO for dimethyl sulfoxide; ESI for electrospray ionization; HPLC for high performance liquid chromatography; and psi for pounds per square inch.

Example 1

N-(2-methyl-2H-indazol-5-yl)-4-oxo-4,5,6,7-tetrahydrofuro[3,2-c]pyridine-3-carboxamide Example 1A ethyl 3-(3-ethoxy-3-oxopropylamino)-3-oxopropanoate To a solution of ethyl 3-aminopropanoate hydrochloride (20 g, 0.13 mol) dissolved in dichloromethane (400 mL) at 0° C. was added triethylamine (37.2 mL, 0.272 mol) dropwise. The mixture was stirred for 1 hour at 0° C., and then ethyl malonyl chloride (16.8 mL, 0.13 mol) was added dropwise. The mixture was stirred for 1 hour, then poured into 75 mL of a saturated aqueous solution of ammonium chloride, and extracted with dichloromethane (3×50 mL). The combined organic layers were washed with saturated aqueous sodium bicarbonate (2×50 mL), washed with water (50 mL), dried with $Na_2SO_4$, filtered, concentrated and purified by silica gel column chromatography eluted with petroleum ether/ethyl acetate (50:1) to give the titled compound. $^1$H NMR (400 MHz, $CDCl_3$) δ ppm 7.50 (s, 1H), 4.14-4.22 (m, 4H), 3.54-3.59 (m, 2H), 3.29 (s, 2H), 2.55 (t, J=6.2 Hz, 2H), 1.25-1.30 (m, 6H).

Example 1B ethyl 2,4-dioxopiperidine-3-carboxylate

Sodium metal (4.84 g, 0.21 mmol) was added to dry ethanol (200 mL) at room temperature with stirring under $N_2$. After complete disappearance of the sodium, the mixture was stirred for another 10 minutes, then a solution of the product from Example 1A (28.6 g, 0.123 mol) in dry ethanol (50 mL) was added dropwise. After the addition was complete, the reaction mixture was stirred at 90° C. for 6 hours, and then the mixture was cooled to room temperature. Concentrated HCl (17.5 mL) was added, and the mixture was concentrated under reduced pressure. The resulting residue was treated with water (50 mL), acidified with concentrated HCl (10 mL) and extracted thoroughly with a mixture of dichloromethane/methanol (5:1). The organic layers were combined, dried over $Na_2SO_4$, filtered and concentrated to give the titled compound. $^1$H NMR (400 MHz, $CDCl_3$) δ ppm 4.19-4.24 (m, 2H), 3.29 (t, J=7.0 Hz, 2H), 2.51-2.55 (m, 3H), 1.23 (t, J=7.2 Hz, 3H).

Example 1C piperidine-2,4-dione

The product from Example 1B (20.5 g, 0.11 mol) was dissolved in acetonitrile (500 mL) and water (5 mL) was added. The resulting mixture was refluxed for 4 hours and then concentrated under reduced pressure to give a residue which was purified by silica gel column chromatography eluted with a gradient of 0% to 100% methanol in ethyl acetate to give the titled compound. $^1$H NMR (400 MHz, DMSO-$d_6$) δ ppm 8.07 (s, 1H), 3.28-3.45 (m, 2H), 3.24 (s, 2H), 2.43-2.49 (m, 2H).

Example 1D ethyl 3-hydroxy-4-oxo-2,3,4,5,6,7-hexahydrofuro[3,2-c]pyridine-3-carboxylate To a stirred solution of potassium hydroxide (2.97 g, 53 mmol) in methanol (60 mL) under nitrogen at 0° C. was added a solution of the product from Example 1C (6 g, 53 mmol) in methanol (10 mL) dropwise. After the addition was complete, the mixture was stirred at 0° C. for 1 hour, and then a solution of ethyl bromopyruvate (7.01 mL, 55.7 mmol) in methanol (10 mL) was added dropwise. After allowing the mixture to stir at ambient temperature for 2.5 hours, the solvent was removed, and the residue was purified by silica gel column chromatography eluted with methanol/dichloromethane (0-10%) to afford 3.4 g of crude product which was further purified via Teledyne Isco CombiFlash® Companion® XL eluted with methanol/10 mM ammonium acetate in water (0-50%) on a 120 g RediSep® $C_{18}$ column to provide the titled compound. $^1$H NMR (400 MHz, DMSO-$d_6$) δ ppm 6.87 (s, 1H), 4.59 (d, J=10.0 Hz, 1H), 4.34 (d, J=10.4 Hz, 1H), 4.11 (m, 2H), 3.27-3.34 (m, 2H), 2.50-2.55 (m, 2H), 1.16 (t, J=7.2 Hz, 3H).

Example 1E 4-oxo-4,5,6,7-tetrahydrofuro[3,2-c]pyridine-3-carboxylic acid

A mixture of the product from Example 1D (3.4 g, 16.3 mmol), tetrahydrofuran (163. mL) and 2 M HCl (16.3 mL) was heated to 80° C. for 2 hours and then cooled to room temperature. The precipitate was filtered, washed with water and dried to afford the titled compound. $^1$H NMR (400 MHz, DMSO-$d_6$) δ ppm 15.01 (s, 1H), 8.68 (s, 1H), 8.43 (s, 1H), 3.59-3.63 (m, 2H), 3.04 (t, J=7.4 Hz, 2H).

Example 1F

N-(2-methyl-2H-indazol-5-yl)-4-oxo-4,5,6,7-tetrahydrofuro[3,2-c]pyridine-3-carboxamide To a solution of the product from Example 1E (0.1 g, 0.552 mmol) in N,N-dimethylformamide (4 mL) was added 2-(7-azabenzotriazol-1-yl)-N,N,N',N'-tetramethyluronium hexafluorophosphate (0.210 g, 0.552 mmol) and triethylamine (0.077 mL, 0.552 mmol). After mixing, 2-methyl-2H-indazol-5-amine (0.081 g, 0.552 mmol) was added and the vial was shaken for 4 hours. The mixture was concentrated and triturated with methanol to provide the titled compound. $^1$H NMR (DMSO-d$_6$) δ ppm 12.70 (s, 1H), 8.33 (s, 1H), 8.27 (m, 2H), 8.22 (bt, 1H), 7.59 (d, J=8 Hz, 1H), 7.25 (d, J=8 Hz, 1H), 4.14 (s, 3H), 3.56 (t, J=4 Hz, 2H), 3.02 (t, J=4 Hz, 2H); MS (APCI) m/z 311 (M+H)$^+$.

Example 2

5-methyl-N-(2-methyl-2H-indazol-5-yl)-4-oxo-4,5,6,7-tetrahydrofuro[3,2-c]pyridine-3-carboxamide

Example 2A methyl 5-methyl-4-oxo-4,5,6,7-tetrahydrofuro[3,2-c]pyridine-3-carboxylate A solution of the product from Example 1E (7.9 g, 43.6 mmol) in N,N-dimethylformamide (450 mL) was cooled to 0° C. in an ice bath, and NaH (60%, 5.23 g, 131 mmol) was added. The mixture was stirred for 1 hour at room temperature and then cooled to 0° C. Methyl iodide (14 mL, 218 mmol) was added, and the mixture was stirred at room temperature overnight. The solvent was removed under reduced pressure. The residue was treated with 100 mL of water and extracted with ethyl acetate (10×30 mL). The combined organic layers were dried with Na$_2$SO$_4$, filtered and concentrated to give a residue which was purified by silica gel column chromatography (100% ethyl acetate) to afford the titled compound. $^1$H NMR (400 MHz, CD$_3$OD) δ ppm 7.96 (s, 1H), 3.72 (s, 3H), 3.59 (t, J=7.2 Hz, 2H), 2.89-2.94 (m, 5H).

Example 2B 5-methyl-4-oxo-4,5,6,7-tetrahydrofuro[3,2-c]pyridine-3-carboxylic acid A mixture of the product from Example 2A (5.3 g, 25.3 mmol), tetrahydrofuran (25.3 mL) and 2 M HCl (25.3 mL) was heated to 80° C. for 2 hours and then cooled to room temperature. The precipitate was filtered, washed with cold water and dried to afford the titled compound. $^1$H NMR (400 MHz, DMSO-d$_6$) δ ppm 15.01 (s, 1H), 8.42 (s, 1H), 3.79 (t, J=7.6 Hz, 2H), 3.13 (t, J=7.6 Hz, 2H), 3.02 (s, 3H).

Example 2C 5-methyl-N-(2-methyl-2H-indazol-5-yl)-4-oxo-4,5,6,7-tetrahydrofuro[3,2-c]pyridine-3-carboxamide To a solution of the product from Example 2B (0.1 g, 0.512 mmol) in N,N-dimethylformamide (4 mL) was added 2-(7-azabenzotriazol-1-yl)-N,N,N',N'-tetramethyluronium hexafluorophosphate (0.195 g, 0.512 mmol) and triethylamine (0.071 mL, 0.512 mmol). After mixing, 2-methyl-2H-indazol-5-amine (0.075 g, 0.512 mmol) was added, and the vial was shaken for 4 hours. The mixture was concentrated and triturated with methanol to provide the titled compound. $^1$H NMR (DMSO-d$_6$) δ ppm 12.76 (s, 1H), 8.32 (s, 1H), 8.29 (s, 1H), 8.25 (d, J=4 Hz, 1H), 7.60 (d, J=12 Hz, 1H), 7.29 (d, J=12 Hz, 1H), 4.41 (s, 3H), 3.75 (t, J=8 Hz, 2H), 3.11 (t, J=8 Hz, 2H), 3.06 (s, 3H); MS (ESI) m/z 325 (M+H)$^+$.

Example 3

N-[4-(morpholin-4-yl)phenyl]-4-oxo-4,5,6,7-tetrahydrofuro[3,2-c]pyridine-3-carboxamide In a 4 mL vial, a solution of the product from Example 1E (31 mg, 0.17 mmol) dissolved in N,N-dimethylacetamide (1.0 mL) was treated with a solution of 2-(7-azabenzotriazol-1-yl)-N,N,N',N'-tetramethyluronium hexafluorophosphate (76 mg, 0.2 mmol) dissolved in N,N-dimethylacetamide (1.0 mL). Then a solution of 4-morpholinoaniline (36 mg, 0.2 mmol) dissolved in N,N-dimethylacetamide (0.7 mL) was added followed by neat triethylamine (73 μL, 0.5 mmol). The reaction was shaken at 60° C. overnight and concentrated to dryness. The residue were dissolved in 1:1 dimethyl sulfoxide/methanol and purified by preparative HPLC on a Phenomenex® Luna® C8(2) 5 μm 100 Å AXIA™ column (30 mm×75 mm) A gradient of acetonitrile (A) and 0.1% trifluoroacetic acid in water (B) was used at a flow rate of 50 mL/minute (0-0.5 minutes 10% A, 0.5-6.0 minutes linear gradient 10-100% A, 6.0-7.0 minutes 100% A, 7.0-8.0 minutes linear gradient 100-10% A). Samples were injected in dimethyl sulfoxide/methanol (1:1, 1.5 mL). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/autosampler. The make-up pump for the mass spectrometer used 3:1 methanol/water with 0.1% formic acid at a flow rate of 1 mL/minute. Fraction collection was automatically triggered when the extracted ion chromatogram (EIC) for the target mass exceeded the threshold. Concentration of selected fractions provided the titled compound as the trifluoroacetate. $^1$H NMR (500 MHz, DMSO-d$_6$/D$_2$O) δ ppm 8.26 (s, 1H), 7.51-7.57 (m, 2H), 6.95-7.00 (m, 2H), 3.72-3.77 (m, 4H), 3.56 (t, J=7.32 Hz, 2H), 3.06-3.10 (m, 4H), 3.01 (t, J=7.32 Hz, 2H); MS (ESI) m/z 342 (M+H)$^+$.

Example 4

5-methyl-N-(4-methylphenyl)-4-oxo-4,5,6,7-tetrahydrofuro[3,2-c]pyridine-3-carboxamide In a 4 mL vial, a solution of the product from Example 2B (31 mg, 0.16 mmol) dissolved in N,N-dimethylacetamide (1.0 mL) was treated with a solution of 2-(7-azabenzotriazol-1-yl)-N,N,N',N'-tetramethyluronium hexafluorophosphate (73 mg, 0.2 mmol) dissolved in N,N-dimethylacetamide (1.0 mL). Then a solution of p-toluidine (30 mg, 0.2 mmol) dissolved in N,N-dimethylacetamide (0.6 mL) was added followed by neat triethylamine (68 μL, 0.5 mmol). The reaction was shaken at 60° C. overnight. The residue was dissolved in 1:1 dimethyl sulfoxide/methanol and purified by preparative HPLC on a Phenomenex® Luna® C8(2) 5 μm 100 Å AXIA™ column (30 mm×75 mm) A gradient of acetonitrile (A) and 0.1% trifluoroacetic acid in water (B)

was used, at a flow rate of 50 mL/minute (0-0.5 minutes 10% A, 0.5-6.0 minutes linear gradient 10-100% A, 6.0-7.0 minutes 100% A, 7.0-8.0 minutes linear gradient 100-10% A). Samples were injected in dimethyl sulfoxide/methanol (1:1, 1.5 mL). An Agilent 1100 Series Purification system was used consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/autosampler. The make-up pump for the mass spectrometer used 3:1 methanol/water with 0.1% formic acid at a flow rate of 1 mL/minute. Fraction collection was automatically triggered when the extracted ion chromatogram (EIC) for the target mass exceeded the threshold. Concentration of selected fractions provided the titled compound. $^1$H NMR (500 MHz, DMSO-$d_6$) δ ppm 12.70 (s, 1H), 8.30 (s, 1H), 7.57 (d, J=8.4 Hz, 2H), 7.17 (d, J=8.3 Hz, 2H), 3.74 (t, J=7.5 Hz, 2H), 3.10 (t, J=7.5 Hz, 2H), 3.04 (s, 3H), 2.27 (s, 3H); MS (APCI) m/z 285 (M+H)$^+$.

Example 5 tert-butyl 4-(3-methoxy-4-{[(4-oxo-4,5,6,7-tetrahydrofuro[3,2-c]pyridin-3-yl)carbonyl]amino}phenyl)piperazine-1-carboxylate A solution of the product from Example 1E (295 mg, 1.627 mmol), tert-butyl 4-(4-amino-3-methoxyphenyl)piperazine-1-carboxylate (CAS#1246532-96-6) (500 mg, 1.627 mmol) and 2-(7-azabenzotriazol-1-yl)-N,N,N',N'-tetramethyluronium hexafluorophosphate (680 mg, 1.789 mmol) in acetonitrile (15 mL) was treated with diisopropylethylamine (0.426 mL, 2.440 mmol) and stirred for 16 hours. The reaction mixture was partitioned between ethyl acetate (50 mL) and H$_2$O (20 mL). The organic layer was separated, washed with brine and dried with MgSO$_4$. After filtration, the filtrate was concentrated under reduced pressure. The resulting residue was chromatographed on a silica gel column eluted with 30-80% ethyl acetate in hexanes to provide the titled compound. $^1$H NMR (300 MHz, DMSO-$d_6$) δ ppm 11.91 (s, 1H), 8.25 (s, 1H), 8.04 (s, 1H), 7.94 (d, J=8.8 Hz, 1H), 6.65 (d, J=2.4 Hz, 1H), 6.49 (dd, J=8.9, 2.5 Hz, 1H), 3.79 (s, 3H), 3.52 (td, J=7.2, 2.5 Hz, 2H), 3.48-3.42 (m, 4H), 3.11-3.06 (m, 4H), 2.99 (t, J=7.3 Hz, 2H), 1.42 (s, 9H); MS (DCI) m/z 471 (M+H)$^+$.

Example 6

N-[2-methoxy-4-(piperazin-1-yl)phenyl]-4-oxo-4,5,6,7-tetrahydrofuro[3,2-c]pyridine-3-carboxamide The product from Example 5, tert-butyl 4-(3-methoxy-4-{[(4-oxo-4,5,6,7-tetrahydrofuro[3,2-c]pyridin-3-yl)carbonyl]amino}phenyl)piperazine-1-carboxylate (753 mg, 1.6 mmol), was treated with trifluoroacetic acid (2 mL) at room temperature for 5 minutes. The mixture was concentrated under reduced pressure. The residue was dissolved in dichloromethane (50 mL) and washed with saturated K$_2$CO$_3$ solution. The organic layer was separated, dried with MgSO$_4$ and concentrated under reduced pressure. The resulting residue was chromatographed on silica gel eluted with concentrated NH$_4$OH/methanol/dichloromethane (0.3/3/97) to provide the titled compound. $^1$H NMR (300 MHz, CD$_3$OD) δ ppm 8.13 (s, 1H), 7.90 (s, 1H), 7.88 (d, J=6.1 Hz, 1H), 6.65 (d, J=2.5 Hz, 1H), 6.55 (dd, J=8.8, 2.6 Hz, 1H), 3.87 (s, 3H), 3.65 (t, J=7.3 Hz, 2H), 3.14 (dd, J=6.2, 3.8 Hz, 4H), 3.02 (dd, J=12.0, 4.6 Hz, 2H), 2.98 (dd, J=6.2, 3.8 Hz, 4H); MS (DCI) m/z 371 (M+H)$^+$.

Example 7

N-[2-methoxy-6-(4-methylpiperazin-1-yl)pyridin-3-yl]-4-oxo-5,6,7,8-tetrahydro-4H-furo[3,2-c]azepine-3-carboxamide Example 7A ethyl 3-hydroxy-4-oxo-3,4,5,6,7,8-hexahydro-2H-furo[3,2-c]azepine-3-carboxylate A solution of azepane-2,4-dione (CAS #29520-88-5, Coleman R S, et al. Organic Letters 2009; 11: 2133-2136) (2.18 g, 17.15 mmol) in methanol (40 mL) was added dropwise to a solution of KOH (1.14 g, 17.27 mmol) in water (10 mL). The resulting mixture was stirred at 0° C. for 1 hour, and then ethyl 3-bromo-2-oxopropanoate (3.35 g, 17.18 mmol) was added dropwise. The resulting mixture was stirred at 25° C. for 1 hour. The solvent was removed under reduced pressure, and the crude material was used in the next step without purification. MS (CI) m/z 224 (M–H$_2$O+H)$^+$.

Example 7B 4-oxo-5,6,7,8-tetrahydro-4H-furo[3,2-c]azepine-3-carboxylic acid

A solution of the product from Example 7A, ethyl 3-hydroxy-4-oxo-3,4,5,6,7,8-hexahydro-2H-furo[3,2-c]azepine-3-carboxylate (184 mg, 0.763 mmol) in H$_2$O (2 mL) and 10% HCl (1.159 mL, 3.81 mmol) was stirred at 100° C. for 3 hours. Solvent was removed under reduced pressure, and the crude material was purified via Teledyne Isco CombiFlash® Companion® XL eluted with acetonitrile/10 mM ammonium acetate in water (0-20%) on a 120 g RediSep® C$_{18}$ column to provide the titled compound. $^1$H NMR (300 MHz, DMSO-$d_6$) δ ppm 16.23 (s, 1H), 9.10 (bt, 1H), 8.37 (s, 1H), 3.34-3.28 (m, 2H), 3.09 (t, J=6.7 Hz, 2H), 2.03-1.91 (m, 2H); MS (ESI) m/z 196 (M+H)$^+$.

Example 7C

N-[2-methoxy-6-(4-methylpiperazin-1-yl)pyridin-3-yl]-4-oxo-5,6,7,8-tetrahydro-4H-furo[3,2-c]azepine-3-carboxamide A solution of the product from Example 7B, 4-oxo-5,6,7,8-tetrahydro-4H-furo[3,2-c]azepine-3-carboxylic acid (30 mg, 0.154 mmol), and triethylamine (0.032 mL, 0.231 mmol) in acetonitrile (5 mL) was treated with ethyl chloroformate (0.019 mL, 0.200 mmol) at 0° C. and stirred for 20 minutes. A solution of 2-methoxy-6-(4-methylpiperazin-1-yl)pyridin-3-amine (CAS #1094787-95-7) in acetonitrile (5 mL) was added, and the mixture was stirred at ambient temperature for 16 hours. The reaction mixture was diluted with water (20 mL) and stirred for 10 minutes. The precipitate was filtered and washed with small amount of ether (5 mL). The solid was purified on a silica gel column eluted with concentrated NH$_4$OH/methanol/dichloromethane (0.2/2/98) to provide the titled compound. $^1$H NMR (400 MHz, DMSO-$d_6$) δ ppm 12.15 (s, 1H), 8.53 (t, J=5.8 Hz, 1H), 8.29-8.09 (m, 2H), 6.29 (d, J=8.6 Hz, 1H), 3.80 (s, 3H), 3.25-3.13 (m, 3H), 3.04 (t, J=7.1 Hz, 2H), 2.42-2.34 (m, 4H), 2.20 (s, 3H), 2.02-1.90 (m, 2H); MS (DCI) m/z 400 (M+H)+.

Example 8

N-[6-(4-acetylpiperazin-1-yl)-2-ethoxypyridin-3-yl]-5-[2-(benzyloxy)ethyl]-4-oxo-4,5,6,7-tetrahydrofuro[3,2-c]pyridine-3-carboxamide Example 8A 5-(2-(benzyloxy)ethyl)-4-oxo-4,5,6,7-tetrahydrofuro[3,2-c]pyridine-3-carboxylic acid A mixture of a 60% dispersion of sodium hydride in mineral oil (55.2 mg, 1.38 mmol) and benzyl 2-bromoethyl ether (356 mg, 1.66 mmol) in N,N-dimethylformamide (2 mL) was cooled to 0° C. and treated with the product from Example 1E (100 mg, 0.55 mmol). The reaction mixture was stirred at 0° C. for 15 minutes, and then it was stirred at room temperature overnight. The reaction mixture was treated with water (10 mL) and 1 MNaOH (1 mL) and then washed with Et$_2$O (2×30 mL, discarded). The aqueous layer was acidified with concentrated HCl and extracted with Et$_2$O (50 mL). This Et$_2$O layer was washed with brine, dried (MgSO$_4$), filtered, concentrated and chromatographed on silica gel eluted with a gradient of 0% to 50% ethyl acetate in [9:1 CH$_2$Cl$_2$:ethyl acetate] to provide the titled compound. $^1$H NMR (300 MHz, CDCl$_3$) δ ppm 14.59 (s, 1H), 8.04 (s, 1H), 7.38-7.26 (m, 5H), 4.53 (s, 2H), 3.89 (t, J=7.4 Hz, 2H), 3.81-3.64 (m, 4H), 3.02 (t, J=7.4 Hz, 2H).

Example 8B

N-[6-(4-acetylpiperazin-1-yl)-2-ethoxypyridin-3-yl]-5-[2-(benzyloxy)ethyl]-4-oxo-4,5,6,7-tetrahydrofuro[3,2-c]pyridine-3-carboxamide A solution of the product from Example 8A (30 mg, 0.095 mmol) in tetrahydrofuran (3 mL) was treated with triethylamine (33.2 μL, 0.238 mmol) followed by treatment with ethyl chloroformate (9.14 μL, 0.095 mmol). The mixture was stirred at room temperature for 45 minutes and then treated with 1-(4-(5-amino-6-ethoxypyridin-2-yl)piperazin-1-yl)ethanone (CAS#1094927-44-2) (20.96 mg, 0.079 mmol). The reaction mixture was stirred for approximately 60 hours and then partitioned between 1 MNaOH (5 mL) and CH$_2$Cl$_2$ (25 mL). The layers were separated and the aqueous layer was extracted with CH$_2$Cl$_2$ (25 mL). The combined CH$_2$Cl$_2$ layers were washed with 1 M HCl (10 mL), dried (MgSO$_4$), filtered, concentrated and chromatographed on silica gel eluted with a gradient of 0% to 100% [20% ethanol in ethyl acetate] in ethyl acetate to provide the titled compound. $^1$H NMR (300 MHz, CDCl$_3$) δ ppm 12.00 (s, 1H), 8.53 (d, J=8.5 Hz, 1H), 8.06 (s, 1H), 7.37-7.27 (m, 5H), 6.19 (d, J=8.6 Hz, 1H), 4.53 (s, 2H), 4.39 (q, J=7.1 Hz, 2H), 3.82 (t, J=7.3 Hz, 2H), 3.77-3.70 (m, 6H), 3.61-3.41 (m, 6H), 2.98 (t, J=7.2 Hz, 2H), 2.14 (s, 3H), 1.46 (t, J=7.1 Hz, 3H); MS (ESI) m/z 562 (M+H)+.

Example 9

N-[6-(4-acetylpiperazin-1-yl)-2-ethoxypyridin-3-yl]-5-(2-hydroxyethyl)-4-oxo-4,5,6,7-tetrahydrofuro[3,2-c]pyridine-3-carboxamide A mixture of the product from Example 8B and 10% Pd/C (~75 mg) in tetrahydrofuran (5 mL) was stirred under H$_2$ using a balloon for 2 hours, diluted with CH$_2$Cl$_2$ and filtered. The filtrate was concentrated and chromatographed on silica gel eluted with a gradient of 0% to 100% [20% ethanol in ethyl acetate] in ethyl acetate to provide the titled compound. $^1$H NMR (300 MHz, CDCl$_3$) δ ppm 11.84 (s, 1H), 8.54 (d, J=8.5 Hz, 1H), 8.08 (s, 1H), 6.20 (d, J=8.6 Hz, 1H), 4.41 (q, J=7.0 Hz, 2H), 3.90 (t, J=4.7 Hz, 2H), 3.82 (t, J=7.3 Hz, 2H), 3.73 (dd, J=9.6, 4.3 Hz, 4H), 3.63-3.40 (m, 6H), 3.06 (t, J=7.3 Hz, 2H), 2.14 (s, 3H), 1.47 (t, J=7.0 Hz, 3H); MS (ESI) m/z 472 (M+H)+.

Example 10

N-[4-(4-acetylpiperazin-1-yl)phenyl]-4-oxo-4,5,6,7-tetrahydrofuro[3,2-c]pyridine-3-carboxamide The titled compound was prepared using the procedure described for Example 1F substituting 1-(4-(4-aminophenyl)piperazin-1-yl)ethanone for 2-methyl-2H-indazol-5-amine. $^1$H NMR (DMSO-d$_6$) δ ppm 12.54 (s, 1H), 8.29 (s, 1H), 8.16 (s, 1H), 7.54 (d, J=8 Hz, 2H), 6.97 (d, J=8 Hz, 2H), 3.35-3.59 (m, 6H), 3.11 (t, J=4 Hz, 2H), 2.99-3.06 (m, 4H), 2.04 (s, 3H); MS (APCI) m/z 383 (M+H)+.

Example 11

N-(1-methyl-1H-indazol-5-yl)-4-oxo-4,5,6,7-tetrahydrofuro[3,2-c]pyridine-3-carboxamide The titled compound was prepared using the procedure described for Example 1F substituting 1-methyl-1H-indazol-5-amine for 2-methyl-2H-indazol-5-amine $^1$H NMR (DMSO-d$_6$) δ ppm 12.79 (s, 1H), 8.34 (s, 1H), 8.27 (s, 1H), 8.22 (s, 1H), 7.64 (d, J=8 Hz, 1H), 7.47 (d, J=12 Hz, 1H), 4.03 (s, 3H), 3.57 (t, J=8 Hz, 2H), 3.03 (t, J=8 Hz, 2H); MS (APCI) m/z 311 (M+H)+.

Example 12

N-(1H-benzimidazol-5-yl)-4-oxo-4,5,6,7-tetrahydrofuro[3,2-c]pyridine-3-carboxamide The titled compound was prepared using the procedure described for Example 1F substituting 1H-benzo[d]imidazol-5-amine for 2-methyl-2H-indazol-5-amine $^1$H NMR (DMSO-d$_6$) δ ppm 12.80 (d, br, 1H), 12.39 (s, 1H), 8.34 (s, 1H), 8.22 (s, 1H), 8.17 (s, 1H), 7.50-7.59 (m, 1H), 7.20-7.34 (d, br, 1H), 3.54-3.59 (m, 2H), 3.03 (t, J=8 Hz, 2H); MS (APCI) m/z 297 (M+H)+.

Example 13

N-(4-carbamoylphenyl)-4-oxo-4,5,6,7-tetrahydrofuro[3,2-c]pyridine-3-carboxamide

The titled compound was prepared using the procedure described for Example 1F substituting 4-aminobenzamide for 2-methyl-2H-indazol-5-amine $^1$H NMR (DMSO-d$_6$) δ ppm 12.99 (s, 1H), 8.38 (s, 1H), 8.26 (s, 1H), 7.89 (d, J=8 Hz, 2H), 7.71 (d, J=8 Hz, 2H), 7.26 (s, 1H), 3.56 (t, J=8 Hz, 2H), 3.03 (t, J=8 Hz, 2H); MS (APCI) m/z 300 (M+H)+.

Example 14

N-(1H-indazol-5-yl)-4-oxo-4,5,6,7-tetrahydrofuro[3,2-c]pyridine-3-carboxamide

The titled compound was prepared using the procedure described for Example 1F substituting 1H-indazol-5-amine for 2-methyl-2H-indazol-5-amine $^1$H NMR (DMSO-d$_6$) δ ppm 13.02 (s, 1H), 12.76 (s, 1H), 8.34 (s, 1H), 8.27 (s, 1H), 8.21 (s, 1H), 8.05 (s, 1H), 7.54 (d, J=8 Hz, 1H), 7.43 (d, J=8 Hz, 1H), 3.57 (t, J=8 Hz, 2H), 3.03 (t, J=8 Hz, 2H); MS (ESI) m/z 297 (M+H)$^+$.

Example 15

N-(2-methyl-1,3-benzothiazol-6-yl)-4-oxo-4,5,6,7-tetrahydrofuro[3,2-c]pyridine-3-carboxamide The titled compound was prepared using the procedure described for Example 1F substituting 2-methylbenzo[d]thiazol-6-amine for 2-methyl-2H-indazol-5-amine. $^1$H NMR (DMSO-d$_6$) δ ppm 12.98 (s, 1H), 8.51 (s, 1H), 8.37 (s, 1H), 8.26 (s, 1H), 7.88 (d, J=8 Hz, 1H), 7.55 (d, J=8 Hz, 1H), 3.58 (t, J=8 Hz, 2H), 3.03 (t, J=8 Hz, 2H), 2.77 (s, 3H); MS (APCI) m/z 327 (M+H)$^+$.

Example 16

N-[5-(4-methylpiperazin-1-yl)pyridin-2-yl]-4-oxo-4,5,6,7-tetrahydrofuro[3,2-c]pyridine-3-carboxamide The titled compound was prepared using the procedure described for Example 1F substituting 5-(4-methylpiperazin-1-yl)pyridin-2-amine for 2-methyl-2H-indazol-5-amine $^1$H NMR (DMSO-d$_6$) δ ppm 12.73 (s, 1H), 8.33 (s, 1H), 8.08 (s, 1H), 8.06 (s, 1H), 8.01 (s, 1H), 7.40 (dd, J=4, 8 Hz, 1H), 3.52 (t, J=8 Hz, 2H), 3.13 (t, J=8 Hz, 4H), 2.99 (t, J=8 Hz, 2H), 2.44 (t, J=8 Hz, 4H), 2.21 (s, 3H); MS (APCI) m/z 356 (M+H)$^+$.

Example 17

N-[4-(4-methylpiperazin-1-yl)phenyl]-4-oxo-4,5,6,7-tetrahydrofuro[3,2-c]pyridine-3-carboxamide The titled compound was prepared using the procedure described for Example 1F substituting 4-(4-methylpiperazin-1-yl)aniline for 2-methyl-2H-indazol-5-amine $^1$H NMR (DMSO-d$_6$) δ ppm 12.5 (s, 1H), 8.26 (s, 1H), 8.16 (s, 1H), 7.50 (d, J=8 Hz, 2H), 6.92 (d, J=8 Hz, 2H), 3.53 (td, H=4, 8, 2H), 3.07 (t, J=4 Hz, 4H), 2.99 (t, J=8 Hz, 2H), 2.43 (t, J=8 Hz, 4H), 2.20 (s, 3H); MS (APCI) m/z 355 (M+H)$^+$.

Example 18

N-[4-(4-acetylpiperazin-1-yl)-2-methoxyphenyl]-4-oxo-4,5,6,7-tetrahydrofuro[3,2-c]pyridine-3-carboxamide To a solution of the product from Example 6 (40 mg, 0.108 mmol) and triethylamine (0.023 mL, 0.15 mmol) in dichloromethane (10 mL) was added acetyl chloride (0.01 mL, 0.14 mmol). The mixture was stirred at room temperature for 10 minutes. The reaction mixture was concentrated under reduced pressure. The resulting residue was chromatographed on a silica gel column eluted with concentrated NH$_4$OH/methanol/dichloromethane (0.2/2/98) to provide the titled compound. $^1$H NMR (300 MHz, CDCl$_3$) δ ppm 11.73 (d, J=28.1 Hz, 1H), 8.28 (d, J=8.6 Hz, 1H), 8.11 (s, 1H), 6.56 (d, J=9.2 Hz, 2H), 5.68 (s, 1H), 3.92 (s, 3H), 3.78-3.55 (m, 6H), 3.17 (m, 4H), 3.04 (t, J=7.2 Hz, 2H), 2.14 (s, 3H); MS (DCI) m/z 413 (M+H)$^+$.

Example 19

N-[6-(4-acetylpiperazin-1-yl)-2-ethoxypyridin-3-yl]-4-oxo-4,5,6,7-tetrahydrofuro[3,2-c]pyridine-3-carboxamide A solution of the product from Example 1E (50 mg, 0.276 mmol) in tetrahydrofuran (5 mL) was treated with triethylamine (96 μL, 0.69 mmol) followed by treatment with ethyl chloroformate (26.5 μL, 0.276 mmol). The mixture was stirred at room temperature for 45 minutes and then treated with 1-(4-(5-amino-6-ethoxypyridin-2-yl)piperazin-1-yl)ethanone (CAS#1094927-44-2) (60.8 mg, 0.230 mmol). The reaction mixture was stirred for overnight and then partitioned between 1 MNaOH (5 mL) and CH$_2$Cl$_2$ (25 mL). The layers were separated and the aqueous layer was extracted with CH$_2$Cl$_2$ (25 mL). The combined CH$_2$Cl$_2$ layers were washed with 1 M HCl (10 mL), dried (MgSO$_4$), filtered, concentrated and chromatographed on silica gel eluted with a gradient of 0% to 100% [20% ethanol in ethyl acetate] in ethyl acetate to provide the titled compound. $^1$H NMR (300 MHz, CDCl$_3$) δ ppm 11.67 (s, 1H), 8.49 (d, J=8.5 Hz, 1H), 8.09 (s, 1H), 6.19 (d, J=8.6 Hz, 1H), 5.62 (s, 1H), 4.43 (q, J=7.0 Hz, 2H), 3.78-3.41 (m, 10H), 3.03 (t, J=7.2 Hz, 2H), 2.14 (s, 3H), 1.45 (t, J=7.0 Hz, 3H); MS (ESI) m/z 428 (M+H)$^+$.

Example 20

N-[6-(4-acetylpiperazin-1-yl)-2-(2-methoxyethoxyl)pyridin-3-yl]-4-oxo-4,5,6,7-tetrahydrofuro[3,2-c]pyridine-3-carboxamide Example 20A 6-chloro-2-(2-methoxyethoxy)-3-nitropyridine A solution of 2-methoxyethanol (1.348 mL, 17.10 mmol) in xylenes (100 mL) was treated with a 60% dispersion of sodium hydride in mineral oil (0.808 g, 20.21 mmol) followed by stirring at room temperature for 20 minutes. The mixture was cooled to 0° C. and treated with a solution of 2,6-dichloro-3-nitropyridine (3 g, 15.55 mmol) in xylenes (70 mL). The reaction mixture was then stirred overnight at room temperature, treated with water (50 mL) and transferred to a separatory funnel with ether. The layers were separated, and the aqueous layer was extracted with ether (50 mL). The combined organic layers were washed with brine, dried (MgSO$_4$), filtered and concentrated to provide the titled compound which was used without purification in the next step. $^1$H NMR (300 MHz, CDCl$_3$) δ ppm 8.27 (d, J=8.2 Hz, 1H), 7.03 (d, J=8.2 Hz, 1H), 4.68-4.64 (m, 2H), 3.83-3.79 (m, 2H), 3.46 (s, 3H).

Example 20B 1-(4-(6-(2-methoxyethoxy)-5-nitropyridin-2-yl)piperazin-1-yl)ethanone A solution of the product from Example 20A (1.86 g, 8 mmol), 1-acetylpiperazine (1.538 g, 12.00 mmol) and triethylamine (3.35 mL, 24.00 mmol) in acetonitrile (20 mL) was heated to 80° C. for 1 hour, cooled and partitioned between ethyl acetate (100 mL) and 1 M HCl (60 mL). The ethyl acetate layer was washed with brine, dried (MgSO$_4$), filtered and concentrated to ~20 mL. The flask was scratched with a spatula, and a yellow solid precipitated. After standing for 1 hour, the solid was collected by filtration, washed with ethyl acetate and dried under vacuum to provide the titled compound. $^1$H NMR (300 MHz, CDCl$_3$) δ ppm 8.30 (d, J=9.1 Hz, 1H), 6.18 (d, J=9.1 Hz, 1H), 4.55 (dd, J=5.6, 4.5 Hz, 2H), 3.85-3.66 (m, 8H), 3.64-3.58 (m, 2H), 3.48 (s, 3H), 2.16 (s, 3H).

Example 20C 1-(4-(5-amino-6-(2-methoxyethoxyl)pyridin-2-yl) piperazin-1-yl)ethanone The product from Example 20B (5 g, 15 mmol) and tetrahydrofuran (30 mL) were added to Raney®-nickel 2800, water slurry, (2.5 g, 43 mmol) in a stainless steel pressure bottle and stirred at room temperature for 6 hours under a hydrogen atmosphere (30 psi). The mixture was filtered through a nylon membrane and concentrated to provide the titled compound. $^1$H NMR (300 MHz, CDCl$_3$) δ ppm 6.92 (d, J=8.1 Hz, 1H), 6.11 (d, J=8.1 Hz, 1H), 4.50-4.45 (m, 2H), 3.79-3.71 (m, 4H), 3.58 (dd, J=6.2, 4.2 Hz, 2H), 3.43 (s, 3H), 3.37 (dd, J=6.3, 4.1 Hz, 2H), 3.32-3.26 (m, 2H), 2.13 (s, 3H).

Example 20D

N-[6-(4-acetylpiperazin-1-yl)-2-(2-methoxyethoxy) pyridin-3-yl]-4-oxo-4,5,6,7-tetrahydrofuro[3,2-c] pyridine-3-carboxamide The titled compound was prepared using the procedure described for Example 19 substituting the product from Example 20C for 1-(4-(5-amino-6-ethoxypyridin-2-yl)piperazin-1-yl)ethanone. $^1$H NMR (300 MHz, DMSO-d$_6$) δ ppm 11.98 (s, 1H), 8.28-8.23 (m, 2H), 8.01 (t, J=2.4 Hz, 1H), 6.36 (d, J=8.6 Hz, 1H), 4.43-4.36 (m, 2H), 3.76-3.71 (m, 2H), 3.58-3.45 (m, 8H), 3.41 (d, J=5.4 Hz, 2H), 3.29 (s, 3H), 2.99 (t, J=7.3 Hz, 2H), 2.04 (s, 3H); MS (ESI) m/z 458 (M+H)$^+$.

Example 21

N-[6-(4-acetylpiperazin-1-yl)-2-(oxetan-3-yloxy) pyridin-3-yl]-4-oxo-4,5,6,7-tetrahydrofuro[3,2-c] pyridine-3-carboxamide Example 21A 6-chloro-3-nitro-2-(oxetan-3-yloxy)pyridine The titled compound was prepared using the procedure described for Example 20A substituting oxetan-3-ol for 2-methoxyethanol and substituting a 3:1 mixture of tetrahydrofuran/xylenes for xylenes. The residue was chromatographed on a silica gel column eluted with 20-100% [9:1 dichloromethane/ethyl acetate] in hexanes. $^1$H NMR (300 MHz, CDCl$_3$) δ ppm 8.32 (d, J=8.4 Hz, 1H), 7.09 (d, J=8.4 Hz, 1H), 5.80-5.70 (m, 1H), 5.05-4.98 (m, 2H), 4.82 (ddd, J=7.5, 5.4, 1.0 Hz, 2H).

Example 21B 1-(4-(5-nitro-6-(oxetan-3-yloxy)pyridin-2-yl)piperazin-1-yl)ethanone The titled compound was prepared using the procedure described for Example 20B substituting the product from Example 21A for the product from Example 20A. $^1$H NMR (300 MHz, CDCl$_3$) δ ppm 8.32 (d, J=9.1 Hz, 1H), 6.23 (d, J=9.1 Hz, 1H), 5.68 (p, J=6.0 Hz, 1H), 4.96 (dd, J=7.6, 6.7 Hz, 2H), 4.90-4.82 (m, 2H), 3.83-3.57 (m, 8H), 2.16 (s, 3H).

Example 21C 1-(4-(5-amino-6-(oxetan-3-yloxy)pyridin-2-yl)piperazin-1-yl)ethanone The titled compound was prepared using the procedure described for Example 20C substituting the product from Example 21B for the product from Example 20B.

Example 21D

N-[6-(4-acetylpiperazin-1-yl)-2-(oxetan-3-yloxy) pyridin-3-yl]-4-oxo-4,5,6,7-tetrahydrofuro[3,2-c] pyridine-3-carboxamide The titled compound was prepared using the procedure described for Example 19 substituting the product from Example 21C for 1-(4-(5-amino-6-ethoxypyridin-2-yl)piperazin-1-yl)ethanone. $^1$H NMR (300 MHz, CDCl$_3$) δ ppm 11.86 (s, 1H), 8.57 (d, J=8.6 Hz, 1H), 8.10 (s, 1H), 6.27 (d, J=8.7 Hz, 1H), 5.70-5.59 (m, 1H), 5.55 (bs, 1H), 4.98 (t, J=6.9 Hz, 2H), 4.95-4.89 (m, 2H), 3.77-3.67 (m, 4H), 3.61-3.53 (m, 2H), 3.52-3.35 (m, 4H), 3.05 (t, J=7.2 Hz, 2H), 2.14 (s, 3H); MS (ESI) m/z 456 (M+H)$^+$.

Example 22

5-methyl-N-[4-(4-methylpiperazin-1-yl)phenyl]-4-oxo-4,5,6,7-tetrahydrofuro[3,2-c]pyridine-3-carboxamide The titled compound was prepared using the procedure described for Example 2C substituting 4-(4-methylpiperazin-1-yl)aniline for 2-methyl-2H-indazol-5-amine $^1$H NMR (DMSO-d$_6$) δ ppm 12.62 (s, 1H), 8.27 (s, 1H), 7.57 (d, J=8 Hz, 2H), 7.01 (d, J=8 Hz, 2H), 3.73 (t, J=8 Hz, 2H), 3.32 (m, 4H), 3.09 (t, J=8 Hz, 2H), 3.08 (s, 3H), 3.03 (s, 3H), 2.51 (m, 4H); MS (APCI) m/z 369 (M+H)$^+$.

Example 23

N-(1H-indazol-5-yl)-5-methyl-4-oxo-4,5,6,7-tetrahydrofuro[3,2-c]pyridine-3-carboxamide The titled compound was prepared using the procedure described for Example 2C substituting 1H-indazol-5-amine for 2-methyl-2H-indazol-5-amine $^1$H NMR (DMSO-d$_6$) δ ppm 13.02 (s, 1H), 12.80, (s, 1H), 8.31 (s, 1H), 8.26 (s, 1H), 8.05 (s, 1H), 7.54 (d, J=8 Hz, 1H), 7.47 (d, J=8 Hz, 1H), 3.73 (t, J=8 Hz, 2H), 3.11 (t, J=8 Hz, 2H), 3.01 (s, 3H); MS (APCI) m/z 311 (M+H)$^+$.

Example 24

5-methyl-N-(1-methyl-1H-indazol-5-yl)-4-oxo-4,5,6,7-tetrahydrofuro[3,2-c]pyridine-3-carboxamide The titled compound was prepared using the procedure described for Example 2C substituting 1-methyl-1H-indazol-5-amine for 2-methyl-2H-indazol-5-amine $^1$H NMR (DMSO-d$_6$) δ ppm 12.82 (s, 1H), 8.32 (s, 1H), 8.25 (s, 1H), 8.02 (s, 1H), 7.63 (d, J=8 Hz, 1H), 7.50 (d, J=8 Hz, 1H), 4.02

(s, 3H), 3.74 (t, J=8 Hz, 2H), 3.10 (t, J=8 Hz, 2H), 3.05 (s, 3H); MS (APCI) m/z 325 (M+H)+.

Example 25

5-methyl-N-[4-(morpholin-4-yl)phenyl]-4-oxo-4,5,6,7-tetrahydrofuro[3,2-c]pyridine-3-carboxamide The titled compound was prepared using the procedure described for Example 2C substituting 4-morpholinoaniline for 2-methyl-2H-indazol-5-amine $^1$H NMR (DMSO-d$_6$) δ ppm 12.57 (s, 1H), 8.26 (s, 1H), 7.54 (d, J=8 Hz, 2H), 6.94 (d, J=8 Hz, 2H), 3.71-3.73 (m, 6H), 3.03-3.10 (m, 9H); MS (APCI) m/z 356 (M+H)+.

Example 26

N-(4-carbamoylphenyl)-5-methyl-4-oxo-4,5,6,7-tetrahydrofuro[3,2-c]pyridine-3-carboxamide The titled compound was prepared using the procedure described for Example 2C substituting 4-aminobenzamide for 2-methyl-2H-indazol-5-amine $^1$H NMR (DMSO-d$_6$) δ ppm 13.01 (s, 1H), 8.35 (s, 1H), 7.87-7.89 (m, 3H), 7.72 (d, J=8 Hz, 2H), 7.25 (s, 1H), 3.74 (t, J=8 Hz, 2H), 3.10 (t, J=8 Hz, 2H), 3.04 (s, 3H); MS (APCI) m/z 314 (M+H)+.

Example 27

N-(1H-benzimidazol-5-yl)-5-methyl-4-oxo-4,5,6,7-tetrahydrofuro[3,2-c]pyridine-3-carboxamide The titled compound was prepared using the procedure described for Example 2C substituting 1H-benzo[d]imidazol-5-amine for 2-methyl-2H-indazol-5-amine $^1$H NMR (DMSO-d$_6$) δ ppm 13.04 (s, 1H), 8.82 (s, 1H), 8.36-8.38 (m, 2H), 7.72 (d, J=8 Hz, 1H), 7.42 (d, J=9 Hz, 2H), 3.76 (t, J=8 Hz, 2H), 3.12 (t, J=8 Hz, 2H), 3.07 (s, 3H); MS (APCI) m/z 311 (M+H)+.

Example 28

N-[4-(4-acetylpiperazin-1-yl)phenyl]-5-methyl-4-oxo-4,5,6,7-tetrahydrofuro[3,2-c]pyridine-3-carboxamide The titled compound was prepared using the procedure described for Example 2C substituting 1-(4-(4-aminophenyl)piperazin-1-yl)ethanone for 2-methyl-2H-indazol-5-amine. $^1$H NMR (DMSO-d$_6$) δ ppm 12.60 (s, 1H), 8.28 (s, 1H), 7.54 (d, J=12 Hz, 2H), 6.97 (d, J=12 Hz, 2H), 3.74 (d, J=4 Hz, 2H), 3.56-3.58 (m, 4H), 3.05-2.12 (m, 6H), 3.04 (s, 3H), 2.04 (s, 3H); MS (APCI) m/z 397 (M+H)+.

Example 29

5-methyl-N-(2-methyl-1,3-benzothiazol-6-yl)-4-oxo-4,5,6,7-tetrahydrofuro[3,2-c]pyridine-3-carboxamide The titled compound was prepared using the procedure described for Example 2C substituting 2-methylbenzo[d]thiazol-6-amine for 2-methyl-2H-indazol-5-amine. $^1$H NMR (DMSO-d$_6$) δ ppm 13.03 (s, 1H), 8.50 (s, 1H), 8.36 (s, 1H), 7.89 (d, J=8 Hz, 1H), 7.60 (d, J=8 Hz, 1H), 3.76 (t, J=8 Hz, 2H), 3.12 (t, J=8 Hz, 2H), 3.06 (s, 3H), 2.77 (s, 3H); MS (APCI) m/z 342 (M+H)+.

Example 30

N-(4-methylphenyl)-4-oxo-4,5,6,7-tetrahydrofuro[3,2-c]pyridine-3-carboxamide

The titled compound was prepared using the procedure described for Example 3, substituting 4-methylaniline for 4-morpholinoaniline. $^1$H NMR (500 MHz, DMSO-d$_6$) δ ppm 12.65 (s, 1H), 8.31 (s, 1H), 8.19 (s, 1H), 7.55 (d, J=8.4 Hz, 2H), 7.16 (d, J=8.3 Hz, 2H), 3.55 (td, J=7.4, 2.6 Hz, 2H), 3.01 (t, J=7.4 Hz, 2H), 2.27 (s, 3H); MS (APCI) m/z 271 (M+H)+.

Example 31

N-(4-hydroxyphenyl)-4-oxo-4,5,6,7-tetrahydrofuro[3,2-c]pyridine-3-carboxamide

The procedure for Example 3, substituting 4-aminophenol for 4-morpholinoaniline, provided the titled compound. $^1$H NMR (500 MHz, DMSO-d$_6$/D$_2$O) δ ppm 8.25 (s, 1H), 7.43-7.49 (m, 2H), 6.72-6.80 (m, 2H), 3.56 (t, J=7.17 Hz, 2H), 3.01 (t, J=7.48 Hz, 2H); MS (ESI) m/z 273 (M+H)+.

Example 32

N-(4-acetamidophenyl)-4-oxo-4,5,6,7-tetrahydrofuro[3,2-c]pyridine-3-carboxamide

The procedure for Example 3, substituting N-(4-aminophenyl)acetamide for 4-morpholinoaniline, provided the titled compound. $^1$H NMR (500 MHz, DMSO-d$_6$/D$_2$O) δ ppm 8.29 (s, 1H), 7.51-7.62 (m, 4H), 3.57 (t, J=7.48 Hz, 2H), 3.02 (t, J=7.32 Hz, 2H), 2.04 (s, 3H); MS (ESI) m/z 314 (M+H)+.

Example 33

4-oxo-N-(quinolin-6-yl)-4,5,6,7-tetrahydrofuro[3,2-c]pyridine-3-carboxamide

The procedure for Example 3, substituting quinolin-6-amine for 4-morpholinoaniline, provided the titled compound as the trifluoroacetate. $^1$H NMR (500 MHz, DMSO-d$_6$/D$_2$O) δ ppm 8.99 (dd, J=4.88, 1.53 Hz, 1H), 8.78 (d, J=8.24 Hz, 1H), 8.64 (d, J=2.44 Hz, 1H), 8.41 (s, 1H), 8.18 (d, J=9.16 Hz, 1H), 8.05 (dd, J=9.16, 2.44 Hz, 1H), 7.80-7.83 (m, 1H), 3.60 (t, J=7.32 Hz, 2H), 3.06 (t, J=7.32 Hz, 2H); MS (ESI) m/z 308 (M+H)+.

Example 34

N-(1H-indazol-6-yl)-4-oxo-4,5,6,7-tetrahydrofuro[3,2-c]pyridine-3-carboxamide

The procedure for Example 3, substituting 1H-indazol-6-amine for 4-morpholinoaniline, provided the titled compound. $^1$H NMR (500 MHz, DMSO-d$_6$/D$_2$O) δ ppm 8.34 (s, 1H), 8.27 (s, 1H), 8.02 (s, 1H), 7.76 (d, J=8.54 Hz, 1H), 7.10 (dd, J=8.70, 1.68 Hz, 1H), 3.58 (t, J=7.48 Hz, 2H), 3.04 (t, J=7.48 Hz, 2H); MS (ESI) m/z 297 (M+H)+.

Example 35

N-(2,6-dimethoxypyridin-3-yl)-4-oxo-4,5,6,7-tetrahydrofuro[3,2-c]pyridine-3-carboxamide The procedure for Example 3, substituting 2,6-dimethoxypyridin-3-amine hydrochloride for 4-morpholinoaniline, provided the titled compound as the trifluoroacetate. ¹H NMR (500 MHz, DMSO-$d_6$/$D_2O$) δ ppm 8.25-8.31 (m, 2H), 6.40 (d, J=8.54 Hz, 1H), 3.92 (s, 3H), 3.85 (s, 3H), 3.55 (t, J=7.32 Hz, 2H), 3.01 (t, J=7.32 Hz, 2H); MS (ESI) m/z 318 (M+H)⁺.

Example 36

N-(1,2-oxazol-3-yl)-4-oxo-4,5,6,7-tetrahydrofuro[3,2-c]pyridine-3-carboxamide

The procedure for Example 3, substituting isoxazol-3-amine for 4-morpholinoaniline, provided the titled compound. ¹H NMR (500 MHz, DMSO-$d_6$/$D_2O$) δ ppm 8.80 (d, J=1.83 Hz, 1H), 8.41 (s, 1H), 7.04 (d, J=1.83 Hz, 1H), 3.57 (t, J=7.48 Hz, 2H), 3.03 (t, J=7.48 Hz, 2H); MS (ESI) m/z 248 (M+H)⁺.

Example 37

4-oxo-N-(pyrazin-2-yl)-4,5,6,7-tetrahydrofuro[3,2-c]pyridine-3-carboxamide

The procedure for Example 3, substituting pyrazin-2-amine for 4-morpholinoaniline, provided the titled compound as the trifluoroacetate. ¹H NMR (500 MHz, DMSO-$d_6$/$D_2O$) δ ppm 9.47 (d, J=1.53 Hz, 1H), 8.39-8.46 (m, 3H), 3.57 (t, J=7.48 Hz, 2H), 3.04 (t, J=7.32 Hz, 2H); MS (ESI) m/z 259 (M+H)⁺.

Example 38

N-(5-methyl-1,2-oxazol-3-yl)-4-oxo-4,5,6,7-tetrahydrofuro[3,2-c]pyridine-3-carboxamide The procedure for Example 3, substituting 5-methylisoxazol-3-amine for 4-morpholinoaniline, provided the titled compound. ¹H NMR (500 MHz, DMSO-$d_6$/$D_2O$) δ ppm 8.39 (s, 1H), 6.73 (s, 1H), 3.56 (t, J=7.48 Hz, 2H), 3.02 (t, J=7.32 Hz, 2H), 2.40 (s, 3H); MS (ESI) m/z 262 (M+H)⁺.

Example 39

N-(4-cyanophenyl)-4-oxo-4,5,6,7-tetrahydrofuro[3,2-c]pyridine-3-carboxamide

The procedure for Example 3, substituting 4-aminobenzonitrile for 4-morpholinoaniline, provided the titled compound. ¹H NMR (500 MHz, DMSO-$d_6$/$D_2O$) δ ppm 8.39 (s, 1H), 7.84 (s, 4H), 3.57 (t, J=7.32 Hz, 2H), 3.03 (t, J=7.32 Hz, 2H); MS (ESI) m/z 282 (M+H)⁺.

Example 40

N-(5-fluoropyridin-2-yl)-4-oxo-4,5,6,7-tetrahydrofuro[3,2-c]pyridine-3-carboxamide The procedure for Example 3, substituting 5-fluoropyridin-2-amine for 4-morpholinoaniline, provided the titled compound as the trifluoroacetate. ¹H NMR (500 MHz, DMSO-$d_6$/$D_2O$) δ ppm 8.38 (s, 1H), 8.34 (d, J=3.05 Hz, 1H), 8.27 (dd, J=9.00, 4.12 Hz, 1H), 7.73-7.80 (m, 1H), 3.56 (t, J=7.48 Hz, 2H), 3.02 (t, J=7.32 Hz, 2H); MS (ESI) m/z 276 (M+H)⁺.

Example 41

N-(6-methoxypyridin-3-yl)-4-oxo-4,5,6,7-tetrahydrofuro[3,2-c]pyridine-3-carboxamide The procedure for Example 3, substituting 6-methoxypyridin-3-amine for 4-morpholinoaniline, provided the titled compound as the trifluoroacetate. ¹H NMR (500 MHz, DMSO-$d_6$/$D_2O$) δ ppm 8.43 (t, J=2.14 Hz, 1H), 8.31 (s, 1H), 7.96 (dd, J=8.85, 2.75 Hz, 1H), 6.88 (d, J=8.85 Hz, 1H), 3.84 (s, 3H), 3.57 (t, J=7.32 Hz, 2H), 3.03 (t, J=7.32 Hz, 2H); MS (ESI) m/z 288 (M+H)⁺.

Example 42

N-(5-chloropyridin-2-yl)-4-oxo-4,5,6,7-tetrahydrofuro[3,2-c]pyridine-3-carboxamide The procedure for Example 3, substituting 5-chloropyridin-2-amine for 4-morpholinoaniline, provided the titled compound as the trifluoroacetate. ¹H NMR (500 MHz, DMSO-$d_6$/$D_2O$) δ ppm 8.38-8.40 (m, 2H), 8.26 (d, J=9.77 Hz, 1H), 7.94 (dd, J=9.16, 2.75 Hz, 1H), 3.56 (t, J=7.32 Hz, 2H), 3.02 (t, J=7.32 Hz, 2H); MS (ESI) m/z 292 (M+H)⁺.

Example 43

N-(3-cyanophenyl)-4-oxo-4,5,6,7-tetrahydrofuro[3,2-c]pyridine-3-carboxamide

The procedure for Example 3, substituting 3-aminobenzonitrile for 4-morpholinoaniline, provided the titled compound. ¹H NMR (500 MHz, DMSO-$d_6$/$D_2O$) δ ppm 8.38 (s, 1H), 8.18-8.21 (m, 1H), 7.78-7.82 (m, 1H), 7.54-7.62 (m, 2H), 3.58 (t, J=7.48 Hz, 2H), 3.03 (t, J=7.48 Hz, 2H); MS (ESI) m/z 282 (M+H)⁺.

Example 44

N-(6-ethoxypyridin-3-yl)-4-oxo-4,5,6,7-tetrahydrofuro[3,2-c]pyridine-3-carboxamide The procedure for Example 3, substituting 6-ethoxypyridin-3-amine for 4-morpholinoaniline, provided the titled compound as the trifluoroacetate. ¹H NMR (500 MHz, DMSO-$d_6$/$D_2O$) δ ppm 8.41 (t, J=1.98 Hz, 1H), 8.31 (s, 1H), 7.94 (dd, J=8.39, 3.20 Hz, 1H), 6.85 (d, J=8.85 Hz, 1H), 4.27 (q, J=7.02 Hz, 2H), 3.57 (t, J=7.32 Hz, 2H), 3.02 (t, J=7.63 Hz, 2H), 1.31 (t, J=7.02 Hz, 3H); MS (ESI) m/z 302 (M+H)⁺.

Example 45

N-(3-methyl-1H-indazol-5-yl)-4-oxo-4,5,6,7-tetrahydrofuro[3,2-c]pyridine-3-carboxamide The procedure for Example 3, substituting 3-methyl-1H-indazol-5-amine for 4-morpholinoaniline, provided the titled compound. ¹H NMR (500 MHz, DMSO-$d_6$/$D_2O$) δ ppm 8.30 (s, 1H), 8.17 (s, 1H), 7.42-7.52 (m, 2H), 3.58 (t, J=7.32 Hz, 2H), 3.03 (t, J=7.32 Hz, 2H), 2.48 (s, 3H); MS (ESI) m/z 311 (M+H)⁺.

Example 46

N-(6-methyl-1H-indazol-5-yl)-4-oxo-4,5,6,7-tetrahydrofuro[3,2-c]pyridine-3-carboxamide The procedure for Example 3, substituting 6-methyl-1H-indazol-5-amine for 4-morpholinoaniline, provided the titled compound. $^1$H NMR (500 MHz, DMSO-$d_6$/$D_2$O) δ ppm 8.30 (s, 1H), 8.00-8.07 (m, 2H), 7.43 (s, 1H), 3.57 (t, J=7.32 Hz, 2H), 3.03 (t, J=7.48 Hz, 2H), 2.41 (s, 3H); MS (ESI) m/z 311 (M+H)$^+$.

Example 47

N-(1,3-benzothiazol-2-yl)-4-oxo-4,5,6,7-tetrahydrofuro[3,2-c]pyridine-3-carboxamide The procedure for Example 3, substituting benzo[d]thiazol-2-amine for 4-morpholinoaniline, provided the titled compound. $^1$H NMR (500 MHz, DMSO-$d_6$/$D_2$O) δ ppm 8.55 (s, 1H), 8.01 (d, J=7.32 Hz, 1H), 7.80 (d, J=7.63 Hz, 1H), 7.44-7.54 (m, 1H), 7.32-7.39 (m, 1H), 3.60 (t, J=7.48 Hz, 2H), 3.07 (t, J=7.48 Hz, 2H); MS (ESI) m/z 314 (M+H)$^+$.

Example 48 methyl 5-{[(4-oxo-4,5,6,7-tetrahydrofuro[3,2-c]pyridin-3-yl)carbonyl]amino}-1H-indazole-3-carboxylate The procedure for Example 3, substituting methyl 5-amino-1H-indazole-3-carboxylate for 4-morpholinoaniline, provided the titled compound. $^1$H NMR (500 MHz, DMSO-$d_6$/$D_2$O) δ ppm 8.60 (s, 1H), 8.34 (s, 1H), 7.68-7.73 (m, 1H), 7.57-7.63 (m, 1H), 3.93 (s, 3H), 3.58 (t, J=7.48 Hz, 2H), 3.04 (t, J=7.32 Hz, 2H); MS (ESI) m/z 355 (M+H)$^+$.

Example 49

N-[4-(diethylamino)phenyl]-4-oxo-4,5,6,7-tetrahydrofuro[3,2-c]pyridine-3-carboxamide The procedure for Example 3, substituting $N^1,N^1$-diethylbenzene-1,4-diamine for 4-morpholinoaniline, provided the titled compound as the trifluoroacetate. $^1$H NMR (500 MHz, DMSO-$d_6$/$D_2$O) δ ppm 8.35 (s, 1H), 7.83 (d, J=8.85 Hz, 2H), 7.51 (d, J=8.54 Hz, 2H), 3.52-3.63 (m, 6H), 3.04 (t, J=7.48 Hz, 2H), 1.03 (t, J=7.17 Hz, 6H); MS (ESI) m/z 328 (M+H)$^+$.

Example 50

N-[1-(2-hydroxypropyl)-1H-indazol-5-yl]-4-oxo-4,5,6,7-tetrahydrofuro[3,2-c]pyridine-3-carboxamide

Example 50A 1-(5-nitro-1H-indazol-1-yl)propan-2-ol

To a mixture of 5-nitro-1H-indazole (44.0 g, 270 mmol), cesium carbonate (176 g, 539 mmol) and potassium iodide (4.48 g, 27.0 mmol) in N,N-dimethylformamide (500 mL) was added 1-bromopropan-2-ol (48.7 g, 351 mmol) at room temperature, and the mixture was stirred at 80° C. for 2 hours. The mixture was treated with $H_2O$ and extracted with ethyl acetate. The organic phase was washed with $H_2O$ and brine. The organic phase was dried over $Na_2SO_4$, filtered and concentrated. The residue was purified by column chromatography on silica gel eluted with petroleum ether/ethyl acetate 2:1 to give the titled compound as the first isomer to elute from the column. $^1$H NMR (400 MHz, CDCl$_3$) δ ppm 8.71 (d, 1H), 8.22-8.27 (m, 2H), 7.53 (d, 1H), 4.27-4.45 (m, 3H), 2.84 (s, 1H), 1.29 (d, 3H).

Example 50B 1-(5-nitro-2H-indazol-2-yl)propan-2-ol

The procedure for Example 50A provided the titled compound as the second isomer to elute from the column. $^1$H NMR (400 MHz, CDCl$_3$) δ ppm 8.66 (dd, 1H), 8.21 (d, 1H), 8.05 (dd, 1H), 7.68 (dt, 1H), 4.46 (dd, 1H), 4.25-4.33 (m, 2H), 3.16 (d, 1H), 1.24 (d, 3H).

Example 50C 1-(5-amino-1H-indazol-1-yl)propan-2-ol

A mixture of the product from Example 50A (18 g, 81 mmol), 10% palladium on carbon (4.33 g) and methanol (75 mL) was hydrogenated (50 psi) at room temperature for 6 hours. The mixture was filtered through diatomaceous earth, and the filtrate was concentrated to dryness. The resulting residue was chromatographed on a silica gel column eluted with 1:2 petroleum ether/ethyl acetate to provide the titled compound. $^1$H NMR (500 MHz, DMSO-$d_6$/$D_2$O) δ ppm 7.71 (s, 1H), 7.36 (d, J=8.8 Hz, 1H), 6.83 (dd, J=8.8, 2.1 Hz, 1H), 6.77 (d, J=2.0 Hz, 1H), 4.22 (dd, J=14.0, 6.5 Hz, 1H), 4.14 (dd, J=14.0, 5.7 Hz, 1H), 4.03 (h, J=6.2 Hz, 1H), 1.02 (d, J=6.2 Hz, 3H); MS (ESI+) m/z 192 (M+H)$^+$.

Example 50D

N-[1-(2-hydroxypropyl)-1H-indazol-5-yl]-4-oxo-4,5,6,7-tetrahydrofuro[3,2-c]pyridine-3-carboxamide The procedure for Example 3, substituting the product from Example 50C for 4-morpholinoaniline, provided the titled compound. $^1$H NMR (500 MHz, DMSO-$d_6$/$D_2$O) δ ppm 8.33 (s, 1H), 8.25 (s, 1H), 8.03-8.05 (m, 1H), 7.67 (d, J=8.85 Hz, 1H), 7.45 (dd, J=9.00, 1.98 Hz, 1H), 4.20-4.39 (m, 2H), 4.01-4.10 (m, 1H), 3.57 (t, J=7.32 Hz, 2H), 3.03 (t, J=7.32 Hz, 2H), 1.06 (d, J=6.10 Hz, 3H); MS (ESI) m/z 355 (M+H)$^+$.

Example 51

N-(2-{2-[(methylsulfonyl)amino]ethyl}-2H-indazol-5-yl)-4-oxo-4,5,6,7-tetrahydrofuro[3,2-c]pyridine-3-carboxamide

Example 51A tert-butyl 2-(5-nitro-2H-indazol-2-yl)ethylcarbamate

To a mixture of 5-nitro-1H-indazole (10 g, 61.3 mmol), cesium carbonate (39.9 g, 123 mmol) and KI (1.018 g, 6.13 mmol) in N,N-dimethylformamide (500 mL) was added tert-butyl 2-bromoethylcarbamate (17.86 g, 80 mmol) at room temperature, and the mixture was stirred at 80° C. for 3 hours. The mixture was diluted with $H_2O$ and extracted with ethyl acetate. The combined organic layers were washed with $H_2O$ and brine. The organic layer was dried (Na$_2$SO$_4$), filtered and concentrated. The crude product was purified by chromatography on silica gel eluted with petroleum ether/ethyl acetate 2:1 to provide the titled compound as the second isomer to elute from the column.

Example 51B tert-butyl 2-(5-nitro-1H-indazol-1-yl)ethylcarbamate

The procedure for Example 51A provided the titled compound as the first isomer to elute from the column. $^1$H NMR (400 MHz, DMSO-d$_6$) δ ppm 8.78 (d, 1H), 8.37 (s, 1H), 8.19 (dd, 1H), 7.73 (d, 1H), 6.67 (t, 1H), 4.49 (t, 2H), 3.35 (t, 2H), 1.21 (s, 9H).

Example 51C 2-(5-nitro-2H-indazol-2-yl)ethanamine hydrochloride

A mixture of the product from Example 51A (65 g, 212 mmol) in ethyl acetate (500 mL) at 0° C. was treated with a stream of HCl gas for 10 minutes. The mixture was allowed to warm to 15° C. with continued stirring at that temperature for 3 hours. The reaction mixture was filtered through a Büchner funnel, and the filter cake was washed with ethyl acetate. The solid was dried under vacuum to yield the titled compound.

Example 51D

N-(2-(5-nitro-2H-indazol-2-yl)ethyl)methanesulfonamide

To a mixture of the product from Example 51C (50 g, 206 mmol) and triethylamine (41.7 g, 412 mmol) in dichloromethane (1000 mL) at 15° C. was added methanesulfonyl chloride (36.6 g, 320 mmol). The mixture was stirred at 15° C. for 3 hours. The reaction mixture was partitioned between water and dichloromethane. The aqueous layer was further extracted with dichloromethane. The combined organic layers were washed with 2 N HCl, brine and water, dried over Na$_2$SO$_4$, and concentrated to dryness. The residue was purified via flash chromatography (petroleum ether/ethyl acetate=1:2) to yield the titled compound.

Example 51E

N-(2-(5-amino-2H-indazol-2-yl)ethyl)methanesulfonamide

The product from Example 51D (20 g, 70.4 mmol) and 10% Pd/C (2 g) were added to methanol (200 mL). The mixture was stirred at 25° C. under H$_2$ (50 psi) for 12 hours. The reaction mixture was filtered through diatomaceous earth. The filtrate was concentrated to dryness, and the residue was purified by column chromatography on silica gel (ethyl acetate) to give the titled compound. $^1$H NMR (500 MHz, DMSO-d$_6$/D$_2$O) δ ppm 7.91 (d, J=0.9 Hz, 1H), 7.36 (d, J=9.0 Hz, 1H), 6.79 (dd, J=9.1, 2.1 Hz, 1H), 6.62 (dd, J=2.1, 0.8 Hz, 1H), 4.39 (t, J=6.2 Hz, 2H), 3.47 (t, J=6.2 Hz, 2H), 2.78 (s, 3H); MS (ESI+) m/z 255 (M+H)$^+$.

Example 51F

N-(2-{2-[(methylsulfonyl)amino]ethyl}-2H-indazol-5-yl)-4-oxo-4,5,6,7-tetrahydrofuro[3,2-c]pyridine-3-carboxamide The procedure for Example 3, substituting the product from Example 51E, (N-(2-(5-amino-2H-indazol-2-yl)ethyl) methanesulfonamide), for 4-morpholinoaniline, provided the titled compound. $^1$H NMR (500 MHz, DMSO-d$_6$/D$_2$O) δ ppm 8.33 (d, J=6.10 Hz, 2H), 8.29 (s, 1H), 7.62 (d, J=9.16 Hz, 1H), 7.27 (dd, J=9.16, 1.83 Hz, 1H), 4.49 (t, J=6.26 Hz, 2H), 3.49-3.59 (m, 4H), 3.03 (t, J=7.48 Hz, 2H), 2.81 (s, 3H); MS (ESI) m/z 418 (M+H)$^+$.

Example 52

N-{2-[2-(4-methylpiperazin-1-yl)ethyl]-2H-indazol-5-yl}-4-oxo-4,5,6,7-tetrahydrofuro[3,2-c]pyridine-3-carboxamide Example 52A 2-(5-nitro-2H-indazol-2-yl)ethanol The procedure for Example 50A, substituting 2-bromoethanol for 1-bromopropan-2-ol, provided the titled compound as the as the second isomer to elute from the column. $^1$H NMR (400 MHz, DMSO-d$_6$) δ ppm 8.87 (dd, 1H), 8.76 (s, 1H), 7.99 (dd, 1H), 7.76 (dd, 1H), 5.01 (t, 1H), 4.52 (t, 2H), 3.88 (m, 2H).

Example 52B 2-(5-nitro-1H-indazol-1-yl)ethanol

The procedure for Example 50A, substituting 2-bromoethanol for 1-bromopropan-2-ol, provided the titled compound as the as the first isomer to elute from the column.

Example 52C 2-(5-nitro-2H-indazol-2-yl)ethyl methanesulfonate

To a mixture of the product from Example 52A (40 g, 193 mmol) and triethylamine (40 g, 396 mmol) in dichloromethane (400 mL) was added methanesulfonyl chloride (79.5 g, 697 mmol) at 15° C. The mixture was stirred at 15° C. for 3 hours. The reaction mixture was partitioned between water (200 mL) and dichloromethane (200 mL). The aqueous layer was extracted with dichloromethane (200 mL). The combined organic layers were washed with brine and water, dried over Na$_2$SO$_4$ and concentrated to provide the titled compound. $^1$H NMR (400 MHz, DMSO-d$_6$) δ ppm 8.76 (dd, 1H), 8.37 (s, 1H), 8.14 (dd, 1H), 7.77 (dt, 1H), 4.81 (m, 4H), 2.91 (s, 3H).

Example 52D 2-(2-(4-methylpiperazin-1-yl)ethyl)-5-nitro-2H-indazole

The product from Example 52C (30 g, 105 mmol) was added to 1-methyl-piperazine (30 g). The mixture was stirred at 60° C. for 6 hours. The mixture was cooled to 20° C. and partitioned between ethyl acetate (150 mL) and H$_2$O (150 mL). The aqueous layer was extracted with ethyl acetate (2×150 mL). The combined organic phases were washed with water (200 mL) and brine (200 mL). The organic layer was dried over Na$_2$SO$_4$, filtered and concentrated to give the titled compound. $^1$H NMR (400 MHz, CDCl$_3$) δ ppm 8.68 (dd, 1H), 8.27 (d, 1H), 8.03 (dd, 1H), 7.67 (d, 1H), 4.50 (t, 2H), 2.92 (t, 2H), 2.35-2.47 (m, 4H), 2.47-2.55 (m, 4H), 2.27 (s, 3H).

Example 52E 2-(2-(4-methylpiperazin-1-yl)ethyl)-2H-indazol-5-amine

The procedure for Example 51E, substituting the product from Example 52D for the product from Example 51D, provided the titled compound. $^1$H NMR (500 MHz, DMSO-d$_6$/D$_2$O) δ ppm 7.91 (d, J=0.9 Hz, 1H), 7.34 (d, J=9.0 Hz, 1H), 6.77 (dd, J=9.0, 2.1 Hz, 1H), 6.61 (dd, J=2.1, 0.8 Hz, 1H), 4.39 (t, J=6.6 Hz, 2H), 2.79 (t, J=6.7 Hz, 2H), 2.47-2.16 (m, 8H), 2.12 (s, 3H); MS (ESI+) m/z 260 (M+H)$^+$.

Example 52F

N-{2-[2-(4-methylpiperazin-1-yl)ethyl]-2H-indazol-5-yl}-4-oxo-4,5,6,7-tetrahydrofuro[3,2-c]pyridine-3-carboxamide bis(2,2,2-trifluoroacetate)

The procedure for Example 3, substituting the product from Example 52E for 4-morpholinoaniline, provided the titled compound as the bistrifluoroacetate. MS (ESI) m/z 423 (M+H)$^+$.

Example 53

N-[1-(2-hydroxyethyl)-1H-indazol-5-yl]-4-oxo-4,5,6,7-tetrahydrofuro[3,2-c]pyridine-3-carboxamide The procedure for Example 3, substituting 2-(5-amino-1H-indazol-1-yl)ethanol (CAS#885270-96-2) for 4-morpholinoaniline, provided the titled compound. $^1$H NMR (500 MHz, DMSO-d$_6$/D$_2$O) δ ppm 8.36 (s, 1H), 8.29 (d, J=1.22 Hz, 1H), 8.25 (s, 1H), 8.08 (s, 1H), 7.69 (d, J=8.85 Hz, 1H), 7.48 (dd, J=9.16, 1.83 Hz, 1H), 4.45 (t, J=5.65 Hz, 2H), 3.82 (t, J=5.80 Hz, 2H), 3.57-3.64 (m, 2H), 3.06 (t, J=7.32 Hz, 2H); MS (ESI) m/z 341 (M+H)$^+$.

Example 54

4-oxo-N-{1-[2-(pyrrolidin-1-yl)ethyl]-1H-indazol-5-yl}-4,5,6,7-tetrahydrofuro[3,2-c]pyridine-3-carboxamide The procedure for Example 3, substituting 1-(2-(pyrrolidin-1-yl)ethyl)-1H-indazol-5-amine (CAS #690265-60-2) for 4-morpholinoaniline, provided the titled compound as the trifluoroacetate. $^1$H NMR (500 MHz, DMSO-d$_6$/D$_2$O) δ ppm 8.35 (s, 1H), 8.32 (s, 1H), 8.19 (s, 1H), 7.77 (d, J=9.16 Hz, 1H), 7.55 (dd, J=8.85, 1.83 Hz, 1H), 4.77 (t, J=6.26 Hz, 2H), 3.73 (t, J=6.26 Hz, 2H), 3.53-3.62 (m, 4H), 3.00-3.10 (m, 4H), 1.95-2.07 (m, 2H), 1.79-1.91 (m, 2H); MS (ESI) m/z 394 (M+H)$^+$.

Example 55

N-[2-(2-hydroxypropyl)-2H-indazol-5-yl]-4-oxo-4,5,6,7-tetrahydrofuro[3,2-c]pyridine-3-carboxamide

Example 55A 1-(5-amino-2H-indazol-2-yl)propan-2-ol

The procedure for Example 51E, substituting the product from Example 50B for the product from Example 51D, provided the titled compound. $^1$H NMR (500 MHz, DMSO-d$_6$/D$_2$O) δ ppm 7.87 (s, 1H), 7.34 (d, J=9.0 Hz, 1H), 6.78 (dd, J=9.0, 2.1 Hz, 1H), 6.62 (d, J=2.0 Hz, 1H), 4.19 (dd, J=6.0, 1.4 Hz, 2H), 4.08 (h, J=6.1 Hz, 1H), 1.06 (d, J=6.2 Hz, 3H); MS (ESI+) m/z 192 (M+H)$^+$.

Example 55B

N-[2-(2-hydroxypropyl)-2H-indazol-5-yl]-4-oxo-4,5,6,7-tetrahydrofuro[3,2-c]pyridine-3-carboxamide The procedure for Example 3, substituting the product from Example 55A, (1-(5-amino-2H-indazol-2-yl)propan-2-ol), for 4-morpholinoaniline, provided the titled compound. $^1$H NMR (500 MHz, DMSO-d$_6$/D$_2$O) δ ppm 8.32 (s, 1H), 8.28 (s, 2H), 7.60 (d, J=8.85 Hz, 1H), 7.26 (dd, J=9.16, 1.83 Hz, 1H), 4.23-4.34 (m, 2H), 4.09-4.16 (m, 1H), 3.56 (t, J=7.32 Hz, 2H), 3.03 (t, J=7.32 Hz, 2H), 1.08 (d, J=6.41 Hz, 3H); MS (ESI) m/z 355 (M+H)$^+$.

Example 56

N-{1-[2-(morpholin-4-yl)ethyl]-1H-indazol-5-yl}-4-oxo-4,5,6,7-tetrahydrofuro[3,2-c]pyridine-3-carboxamide The procedure for Example 3, substituting 1-(2-morpholinoethyl)-1H-indazol-5-amine (CAS #854921-80-5) for 4-morpholinoaniline, provided the titled compound as the trifluoroacetate. MS (ESI) m/z 410 (M+H)$^+$.

Example 57

N-{1-[2-(4-methylpiperazin-1-yl)ethyl]-1H-indazol-5-yl}-4-oxo-4,5,6,7-tetrahydrofuro[3,2-c]pyridine-3-carboxamide

Example 57A 2-(5-nitro-1H-indazol-1-yl)ethyl methanesulfonate

The procedure for Example 52C, substituting the product from Example 52B for the product from Example 52A, provided the titled compound. $^1$H NMR (400 MHz, DMSO-d$_6$) δ ppm 8.81 (d, J=2.0 Hz, 1H), 8.44 (s, 1H), 8.23 (dd, J=9.2, 2.0 Hz, 1H), 7.89 (d, J=9.2 Hz, 1H), 4.84 (t, J=5.2 Hz, 2H), 4.62 (t, J=5.2 Hz, 2H), 3.01 (s, 3H).

Example 57B 1-(2-(4-methylpiperazin-1-yl)ethyl)-5-nitro-1H-indazole

The procedure for Example 52D, substituting the product from Example 57A for the product from Example 52C, provided the titled compound.

Example 57C 1-(2-(4-methylpiperazin-1-yl)ethyl)-1H-indazol-5-amine

The procedure for Example 51E, substituting the product from Example 57B for the product from Example 51D, provided the titled compound. $^1$H NMR (500 MHz, DMSO-d$_6$/D$_2$O) δ ppm 7.71 (d, J=0.9 Hz, 1H), 7.36 (d, J=8.8 Hz, 1H), 6.84 (dd, J=8.8, 2.1 Hz, 1H), 6.77 (d, J=2.0 Hz, 1H), 4.37 (t, J=6.8 Hz, 2H), 2.70 (t, J=6.8 Hz, 2H), 2.46-2.19 (m, 8H), 2.12 (s, 3H); MS (ESI+) m/z 260 (M+H)⁺.

Example 57D

N-{1-[2-(4-methylpiperazin-1-yl)ethyl]-1H-indazol-5-yl}-4-oxo-4,5,6,7-tetrahydrofuro[3,2-c]pyridine-3-carboxamide bis(2,2,2-trifluoroacetate)

The procedure for Example 3, substituting the product from Example 57C for 4-morpholinoaniline, provided the titled compound as the bistrifluoroacetate. MS (ESI) m/z 423 (M+H)⁺.

Example 58

N-(1-{2-[(methylsulfonyl)amino]ethyl}-1H-indazol-5-yl)-4-oxo-4,5,6,7-tetrahydrofuro[3,2-c]pyridine-3-carboxamide

Example 58A

N-(2-(5-amino-1H-indazol-1-yl)ethyl)methanesulfonamide

The procedures for Examples 51C, 51D and 51E, substituting the product of Example 51B for the product of Example 51A, provided the titled compound. ¹H NMR (500 MHz, DMSO-d₆/D₂O) δ ppm 7.76 (s, 1H), 7.36 (d, J=8.8 Hz, 1H), 6.86 (dd, J=8.8, 2.1 Hz, 1H), 6.79 (d, J=2.0 Hz, 1H), 4.37 (t, J=6.3 Hz, 2H), 3.38 (t, J=6.3 Hz, 2H), 2.72 (s, 3H); MS (ESI+) m/z 255 (M+H)⁺.

Example 58B

N-(1-{2-[(methylsulfonyl)amino]ethyl}-1H-indazol-5-yl)-4-oxo-4,5,6,7-tetrahydrofuro[3,2-c]pyridine-3-carboxamide The procedure for Example 3, substituting the product from Example 58A for 4-morpholinoaniline, provided the titled compound. ¹H NMR (500 MHz, DMSO-d₆/D₂O) δ ppm 8.34 (s, 1H), 8.27 (d, J=1.53 Hz, 1H), 8.09 (s, 1H), 7.66 (d, J=9.16 Hz, 1H), 7.49 (dd, J=8.85, 1.83 Hz, 1H), 4.47 (t, J=6.41 Hz, 2H), 3.54-3.61 (m, 2H), 3.42 (t, J=6.26 Hz, 2H), 3.03 (t, J=7.32 Hz, 2H), 2.73-2.79 (m, 3H); MS (ESI) m/z 418 (M+H)⁺.

Example 59

N-(4-hydroxyphenyl)-5-methyl-4-oxo-4,5,6,7-tetrahydrofuro[3,2-c]pyridine-3-carboxamide The procedure for Example 4, substituting 4-aminophenol for p-toluidine, provided the titled compound. ¹H NMR (500 MHz, DMSO-d₆/D₂O) δ ppm 8.24 (s, 1H), 7.47 (dd, J=8.70, 1.37 Hz, 2H), 6.74-6.81 (m, 2H), 3.74 (t, 2H), 3.09 (t, J=7.48 Hz, 2H), 3.04 (s, 3H); MS (ESI) m/z 287 (M+H)⁺.

Example 60

N-(4-acetamidophenyl)-5-methyl-4-oxo-4,5,6,7-tetrahydrofuro[3,2-c]pyridine-3-carboxamide The procedure for Example 4, substituting N-(4-aminophenyl)acetamide for p-toluidine, provided the titled compound. ¹H NMR (500 MHz, DMSO-d₆/D₂O) δ ppm 8.27 (s, 1H), 7.53-7.62 (m, 4H), 3.74 (t, J=7.48 Hz, 2H), 3.10 (t, J=7.48 Hz, 2H), 3.05 (s, 3H), 2.04 (s, 3H); MS (ESI) m/z 328 (M+H)⁺.

Example 61

5-methyl-4-oxo-N-[4-(piperidin-1-yl)phenyl]-4,5,6,7-tetrahydrofuro[3,2-c]pyridine-3-carboxamide The procedure for Example 4, substituting 4-(piperidin-1-yl)aniline for p-toluidine, provided the titled compound as the trifluoroacetate. ¹H NMR (500 MHz, DMSO-d₆/D₂O) δ ppm 8.34 (s, 1H), 7.76-7.88 (m, 2H), 7.59-7.72 (m, 2H), 3.77 (t, 2H), 3.49-3.57 (m, 4H), 3.11 (t, J=7.48 Hz, 2H), 3.05 (s, 3H), 1.85-1.97 (m, 4H), 1.67 (s, 2H); MS (ESI) m/z 354 (M+H)⁺.

Example 62

5-methyl-4-oxo-N-(quinolin-3-yl)-4,5,6,7-tetrahydrofuro[3,2-c]pyridine-3-carboxamide The procedure for Example 4, substituting quinolin-3-amine for p-toluidine, provided the titled compound as the trifluoroacetate. ¹H NMR (500 MHz, DMSO-d₆/D₂O) δ ppm 9.12 (s, 1H), 8.85 (d, J=2.14 Hz, 1H), 8.40 (s, 1H), 8.02-8.08 (m, 2H), 7.64-7.81 (m, 2H), 3.77 (t, J=7.63 Hz, 2H), 3.13 (t, J=7.48 Hz, 2H), 3.08 (s, 3H); MS (ESI) m/z 322 (M+H)⁺.

Example 63

5-methyl-4-oxo-N-(quinolin-6-yl)-4,5,6,7-tetrahydrofuro[3,2-c]pyridine-3-carboxamide The procedure for Example 4, substituting quinolin-6-amine for p-toluidine, provided the titled compound as the trifluoroacetate. ¹H NMR (500 MHz, DMSO-d₆/D₂O) δ ppm 9.01 (d, J=4.58 Hz, 1H), 8.84 (d, J=8.55 Hz, 1H), 8.65 (d, J=1.83 Hz, 1H), 8.39 (s, 1H), 8.15-8.22 (m, 1H), 8.08 (dd, J=9.16, 2.14 Hz, 1H), 7.85 (dd, J=8.54, 4.88 Hz, 1H), 3.78 (t, 2H), 3.13 (t, J=7.48 Hz, 2H), 3.08 (s, 3H); MS (ESI) m/z 322 (M+H)⁺.

Example 64

N-(1H-indazol-6-yl)-5-methyl-4-oxo-4,5,6,7-tetrahydrofuro[3,2-c]pyridine-3-carboxamide The procedure for Example 4, substituting 1H-indazol-6-amine for p-toluidine, provided the titled compound. ¹H NMR (500 MHz, DMSO-d₆/D₂O) δ ppm 8.33 (s, 1H), 8.26 (s, 1H), 8.03 (s, 1H), 7.77 (d, J=8.54 Hz, 1H), 7.14 (dd, J=8.70, 1.68 Hz, 1H), 3.76 (t, J=7.48 Hz, 2H), 3.11 (t, J=7.48 Hz, 2H), 3.07 (s, 3H); MS (ESI) m/z 311 (M+H)⁺.

Example 65

N-(2,6-dimethoxypyridin-3-yl)-5-methyl-4-oxo-4,5,6,7-tetrahydrofuro[3,2-c]pyridine-3-carboxamide The procedure for Example 4, substituting 2,6-dimethoxypyridin-3-amine hydrochloride for p-toluidine, provided the titled compound as the trifluoroacetate. ¹H NMR (500 MHz, DMSO-d₆/D₂O) δ ppm 8.20-8.28 (m, 2H), 6.40

(d, J=8.54 Hz, 1H), 3.93 (s, 3H), 3.86 (s, 3H), 3.73 (t, 2H), 3.09 (t, J=7.48 Hz, 2H), 3.02 (s, 3H); MS (ESI) m/z 332 (M+H)$^+$.

Example 66

5-methyl-N-(5-methyl-1,2-oxazol-3-yl)-4-oxo-4,5,6, 7-tetrahydrofuro[3,2-c]pyridine-3-carboxamide The procedure for Example 4, substituting 5-methylisoxazol-3-amine for p-toluidine, provided the titled compound. $^1$H NMR (500 MHz, DMSO-d$_6$/D$_2$O) δ ppm 8.38 (s, 1H), 6.73 (s, 1H), 3.74 (t, J=7.48 Hz, 2H), 3.10 (t, J=7.48 Hz, 2H), 3.03 (s, 3H), 2.40 (s, 3H); MS (ESI) m/z 276 (M+H)$^+$.

Example 67

N-(4-cyanophenyl)-5-methyl-4-oxo-4,5,6,7-tetrahydrofuro[3,2-c]pyridine-3-carboxamide The procedure for Example 4, substituting 4-aminobenzonitrile for p-toluidine, provided the titled compound. $^1$H NMR (500 MHz, DMSO-d$_6$/D$_2$O) δ ppm 8.37 (s, 1H), 7.85 (s, 4H), 3.76 (t, 2H), 3.11 (t, J=7.48 Hz, 2H), 3.06 (s, 3H); MS (ESI) m/z 296 (M+H)$^+$.

Example 68

N-(5-fluoropyridin-2-yl)-5-methyl-4-oxo-4,5,6,7-tetrahydrofuro[3,2-c]pyridine-3-carboxamide The procedure for Example 4, substituting 5-fluoropyridin-2-amine for p-toluidine, provided the titled compound as the trifluoroacetate. $^1$H NMR (500 MHz, DMSO-d$_6$/D$_2$O) δ ppm 8.37 (s, 1H), 8.36 (d, J=3.05 Hz, 1H), 8.28 (dd, J=9.31, 4.12 Hz, 1H), 7.74-7.80 (m, 1H), 3.74 (t, 2H), 3.10 (t, J=7.48 Hz, 2H), 3.04 (s, 3H); MS (ESI) m/z 290 (M+H)$^+$.

Example 69

N-(6-methoxypyridin-3-yl)-5-methyl-4-oxo-4,5,6,7-tetrahydrofuro[3,2-c]pyridine-3-carboxamide The procedure for Example 4, substituting 6-methoxypyridin-3-amine for p-toluidine, provided the titled compound as the trifluoroacetate. $^1$H NMR (500 MHz, DMSO-d$_6$/D$_2$O) δ ppm 8.48 (d, J=2.75 Hz, 1H), 8.30 (s, 1H), 7.94 (dd, J=8.85, 2.75 Hz, 1H), 6.89 (d, J=8.85 Hz, 1H), 3.85 (s, 3H), 3.76 (t, 2H), 3.10 (t, J=7.63 Hz, 2H), 3.04 (s, 3H); MS (ESI) m/z 302 (M+H)$^+$.

Example 70

N-(5-chloropyridin-2-yl)-5-methyl-4-oxo-4,5,6,7-tetrahydrofuro[3,2-c]pyridine-3-carboxamide The procedure for Example 4, substituting 5-chloropyridin-2-amine for p-toluidine, provided the titled compound as the trifluoroacetate. $^1$H NMR (500 MHz, DMSO-d$_6$/D$_2$O) δ ppm 8.38-8.42 (m, 2H), 8.27 (d, J=8.85 Hz, 1H), 7.94 (dd, J=9.00, 2.59 Hz, 1H), 3.74 (t, 2H), 3.10 (t, J=7.48 Hz, 2H), 3.04 (s, 3H); MS (ESI) m/z 306 (M+H)$^+$.

Example 71

N-(3-cyanophenyl)-5-methyl-4-oxo-4,5,6,7-tetrahydrofuro[3,2-c]pyridine-3-carboxamide The procedure for Example 4, substituting 3-aminobenzonitrile for p-toluidine, provided the titled compound. $^1$H NMR (500 MHz, DMSO-d$_6$/D$_2$O) δ ppm 8.36 (s, 1H), 8.20 (s, 1H), 7.79-7.84 (m, 1H), 7.54-7.64 (m, 2H), 3.76 (t, J=7.48 Hz, 2H), 3.11 (t, J=7.48 Hz, 2H), 3.06 (s, 3H); MS (ESI) m/z 296 (M+H)$^+$.

Example 72

N-(6-ethoxypyridin-3-yl)-5-methyl-4-oxo-4,5,6,7-tetrahydrofuro[3,2-c]pyridine-3-carboxamide The procedure for Example 4, substituting 6-ethoxypyridin-3-amine for p-toluidine, provided the titled compound as the trifluoroacetate. $^1$H NMR (500 MHz, DMSO-d$_6$/D$_2$O) δ ppm 8.45 (d, J=2.75 Hz, 1H), 8.30 (s, 1H), 7.93 (dd, J=8.85, 2.75 Hz, 1H), 6.86 (d, J=8.85 Hz, 1H), 4.28 (q, J=7.02 Hz, 2H), 3.75 (t, 2H), 3.10 (t, J=7.48 Hz, 2H), 3.04 (s, 3H), 1.32 (t, 3H); MS (ESI) m/z 316 (M+H)$^+$.

Example 73

5-methyl-N-(3-methyl-1H-indazol-5-yl)-4-oxo-4,5,6, 7-tetrahydrofuro[3,2-c]pyridine-3-carboxamide The procedure for Example 4, substituting 3-methyl-1H-indazol-5-amine for p-toluidine, provided the titled compound. $^1$H NMR (500 MHz, DMSO-d$_6$/D$_2$O) δ ppm 8.29 (s, 1H), 8.19 (s, 1H), 7.41-7.53 (m, 2H), 3.75 (t, J=7.63 Hz, 2H), 3.11 (t, J=7.32 Hz, 2H), 3.07 (s, 3H), 2.48 (s, 3H); MS (ESI) m/z 325 (M+H)$^+$.

Example 74

5-methyl-N-(6-methyl-1H-indazol-5-yl)-4-oxo-4,5,6, 7-tetrahydrofuro[3,2-c]pyridine-3-carboxamide The procedure for Example 4, substituting 6-methyl-1H-indazol-5-amine for p-toluidine, provided the titled compound. $^1$H NMR (500 MHz, DMSO-d$_6$/D$_2$O) δ ppm 8.29 (s, 1H), 7.99-8.05 (m, 2H), 7.44 (s, 1H), 3.75 (t, J=7.63 Hz, 2H), 3.11 (t, J=7.48 Hz, 2H), 3.02 (s, 3H), 2.42 (s, 3H); MS (ESI) m/z 325 (M+H)$^+$.

Example 75

N-(1,3-benzothiazol-2-yl)-5-methyl-4-oxo-4,5,6,7-tetrahydrofuro[3,2-c]pyridine-3-carboxamide The procedure for Example 4, substituting benzo[d]thiazol-2-amine for p-toluidine, provided the titled compound. $^1$H NMR (500 MHz, DMSO-d$_6$/D$_2$O) δ ppm 8.54 (s, 1H), 8.01 (d, J=7.63 Hz, 1H), 7.82 (d, J=7.93 Hz, 1H), 7.43-7.53 (m, 1H), 7.36 (t, J=7.63 Hz, 1H), 3.78 (t, J=7.48 Hz, 2H), 3.15 (t, 2H), 3.09 (s, 3H); MS (ESI) m/z 328 (M+H)$^+$.

Example 76

5-methyl-4-oxo-N-[5-(trifluoromethyl)pyridin-2-yl]-4,5,6,7-tetrahydrofuro[3,2-c]pyridine-3-carboxamide The procedure for Example 4, substituting 5-(trifluoromethyl)pyridin-2-amine for p-toluidine, provided the titled compound as the trifluoroacetate. $^1$H NMR (500 MHz, DMSO-d$_6$/D$_2$O) δ ppm 8.74-8.76 (m, J=2.44 Hz, 1H), 8.41-8.45 (m, 2H), 8.23 (dd, J=9.00, 2.29 Hz, 1H), 3.75 (t, J=7.48 Hz, 2H), 3.11 (t, J=7.48 Hz, 2H), 3.05 (s, 3H); MS (ESI) m/z 340 (M+H)$^+$.

Example 77

N-(6-chloro-1H-indazol-5-yl)-5-methyl-4-oxo-4,5,6,7-tetrahydrofuro[3,2-c]pyridine-3-carboxamide The procedure for Example 4, substituting 6-chloro-1H-indazol-5-amine for p-toluidine, provided the titled compound. MS (ESI) m/z 345 (M+H)$^+$.

Example 78

5-methyl-N-(2-methyl-1H-benzimidazol-5-yl)-4-oxo-4,5,6,7-tetrahydrofuro[3,2-c]pyridine-3-carboxamide The procedure for Example 2C, substituting 2-methyl-1H-benzo[d]imidazol-5-amine for 2-methyl-2H-indazol-5-amine, provided the titled compound as the trifluoroacetate. $^1$H NMR (400 MHz, DMSO-d$_6$) δ ppm 14.37 (bs, 1H), 13.13 (s, 1H), 8.40-8.37 (m, 2H), 7.72 (d, J=8.7 Hz, 1H), 7.44 (dd, J=8.8, 1.8 Hz, 1H), 3.75 (t, J=7.5 Hz, 2H), 3.12 (t, J=7.5 Hz, 2H), 3.06 (s, 3H), 2.73 (s, 3H); MS (APCI) m/z 325 (M+H)$^+$.

Example 79

N-{4-[4-(3,3-dimethylbutanoyl)piperazin-1-yl]-2-methoxyphenyl}-4-oxo-4,5,6,7-tetrahydrofuro[3,2-c]pyridine-3-carboxamide The titled compound was prepared using the procedure described in Example 18 substituting 3,3-dimethylbutanoyl chloride for acetyl chloride. $^1$H NMR (300 MHz, CDCl$_3$) δ ppm 11.82-11.63 (m, 1H), 8.40-8.22 (m, 1H), 8.11 (s, 1H), 6.77-6.39 (m, 2H), 5.72-5.46 (m, 1H), 3.95 (s, 3H), 3.86-3.59 (m, 6H), 3.26-3.11 (m, 4H), 3.04 (t, J=7.2 Hz, 2H), 2.31 (s, 2H), 1.08 (s, 9H); MS (DCI) m/z 469 (M+H)$^+$.

Example 80

N-{2-methoxy-4-[4-(pyrrolidin-1-ylcarbonyl)piperazin-1-yl]phenyl}-4-oxo-4,5,6,7-tetrahydrofuro[3,2-c]pyridine-3-carboxamide The titled compound was prepared using the procedure described in Example 18 substituting pyrrolidine-1-carbonyl chloride for acetyl chloride. $^1$H NMR (300 MHz, CDCl$_3$) δ ppm 11.88-11.70 (m, 1H), 8.62-8.39 (m, 1H), 8.32-8.01 (m, 2H), 6.79-6.51 (m, 1H), 5.70-5.41 (m, 1H), 4.01-3.93 (m, 4H), 3.93 (s, 3H), 3.78-3.64 (m, 6H), 3.55-3.46 (m, 2H), 3.45-3.34 (m, 4H), 1.93-1.81 (m, 4H); MS (DCI) m/z 485 (M+NH$_4$)$^+$.

Example 81

N-{4-[4-(dimethylsulfamoyl)piperazin-1-yl]-2-methoxyphenyl}-4-oxo-4,5,6,7-tetrahydrofuro[3,2-c]pyridine-3-carboxamide The titled compound was prepared using the procedure described in Example 18 substituting dimethylsulfamoyl chloride for acetyl chloride. $^1$H NMR (300 MHz, CDCl$_3$) δ ppm 11.79 (s, 1H), 8.36 (s, 1H), 8.12 (s, 1H), 6.60 (s, 1H), 5.54 (s, 1H), 5.54 (s, 1H), 3.94 (s, 3H), 3.70 (td, J=7.2, 2.6 Hz, 2H), 3.65-3.44 (m, 3H), 3.31 (m, 3H), 3.15-2.98 (m, 3H), 2.87 (s, 6H); MS (DCI) m/z 478 (M+H)$^+$.

Example 82 methyl 4-{[6-(4-methylpiperazin-1-yl)-3-{[(4-oxo-5,6,7,8-tetrahydro-4H-furo[3,2-c]azepin-3-yl)carbonyl]amino}pyridin-2-yl]oxy}benzoate

Example 82A methyl 4-(6-chloro-3-nitropyridin-2-yloxy)benzoate

To a solution of methyl 4-hydroxybenzoate (1 g, 6.57 mmol) in tetrahydrofuran (30 mL) was added NaH (0.342 g, 8.54 mmol) at 0° C. After stirring for 25 minutes at 0° C., a solution of 2,6-dichloro-3-nitropyridine (1.379 g, 6.57 mmol) in xylene (20 mL) was added over 5 minutes. After stirring for 16 hours, the reaction mixture was diluted with ether (100 mL) and quenched with H$_2$O (30 mL). The organic phase was separated, and the aqueous layer was extracted with additional ether (20 mL). The combined organic phases were washed with brine, dried with MgSO$_4$ and concentrated under reduced pressure. The resulting residue was purified on a silica gel column eluted with a gradient of 0-15% ethyl acetate/hexanes to provide the titled compound. MS (DCI) m/z 326 (M+NH$_4$)$^+$.

Example 82B methyl 4-(6-(4-methylpiperazin-1-yl)-3-nitropyridin-2-yloxy)benzoate To a solution of the product from Example 82A, methyl 4-(6-chloro-3-nitropyridin-2-yloxy)benzoate (400 mg, 1.296 mmol), and K$_2$CO$_3$ (358 mg, 2.59 mmol) in N,N-dimethylformamide (20 mL) was added 1-methylpiperazine (260 mg, 2.59 mmol), and the mixture was heated to 60° C. for 30 minutes. The reaction mixture was cooled to ambient temperature and then partitioned between ether (50 mL) and H$_2$O (30 mL). The organic phase was separated, and the aqueous layer was extracted with additional ether (50 mL). The combined organics were washed with brine, dried with MgSO$_4$ and concentrated under reduced pressure to provide the titled compound. MS (DCI) m/z 373 (M+H)$^+$.

Example 82C methyl 4-(3-amino-6-(4-methylpiperazin-1-yl)pyridin-2-yloxy)benzoate To a solution of the product from Example 82B (450 mg, 1.2 mmol) in methanol (30 mL) was added Raney®-nickel, 2800 slurry in H$_2$O (500 mg), and the mixture was stirred under a hydrogen atmosphere using a balloon for 3 hours. The mixture was filtered and washed with additional methanol. The filtrate was concentrated under reduced pressure and azeotropically dried with toluene to provide the titled compound. MS (DCI) m/z 343 (M+H)$^+$.

Example 82D methyl 4-{[6-(4-methylpiperazin-1-yl)-3-{[(4-oxo-5,6,7,8-tetrahydro-4H-furo[3,2-c]azepin-3-yl)carbonyl]amino}pyridin-2-yl]oxy}benzoate A solution of the product from Example 7B (220 mg, 1.13 mmol), and triethylamine (0.220 mL, 1.577 mmol) in acetonitrile (10 mL) was treated with ethyl chloroformate (0.131 mL, 1.367 mmol) at 0° C. and stirred for 20 minutes.

A solution of the product from Example 82C, methyl 4-(3-amino-6-(4-methylpiperazin-1-yl)pyridin-2-yloxy)benzoate (360 mg, 1.051 mmol) in acetonitrile (5 mL) was added, and the mixture was stirred for 16 hours. The mixture was diluted with ethyl acetate (50 mL) and H$_2$O (20 mL). The organic phase was separated, and the aqueous phase was extracted with additional ethyl acetate (50 mL). The combined organic phases were washed with brine, dried with MgSO$_4$ and concentrated under reduced pressure. The residue was chromatographed on a silica gel column eluted with concentrated NH$_4$OH/methanol/dichloromethane (0.2/2/98) to provide the titled compound. $^1$H NMR (300 MHz, CDCl$_3$) δ ppm 12.21 (s, 1H), 8.58 (d, J=8.7 Hz, 1H), 8.15 (s, 1H), 8.11-7.95 (m, 2H), 7.37-7.28 (m, 2H), 6.39 (d, J=8.8 Hz, 1H), 6.17 (t, J=5.8 Hz, 1H), 3.91 (s, 3H), 3.45-3.29 (m, 6H), 3.08 (t, J=7.2 Hz, 2H), 2.50-2.37 (m, 4H), 2.30 (s, 3H), 2.17-2.03 (m, 2H); MS (ESI) m/z 520 (M+H)$^+$.

Example 83

N-{2-[4-(hydroxymethyl)phenoxy]-6-(4-methylpiperazin-1-yl)pyridin-3-yl}-4-oxo-5,6,7,8-tetrahydro-4H-furo[3,2-c]azepine-3-carboxamide A solution of the product from Example 82, (30 mg, 0.056 mmol) in anhydrous tetrahydrofuran (10 mL) was treated with lithium aluminum hydride (0.225 mL, 0.225 mmoL, 1 M solution in tetrahydrofuran) and stirred at room temperature for 30 minutes. The reaction was quenched with 2 drops of H$_2$O, 2 drops of 1 MNaOH and 6 drops of H$_2$O, and stirred for 30 minutes. The mixture was filtered through diatomaceous earth that was then washed with ethyl acetate. The combined filtrates were concentrated under reduced pressure. The resulting residue was chromatographed on a silica gel column eluted with concentrated NH$_4$OH/methanol/dichloromethane (0.3/3/97) to provide the titled compound. $^1$H NMR (300 MHz, CDCl$_3$) δ ppm 12.17 (s, 1H), 8.56 (d, J=8.7 Hz, 1H), 8.15 (s, 1H), 7.36-7.31 (m, 2H), 7.26 (d, J=2.8 Hz, 2H), 6.34 (d, J=8.7 Hz, 1H), 6.16 (s, 1H), 5.30 (s, 1H), 4.68 (s, 2H), 3.43-3.29 (m, 6H), 3.08 (t, J=7.2 Hz, 2H), 2.49-2.35 (m, 4H), 2.29 (s, 3H), 2.10 (dt, J=6.8, 6.2 Hz, 2H); MS (ESI) m/z 492 (M+H)$^+$.

Example 84

N-[6-(4-acetylpiperazin-1-yl)-2-ethoxypyridin-3-yl]-5-(2-methoxyethyl)-4-oxo-4,5,6,7-tetrahydrofuro[3,2-c]pyridine-3-carboxamide Example 84A 5-(2-methoxyethyl)-4-oxo-4,5,6,7-tetrahydrofuro[3,2-c]pyridine-3-carboxylic acid The procedure for Example 8A, substituting 2-bromoethyl methylether for benzyl 2-bromoethyl ether, provided the titled compound. $^1$H NMR (300 MHz, CDCl$_3$) δ ppm 14.61 (s, 1H), 8.04 (s, 1H), 3.88 (t, J=7.5 Hz, 2H), 3.74-3.68 (m, 2H), 3.64-3.58 (m, 2H), 3.36 (s, 3H), 3.07 (t, J=7.5 Hz, 2H).

Example 84B

N-[6-(4-acetylpiperazin-1-yl)-2-ethoxypyridin-3-yl]-5-(2-methoxyethyl)-4-oxo-4,5,6,7-tetrahydrofuro[3,2-c]pyridine-3-carboxamide The procedure for Example 8B, substituting the product from Example 84A for the product from Example 8A, provided the titled compound. $^1$H NMR (300 MHz, CDCl$_3$) δ ppm 12.00 (s, 1H), 8.53 (d, J=8.6 Hz, 1H), 8.06 (s, 1H), 6.18 (d, J=8.6 Hz, 1H), 4.40 (q, J=7.1 Hz, 2H), 3.81 (t, J=7.3 Hz, 2H), 3.72 (dd, J=11.3, 5.6 Hz, 4H), 3.65-3.55 (m, 4H), 3.53-3.48 (m, 2H), 3.47-3.42 (m, 2H), 3.37 (s, 3H), 3.01 (t, J=7.2 Hz, 2H), 2.14 (s, 3H), 1.48 (t, J=7.1 Hz, 3H); MS (ESI) m/z 486 (M+H)$^+$.

Example 85

N-[6-(4-acetylpiperazin-1-yl)-2-(2-methoxyethoxyl)pyridin-3-yl]-5-[2-(benzyloxy)ethyl]-4-oxo-4,5,6,7-tetrahydrofuro[3,2-c]pyridine-3-carboxamide The procedure for Example 8B, substituting the product from Example 20C for 1-(4-(5-amino-6-ethoxypyridin-2-yl)piperazin-1-yl)ethanone, provided the titled compound. $^1$H NMR (300 MHz, CDCl$_3$) δ ppm 11.98 (s, 1H), 8.53 (d, J=8.6 Hz, 1H), 8.06 (s, 1H), 7.37-7.27 (m, 5H), 6.20 (d, J=8.6 Hz, 1H), 4.54 (s, 2H), 4.50 (t, J=5.4 Hz, 2H), 3.90-3.85 (m, 2H), 3.82 (t, J=7.3 Hz, 2H), 3.78-3.70 (m, 6H), 3.60-3.55 (m, 2H), 3.54-3.48 (m, 2H), 3.48-3.42 (m, 2H), 3.41 (s, 3H), 2.98 (t, J=7.2 Hz, 2H), 2.14 (s, 3H); MS (ESI) m/z 592 (M+H)$^+$.

Example 86

N-{6-(4-acetylpiperazin-1-yl)-2-[2-(benzyloxy)ethoxy]pyridin-3-yl}-5-[2-(benzyloxy)ethyl]-4-oxo-4,5,6,7-tetrahydrofuro[3,2-c]pyridine-3-carboxamide Example 86A 2-(2-(benzyloxy)ethoxy)-6-chloro-3-nitropyridine The procedure for Example 20A, substituting 2-benzyloxyethanol for 2-methoxyethanol, provided the titled compound. $^1$H NMR (300 MHz, CDCl$_3$) δ ppm 8.27 (d, J=8.2 Hz, 1H), 7.37-7.26 (m, 5H), 7.03 (d, J=8.3 Hz, 1H), 4.70-4.66 (m, 2H), 4.65 (s, 2H), 3.91-3.87 (m, 2H).

Example 86B 1-(4-(6-(2-(benzyloxy)ethoxy)-5-nitropyridin-2-yl)piperazin-1-yl)ethanone The procedure for Example 20B, substituting the product from Example 86A for the product from Example 20A, provided the titled compound. $^1$H NMR (300 MHz, CDCl$_3$) δ ppm 8.30 (d, J=9.0 Hz, 1H), 7.40-7.27 (m, 5H), 6.17 (d, J=9.1 Hz, 1H), 4.68 (s, 2H), 4.62-4.55 (m, 2H), 3.95-3.87 (m, 2H), 3.81-3.71 (m, 4H), 3.67 (dd, J=6.5, 3.2 Hz, 2H), 3.57 (dd, J=6.2, 4.2 Hz, 2H), 2.15 (s, 3H); MS (ESI) m/z 401 (M+H)$^+$.

Example 86C 1-(4-(5-amino-6-(2-(benzyloxy)ethoxy)pyridin-2-yl)piperazin-1-yl)ethanone A mixture of the product from Example 86B (1.95 g, 4.87 mmol), platinum(IV) oxide (195 mg), potassium carbonate (337 mg, 2.4 mmol) in ethyl acetate (30 mL) and ethanol (30 mL) was hydrogenated (50 psi) at room temperature for 3 hours. Filtration of the solids and evaporation of the filtrate provided the titled compound. $^1$H NMR (300 MHz, CDCl$_3$) δ ppm 7.39-7.27 (m, 5H), 6.90 (d, J=8.1 Hz, 1H), 6.09 (d, J=8.1 Hz, 1H), 4.61 (s, 2H), 4.53-4.48 (m, 2H), 3.87-3.82 (m, 2H), 3.75-3.69 (m, 2H), 3.58-3.53 (m, 2H), 3.40 (bs, 2H), 3.37-3.32 (m, 2H), 3.29-3.24 (m, 2H), 2.13 (s, 3H); MS (ESI) m/z 371 (M+H)$^+$.

Example 86D

N-{6-(4-acetylpiperazin-1-yl)-2-[2-(benzyloxy)ethoxy]pyridin-3-yl}-5-[2-(benzyloxy)ethyl]-4-oxo-4,5,6,7-tetrahydrofuro[3,2-c]pyridine-3-carboxamide The procedure for Example 8B, substituting the product from Example 86C for 1-(4-(5-amino-6-ethoxypyridin-2-yl)piperazin-1-yl)ethanone, provided the titled compound. $^1$H NMR (300 MHz, CDCl$_3$) δ ppm 11.98 (s, 1H), 8.49 (d, J=8.5 Hz, 1H), 8.06 (s, 1H), 7.36-7.19 (m, 10H), 6.20 (d, J=8.6 Hz, 1H), 4.61 (s, 2H), 4.54 (t, J=5.6 Hz, 2H), 4.48 (s, 2H), 3.97 (t, J=5.6 Hz, 2H), 3.78 (t, J=7.3 Hz, 2H), 3.75-3.70 (m, 2H), 3.68-3.64 (m, 4H), 3.53 (dd, J=14.1, 6.2 Hz, 4H), 3.46-3.40 (m, 2H), 2.96 (t, J=7.2 Hz, 2H), 2.14 (s, 3H); MS (ESI) m/z 668 (M+H)$^+$.

Example 87

N-[6-(4-acetylpiperazin-1-yl)-2-(2-methoxyethoxy)pyridin-3-yl]-5-(2-hydroxyethyl)-4-oxo-4,5,6,7-tetrahydrofuro[3,2-c]pyridine-3-carboxamide The procedure for Example 9, substituting the product from Example 85 for the product from Example 8B, provided the titled compound. $^1$H NMR (300 MHz, CDCl$_3$) δ ppm 11.94 (s, 1H), 8.57 (d, J=8.6 Hz, 1H), 8.07 (s, 1H), 6.20 (d, J=8.6 Hz, 1H), 4.53-4.48 (m, 2H), 3.93-3.86 (m, 4H), 3.80 (t, J=7.3 Hz, 2H), 3.76-3.70 (m, 4H), 3.61-3.54 (m, 2H), 3.53-3.48 (m, 2H), 3.47-3.42 (m, 2H), 3.44 (s, 3H), 3.05 (t, J=7.3 Hz, 2H), 2.14 (s, 3H); MS (ESI) m/z 502 (M+H)$^+$.

Example 88

N-[6-(4-acetylpiperazin-1-yl)-2-(2-hydroxyethoxy)pyridin-3-yl]-5-(2-hydroxyethyl)-4-oxo-4,5,6,7-tetrahydrofuro[3,2-c]pyridine-3-carboxamide The procedure for Example 9, substituting the product from Example 86D for the product from Example 8B, provided the titled compound. $^1$H NMR (300 MHz, DMSO-d$_6$) δ ppm 12.07 (s, 1H), 8.46 (d, J=8.6 Hz, 1H), 8.29 (s, 1H), 6.37 (d, J=8.7 Hz, 1H), 4.81 (dt, J=6.7, 6.0 Hz, 2H), 4.27 (t, J=5.0 Hz, 2H), 3.84-3.76 (m, 4H), 3.63-3.58 (m, 2H), 3.57-3.51 (m, 6H), 3.49-3.44 (m, 2H), 3.42-3.37 (m, 2H), 3.07 (t, J=7.3 Hz, 2H), 2.04 (s, 3H); MS (ESI) m/z 488 (M+H)$^+$.

Example 89

N-[6-(4-acetylpiperazin-1-yl)-2-ethoxypyridin-3-yl]-5-(3-hydroxypropyl)-4-oxo-4,5,6,7-tetrahydrofuro[3,2-c]pyridine-3-carboxamide Example 89A 5-(3-(benzyloxy)propyl)-4-oxo-4,5,6,7-tetrahydrofuro[3,2-c]pyridine-3-carboxylic acid The procedure for Example 8A, substituting benzyl 3-bromopropyl ether for benzyl 2-bromoethyl ether, provided the titled compound. $^1$H NMR (300 MHz, CDCl$_3$) δ ppm 14.70 (s, 1H), 8.01 (s, 1H), 7.36-7.27 (m, 5H), 4.48 (s, 2H), 3.72 (t, J=7.5 Hz, 2H), 3.64 (t, J=6.9 Hz, 2H), 3.57 (t, J=5.8 Hz, 2H), 2.95 (t, J=7.4 Hz, 2H), 2.00-1.88 (m, 2H); MS (ESI) m/z 330 (M+H)$^+$.

Example 89B

N-(6-(4-acetylpiperazin-1-yl)-2-ethoxypyridin-3-yl)-5-(3-(benzyloxy)propyl)-4-oxo-4,5,6,7-tetrahydrofuro[3,2-c]pyridine-3-carboxamide The procedure for Example 8B, substituting the product from Example 89A for the product from Example 8A, provided the titled compound.

Example 89C

N-[6-(4-acetylpiperazin-1-yl)-2-ethoxypyridin-3-yl]-5-(3-hydroxypropyl)-4-oxo-4,5,6,7-tetrahydrofuro[3,2-c]pyridine-3-carboxamide The procedure for Example 9, substituting the product from Example 89B for the product from Example 8B, provided the titled compound. $^1$H NMR (300 MHz, CDCl$_3$) δ ppm 11.80 (s, 1H), 8.56 (d, J=8.6 Hz, 1H), 8.09 (s, 1H), 6.18 (d, J=8.6 Hz, 1H), 4.45 (q, J=7.1 Hz, 2H), 3.72 (m, 6H), 3.65-3.49 (m, 8H), 3.44 (dd, J=6.2, 4.4 Hz, 2H), 3.06 (t, J=7.3 Hz, 2H), 2.14 (s, 3H), 1.46 (t, J=7.1 Hz, 3H); MS (ESI) m/z 486 (M+H)$^+$.

Example 90

N-[6-(4-acetylpiperazin-1-yl)-2-ethoxypyridin-3-yl]-5-(4-hydroxybutyl)-4-oxo-4,5,6,7-tetrahydrofuro[3,2-c]pyridine-3-carboxamide Example 90A 5-(4-(benzyloxy)butyl)-4-oxo-4,5,6,7-tetrahydrofuro[3,2-c]pyridine-3-carboxylic acid The procedure for Example 8A, substituting benzyl 4-bromobutyl ether for benzyl 2-bromoethyl ether, provided the titled compound. $^1$H NMR (300 MHz, CDCl$_3$) δ ppm 14.70 (s, 1H), 8.03 (s, 1H), 7.38-7.27 (m, 5H), 4.50 (s, 2H), 3.73 (t, J=7.5 Hz, 2H), 3.54 (dt, J=11.9, 4.3 Hz, 4H), 3.05 (t, J=7.4 Hz, 2H), 1.80-1.60 (m, 4H); MS (ESI) m/z 344 (M+H)$^+$.

Example 90B

N-(6-(4-acetylpiperazin-1-yl)-2-ethoxypyridin-3-yl)-5-(4-(benzyloxy)butyl)-4-oxo-4,5,6,7-tetrahydrofuro[3,2-c]pyridine-3-carboxamide The procedure for Example 8B, substituting the product from Example 90A for the product from Example 8A, provided the titled compound.

Example 90C

N-[6-(4-acetylpiperazin-1-yl)-2-ethoxypyridin-3-yl]-5-(4-hydroxybutyl)-4-oxo-4,5,6,7-tetrahydrofuro[3,2-c]pyridine-3-carboxamide The procedure for Example 9, substituting the product from Example 90B for the product from Example 8B, provided the titled compound. $^1$H NMR (300 MHz, CDCl$_3$) δ ppm 12.04 (s, 1H), 8.55 (d, J=8.5 Hz, 1H), 8.07 (s, 1H), 6.23 (d, J=8.6 Hz, 1H), 4.42 (q, J=7.1 Hz, 2H), 3.78-3.66 (m, 6H), 3.63-3.56 (m, 4H), 3.54-3.41 (m, 4H), 3.03 (t, J=7.3 Hz, 2H), 2.14 (s, 3H), 1.82-1.60 (m, 4H), 1.49 (t, J=7.1 Hz, 3H); MS (ESI) m/z 500 (M+H)$^+$.

Example 91

N-[6-(4-acetylpiperazin-1-yl)-2-ethoxypyridin-3-yl]-5-[2-(2-hydroxyethoxyl)ethyl]-4-oxo-4,5,6,7-tetrahydrofuro[3,2-c]pyridine-3-carboxamide Example 91A 5-(2-(2-(benzyloxy)ethoxy)ethyl)-4-oxo-4,5,6,7-tetrahydrofuro[3,2-c]pyridine-3-carboxylic acid The procedure for Example 8A, substituting ((2-(2-bromoethoxy)ethoxy)methyl)benzene for benzyl 2-bromoethyl ether, provided the titled compound. $^1$H NMR (300 MHz, CDCl$_3$) δ ppm 14.64 (s, 1H), 8.02 (s, 1H), 7.38-7.27 (m, 5H), 4.53 (s, 2H), 3.87 (t, J=7.5 Hz, 2H), 3.71 (s, 4H), 3.69-3.57 (m, 4H), 2.94 (t, J=7.5 Hz, 2H); MS (ESI) m/z 360 (M+H)$^+$.

Example 91B

N-(6-(4-acetylpiperazin-1-yl)-2-ethoxypyridin-3-yl)-5-(2-(2-(benzyloxy)ethoxy)ethyl)-4-oxo-4,5,6,7-tetrahydrofuro[3,2-c]pyridine-3-carboxamide The procedure for Example 8B, substituting the product from Example 91A for the product from Example 8A, provided the titled compound. $^1$H NMR (300 MHz, CDCl$_3$) δ ppm 12.08-11.89 (m, 1H), 8.52 (d, J=8.5 Hz, 1H), 8.05 (s, 1H), 7.36-7.26 (m, 5H), 6.18 (d, J=8.6 Hz, 1H), 4.54 (s, 2H), 4.39 (q, J=7.0 Hz, 2H), 3.80 (t, J=7.3 Hz, 2H), 3.74 (d, J=8.2 Hz, 6H), 3.69-3.54 (m, 6H), 3.54-3.41 (m, 4H), 2.92 (t, J=7.2 Hz, 2H), 2.14 (s, 3H), 1.46 (t, J=7.1 Hz, 3H); MS (ESI) m/z 606 (M+H)$^+$.

Example 91C

N-[6-(4-acetylpiperazin-1-yl)-2-ethoxypyridin-3-yl]-5-[2-(2-hydroxyethoxyl)ethyl]-4-oxo-4,5,6,7-tetrahydrofuro[3,2-c]pyridine-3-carboxamide The procedure for Example 9, substituting the product from Example 91B for the product from Example 8B, provided the titled compound. $^1$H NMR (300 MHz, DMSO-d$_6$) δ ppm 12.06 (s, 1H), 8.31 (d, J=8.6 Hz, 1H), 8.26 (s, 1H), 6.34 (d, J=8.7 Hz, 1H), 4.56 (t, J=5.3 Hz, 1H), 4.31 (q, J=7.0 Hz, 2H), 3.79 (t, J=7.3 Hz, 2H), 3.63 (s, 4H), 3.58-3.35 (m, 12H), 3.05 (t, J=7.3 Hz, 2H), 2.04 (s, 3H), 1.38 (t, J=7.1 Hz, 3H); MS (ESI) m/z 516 (M+H)$^+$.

Example 92 tert-butyl 4-(6-ethoxy-5-{[(4-oxo-4,5,6,7-tetrahydrofuro[3,2-c]pyridin-3-yl)carbonyl]amino}pyridin-2-yl)piperazine-1-carboxylate Example 92A 6-chloro-2-ethoxy-3-nitropyridine The titled compound was prepared using the procedure described for Example 20A substituting ethanol for 2-methoxyethanol. $^1$H NMR (300 MHz, CDCl$_3$) δ ppm 8.24 (d, J=8.4 Hz, 1H), 7.00 (d, J=8.3 Hz, 1H), 4.58 (q, J=7.1 Hz, 2H), 1.47 (t, J=7.0 Hz, 3H).

Example 92B tert-butyl 4-(6-ethoxy-5-nitropyridin-2-yl)piperazine-1-carboxylate

The titled compound was prepared using the procedure described for Example 20B, substituting the product from Example 92A for the product from Example 20A, and substituting tert-butyl piperazine-1-carboxylate for 1-acetylpiperazine. $^1$H NMR (500 MHz, CDCl$_3$) δ ppm 8.28 (d, J=9.1 Hz, 1H), 6.15 (d, J=9.1 Hz, 1H), 4.49 (q, J=7.1 Hz, 2H), 3.75-3.67 (m, 4H), 3.58-3.52 (m, 4H), 1.49 (s, 9H), 1.46 (t, J=7.1 Hz, 3H).

Example 92C tert-butyl 4-(5-amino-6-ethoxypyridin-2-yl)piperazine-1-carboxylate

The titled compound was prepared using the procedure described for Example 20C, substituting the product from Example 92B for the product from Example 20B. $^1$H NMR (300 MHz, CDCl$_3$) δ ppm 6.89 (d, J=8.0 Hz, 1H), 6.10 (d, J=8.4 Hz, 1H), 4.37 (q, J=7.0 Hz, 2H), 3.60-3.51 (m, 4H), 3.33-3.26 (m, 4H), 1.48 (s, 9H), 1.39 (t, J=7.1 Hz, 3H).

Example 92D tert-butyl 4-(6-ethoxy-5-{[(4-oxo-4,5,6,7-tetrahydrofuro[3,2-c]pyridin-3-yl)carbonyl]amino}pyridin-2-yl)piperazine-1-carboxylate The titled compound was prepared using the procedure described for Example 19, substituting the product from Example 92C for 1-(4-(5-amino-6-ethoxypyridin-2-yl)piperazin-1-yl)ethanone. $^1$H NMR (300 MHz, DMSO-d$_6$) δ ppm 11.96 (s, 1H), 8.23-8.26 (m, 2H), 8.02 (m, 1H), 6.34 (d, J=8.8 Hz, 1H), 4.32 (q, J=7.1 Hz, 2H), 3.52 (m, 2H), 3.42 (m, 8H), 2.99 (m, 2H), 1.42 (s, 9H), 1.34 (t, J=7.1 Hz, 3H); MS (ESI) m/z 486 (M+H)$^+$.

Example 93

N-{6-[4-(N'-cyano-N-methylcarbamimidoyl)piperazin-1-yl]-2-ethoxypyridin-3-yl}-4-oxo-4,5,6,7-tetrahydrofuro[3,2-c]pyridine-3-carboxamide Example 93A N-[2-ethoxy-6-(piperazin-1-yl)pyridin-3-yl]-4-oxo-4,5,6,7-tetrahydrofuro[3,2-c]pyridine-3-carboxamide 2,2,2-trifluoroacetate A mixture of Example 92D (0.222 g, 0.457 mmol) and trifluoroacetic acid (2 mL, 26.0 mmol) was stirred at room temperature for 1 hour. The mixture was then concentrated in vacuo to afford the titled compound as the trifluoroacetate.

Example 93B

N-{6-[4-(N'-cyano-N-methylcarbamimidoyl)piperazin-1-yl]-2-ethoxypyridin-3-yl}-4-oxo-4,5,6,7-tetrahydrofuro[3,2-c]pyridine-3-carboxamide bis(2,2,2-trifluoroacetate)

A mixture of Example 93A (0.228 g, 0.457 mmol), methyl N-cyano-N-methylcarbamimidothioate (0.065 g, 0.503 mmol), mercury(II) chloride (0.170 g, 0.626 mmol), and triethylamine (0.8 mL, 5.74 mmol) in N,N-dimethylformamide (4 mL) was stirred overnight at room temperature. The mixture was concentrated in vacuo. The residue was taken up in a 1:1 mixture of methanol and dimethylsulfoxide (2.5 mL) and filtered, and the filtrate was purified by preparative HPLC on a Phenomenex® Luna® C8(2) 5 µm 100 Å AXIA™ column (30 mm×75 mm) A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A). Samples were injected in dimethyl sulfoxide/methanol (1:1, 2.5 mL). A custom purification system was used, consisting of the following modules: Waters LC4000 preparative pump; Waters 996 diode-array detector; Waters 717+ autosampler; Waters SAT/IN module, Alltech Varex III evaporative light-scattering detector; Gilson 506C interface box; and two Gilson FC204 fraction collectors. The system was controlled using Waters Millennium32 software, automated using an AbbVie developed Visual Basic application for fraction collector control and fraction tracking. Fractions were collected based upon UV signal threshold and selected fractions subsequently analyzed by flow injection analysis mass spectrometry using positive APCI ionization on a Finnigan LCQ using 70:30 methanol:10 mM $NH_4OH$(aqueous) at a flow rate of 0.8 mL/minute. Loop-injection mass spectra were acquired using a Finnigan LCQ running LCQ Navigator 1.2 software and a Gilson 215 liquid handler for fraction injection controlled by an AbbVie developed Visual Basic application. Concentration of selected fractions provided the titled compound as the bistrifluoroacetate. $^1H$ NMR (300 MHz, DMSO-$d_6$) δ ppm 11.97 (s, 1H), 8.24-8.26 (m, 2H), 8.02 (m, 1H), 7.31 (m, 1H), 6.35 (d, J=8.5 Hz, 1H), 4.33 (q, J=7.1 Hz, 2H), 3.39-3.59 (m, 10H), 2.99 (m, 2H), 2.87 (d, J=4.4 Hz, 3H), 1.34 (t, J=7.1 Hz, 3H); MS (ESI) m/z 467 $(M+H)^+$.

Example 94

(2R)-1-[3-{[6-(4-acetylpiperazin-1-yl)-2-ethoxypyridin-3-yl]carbamoyl}-4-oxo-6,7-dihydrofuro[3,2-c]pyridin-5(4H)-yl]propan-2-yl acetate

Example 94A (R)-ethyl 3-(2-hydroxypropylamino)propanoate (R)-(−)-1-Amino-2-propanol (0.296 g, 3.94 mmol) was cooled to 0° C., treated dropwise with ethyl acrylate (0.427 mL, 3.94 mmol) and stirred overnight at room temperature to provide the titled compound. $^1H$ NMR (300 MHz, CDCl$_3$) δ ppm 4.15 (q, J=7.1 Hz, 2H), 3.75 (dqd, J=9.3, 6.2, 3.1 Hz, 1H), 3.00-2.82 (m, 2H), 2.73 (dd, J=12.1, 3.1 Hz, 1H), 2.49 (t, J=6.4 Hz, 2H), 2.39 (dd, J=12.1, 9.4 Hz, 1H), 1.27 (t, J=7.2 Hz, 3H), 1.14 (d, J=6.2 Hz, 3H); MS (ESI) m/z 176 $(M+H)^+$.

Example 94B ethyl 1-((R)-2-hydroxypropyl)-2,4-dioxopiperidine-3-carboxylate

A solution of the product from Example 94A (0.690 g, 3.94 mmol) in tetrahydrofuran (12 mL) was cooled to 0° C. under $N_2$, treated with triethylamine (0.604 mL, 4.33 mmol), treated with trimethylsilyl chloride (0.554 mL, 4.33 mmol), stirred at room temperature for 30 minutes, concentrated to dryness, and partitioned between ether (100 mL) and brine (20 mL). The ether layer was isolated, dried (MgSO$_4$), filtered, and concentrated to provide (R)-ethyl 3-(2-(trimethylsilyloxy)propylamino)propanoate. $^1H$ NMR (300 MHz, CDCl$_3$) δ ppm 4.15 (q, J=7.1 Hz, 2H), 3.99-3.88 (m, 1H), 2.89 (t, J=6.7 Hz, 2H), 2.63-2.43 (m, 4H), 1.27 (t, J=7.1 Hz, 3H), 1.15 (d, J=6.2 Hz, 3H), 0.13 (s, 9H); MS (ESI) m/z 248 $(M+H)^+$.

The (R)-ethyl 3-(2-(trimethylsilyloxy)propylamino)propanoate was dissolved in CH$_2$Cl$_2$ (12 mL) under $N_2$, cooled to 0° C. and treated with triethylamine (0.604 mL, 4.33 mmol). Ethyl malonyl chloride (0.549 mL, 4.33 mmol) was then added over 5 minutes, and the mixture was stirred at room temperature overnight. The mixture was concentrated to dryness and partitioned between ether (100 mL) and brine (20 mL). The ether layer was isolated, dried (MgSO$_4$), filtered, and concentrated to provide (R)-ethyl 3-((3-ethoxy-3-oxopropyl)(2-(trimethylsilyloxy)propyl)amino)-3-oxopropanoate.

A solution of ethanol (4.60 mL, 79 mmol) in tetrahydrofuran (30 mL) under $N_2$ was treated with potassium tert-butoxide (0.973 g, 8.67 mmol) and stirred until the mixture was homogeneous. This mixture was cooled to 0° C. and treated dropwise with a solution of (R)-ethyl 3-((3-ethoxy-3-oxopropyl)(2-(trimethylsilyloxy)propyl)amino)-3-oxopropanoate in tetrahydrofuran (10 mL). After stirring at room temperature overnight, the mixture was concentrated to dryness, dissolved in 1 M HCl (15 mL) and stirred for 10 minutes. The mixture was then treated with silica gel (2.5 g) and concentrated to dryness. This silica gel mixture was placed on top of a silica gel column and chromatographed eluting with a gradient of 0% to 100% [22:1:1 ethyl acetate/formic acid/water] in ethyl acetate to provide the titled compound. $^1H$ NMR (400 MHz, CDCl$_3$) δ ppm 14.10 (s, 1H), 8.06 (s, 1H), 4.36 (q, J=7.1 Hz, 2H), 4.11-4.03 (m, 1H), 3.54 (t, J=6.9 Hz, 2H), 3.45 (d, J=5.8 Hz, 2H), 2.70 (dd, J=11.5, 6.6 Hz, 2H), 1.37 (t, J=7.1 Hz, 3H), 1.21 (d, J=6.3 Hz, 3H); MS (ESI) m/z 244 $(M+H)^+$.

Example 94C (R)-5-(2-acetoxypropyl)-4-oxo-4,5,6,7-tetrahydrofuro[3,2-c]pyridine-3-carboxylic acid A solution of the product from Example 94B (0.70 g, 2.88 mmol) in water (12 mL) was heated to reflux for 30 minutes and then cooled to 0° C. This mixture was treated with sodium bicarbonate (0.967 g, 11.5 mmol), then treated portion-wise over 45 minutes with a solution of 3-bromopyruvic acid (0.577 g, 3.45 mmol) in methanol (12 mL) and stirred at room temperature overnight. The mixture was concentrated to dryness, and the residue was treated with acetic acid (30 mL) and acetic anhydride (15 mL). This mixture was heated to 110° C. for 2 hours, cooled and concentrated to dryness. The residue was partitioned between ethyl acetate (200 mL) and 1 M HCl (50 mL). The layers were separated, and the aqueous layer was extracted with ethyl acetate (25 mL). The combined ethyl acetate layers were washed with brine, dried (MgSO$_4$), filtered and concentrated. The residue was chromatographed on silica gel eluting with at gradient of 50-100% [200:1:1 ethyl acetate/formic acid/water] in heptanes to provide the titled compound. $^1$H NMR (400 MHz, CDCl$_3$) δ ppm 14.44 (s, 1H), 8.04 (s, 1H), 5.21 (dqd, J=12.9, 6.4, 3.6 Hz, 1H), 3.94-3.72 (m, 3H), 3.56 (dd, J=14.3, 3.6 Hz, 1H), 3.16-3.01 (m, 2H), 2.04 (s, 3H), 1.30 (d, J=6.4 Hz, 3H); MS (ESI) m/z 282 (M+H)$^+$.

Example 94D (2R)-1-[3-{[6-(4-acetylpiperazin-1-yl)-2-ethoxypyridin-3-yl]carbamoyl}-4-oxo-6,7-dihydrofuro[3,2-c]pyridin-5(4H)-yl]propan-2-yl acetate A solution of the product from Example 94C (113 mg, 0.402 mmol) in tetrahydrofuran (8 mL) under nitrogen was treated with triethylamine (168 μL, 1.21 mmol) followed by treatment with ethyl chloroformate (38.6 μL, 0.402 mmol). The mixture was stirred at room temperature for 45 minutes and then 1-(4-(5-amino-6-ethoxypyridin-2-yl)piperazin-1-yl)ethanone (CAS#1094927-44-2) (106 mg, 0.402 mmol) was added. The reaction mixture was stirred overnight and then diluted with ethyl acetate (100 mL). This organic layer was washed with 1 M HCl (25 mL), washed with saturated sodium bicarbonate solution (15 mL), washed with brine, dried (MgSO$_4$), filtered, concentrated and chromatographed on silica gel eluted with a gradient of 0% to 100% [10% ethanol in ethyl acetate] in ethyl acetate to provide the titled compound. $^1$H NMR (300 MHz, CDCl$_3$) δ ppm 11.92 (s, 1H), 8.53 (d, J=8.6 Hz, 1H), 8.07 (s, 1H), 6.18 (d, J=8.6 Hz, 1H), 5.27-5.14 (m, 1H), 4.41 (q, J=7.1 Hz, 2H), 3.85-3.41 (m, 11H), 3.12-2.92 (m, 3H), 2.14 (s, 3H), 2.04 (s, 3H), 1.49 (t, J=7.1 Hz, 3H), 1.30 (d, J=6.4 Hz, 3H); MS (ESI) m/z 528 (M+H)$^+$.

Example 95

N-[6-(4-acetylpiperazin-1-yl)-2-ethoxypyridin-3-yl]-5-[(2R)-2-hydroxypropyl]-4-oxo-4,5,6,7-tetrahydrofuro[3,2-c]pyridine-3-carboxamide A solution of the product from Example 94 (126 mg, 0.239 mmol) in tetrahydrofuran (2 mL) and methanol (2 mL) was treated with 1 MNaOH (1 mL). After stirring for 15 minutes, the mixture was partitioned between water (10 mL) and CH$_2$Cl$_2$ (50 mL). The layers were separated, and the aqueous layer was extracted with CH$_2$Cl$_2$ (25 mL). The combined CH$_2$Cl$_2$ layers were dried (MgSO$_4$), filtered and concentrated to provide the titled compound. $^1$H NMR (300 MHz, CDCl$_3$) δ ppm 11.87 (s, 1H), 8.54 (d, J=8.6 Hz, 1H), 8.07 (s, 1H), 6.17 (d, J=8.6 Hz, 1H), 4.40 (q, J=7.1 Hz, 2H), 4.22-4.09 (m, 1H), 3.82 (t, J=7.3 Hz, 2H), 3.77-3.70 (m, 2H), 3.61-3.41 (m, 8H), 3.04 (dd, J=7.5, 6.7 Hz, 2H), 2.74 (d, J=4.6 Hz, 1H), 2.14 (s, 3H), 1.48 (t, J=7.1 Hz, 3H), 1.26 (d, J=6.3 Hz, 3H); MS (ESI) m/z 486 (M+H)$^+$.

Example 96

(2S)-1-[3-{[6-(4-acetylpiperazin-1-yl)-2-ethoxypyridin-3-yl]carbamoyl}-4-oxo-6,7-dihydrofuro[3,2-c]pyridin-5(4H)-yl]propan-2-yl acetate The titled compound was prepared using the procedures described for Example 94 substituting (S)-1-aminopropan-2-ol for (R)-(−)-1-amino-2-propanol. $^1$H NMR (300 MHz, CDCl$_3$) δ ppm 11.92 (s, 1H), 8.53 (d, J=8.5 Hz, 1H), 8.07 (s, 1H), 6.18 (d, J=8.6 Hz, 1H), 5.27-5.15 (m, 1H), 4.41 (q, J=7.1 Hz, 2H), 3.86-3.42 (m, 12H), 3.12-2.92 (m, 2H), 2.14 (s, 3H), 2.04 (s, 3H), 1.49 (t, J=7.1 Hz, 3H), 1.30 (d, J=6.4 Hz, 3H); MS (ESI) m/z 528 (M+H)$^+$.

Example 97

N-[6-(4-acetylpiperazin-1-yl)-2-ethoxypyridin-3-yl]-5-[(2S)-2-hydroxypropyl]-4-oxo-4,5,6,7-tetrahydrofuro[3,2-c]pyridine-3-carboxamide The titled compound was prepared using the procedure described for Example 95 substituting the product from Example 96 for the product from Example 94. $^1$H NMR (300 MHz, CDCl$_3$) δ ppm 11.86 (s, 1H), 8.54 (d, J=8.6 Hz, 1H), 8.08 (s, 1H), 6.17 (d, J=8.6 Hz, 1H), 4.40 (q, J=7.1 Hz, 2H), 4.22-4.09 (m, 1H), 3.82 (t, J=7.3 Hz, 2H), 3.77-3.71 (m, 2H), 3.61-3.40 (m, 8H), 3.05 (dd, J=7.5, 6.4 Hz, 2H), 2.72 (d, J=4.6 Hz, 1H), 2.14 (s, 3H), 1.48 (t, J=7.1 Hz, 3H), 1.26 (d, J=6.3 Hz, 3H); MS (ESI) m/z 486 (M+H)$^+$.

Example 98

(2R)-2-[3-{[6-(4-acetylpiperazin-1-yl)-2-ethoxypyridin-3-yl]carbamoyl}-4-oxo-6,7-dihydrofuro[3,2-c]pyridin-5(4H)-yl]propyl acetate The titled compound was prepared using the procedures described for Example 94 substituting (R)-2-aminopropan-1-ol for (R)-(−)-1-amino-2-propanol. $^1$H NMR (500 MHz, CDCl$_3$) δ ppm 11.99 (s, 1H), 8.54 (d, J=8.5 Hz, 1H), 8.07 (s, 1H), 6.18 (d, J=8.6 Hz, 1H), 5.13-5.03 (m, 1H), 4.41 (q, J=7.0 Hz, 2H), 4.25 (dd, J=11.6, 8.6 Hz, 1H), 4.14 (dd, J=11.6, 4.6 Hz, 1H), 3.76-3.71 (m, 2H), 3.62 (dd, J=10.1, 4.2 Hz, 2H), 3.60-3.56 (m, 2H), 3.51 (dd, J=6.4, 3.2 Hz, 2H), 3.47-3.42 (m, 2H), 2.99 (dd, J=12.8, 6.7 Hz, 2H), 2.14 (s, 3H), 2.03 (s, 3H), 1.48 (t, J=7.0 Hz, 3H), 1.26 (d, J=7.0 Hz, 3H); MS (ESI) m/z 528 (M+H)$^+$.

Example 99

N-[6-(4-acetylpiperazin-1-yl)-2-ethoxypyridin-3-yl]-5-[(2R)-1-hydroxypropan-2-yl]-4-oxo-4,5,6,7-tetrahydrofuro[3,2-c]pyridine-3-carboxamide The titled compound was prepared using the procedure described for Example 95 substituting the product from Example 98 for the product from Example 94. $^1$H NMR (500 MHz, CDCl$_3$) δ ppm 12.00 (s, 1H), 8.51 (d, J=8.5 Hz, 1H), 8.05 (s, 1H), 6.16 (d, J=8.6 Hz, 1H), 4.75-4.68 (m, 1H), 4.40 (q, J=7.1 Hz, 2H), 3.79-3.66 (m, 5H), 3.64-3.54 (m, 3H), 3.49 (dd, J=6.3, 3.7 Hz, 2H), 3.43 (t, J=4.9 Hz, 2H), 3.02-2.89 (m, 3H), 2.12 (s, 3H), 1.47 (t, J=7.1 Hz, 3H), 1.25 (d, J=7.0 Hz, 3H); MS (ESI) m/z 486 (M+H)$^+$.

Example 100

(2S)-2-[3-{[6-(4-acetylpiperazin-1-yl)-2-ethoxypyridin-3-yl]carbamoyl}-4-oxo-6,7-dihydrofuro[3,2-c]pyridin-5(4H)-yl]propyl acetate The titled compound was prepared using the procedures described for Example 94 substituting (S)-2-aminopropan-1-ol for (R)-(−)-1-amino-2-propanol. $^1$H NMR (500 MHz, CDCl$_3$) δ ppm 11.99 (s, 1H), 8.54 (d, J=8.5 Hz, 1H), 8.07 (s, 1H), 6.18 (d, J=8.6 Hz, 1H), 5.16-5.03 (m, 1H), 4.41 (q, J=7.1 Hz, 2H), 4.25 (dd, J=11.7, 8.6 Hz, 1H), 4.14 (dd, J=11.6, 4.7 Hz, 1H), 3.76-3.71 (m, 2H), 3.67-3.55 (m, 4H), 3.54-3.49 (m, 2H), 3.47-3.43 (m, 2H), 3.06-2.94 (m, 2H), 2.14 (s, 3H), 2.03 (s, 3H), 1.48 (t, J=7.1 Hz, 3H), 1.26 (d, J=7.1 Hz, 3H); MS (ESI) m/z 528 (M+H)$^+$.

Example 101

N-[6-(4-acetylpiperazin-1-yl)-2-ethoxypyridin-3-yl]-5-[(2S)-1-hydroxypropan-2-yl]-4-oxo-4,5,6,7-tetrahydrofuro[3,2-c]pyridine-3-carboxamide The titled compound was prepared using the procedure described for Example 95 substituting the product from Example 100 for the product from Example 94. $^1$H NMR (400 MHz, CDCl$_3$) δ ppm 11.96 (s, 1H), 8.52 (d, J=8.5 Hz, 1H), 8.06 (s, 1H), 6.17 (d, J=8.6 Hz, 1H), 4.76-4.66 (m, 1H), 4.41 (q, J=7.0 Hz, 2H), 3.81-3.55 (m, 8H), 3.50 (dd, J=6.6, 3.7 Hz, 2H), 3.46-3.42 (m, 2H), 3.05-2.90 (m, 2H), 2.62 (t, J=5.6 Hz, 1H), 2.13 (s, 3H), 1.47 (t, J=7.1 Hz, 3H), 1.26 (d, J=7.0 Hz, 3H); MS (ESI) m/z 486 (M+H)$^+$.

Example 102

N-[6-(4-acetylpiperazin-1-yl)-2-ethoxypyridin-3-yl]-5-(1-hydroxy-2-methylpropan-2-yl)-4-oxo-4,5,6,7-tetrahydrofuro[3,2-c]pyridine-3-carboxamide Example 102A 2-(3-(6-(4-acetylpiperazin-1-yl)-2-ethoxypyridin-3-ylcarbamoyl)-4-oxo-6,7-dihydrofuro[3,2-c]pyridin-5(4H)-yl)-2-methylpropyl acetate The titled compound was prepared using the procedures described for Example 94 substituting 2-amino-2-methylpropan-1-ol for (R)-(−)-1-amino-2-propanol.

Example 102B

N-(6-(4-acetylpiperazin-1-yl)-2-ethoxypyridin-3-yl)-5-(1-hydroxy-2-methylpropan-2-yl)-4-oxo-4,5,6,7-tetrahydrofuro[3,2-c]pyridine-3-carboxamide The titled compound was prepared using the procedure described for Example 95 substituting the product from Example 102A for the product from Example 94. $^1$H NMR (300 MHz, CDCl$_3$) δ ppm 11.85 (s, 1H), 8.57 (d, J=8.6 Hz, 1H), 8.07 (s, 1H), 6.18 (d, J=8.6 Hz, 1H), 4.46 (q, J=7.1 Hz, 2H), 4.25 (t, J=7.1 Hz, 1H), 3.91 (d, J=7.1 Hz, 2H), 3.79-3.70 (m, 4H), 3.61-3.41 (m, 6H), 2.93 (t, J=6.9 Hz, 2H), 2.14 (s, 3H), 1.45 (t, J=7.0 Hz, 3H), 1.44 (s, 6H); MS (ESI) m/z 500 (M+H)$^+$.

Example 103

1-[3-{[6-(4-acetylpiperazin-1-yl)-2-ethoxypyridin-3-yl]carbamoyl}-4-oxo-6,7-dihydrofuro[3,2-c]pyridin-5(4H)-yl]-2-methylpropan-2-yl acetate The titled compound was prepared using the procedures described for Example 94 substituting 1-amino-2-methylpropan-2-ol for (R)-(−)-1-amino-2-propanol. $^1$H NMR (300 MHz, CDCl$_3$) δ ppm 11.91 (s, 1H), 8.53 (d, J=8.6 Hz, 1H), 8.08 (s, 1H), 6.18 (d, J=8.6 Hz, 1H), 4.40 (q, J=7.1 Hz, 2H), 3.81 (t, J=7.1 Hz, 2H), 3.80 (s, 2H), 3.76-3.70 (m, 2H), 3.61-3.41 (m, 6H), 3.02 (t, J=7.1 Hz, 2H), 2.14 (s, 3H), 2.02 (s, 3H), 1.54 (s, 6H), 1.47 (t, J=7.1 Hz, 3H); MS (ESI) m/z 542 (M+H)$^+$.

Example 104

N-[6-(4-acetylpiperazin-1-yl)-2-ethoxypyridin-3-yl]-5-(2-hydroxy-2-methylpropyl)-4-oxo-4,5,6,7-tetrahydrofuro[3,2-c]pyridine-3-carboxamide The titled compound was prepared using the procedure described for Example 95 substituting the product from Example 103 for the product from Example 94. $^1$H NMR (300 MHz, CDCl$_3$) δ ppm 11.82 (s, 1H), 8.54 (d, J=8.6 Hz, 1H), 8.08 (s, 1H), 6.17 (d, J=8.6 Hz, 1H), 4.40 (q, J=7.1 Hz, 2H), 3.86 (t, J=7.2 Hz, 2H), 3.77-3.70 (m, 2H), 3.56 (s, 2H), 3.62-3.41 (m, 6H), 3.05 (t, J=7.2 Hz, 2H), 2.14 (s, 3H), 1.47 (t, J=7.1 Hz, 3H), 1.31 (s, 6H); MS (ESI) m/z 500 (M+H)$^+$.

Example 105

N-{6-(4-acetylpiperazin-1-yl)-2-[(3S)-tetrahydrofuran-3-yloxy]pyridin-3-yl}-4-oxo-4,5,6,7-tetrahydrofuro[3,2-c]pyridine-3-carboxamide The titled compound was prepared by sequentially using the procedures described for Example 20A, Example 20B, Example 20C and Example 19, substituting (S)-(+)-3-hydroxytetrahydrofuran for 2-methoxyethanol in Example 20A. $^1$H NMR (300 MHz, CDCl$_3$) δ ppm 11.74 (s, 1H), 8.55 (d, J=8.6 Hz, 1H), 8.08 (s, 1H), 6.21 (d, J=8.6 Hz, 1H), 5.65 (bs, 1H), 5.51 (ddd, J=6.9, 5.2, 2.8 Hz, 1H), 4.16-4.00 (m, 3H), 3.89 (td, J=8.1, 4.4 Hz, 1H), 3.76-3.71 (m, 2H), 3.68 (td, J=7.3, 2.6 Hz, 2H), 3.62-3.41 (m, 6H), 3.03 (t, J=7.2 Hz, 2H), 2.36 (dddd, J=13.4, 6.7, 4.4, 2.4 Hz, 1H), 2.30-2.17 (m, 1H), 2.14 (s, 3H); MS (ESI) m/z 470 (M+H)$^+$.

Example 106

N-[2-ethoxy-6-(morpholin-4-yl)pyridin-3-yl]-4-oxo-4,5,6,7-tetrahydrofuro[3,2-c]pyridine-3-carboxamide The titled compound was prepared by sequentially using the procedures described for Example 20B, Example 20C, and Example 19, substituting the product from Example 92A for the product from Example 20A in the procedure described in Example 20B, and substituting morpholine for 1-acetylpiperazine in the procedure described in Example 20B. $^1$H NMR (300 MHz, CDCl$_3$) δ ppm 11.63 (s, 1H), 8.48 (d, J=8.6 Hz, 1H), 8.09 (s, 1H), 6.16 (d, J=8.6 Hz, 1H), 5.55 (s, 1H), 4.43 (q, J=7.1 Hz, 2H), 3.86-3.79 (m, 4H), 3.69 (td, J=7.2, 2.6 Hz, 2H), 3.45-3.40 (m, 4H), 3.03 (t, J=7.2 Hz, 2H), 1.44 (t, J=7.1 Hz, 3H); MS (ESI) m/z 386 (M+H)$^+$.

Example 107

N-[2-(2-hydroxy-2-methylpropoxy)-6-(morpholin-4-yl)pyridin-3-yl]-4-oxo-4,5,6,7-tetrahydrofuro[3,2-c]pyridine-3-carboxamide Example 107A 2-(2-(benzyloxy)-2-methylpropoxy)-6-morpholinopyridin-3-amine The titled compound was prepared using the procedures described for Example 20A, Example 20B, and Example 86C, substituting 2-(benzyloxy)-2-methylpropan-1-ol for 2-methoxyethanol in Example 20A, and substituting morpholine for 1-acetylpiperazine in Example 20B.

Example 107B

N-(2-(2-(benzyloxy)-2-methylpropoxy)-6-morpholinopyridin-3-yl)-4-oxo-4,5,6,7-tetrahydrofuro[3,2-c]pyridine-3-carboxamide A solution of the product from Example 1E (50 mg, 0.276 mmol) and triethylamine (0.058 mL, 0.414 mmol) in acetonitrile (5 mL) under nitrogen was cooled to 0° C., treated with ethyl chloroformate (0.034 mL, 0.359 mmol) and stirred for 20 minutes at 0° C. A solution of the product from Example 107A (99 mg, 0.276 mmol) in acetonitrile (2 mL) was then added, and the reaction was stirred for 2 hours. The mixture was diluted with ethyl acetate, washed with water, washed with brine, dried (MgSO$_4$), filtered, concentrated and chromatographed on silica gel eluted with a gradient of 20% to 40% ethyl acetate in hexanes to provide the titled compound.

Example 107C

N-[2-(2-hydroxy-2-methylpropoxy)-6-(morpholin-4-yl)pyridin-3-yl]-4-oxo-4,5,6,7-tetrahydrofuro[3,2-c]pyridine-3-carboxamide The titled compound was prepared using the procedure described for Example 9, substituting the product from Example 107B for the product from Example 8B. $^1$H NMR (300 MHz, CDCl$_3$) δ ppm 11.86 (s, 1H), 8.71 (d, J=8.6 Hz, 1H), 8.10 (s, 1H), 6.18 (d, J=8.6 Hz, 1H), 5.80 (s, 1H), 5.20 (s, 1H), 4.19 (s, 2H), 3.87-3.79 (m, 4H), 3.70 (td, J=7.3, 2.7 Hz, 2H), 3.45-3.39 (m, 4H), 3.05 (t, J=7.3 Hz, 2H), 1.32 (s, 6H); MS (ESI) m/z 431 (M+H)$^+$.

Example 108 methyl(6-ethoxy-5-{[(4-oxo-4,5,6,7-tetrahydrofuro[3,2-c]pyridin-3-yl)carbonyl]amino}pyridin-2-yl)acetate

Example 108A 1-tert-butyl 3-methyl 2-(6-ethoxy-5-nitropyridin-2-yl)malonate

A mixture of a 60% dispersion of sodium hydride in mineral oil (1.185 g, 29.6 mmol) and the product from Example 92A (3.0 g, 14.8 mmol) in N,N-dimethylformamide (4 mL) was cooled to 0° C. and treated dropwise with tert-butyl methyl malonate (3.16 mL, 17.77 mmol). The mixture was stirred at room temperature overnight. The mixture was diluted with ether, washed with water, dried (MgSO$_4$), filtered and concentrated. The residue was purified by chromatography on silica gel eluting with a gradient of 10% to 40% ethyl acetate in heptanes. $^1$H NMR (300 MHz, CDCl$_3$) δ ppm 8.26 (d, J=8.1 Hz, 1H), 7.13 (d, J=8.1 Hz, 1H), 4.78 (s, 1H), 4.60-4.49 (m, 2H), 3.79 (s, 3H), 1.47 (s, 9H), 1.43 (t, J=7.1 Hz, 3H).

Example 108B methyl 2-(6-ethoxy-5-nitropyridin-2-yl)acetate

A mixture of the product from Example 108A (4.1 g, 12 mmol) and 2,2,2-trifluoroacetic acid (13.7 g, 120 mmol) was stirred at room temperature for 10 minutes and then concentrated to dryness to provide the titled compound.

Example 108C methyl 2-(5-amino-6-ethoxypyridin-2-yl)acetate

The titled compound was prepared using the procedure described for Example 20C, substituting the product from Example 108B for the product from Example 20B.

Example 108D methyl(6-ethoxy-5-{[(4-oxo-4,5,6,7-tetrahydrofuro[3,2-c]pyridin-3-yl)carbonyl]amino}pyridin-2-yl)acetate The titled compound was prepared using the procedure described for Example 107B, substituting the product from Example 108C for the product from Example 107A. $^1$H NMR (300 MHz, CDCl$_3$) δ ppm 11.86 (s, 1H), 8.64 (d, J=8.0 Hz, 1H), 8.11 (s, 1H), 6.82 (d, J=8.0 Hz, 1H), 5.52 (s, 1H), 4.47 (q, J=7.1 Hz, 2H), 3.74-3.66 (m, 7H), 3.04 (t, J=7.2 Hz, 2H), 1.45 (t, J=7.1 Hz, 3H); MS (ESI) m/z 374 (M+H)$^+$.

Example 109

N-[2-ethoxy-6-(2-hydroxyethyl)pyridin-3-yl]-4-oxo-4,5,6,7-tetrahydrofuro[3,2-c]pyridine-3-carboxamide A solution of the product from Example 108D (70 mg, 0.19 mmoL) in tetrahydrofuran was treated with 1 M lithium aluminum hydride in tetrahydrofuran (0.56 mL, 0.56 mmol) and stirred for 30 minutes. The mixture was treated sequentially with 1 drop of water, 1 drop of 1 M NaOH, and 3 drops of water. After stirring for 1 hour, the mixture was filtered through a Whatman Puradisc™ 25 TF 0.45 μm polytetrafluoroethylene (PTFE) membrane with polypropylene housing 25 mm diameter filter. The filtrate was concentrated and chromatographed on silica gel eluting with a gradient of 0% to 100% ethyl acetate in heptanes, followed by a gradient of 0% to 10% methanol in ethyl acetate to provide the titled compound. $^1$H NMR (400 MHz, CDCl$_3$) δ ppm 11.82 (s, 1H), 8.55 (d, J=7.9 Hz, 1H), 8.05 (s, 1H), 6.66 (d, J=8.0 Hz, 1H), 5.58 (s, 1H), 4.36 (q, J=7.1 Hz, 2H), 4.16 (t, J=5.3 Hz, 1H), 3.91 (dd, J=10.5, 5.2 Hz, 2H), 3.63 (td, J=7.2, 2.6 Hz, 2H), 2.97 (t, J=7.2 Hz, 2H), 2.83 (t, J=5.4 Hz, 2H), 1.42 (t, J=7.1 Hz, 3H); MS (ESI) m/z 346 (M+H)$^+$.

Example 110

N-[6-(4-acetylpiperazin-1-yl)-2-methoxypyridin-3-yl]-4-oxo-2',3',4,5',6',7-hexahydro-5H-spiro[1-benzofuran-6,4'-pyran]-3-carboxamide

Example 110A 1-(dihydro-2H-pyran-4(3H)-ylidene)propan-2-one

A mixture of potassium hydroxide (1.29 g, 22.99 mmol) in water (5 mL) and ethanol (20 mL) was cooled to 0° C. Dihydro-2H-pyran-4(3H)-one (1.5 mL, 16.24 mmol) was added followed by dimethyl 2-oxopropylphosphonate (3.16 mL, 21.21 mmol). The reaction mixture was stirred overnight at room temperature. After this time, the mixture was concentrated in vacuo to remove most of the ethanol, and then the mixture was partitioned between ether (20 mL) and water (20 mL). The phases were separated, and the aqueous layer was extracted twice more with ether (20 mL each). The combined organic layers were dried over $Na_2SO_4$ and concentrated to yield the titled compound as a colorless oil. $^1$H NMR (300 MHz, $CDCl_3$) δ ppm 6.06 (s, 1H), 3.70-3.81 (m, 4H), 2.98 (m, 2H), 2.30 (m, 2H), 2.19 (s, 3H); MS ($DCI^+$) m/z 158 $(M+NH_4)^+$.

Example 110B methyl 8,10-dioxo-3-oxaspiro[5.5]undecane-7-carboxylate

A mixture of Example 110A (2.485 g, 17.73 mmol) and dimethyl malonate (2.342 g, 17.73 mmol) in methanol (13 mL) was treated with sodium methoxide (25% in methanol) (4.8 mL, 20.99 mmol), and the reaction mixture was refluxed for 4 hours. After cooling to room temperature, the mixture was concentrated in vacuo to afford the crude titled compound as an orange, waxy solid which was used in the next reaction without further purification.

Example 110C 3-oxaspiro[5.5]undecane-8,10-dione

A mixture of Example 110B (1 g, 4.16 mmol) and 2 N NaOH (6.9 mL, 13.8 mmol) was refluxed for 2 hours. The mixture was cooled briefly to room temperature, treated with 5 N $H_2SO_4$ (6.9 mL, 34.5 mmol), and refluxed for 1.5 hours before being cooled to room temperature and stirred overnight. After this time, the mixture was extracted with ethyl acetate (50 mL) and $CH_2Cl_2$ (50 mL). The combined organic washes were dried over $Na_2SO_4$ and concentrated to afford the titled compound as a gold oil, 0.445 g (59%). $^1$H NMR (300 MHz, $CDCl_3$) δ ppm 3.67-3.71 (m, 4H), 3.39 (s, 2H), 2.69 (m, 4H), 1.47-1.50 (m, 4H).

Example 110D ethyl 4-oxo-2',3',5,5',6',7-hexahydro-4H-spiro[benzofuran-6,4'-pyran]-3-carboxylate A solution of Example 110C (0.445 g, 2.442 mmol) in ethanol (8.1 mL) was treated sequentially with sodium bicarbonate (2 g, 23.81 mmol) and ethyl bromopyruvate (0.37 mL, 2.94 mmol), and the mixture was stirred overnight at room temperature. After this time, the mixture was diluted with ethanol (15 mL) and filtered. The filtrate was concentrated. The residue was treated with acetic acid (23 mL) and acetic anhydride (11 mL), and the mixture was heated at 110° C. overnight. After cooling to room temperature, the mixture was concentrated. The residue was taken up in ethyl acetate (50 mL) and washed with saturated $NaHCO_3$ solution (15 mL) and brine (15 mL). The organic layer was dried over $Na_2SO_4$ and concentrated. Chromatography on silica gel (20 to 100% ethyl acetate-hexane, eluant) afforded the titled compound as a brown oil. $^1$H NMR (300 MHz, $CDCl_3$) δ ppm 7.92 (m, 1H), 4.34 (m, 2H), 3.68-3.73 (m, 4H), 2.92 (s, 2H), 2.61 (s, 2H), 1.60-1.66 (m, 4H), 1.36 (m, 3H); MS ($DCI^+$) m/z 279 $(M+H)^+$.

Example 110E 4-oxo-2',3',5,5',6',7-hexahydro-4H-spiro[benzofuran-6,4'-pyran]-3-carboxylic acid The product from Example 110D (0.204 g, 0.733 mmol) and 1 M aqueous sodium hydroxide solution (2.2 mL, 2.20 mmol) were stirred in methanol (2.2 mL) and tetrahydrofuran (2.2 mL) overnight at room temperature. After this time, the mixture was concentrated in vacuo, and the aqueous residue was washed with $CH_2Cl_2$ (3×1 mL). The remaining (basic) aqueous layer was acidified to pH 1 with 6 N HCl, and the resulting tan precipitate was collected by filtration, washed with water, and air-dried to give the titled compound, 0.049 g (27%). $^1$H NMR (300 MHz, $CDCl_3$) δ ppm 12.92 (s, 1H), 8.11 (sm, 1H), 3.66-3.79 (m, 4H), 3.02 (s, 2H), 2.73 (s, 2H), 1.67-1.71 (m, 4H); MS ($DCI^+$) m/z 251 $(M+H)^+$.

Example 110F

N-[6-(4-acetylpiperazin-1-yl)-2-methoxypyridin-3-yl]-4-oxo-2',3',4,5',6',7-hexahydro-5H-spiro[1-benzofuran-6,4'-pyran]-3-carboxamide The titled compound was prepared according to the procedure of Example 8B, substituting 1-(4-(5-amino-6-methoxypyridin-2-yl)piperazin-1-yl)ethanone (CAS #1094788-32-5) for 1-(4-(5-amino-6-ethoxypyridin-2-yl)piperazin-1-yl)ethanone and substituting the product from Example 110E for the product from Example 8A. $^1$H NMR (300 MHz, DMSO-$d_6$) δ ppm 11.19 (s, 1H), 8.38 (s, 1H), 8.31 (d, J=8.7 Hz, 1H), 6.38 (d, J=8.7 Hz, 1H), 3.91 (s, 3H), 3.42-3.62 (m, 12H), 3.09 (s, 2H), 2.72 (s, 2H), 2.04 (s, 3H), 1.54-1.58 (m, 4H); MS ($ESI^+$) m/z 483 $(M+H)^+$.

Example 111

N-[6-(4-acetylpiperazin-1-yl)-2-ethoxypyridin-3-yl]-4'-oxo-4',7'-dihydro-5'H-spiro[cyclobutane-1,6'-furo[3,2-c]pyridine]-3'-carboxamide

Example 111A 1-azaspiro[3.3]heptan-2-one

A solution of methylenecyclobutane (5 g, 73.4 mmol) in ether (30 mL) was cooled to −40° C. and treated dropwise with chlorosulfonyl isocyanate (3.3 mL, 38.0 mmol). The mixture was warmed to 10° C., at which point an exothermic reaction and the formation of a precipitate was noted. The mixture was cooled to −20° C. and stirred at this temperature for 1 hour, then warmed to room temperature overnight. The mixture was then treated with saturated $Na_2SO_3$ solution (13 mL) and stirred vigorously at room temperature for 1 hour. After this time, an additional portion of saturated $Na_2SO_3$ solution (13 mL) was added followed by solid $NaHCO_3$ to adjust the pH (~9). $CH_2Cl_2$ (70 mL) was added, and the phases were separated. The organic layer was dried over $Na_2SO_4$ and concentrated to afford the titled compound as a gold oil. $^1$H NMR (300 MHz, $CDCl_3$) δ ppm 6.02 (br, 1H), 2.98 (m, 2H), 2.22-2.42 (m, 4H), 1.67-1.78 (m, 2H); MS ($DCI^+$) m/z 112 $(M+H)^+$.

Example 111B tert-butyl 2-oxo-1-azaspiro[3.3]heptane-1-carboxylate

To a solution of di-tert-butyl dicarbonate (6.13 mL, 26.4 mmol), triethylamine (4.42 mL, 31.7 mmol), and 4-dimethylaminopyridine (0.323 g, 2.64 mmol) in $CH_2Cl_2$ (15 mL) was added a solution of Example 111A (2.936 g, 26.4 mmol) in $CH_2Cl_2$ (15 mL), and the reaction was stirred overnight at room temperature. After this time, the mixture was washed sequentially with 10% aqueous NH$_4$Cl solution, water, and saturated NaHCO$_3$ solution (10 mL each). The organic layer was dried over Na$_2$SO$_4$ and concentrated to afford the titled compound as a brown oil. $^1$H NMR (300 MHz, CDCl$_3$) δ ppm 3.01 (s, 2H), 2.84-2.95 (m, 2H), 2.11-2.19 (m, 2H), 1.73-1.91 (m, 2H), 1.55 (s, 9H); MS (ESI$^+$) m/z 228 (M+NH$_4$)$^+$.

Example 111C 2-(1-(tert-butoxycarbonylamino)cyclobutyl)acetic acid

A solution of Example 111B (5.435 g, 25.7 mmol) in tetrahydrofuran (23 mL) was treated with 1 M aqueous lithium hydroxide solution (25.7 mL, 25.7 mmol), and the reaction mixture was stirred at room temperature for 2 hours. Ether (23 mL) and water (23 mL) were added with continued stirring at room temperature overnight. After this time, the phases were separated. The aqueous (lower) layer was washed twice with ether (50 mL each), then it was acidified to pH ~2 with 10% aqueous NaHSO$_3$ solution. The beige and orange precipitate which formed was collected by filtration, washed with additional water, and air-dried to afford the titled compound. $^1$H NMR (300 MHz, CDCl$_3$) δ ppm 5.21 (br, 1H), 2.91 (m, 2H), 2.14-2.30 (m, 4H), 1.79-1.99 (m, 2H), 1.44 (s, 9H); MS (ESI$^+$) m/z 252 (M+Na)$^+$.

Example 111D tert-butyl 6,8-dioxo-5-azaspiro[3.5]nonane-5-carboxylate

The product from Example 111C (2.0 g, 8.72 mmol), 1-(3-dimethylaminopropyl)-3-ethylcarbodiimide hydrochloride (2.508 g, 13.08 mmol), 4-dimethylaminopyridine (1.599 g, 13.08 mmol), and Meldrum's acid (1.257 g, 8.72 mmol) were mixed in CH$_2$Cl$_2$ (40 mL), and the mixture was stirred overnight at room temperature. After this time, the mixture was poured into a mixture of 1 N HCl (32 mL) and water (160 mL). The phases were separated, and the aqueous layer was extracted twice more with CH$_2$Cl$_2$ (40 mL each). The combined organic phases were dried over Na$_2$SO$_4$ and concentrated in vacuo, then the residue was taken up in ethyl acetate (65 mL) and refluxed for 3 hours. After this time, the mixture was cooled to room temperature and concentrated to afford the titled compound as a yellow-orange waxy residue which was used directly in the next reaction without further purification.

Example 111E ethyl 4'-oxo-5',7'-dihydro-4'H-spiro[cyclobutane-1,6'-furo[3,2-c]pyridine]-3'-carboxylate The titled compound was prepared according to the procedure of Example 110D substituting the product from Example 111C for the product from Example 110C. $^1$H NMR (300 MHz, CDCl$_3$) δ ppm 7.89 (s, 1H), 5.52 (br, 1H), 4.34 (q, J=7.1 Hz, 2H), 3.09 (s, 2H), 2.12-2.22 (m, 4H), 1.73-1.86 (m, 2H), 1.36 (t, J=7.1 Hz, 3H); MS (DCI$^+$) m/z 250 (M+H)$^+$.

Example 111F

4'-oxo-5',7'-dihydro-4'H-spiro[cyclobutane-1,6'-furo[3,2-c]pyridine]-3'-carboxylic acid The titled compound was prepared according to the procedure of Example 110E substituting the product from Example 111E for the product from Example 110D. $^1$H NMR (300 MHz, CDCl$_3$) δ ppm 13.96 (s, 1H), 8.07 (s, 1H), 5.90 (br, 1H), 3.22 (s, 2H), 2.25-2.30 (m, 4H), 1.90-2.23 (m, 2H); MS (ESI$^+$) m/z 222 (M+H)$^+$.

Example 111G

N-[6-(4-acetylpiperazin-1-yl)-2-ethoxypyridin-3-yl]-4'-oxo-4',7'-dihydro-5'H-spiro[cyclobutane-1,6'-furo[3,2-c]pyridine]-3'-carboxamide The titled compound was prepared according to the procedure for Example 8B substituting the product of Example 111F for the product of Example 8A. $^1$H NMR (300 MHz, DMSO-d$_6$) δ ppm 11.89 (s, 1H), 8.50 (s, 1H), 8.27 (m, 1H), 8.24 (m, 1H), 6.35 (m, 1H), 4.33 (q, J=7.1 Hz, 2H), 3.37-3.56 (m, 8H), 3.22 (s, 3H), 2.06-2.27 (m, 6H), 2.04 (s, 3H), 1.72-1.85 (m, 2H), 1.35 (t, J=7.1 Hz, 3H); MS (ESI$^+$) m/z 468 (M+H)$^+$.

Example 112

N-[6-(4-acetylpiperazin-1-yl)-2-ethoxypyridin-3-yl]-4'-oxo-4',7'-dihydro-5'H-spiro[cyclohexane-1,6'-furo[3,2-c]pyridine]-3'-carboxamide

Example 112A ethyl 3-(1-(2-methoxy-2-oxoethyl)cyclohexylamino)-3-oxopropanoate A solution of methyl 2-(1-aminocyclohexyl)acetate hydrochloride (1 g, 4.81 mmol) and triethylamine (2.2 mL, 15.78 mmol) in CH$_2$Cl$_2$ (30 mL) at 0° C. was treated dropwise with ethyl malonyl chloride (0.59 mL, 4.61 mmol). After completion of the addition, the reaction mixture was brought to room temperature and stirred at this temperature for 1 hour. The mixture was then poured into saturated NaHCO$_3$ solution (50 mL) and extracted with CH$_2$Cl$_2$ three times (30 mL each). The combined organic extracts were dried over Na$_2$SO$_4$ and concentrated in vacuo to afford the titled compound as an orange oil which was used in the next reaction without further purification. $^1$H NMR (300 MHz, CDCl$_3$) δ ppm 6.95 (br, 1H), 4.21 (m, 2H), 3.63 (s, 3H), 3.27 (s, 2H), 2.86 (s, 2H), 1.35-1.62 (m, 10H), 1.30 (m, 3H); MS (DCI$^+$) m/z 286 (M+H)$^+$.

Example 112B methyl 2,4-dioxo-1-azaspiro[5.5]undecane-3-carboxylate

Sodium metal (0.106 g, 4.61 mmol) was dissolved in dry methanol (5.6 mL). Then a solution of Example 112A (1.315 g, 4.61 mmol) in dry toluene (17 mL) was added. The reaction mixture was refluxed for 1 hour, then cooled to room temperature and poured into water (50 mL). The mixture was washed three times with ether (20 mL each), and then the aqueous phase was acidified with 6 N HCl and concentrated in vacuo to dryness. The residue was further dried azeotropically with acetonitrile to afford the titled compound as a yellow gel-like residue, which was carried on into the next reaction without further purification.

Example 112C 1-azaspiro[5.5]undecane-2,4-dione

The product from Example 112B (1.103 g, 4.61 mmol) was refluxed in acetonitrile (18 mL) and water (2 mL) for 1 hour, then the mixture was cooled to room temperature and concentrated in vacuo. The residue was taken up in ethyl acetate-methanol (1:1, ~60 mL), and the white solid was removed by filtration. The yellow filtrate was concentrated in vacuo to afford the titled compound as a yellow residue, 1-azaspiro[5.5]undecane-2,4-dione (0.840 g, quantitative). $^1$H NMR (300 MHz, CDCl$_3$) δ ppm 6.37 (br, 1H), 3.25 (s, 2H), 2.60 (s, 2H), 1.40-1.90 (m, 10H); MS (DCI$^+$) m/z 182 (M+H)$^+$.

Example 112D ethyl 4'-oxo-5',7'-dihydro-4'H-spiro[cyclohexane-1,6'-furo[3,2-c]pyridine]-3'-carboxylate The titled compound was prepared according to the procedure for Example 110D substituting the product from Example 112C for the product from Example 110C. $^1$H NMR (300 MHz, CDCl$_3$) δ ppm 7.88 (s, 1H), 5.45 (br, 1H), 4.34 (q, J=7.1 Hz, 2H), 2.88 (s, 2H), 1.46-1.71 (m, 10H), 1.36 (t, J=7.1 Hz, 3H); MS (DCI$^+$) m/z 278 (M+H)$^+$.

Example 112E

4'-oxo-5',7'-dihydro-4'H-spiro[cyclohexane-1,6'-furo[3,2-c]pyridine]-3'-carboxylic acid The titled compound was prepared according to the procedure for Example 110E substituting the product from Example 112D for the product from Example 110D. $^1$H NMR (300 MHz, CDCl$_3$) δ ppm 14.11 (br, 1H), 8.06 (s, 1H), 5.92 (br, 1H), 3.01 (s, 2H), 1.47-1.80 (m, 10H); MS (ESI$^+$) m/z 250 (M+H)$^+$.

Example 112F

N-[6-(4-acetylpiperazin-1-yl)-2-ethoxypyridin-3-yl]-4'-oxo-4',7'-dihydro-5'H-spiro[cyclohexane-1,6'-furo[3,2-c]pyridine]-3'-carboxamide The titled compound was prepared according to the procedure of Example 8B substituting the product from Example 112E for the product from Example 8A. $^1$H NMR (300 MHz, DMSO-d$_6$) δ ppm 11.95 (s, 1H), 8.23-8.26 (m, 2H), 7.97 (s, 1H), 6.35 (m, 1H), 4.33 (q, J=7.1 Hz, 2H), 3.37-3.60 (m, 8H), 3.05 (s, 2H), 2.04 (s, 3H), 1.41-1.78 (m, 10H), 1.34 (t, J=7.1 Hz, 3H); MS (ESI$^+$) m/z 496 (M+H)$^+$.

Example 113

1-acetyl-N-[6-(4-acetylpiperazin-1-yl)-2-ethoxypyridin-3-yl]-4'-oxo-4',7'-dihydro-5'H-spiro[azetidine-3,6'-furo[3,2-c]pyridine]-3'-carboxamide

Example 113A tert-butyl 3-(2-methoxy-2-oxoethylidene)azetidine-1-carboxylate tert-Butyl 3-oxoazetidine-1-carboxylate (5 g, 29.2 mmol) and methoxycarbonylmethylene-triphenylphosphorane (10.25 g, 30.7 mmol) were mixed in toluene (15 mL), and the mixture was refluxed for 2.5 hour before being cooled to room temperature with continued stirring overnight. The precipitate was removed by filtration, and the filter pad was washed with ether. The combined filtrate and wash were concentrated, then the residue was chromatographed on silica gel (10 to 50% ethyl acetate-hexane, eluant) to afford the titled compound as a colorless oil, 5.532 g, (83%). $^1$H NMR (300 MHz, CDCl$_3$) δ ppm 5.79 (m, 1H), 4.80-4.84 (m, 2H), 4.58-4.61 (m, 2H), 3.73 (s, 3H), 1.46 (s, 9H); MS (ESI$^+$) m/z 228 (M+H)$^+$.

Example 113B tert-butyl 3-amino-3-(2-methoxy-2-oxoethyl)azetidine-1-carboxylate The product from Example 113A (2 g, 8.80 mmol) was heated in ammonia (2 M in ethanol) (22 mL, 44 mmol) at 120° C. in a sealed tube overnight. After cooling to room temperature, the mixture was concentrated in vacuo, and then chromatographed on silica gel (50 to 100% ethyl acetate-hexane, eluant) to afford the titled compound as a colorless oil, 2.062 g (96%). $^1$H NMR (300 MHz, CDCl$_3$) δ ppm 3.76-3.89 (m, 4H), 3.72 (s, 3H), 2.79 (s, 2H), 1.44 (s, 9H); MS (DCI$^+$) m/z 245 (M+H)$^+$.

Example 113C tert-butyl 3-(3-ethoxy-3-oxopropanamido)-3-(2-methoxy-2-oxoethyl)azetidine-1-carboxylate The titled compound was prepared according to the procedure for Example 112A substituting the product from Example 113B for methyl 2-(1-aminocyclohexyl)acetate hydrochloride. The material was used in the next reaction without further purification.

Example 113D 2-tert-butyl 7-methyl 6,8-dioxo-2,5-diazaspiro[3.5]nonane-2,7-dicarboxylate The titled compound was prepared according to the procedure of Example 112B substituting the product from Example 113C for the product of Example 112A. $^1$H NMR (300 MHz, CDCl$_3$) δ ppm 5.92 (br, 1H), 3.72 (s, 3H), 3.62-4.04 (m, 5H), 2.90 (m, 2H), 1.44 (s, 9H); MS (ESI$^+$) m/z 313 (M+H)$^+$.

Example 113E tert-butyl 6,8-dioxo-2,5-diazaspiro[3.5]nonane-2-carboxylate

The titled compound was prepared according to the procedure of Example 112C substituting the product of Example 113D for the product of Example 112B. $^1$H NMR (300 MHz, DMSO-d$_6$) δ ppm 3.57-3.95 (m, 6H), 3.06 (m, 2H), 1.37 (s, 9H); MS (ESI$^+$) m/z 255 (M+H)$^+$.

Example 113F 1-tert-butyl 3'-ethyl 4'-oxo-5',7'-dihydro-4'H-spiro[azetidine-3,6'-furo[3,2-c]pyridine]-1,3'-dicarboxylate The product of Example 113E (1.897 g, 7.46 mmol) in ethanol (30 mL) was treated with sodium bicarbonate (6.14 g, 73.1 mmol) and then ethyl bromopyruvate (1.13 mL, 8.95 mmol). The reaction mixture was stirred overnight at room temperature. After this time, the mixture was diluted with ethanol (50 mL) and filtered. The filtrate was concentrated to a dark green oil, which was then taken up in $CH_2Cl_2$ (80 mL) and treated with triethylamine (12 mL, 86.4 mmol). The mixture was cooled to 0° C., and then treated dropwise with methanesulfonyl chloride (4 mL, 51.6 mmol). After the addition was complete, the reaction mixture stirred at 0° C. for 1 hour, and then it was poured into water (100 mL). The mixture was extracted with $CH_2Cl_2$ (3×50 mL), then the extracts were dried over $Na_2SO_4$ and concentrated in vacuo. Chromatography on silica gel (40 to 100% ethyl acetate-hexane, eluant) afforded the titled compound as a tan solid, 0.296 g (11%). $^1$H NMR (300 MHz, DMSO-$d_6$) δ ppm 8.29 (s, 1H), 8.19 (br, 1H), 4.21 (q, J=7.2 Hz, 2H), 3.88 (m, 4H), 3.26 (s, 2H), 1.38 (s, 9%), 1.25 (t, J=7.1 Hz, 3H); MS (ESI$^+$) m/z 351 (M+H)$^+$.

Example 113G 1-(tert-butoxycarbonyl)-4'-oxo-5',7'-dihydro-4'H-spiro[azetidine-3,6'-furo[3,2-c]pyridine]-3'-carboxylic acid The titled compound was prepared according to the procedure of Example 110E substituting the product of Example 113F for the product of Example 110D. $^1$H NMR (300 MHz, DMSO-$d_6$) δ ppm 14.48 (s, 1H), 9.36 (s, 1H), 8.47 (s, 1H), 3.96 (m, 4H), 3.46 (m, 2H), 1.39 (s, 9H); MS (ESI$^+$) m/z 323 (M+H)$^+$.

Example 113H tert-butyl 3'-{[6-(4-acetylpiperazin-1-yl)-2-ethoxypyridin-3-yl]carbamoyl}-4'-oxo-4',7'-dihydro-1H,5'H-spiro[azetidine-3,6'-furo[3,2-c]pyridine]-1-carboxylate The titled compound was prepared according to the procedure of Example 8B substituting the product of Example of Example 113G for the product of Example 8A. $^1$H NMR (300 MHz, DMSO-$d_6$) δ ppm 11.76 (s, 1H), 8.79 (s, 1H), 8.26-8.32 (m, 2H), 6.35 (m, 1H), 4.33 (q, J=7.1 Hz, 2H), 3.93 (m, 4H), 3.40-3.55 (m, 10H), 2.04 (s, 3H), 1.39 (s, 9H), 1.36 (t, J=6.8 Hz, 3H); MS (ESI$^+$) m/z 569 (M+H)$^+$.

Example 113I

N-[6-(4-acetylpiperazin-1-yl)-2-ethoxypyridin-3-yl]-4'-oxo-4',7'-dihydro-5'H-spiro[azetidine-3,6'-furo[3,2-c]pyridine]-3'-carboxamide trifluoroacetate The product of Example 113H (0.040 g, 0.070 mmol) was stirred in trifluoroacetic acid (2 mL) at room temperature for 1 hour. After this time, the mixture was concentrated in vacuo, and the residue was dried under vacuum at 50° C. for 1 hour to provide the titled compound as a brown solid. $^1$H NMR (300 MHz, DMSO-$d_6$) δ ppm 11.64 (s, 1H), 8.71-8.96 (m, 3H), 8.29-8.37 (m, 2H), 6.35 (m, 1H), 4.34 (m, 2H), 3.38-3.78 (m, 14H), 2.04 (s, 3H), 1.36 (m, 3H); MS (ESI$^+$) m/z 469 (M+H)$^+$.

Example 113J 1-acetyl-N-[6-(4-acetylpiperazin-1-yl)-2-ethoxypyridin-3-yl]-4'-oxo-4',7'-dihydro-5'H-spiro[azetidine-3,6'-furo[3,2-c]pyridine]-3'-carboxamide A mixture of Example 113I (29 mg, 0.049 mmol), acetic acid (0.014 mL, 0.245 mmol), N,N-diisopropylethylamine (0.17 mL, 0.980 mmol), 1-(3-dimethylaminopropyl)-3-ethylcarbodiimide hydrochloride (12 mg, 0.064 mmol), and 1-hydroxybenzotriazole (7.5 mg, 0.049 mmol) in N,N-dimethylformamide (2 mL) was stirred overnight at room temperature. The mixture was then diluted with ethyl acetate (10 mL) and washed with water (4×2 mL). The organic layer was dried over $Na_2SO_4$ and concentrated in vacuo, and the residue was triturated with ethyl acetate to afford the titled compound as a tan solid, 3.5 mg (14%). $^1$H NMR (300 MHz, DMSO-$d_6$) δ ppm 11.76 (s, 1H), 8.84 (s, 1H), 8.27-8.33 (m, 2H), 6.35 (m, 1H), 4.33 (m, 2H), 3.33-3.57 (m, 14H), 2.04 (s, 3H), 1.77 (s, 3H), 1.36 (m, 3H); MS (ESI$^+$) m/z 511 (M+H)$^+$.

Example 114

N-[6-(4-acetylpiperazin-1-yl)-2-ethoxypyridin-3-yl]-4-oxo-4,7-dihydro-5H-spiro[furo[3,2-c]pyridine-6,3'-oxetane]-3-carboxamide Example 114A methyl 2-(oxetan-3-ylidene)acetate The titled compound was prepared according to the procedure of Example 113A substituting oxetan-3-one for tert-butyl 3-oxoazetidine-1-carboxylate. $^1$H NMR (300 MHz, CDCl$_3$) δ ppm 5.65 (m, 1H), 5.51 (m, 2H), 5.31 (m, 2H), 3.72 (s, 3H); MS (DCI$^+$) m/z 129 (M+H)$^+$.

Example 114B methyl 2-(3-aminooxetan-3-yl)acetate

The titled compound was prepared according to the procedure of Example 113B substituting the product of Example 114A for the product of Example 113A. $^1$H NMR (300 MHz, CDCl$_3$) δ ppm 4.50-4.57 (m, 4H), 3.72 (s, 3H), 2.90 (s, 2H); MS (DCI$^+$) m/z 146 (M+H)$^+$.

Example 114C ethyl 3-(3-(2-methoxy-2-oxoethyl)oxetan-3-ylamino)-3-oxopropanoate

The titled compound was prepared according to the procedure for Example 112A substituting the product from Example 114B for methyl 2-(1-aminocyclohexyl)acetate hydrochloride. $^1$H NMR (300 MHz, CDCl$_3$) δ ppm 7.74 (br, 1H), 4.57-4.77 (m, 4H), 4.21 (m, 2H), 3.29 (s, 2H), 2.88 (s, 2H), 1.29 (m, 3H); MS (ESI$^+$) m/z 260 (M+H)$^+$.

Example 114D methyl 6,8-dioxo-2-oxa-5-azaspiro[3.5]nonane-7-carboxylate

The titled compound was prepared according to the procedure of Example 112B substituting the product from Example 114C for the product of Example 112A. The compound was used in the next reaction without further purification.

Example 114E 2-oxa-5-azaspiro[3.5]nonane-6,8-dione

The titled compound was prepared according to the procedure of Example 112C substituting the product of Example 114D for the product of Example 112B. $^1$H NMR (300 MHz, CDCl$_3$) δ ppm 4.61-4.71 (m, 4H), 3.25 (s, 2H), 3.07 (s, 2H); MS (DCI$^+$) m/z 173 (M+NH$_4$).

Example 114F ethyl 4-oxo-5,7-dihydro-4H-spiro[furo[3,2-c]pyridine-6,3'-oxetane]-3-carboxylate The titled compound was prepared according to the procedure of Example 113F substituting the product from Example 114E for the product from Example 113E. $^1$H NMR (300 MHz, CDCl$_3$) δ ppm 7.92 (s, 1H), 5.83 (br, 1H), 4.57-4.68 (m, 4H), 4.35 (m, 2H), 3.41 (s, 2H), 1.36 (m, 3H); MS (ESI$^+$) m/z 252 (M+H)$^+$.

Example 114G 4-oxo-5,7-dihydro-4H-spiro[furo[3,2-c]pyridine-6,3'-oxetane]-3-carboxylic acid The titled compound was prepared according to the procedure of Example 110E substituting the product of Example 114F for the product of Example 110D. $^1$H NMR (300 MHz, CDCl$_3$) δ ppm 8.11 (s, 1H), 4.65-4.74 (m, 4H), 3.53 (s, 2H); MS (ESI$^+$) m/z 224 (M+H)$^+$.

Example 114H

N-[6-(4-acetylpiperazin-1-yl)-2-ethoxypyridin-3-yl]-4-oxo-4,7-dihydro-5H-spiro[furo[3,2-c]pyridine-6,3'-oxetane]-3-carboxamide The titled compound was prepared according to the procedure of Example 8B substituting the product of Example of Example 114G for the product of Example 8A. $^1$H NMR (300 MHz, DMSO-d$_6$) δ ppm 11.77 (s, 1H), 9.00 (s, 1H), 8.26-8.32 (m, 2H), 6.35 (m, 1H), 4.50-4.66 (m, 4H), 4.35 (m, 2H), 3.38-3.57 (m, 10H), 2.04 (s, 3H), 1.36 (m, 3H); MS (ESI$^+$) m/z 470 (M+H)$^+$.

Example 115

(6R)—N-[6-(4-acetylpiperazin-1-yl)-2-ethoxypyridin-3-yl]-6-[(1R)-1-hydroxyethyl]-4-oxo-4,5,6,7-tetrahydrofuro[3,2-c]pyridine-3-carboxamide Example 115A (R)-tert-butyl 2-((R)-1-(benzyloxy)ethyl)-4,6-dioxopiperidine-1-carboxylate (3R,4R)-4-(Benzyloxy)-3-(tert-butoxycarbonylamino) pentanoic acid (Aldrich; 1 g, 3.09 mmol), 2,2-dimethyl-1,3-dioxane-4,6-dione (Meldrum's acid) (0.490 g, 3.40 mmol), and 4-dimethylaminopyridine (0.567 g, 4.64 mmol) were mixed in CH$_2$Cl$_2$ (26 mL) and cooled to 0° C. 1-(3-Dimethylaminopropyl)-3-ethylcarbodiimide hydrochloride (0.711 g, 3.71 mmol) was added, and the reaction was stirred overnight at room temperature. The mixture was then washed with 5% aqueous sodium bisulfate (4×10 mL), and the organic layer was dried over Na$_2$SO$_4$ and concentrated. The crude material was taken up in ethyl acetate (25 mL) and refluxed for 4 hours, then cooled to room temperature and concentrated in vacuo to afford the titled compound as a yellow oil, 1.2 g (quantitative). $^1$H NMR (300 MHz, CDCl$_3$) δ ppm 7.21-7.37 (m, 5H), 4.74 (m, 1H), 4.26-4.52 (m, 2H), 3.58 (m, 1H), 3.10-3.40 (m, 2H), 2.56-2.75 (m, 2H), 1.54 (s, 9H), 1.22 (d, J=6.3 Hz, 3H); MS (ESI$^-$) m/z 347 (M–H).

Example 115B (R)-5-tert-butyl 3-ethyl 6-((R)-1-(benzyloxy)ethyl)-4-oxo-6,7-dihydrofuro[3,2-c]pyridine-3,5(4H)-dicarboxylate The titled compound was prepared according to the procedure of Example 113F substituting the product from Example 115A for the product from Example 113E. $^1$H NMR (300 MHz, DMSO-d$_6$) δ ppm 8.26 (s, 1H), 7.08-7.33 (m, 5H), 4.77 (m, 1H), 4.27-4.50 (m, 2H), 4.23 (m, 2H), 3.65 (m, 1H), 3.41 (m, 1H), 2.97 (m, 1H), 1.44 (s, 9H), 1.26 (m, 3H), 1.07 (d, J=6.3 Hz, 3H); MS (ESI$^+$) m/z 444 (M+H)$^+$.

Example 115C (R)-6-((R)-1-(benzyloxy)ethyl)-4-oxo-4,5,6,7-tetrahydrofuro[3,2-c]pyridine-3-carboxylic acid The titled compound was prepared according to the procedure of Example 110E substituting the product of Example 115B for the product of Example 110D. $^1$H NMR (300 MHz, CDCl$_3$) δ ppm 8.05 (s, 1H), 7.25-7.47 (m, 5H), 4.41-4.76 (m, 2H), 3.87 (m, 1H), 3.62 (m, 1H), 3.35 (m, 1H), 2.92 (m, 1H), 1.31 (d, J=6.1 Hz, 3H); MS (ESI$^+$) m/z 316 (M+H)$^+$.

Example 115D (6R)—N-[6-(4-acetylpiperazin-1-yl)-2-ethoxypyridin-3-yl]-6-[(1R)-1-(benzyloxy)ethyl]-4-oxo-4,5,6,7-tetrahydrofuro[3,2-c]pyridine-3-carboxamide The titled compound was prepared according to the procedure of Example 8B substituting the product of Example of Example 115C for the product of Example 8A. $^1$H NMR (300 MHz, DMSO-d$_6$) δ ppm 11.91 (s, 1H), 8.24-8.27 (m, 2H), 7.83 (m, 1H), 7.23-7.34 (m, 5H), 6.35 (m, 1H), 4.44-4.59 (m, 2H), 4.33 (q, J=6.8 Hz, 2H), 3.90 (m, 1H), 3.67 (m, 1H), 3.41-3.56 (m, 8H), 2.91-3.16 (m, 2H), 2.04 (s, 3H), 1.34 (t, J=7.1 Hz, 3H), 1.16 (d, J=6.1 Hz, 3H); MS (ESI$^+$) m/z 562 (M+H)$^+$.

Example 115E (6R)—N-[6-(4-acetylpiperazin-1-yl)-2-ethoxypyridin-3-yl]-6-[(1R)-1-hydroxyethyl]-4-oxo-4,5,6,7-tetrahydrofuro[3,2-c]pyridine-3-carboxamide The product from Example 115D (0.010 g, 0.018 mmol) in tetrahydrofuran (1 mL) was hydrogenated (balloon) over 10% palladium on carbon at room temperature overnight. After this time, the catalyst was removed by filtration, and the filtrate was concentrated in vacuo. The residue was purified by reverse-phase HPLC (Phenomenex® Luna® C8(2) 5 μm 100 Å AXIA™ column (30 mm×75 mm); acetonitrile (A) and 0.1% trifluoroacetic acid in water (B) eluant; 20 to 50% (A), gradient; flow rate=50 mL/minute) to afford the trifluoroacetate salt of the titled compound as an off-white solid. $^1$H NMR (300 MHz, DMSO-d$_6$) δ ppm 11.92 (s, 1H), 8.24-8.27 (m, 2H), 7.57 (s, 1H), 6.34 (s, 1H), 4.33 (q, J=7.1 Hz, 2H), 3.53-3.75 (m, 10H), 2.84-3.09 (m, 2H), 2.04 (s, 3H), 1.35 (t, J=7.1 Hz, 3H), 1.07 (d, J=5.7 Hz, 3H); MS (ESI$^+$) m/z 472 (M+H)$^+$.

Example 116

N-[6-(4-acetylpiperazin-1-yl)-2-ethoxypyridin-3-yl]-5'-(2-hydroxyethyl)-4'-oxo-4',7'-dihydro-5'H-spiro [cyclobutane-1,6'-furo[3,2-c]pyridine]-3'-carboxamide

Example 116A

5'-(2-(benzyloxy)ethyl)-4'-oxo-5',7'-dihydro-4'H-spiro[cyclobutane-1,6'-furo[3,2-c]pyridine]-3'-carboxylic acid A solution of the product of Example 111F (0.150 g, 0.678 mmol) in N,N-dimethylformamide (2 mL) was treated with 60% sodium hydride (0.060 g, 1.492 mmol) at room temperature. The mixture stirred at room temperature for 15 minutes and was then treated with a solution of ((2-bromoethoxy)methyl)benzene (0.438 g, 2.034 mmol) in N,N-dimethylformamide (0.5 mL). The reaction mixture was stirred overnight at room temperature. After this time, the mixture was partitioned between ether (20 mL) and 0.5 N HCl (10 mL). The phases were separated, and the ether layer was washed with additional 0.5 N HCl (2×5 mL) and then with brine (5 mL). The organic layer was dried over Na$_2$SO$_4$ and concentrated in vacuo, and the residue was chromatographed on silica gel (0 to 10% ethyl acetate-CH$_2$Cl$_2$, eluant) to afford the titled compound as a colorless oil, 0.099 g (41%). $^1$H NMR (300 MHz, DMSO-d$_6$) δ ppm 8.40 (m, 1H), 7.25-7.34 (m, 5H), 4.50 (s, 2H), 4.02 (m, 2H), 3.86 (m, 2H), 3.55 (m, 2H), 1.70-1.99 (m, 6H); MS (ESI$^+$) m/z 356 (M+H)$^+$.

Example 116B

N-[6-(4-acetylpiperazin-1-yl)-2-ethoxypyridin-3-yl]-5'-[2-(benzyloxy)ethyl]-4'-oxo-4',7'-dihydro-5'H-spiro[cyclobutane-1,6'-furo[3,2-c]pyridine]-3'-carboxamide The titled compound was prepared according to the procedure of Example 8B substituting the product of Example of Example 116A for the product of Example 8A. $^1$H NMR (300 MHz, DMSO-d$_6$) δ ppm 11.98 (s, 1H), 8.28-8.35 (m, 2H), 7.27-7.34 (m, 5H), 6.33 (m, 1H), 4.53 (s, 2H), 4.30 (q, J=6.8 Hz, 2H), 3.87 (m, 2H), 3.23-3.60 (m, 12H), 2.04 (s, 3H), 1.74-2.05 (m, 6H), 1.38 (t, J=7.2 Hz, 3H); MS (ESI$^+$) m/z 602 (M+H)$^+$.

Example 116C

N-[6-(4-acetylpiperazin-1-yl)-2-ethoxypyridin-3-yl]-5'-(2-hydroxyethyl)-4'-oxo-4',7'-dihydro-5'H-spiro [cyclobutane-1,6'-furo[3,2-c]pyridine]-3'-carboxamide The titled compound was prepared according to the procedure of Example 9 substituting the product of Example 116B for the product of Example 8B. $^1$H NMR (300 MHz, DMSO-d$_6$) δ ppm 12.00 (s, 1H), 8.28-8.31 (m, 2H), 6.33 (m, 1H), 4.78 (m, 1H), 4.31 (q, J=7.2 Hz, 2H), 3.71 (m, 2H), 3.37-3.55 (m, 12H), 2.04 (s, 3H), 1.72-2.06 (m, 6H), 1.39 (t, J=7.1 Hz, 3H); MS (ESI$^+$) m/z 512 (M+H)$^+$.

Example 117

N-[6-(4-acetylpiperazin-1-yl)-2-ethoxypyridin-3-yl]-4'-oxo-4',7'-dihydro-5'H-spiro[cyclopropane-1,6'-furo[3,2-c]pyridine]-3'-carboxamide

Example 117A tert-butyl 1-(bromomethyl)cyclopropylcarbamate

A mixture of tert-butyl 1-(hydroxymethyl)cyclopropylcarbamate (CAS#107017-73-2; 5 g, 26.7 mmol), triphenylphosphine (9.5 g, 36.2 mmol), and carbon tetrabromide (11.9 g, 35.9 mmol) in ether (120 mL) was stirred at room temperature for 24 hours. After this time, the mixture was filtered, and the filtrate was concentrated in vacuo. The residue was chromatographed on silica gel (0 to 10% ethyl acetate-CH$_2$Cl$_2$, eluant) to afford the titled compound as a white solid, 3.594 g (54%). $^1$H NMR (300 MHz, CDCl$_3$) δ ppm 5.11 (br, 1H), 3.58 (s, 2H), 1.45 (s, 9H), 1.07 (m, 2H), 0.91 (m, 2H); MS (DC) m/z 250/252 (M+H$^+$; $^{79}$Br/$^{81}$Br).

Example 117B tert-butyl 1-(cyanomethyl)cyclopropylcarbamate

The product from Example 117A (3.594 g, 14.37 mmol), sodium cyanide (3.45 g, 70.4 mmol), and potassium iodide (0.286 g, 1.724 mmol) were stirred in dimethyl sulfoxide (33 mL) at room temperature for 72 hours. After this time, the mixture was poured into 10% aqueous Na$_2$CO$_3$ solution (60 mL) containing some NaCl. The mixture was extracted with ether (3×150 mL), then the combined ethereal extracts were washed with water (25 mL) and brine (25 mL), dried over Na$_2$SO$_4$, and concentrated in vacuo. The residue was chromatographed on silica gel (20 to 100% ethyl acetate-hexane, eluant) to afford the titled compound as a white solid, 1.737 g (62%). $^1$H NMR (300 MHz, CDCl$_3$) δ ppm 5.13 (br, 1H), 2.72 (s, 2H), 1.45 (s, 9H), 0.93 (m, 2H), 0.87 (m, 2H); MS (DCI$^+$) m/z 197 (M+H)$^+$.

Example 117C methyl 2-(1-aminocyclopropyl)acetate

A solution of the product from Example 117B (4.049 g, 20.63 mmol) in methanol (75 mL) was cooled to 0° C., then HCl gas was bubbled through the solution at a moderately strong rate for 15 minutes. The mixture was allowed to stir while slowly warming to ambient temperature overnight. After this time, volatiles were removed in vacuo. The residue was treated with a saturated solution of Na$_2$CO$_3$ (25 mL) and was extracted three times with CH$_2$Cl$_2$ (30 mL each). The combined extracts were dried over Na$_2$SO$_4$ and concentrated in vacuo, then the residue was chromatographed on silica gel (1 to 10% methanol-CH$_2$Cl$_2$, eluant) to yield the titled compound as a pale yellow oil (0.971 g, 36%). $^1$H NMR (300 MHz, CDCl$_3$) δ ppm 3.72 (s, 3H), 2.43 (s, 2H), 0.68 (m, 2H), 0.51 (m, 2H); MS (DCI$^+$) m/z 130 (M+H)$^+$.

Example 117D ethyl 3-(1-(2-methoxy-2-oxoethyl)cyclopropylamino)-3-oxopropanoate The titled compound was prepared according to the procedure for Example 112A substituting the product from Example 117C for methyl 2-(1-aminocyclohexyl)acetate hydrochloride. ¹H NMR (300 MHz, CDCl₃) δ ppm 4.19 (q, J=7.2 Hz, 2H), 3.69 (s, 3H), 3.23 (s, 2H), 2.62 (s, 2H), 1.28 (t, J=7.1 Hz, 3H), 0.88 (m, 2H), 0.79 (m, 2H); MS (ESI⁺) m/z 244 (M+H)⁺.

Example 117E methyl 5,7-dioxo-4-azaspiro[2.5]octane-6-carboxylate

The titled compound was prepared according to the procedure of Example 112B substituting the product from Example 117D for the product of Example 112A. ¹H NMR (300 MHz, CDCl₃) δ ppm 8.67 (br, 1H), 3.96 (m, 1H), 3.92 (s, 3H), 2.60-2.66 (m, 2H), 0.80 (m, 2H), 0.77 (m, 2H); MS (DCI⁺) m/z 198 (M+H)⁺.

Example 117F 4-azaspiro[2.5]octane-5,7-dione

The titled compound was prepared according to the procedure of Example 112C substituting the product of Example 117E for the product of Example 112B. ¹H NMR (300 MHz, CDCl₃) δ ppm 8.66 (br, 1H), 3.43 (s, 2H), 2.52 (s, 2H), 0.96 (m, 2H), 0.85 (m, 2H); MS (DCI⁺) m/z 140 (M+H)⁺.

Example 117G ethyl 4'-oxo-5',7'-dihydro-4'H-spiro[cyclopropane-1, 6'-furo[3,2-c]pyridine]-3'-carboxylate The titled compound was prepared according to the procedure of Example 113F substituting the product from Example 117F for the product from Example 113E. ¹H NMR (300 MHz, CDCl₃) δ ppm 7.90 (s, 1H), 5.16 (br, 1H), 4.35 (q, J=7.1 Hz, 2H), 2.90 (s, 2H), 1.36 (t, J=7.1 Hz, 3H), 0.81-0.85 (m, 4H); MS (ESI⁺) m/z 236 (M+H)⁺.

Example 117H

4'-oxo-5',7'-dihydro-4'H-spiro[cyclopropane-1,6'-furo[3,2-c]pyridine]-3'-carboxylic acid The titled compound was prepared according to the procedure of Example 110E substituting the product of Example 117G for the product of Example 110D. ¹H NMR (300 MHz, CDCl₃) δ ppm 13.98 (s, 1H), 8.10 (s, 1H), 5.57 (br, 1H), 3.03 (s, 2H), 0.92-0.99 (m, 4H); MS (ESI⁺) m/z 208 (M+H)⁺.

Example 117I

N-[6-(4-acetylpiperazin-1-yl)-2-ethoxypyridin-3-yl]-4'-oxo-4',7'-dihydro-5'H-spiro[cyclopropane-1,6'-furo[3,2-c]pyridine]-3'-carboxamide The titled compound was prepared according to the procedure of Example 8B substituting the product of Example 117H for the product of Example 8A. ¹H NMR (300 MHz, DMSO-d₆) δ ppm 11.92 (s, 1H), 8.20-8.29 (m, 3H), 6.35 (m, 1H), 4.33 (q, J=6.8 Hz, 2H), 3.37-3.58 (m, 8H), 3.03 (s, 2H), 2.04 (s, 3H), 1.34 (t, J=7.1 Hz, 3H), 0.87 (m, 2H), 0.79 (m, 2H); MS (ESI⁺) m/z 454 (M+H)⁺.

Example 118

N-{6-[4-(N'-cyano-N-methylcarbamimidoyl)piperazin-1-yl]-2-ethoxypyridin-3-yl}-4'-oxo-4',7'-dihydro-5'H-spiro[cyclobutane-1,6'-furo[3,2-c]pyridine]-3'-carboxamide Example 118A tert-butyl 4-(6-ethoxy-5-{[(4'-oxo-4',7'-dihydro-5'H-spiro[cyclobutane-1,6'-furo[3,2-c]pyridin]-3'-yl)carbonyl]amino}pyridin-2-yl)piperazine-1-carboxylate The titled compound was prepared according to the procedure for Example 8B substituting the product of Example 92C for 1-(4-(5-amino-6-ethoxypyridin-2-yl)piperazin-1-yl)ethanone and the product of Example 111F for the product from Example 8A. ¹H NMR (300 MHz, DMSO-d₆) δ ppm 11.88 (s, 1H), 8.50 (s, 1H), 8.23-8.28 (m, 2H), 6.33 (m, 1H), 4.33 (q, J=7.1 Hz, 2H), 3.42 (m, 8H), 3.22 (s, 2H), 2.05-2.27 (m, 4H), 1.70-1.85 (m, 2H), 1.42 (s, 9H), 1.34 (t, J=7.2 Hz, 3H); MS (ESI⁺) m/z 526 (M+H)⁺.

Example 118B

N-[2-ethoxy-6-(piperazin-1-yl)pyridin-3-yl]-4'-oxo-4',7'-dihydro-5'H-spiro[cyclobutane-1,6'-furo[3,2-c]pyridine]-3'-carboxamide The titled compound was prepared as the trifluoroacetate according to the procedure of Example 93A substituting the product of Example 118A for the product of Example 92D. The resulting trifluoroacetate salt was used in the next reaction without further purification.

Example 118C

N-{6-[4-(N'-cyano-N-methylcarbamimidoyl)piperazin-1-yl]-2-ethoxypyridin-3-yl}-4'-oxo-4',7'-dihydro-5'H-spiro[cyclobutane-1,6'-furo[3,2-c]pyridine]-3'-carboxamide The titled compound was prepared according to the procedure of Example 93B substituting the product of Example 118B for the product of Example 93A. ¹H NMR (300 MHz, DMSO-d₆) δ ppm 11.90 (s, 1H), 8.52 (s, 1H), 8.26 (m, 2H), 7.33 (m, 1H), 6.36 (m, 1H), 4.34 (q, J=7.1 Hz, 2H), 3.47-3.55 (m, 8H), 3.22 (s, 2H), 2.87 (d, J=4.3 HZ, 3H), 2.22 (m, 2H), 2.08 (m, 2H), 1.79 (m, 2H), 1.35 (t, J=6.7 Hz, 3H); MS (ESI⁺) m/z 507 (M+H)⁺.

Example 119

N-[6-(4-acetylpiperazin-1-yl)-2-ethoxypyridin-3-yl]-5-(2,3-dihydroxypropyl)-6,6-dimethyl-4-oxo-4,5,6,7-tetrahydrofuro[3,2-c]pyridine-3-carboxamide Example 119A 5-allyl-6,6-dimethyl-4-oxo-4,5,6,7-tetrahydrofuro[3,2-c]pyridine-3-carboxylic acid A solution of the product from Example 120A (1 g, 4.78 mmol) in N,N-dimethylformamide (15 mL) was treated with 60% dispersion of sodium hydride in mineral oil (0.574 g, 14.34 mmol), and the mixture was stirred at room temperature for 15 minutes. It was then treated with allyl bromide (1.24 mL, 14.34 mmol), stirred at room temperature for 15 minutes, then heated to 50° C. overnight. The mixture was cooled to room temperature, treated with 1 M NaOH (15 mL), and stirred at room temperature for 30 minutes. It was diluted with water (60 mL) and washed with ether (2×50 mL). The aqueous (basic) layer was acidified with concentrated HCl and a white solid formed. The solid was collected by filtration, washed with ether, and dried under vacuum (ambient temperature) to afford the titled compound, 646 mg (54%). $^1$H NMR (300 MHz, CDCl$_3$) δ ppm 14.68 (s, 1H), 8.05 (s, 1H), 5.89 (m, 1H), 5.19-5.27 (m, 2H), 4.19 (m, 2H), 3.01 (s, 2H), 1.48 (s, 6H); MS (ESI$^+$) m/z 250 (M+H)$^+$.

Example 119B

N-[6-(4-acetylpiperazin-1-yl)-2-ethoxypyridin-3-yl]-5-allyl-6,6-dimethyl-4-oxo-4,5,6,7-tetrahydrofuro[3,2-c]pyridine-3-carboxamide The titled compound was prepared according to the procedure of Example 8B substituting the product of Example 119A for the product of Example 8A. $^1$H NMR (300 MHz, CDCl$_3$) δ ppm 12.10 (s, 1H), 8.56 (m, 1H), 8.07 (s, 1H), 6.18 (m, 1H), 5.94 (m, 1H), 5.14-5.28 (m, 2H), 4.40 (q, J=7.2 Hz, 2H), 4.18 (m, 2H), 3.73 (m, 2H), 3.42-3.59 (m, 6H), 2.95 (s, 2H), 2.14 (s, 3H), 1.49 (t, J=7.1 Hz, 3H), 1.44 (s, 6H); MS (ESI$^+$) 496 (M+H)$^+$.

Example 119C

N-[6-(4-acetylpiperazin-1-yl)-2-ethoxypyridin-3-yl]-5-(2,3-dihydroxypropyl)-6,6-dimethyl-4-oxo-4,5,6,7-tetrahydrofuro[3,2-c]pyridine-3-carboxamide A solution of the product of Example 119B (0.269 g, 0.543 mmol) in acetonitrile (20 mL) and tert-butyl alcohol (5 mL) was treated with 4-methylmorpholine N-oxide (50% weight solution in water) (0.16 mL, 0.772 mmol) and then osmium tetroxide (4% weight solution in water) (0.05 mL, 7.87 μmol). The reaction mixture was stirred overnight at room temperature. After this time, the mixture was treated with Na$_2$SO$_3$ (200 mg), stirred for 1 hour, and then filtered through a pad of Na$_2$SO$_3$. The filtrate was concentrated in vacuo to yield a brown oil, which was purified by reverse-phase HPLC (Phenomenex® Luna® C8(2) 5 μm 100 Å AXIA™ column (30 mm×75 mm); acetonitrile (A) and 0.1% trifluoroacetic acid in water (B) eluant; 20 to 50% (A), gradient; flow rate=50 mL/minute) to afford the titled compound (0.119 g, 41%). $^1$H NMR (300 MHz, DMSO-d$_6$) δ ppm 12.09 (s, 1H), 8.37 (m, 1H), 8.28 (s, 1H), 6.33 (m, 1H), 4.32 (q, J=7.1 Hz, 2H), 3.22-3.56 (m, 13H), 3.09 (m, 2H), 2.04 (s, 3H), 1.45 (s, 3H), 1.38 (t, J=7.1 Hz, 3H), 1.35 (s, 3H); MS (ESI$^+$) m/z 530 (M+H)$^+$.

Example 120

N-[2-methoxy-4-(piperazin-1-yl)phenyl]-6,6-dimethyl-4-oxo-4,5,6,7-tetrahydrofuro[3,2-c]pyridine-3-carboxamide Example 120A 6,6-dimethyl-4-oxo-4,5,6,7-tetrahydrofuro[3,2-c]pyridine-3-carboxylic acid To a suspension of 6,6-dimethylpiperidine-2,4-dione (CAS#: 5239-39-4, 2 g, 14.17 mmol) in water (10 mL) was added KOH (1.033 g, 18.42 mmol). The mixture became homogeneous and was cooled in an ice bath before a solution of 3-bromo-2-oxopropanoic acid (2.84 g, 17.00 mmol) in methanol (10 mL) was added dropwise. The mixture was stirred for about 2 hours and concentrated under reduced pressure. Water (20 mL) was added, and the mixture was acidified with 37% HCl and heated to reflux for 2 hours. The mixture was cooled (with stirring) and diluted with ether. The solid was collected by filtration, washed with H$_2$O and ether, and dried. The product 6,6-dimethyl-4-oxo-4,5,6,7-tetrahydrofuro[3,2-c]pyridine-3-carboxylic acid (955 mg, 4.57 mmol, 32.2% yield) was obtained as a brownish solid.

Example 120B tert-butyl 4-(4-{[(6,6-dimethyl-4-oxo-4,5,6,7-tetrahydrofuro[3,2-c]pyridin-3-yl)carbonyl]amino}-3-methoxyphenyl)piperazine-1-carboxylate The titled compound was prepared using the procedure described for Example 5 substituting Example 120A for Example 1E.

Example 120C

N-[2-methoxy-4-(piperazin-1-yl)phenyl]-6,6-dimethyl-4-oxo-4,5,6,7-tetrahydrofuro[3,2-c]pyridine-3-carboxamide The titled compound was prepared using the procedure described for Example 6 substituting Example 120B for Example 5. $^1$H NMR (300 MHz, CDCl$_3$) δ ppm 11.65 (s, 1H), 8.33-8.18 (m, 1H), 8.10 (s, 1H), 6.67-6.36 (m, 2H), 5.32 (s, 1H), 3.91 (s, 3H), 3.13 (dd, J=6.5, 3.1 Hz, 4H), 3.04 (dd, J=6.5, 3.2 Hz, 4H), 2.94 (s, 2H), 1.43 (s, 6H); MS (DCI) m/z 499 (M+H)$^+$.

Example 121

N-{2-methoxy-6-[4-(morpholin-4-ylcarbonyl)piperazin-1-yl]pyridin-3-yl}-6,6-dimethyl-4-oxo-4,5,6,7-tetrahydrofuro[3,2-c]pyridine-3-carboxamide Example 121A 6-chloro-2-methoxy-3-nitropyridine To a solution of methanol (1.929 mL, 47.7 mmol) in xylene (200 mL) was added NaH (2.479 g, 60% dispersed in oil, 62.0 mmol) and the mixture was stirred at 0° C. for 30 minutes. Then, 2,6-dichloro-3-nitropyridine (10 g, 92% 47.7 mmol) in xylene (200 mL) was added over 30 minutes. The mixture was stirred at ambient temperature for 16 hours. The mixture was then diluted with ether (200 mL), quenched with H$_2$O, and partitioned. The aqueous layer was extracted with additional ether. The organic washes were combined, washed with brine, dried (MgSO$_4$) and concentrated under reduced pressure. The residue was passed through a short silica gel pad to provide the titled compound.

Example 121B tert-butyl 4-(6-methoxy-5-nitropyridin-2-yl)piperazine-1-carboxylate To a solution of the product from Example 121A, 6-chloro-2-methoxy-3-nitropyridine, (8.86 g, 47 mmol) and tert-butyl piperazine-1-carboxylate (11.38 g, 61.1 mmol) in N,N-dimethylformamide (60 mL) was added triethylamine (9.17 mL, 65.8 mmol). The mixture was heated to 50° C. for 1 hour and then cooled to room temperature. The reaction mixture was diluted with ether (150 mL) and water (100 mL), and the product precipitated as a yellow solid. The product was collected by filtration and washed with water and small amount of ether to provide the titled compound.

Example 121C tert-butyl 4-(5-amino-6-methoxypyridin-2-yl)piperazine-1-carboxylate To a solution of Example 121B, tert-butyl 4-(6-methoxy-5-nitropyridin-2-yl)piperazine-1-carboxylate (21.9 g, 64.7 mmol) in methanol (300 mL) under a nitrogen atmosphere was added Raney®-nickel (~3.8 g, Aldrich, W.R. Grace and Co. Raney® 2800, slurry in $H_2O$). The atmosphere in the reaction vessel was exchanged with hydrogen, and the reaction was stirred at ambient temperature for 5 hours. The atmosphere was exchanged with nitrogen and the mixture was filtered and washed with methanol. The filtrate was concentrated under reduced pressure to provide the titled compound.

Example 121D tert-butyl 4-(5-{[(6,6-dimethyl-4-oxo-4,5,6,7-tetrahydrofuro[3,2-c]pyridin-3-yl)carbonyl]amino}-6-methoxypyridin-2-yl)piperazine-1-carboxylate The titled compound was prepared using the procedure described for Example 5 substituting Example 120A for Example 1E, and substituting Example 121C for tert-butyl 4-(4-amino-3-methoxyphenyl)piperazine-1-carboxylate.

Example 121E

N-[2-methoxy-6-(piperazin-1-yl)pyridin-3-yl]-6,6-dimethyl-4-oxo-4,5,6,7-tetrahydrofuro[3,2-c]pyridine-3-carboxamide The titled compound was prepared using the procedure described for Example 6 substituting Example 121D for Example 5.

Example 121F

N-{2-methoxy-6-[4-(morpholin-4-ylcarbonyl)piperazin-1-yl]pyridin-3-yl}-6,6-dimethyl-4-oxo-4,5,6,7-tetrahydrofuro[3,2-c]pyridine-3-carboxamide The titled compound was prepared using the procedure described for Example 18 substituting Example 121E for Example 6, and substituting 4-morpholinecarbonyl chloride for acetyl chloride. $^1$H NMR (300 MHz, CDCl$_3$) δ ppm 11.80-11.57 (m, 1H), 8.59-8.42 (m, 1H), 8.19-7.96 (m, 1H), 6.48-6.18 (m, 1H), 5.50-5.25 (m, 1H), 4.00 (s, 3H), 3.76-3.65 (m, 4H), 3.48 (dt, J=14.7, 4.5 Hz, 8H), 3.35-3.28 (m, 4H), 2.94 (d, J=8.7 Hz, 2H), 1.44 (s, 6H); MS (ESI) m/z 513 (M+H)$^+$.

Example 122

N-[6-(4-acetylpiperazin-1-yl)-2-methoxypyridin-3-yl]-6,6-dimethyl-4-oxo-4,5,6,7-tetrahydrofuro[3,2-c]pyridine-3-carboxamide The titled compound was prepared using the procedure described for Example 18 substituting Example 121E for Example 6. $^1$H NMR (300 MHz, CDCl$_3$) δ ppm 11.84-11.63 (m, 1H), 8.62-8.44 (m, 1H), 8.22-8.01 (m, 1H), 6.55-6.35 (m, 1H), 5.48-5.32 (m, 1H), 4.01 (d, J=1.5 Hz, 3H), 3.89-3.76 (m, 2H), 3.72-3.63 (m, 2H), 3.49 (ddd, J=14.0, 9.3, 3.2 Hz, 3H), 2.95 (s, 2H), 2.15 (d, J=3.8 Hz, 3H), 1.44 (s, 5H); MS (DCI) m/z 459 (M+NH$_4$)$^+$.

Example 123

N-{2-methoxy-6-[4-(pyrrolidin-1-ylcarbonyl)piperazin-1-yl]pyridin-3-yl}-6,6-dimethyl-4-oxo-4,5,6,7-tetrahydrofuro[3,2-c]pyridine-3-carboxamide The titled compound was prepared using the procedure described for Example 18 substituting Example 121E for Example 6 and substituting 1-pyrrolidinecarbonyl chloride for acetyl chloride. $^1$H NMR (300 MHz, CDCl$_3$) δ ppm 11.77-11.56 (m, 1H), 8.59-8.37 (m, 1H), 8.17-7.99 (m, 1H), 6.34-6.09 (m, 1H), 5.42-5.33 (m, 1H), 4.00 (s, 3H), 3.57-3.35 (m, 8H), 2.95 (s, 2H), 1.89-1.76 (m, 4H), 1.43 (s, 6H); MS (DCI) m/z 514 (M+NH$_4$)$^+$.

Example 124

N-[2-methoxy-4-(piperazin-1-yl)phenyl]-6-methyl-4-oxo-4,5,6,7-tetrahydrofuro[3,2-c]pyridine-3-carboxamide Example 124A 6-methyl-4-oxo-4,5,6,7-tetrahydrofuro[3,2-c]pyridine-3-carboxylic acid The titled compound was prepared using the procedure described for Example 120A substituting 6-methylpiperidine-2,4-dione (CAS#: 118263-99-3) for 6,6-dimethylpiperidine-2,4-dione.

Example 124B tert-butyl 4-(3-methoxy-4-{[(6-methyl-4-oxo-4,5,6,7-tetrahydrofuro[3,2-c]pyridin-3-yl)carbonyl]amino}phenyl)piperazine-1-carboxylate The titled compound was prepared using the procedure described for Example 5 substituting Example 124A for Example 1E.

Example 124C

N-[2-methoxy-4-(piperazin-1-yl)phenyl]-6-methyl-4-oxo-4,5,6,7-tetrahydrofuro[3,2-c]pyridine-3-carboxamide The titled compound was prepared using the procedure described for Example 6 substituting Example 124B for Example 5. $^1$H NMR (500 MHz, DMSO-d$_6$) δ ppm 11.89 (s, 1H), 8.24 (s, 1H), 8.07 (s, 1H), 7.91 (dd, J=14.0, 8.9 Hz, 1H), 6.59 (d, J=2.5 Hz, 1H), 6.45 (dd, J=8.9, 2.6 Hz, 1H), 4.01-3.85 (m, 1H), 3.79 (s, 3H), 3.14-3.04 (m, 1H), 3.03 (dd, J=5.9, 4.0 Hz, 4H), 2.86-2.79 (m, 4H), 2.74 (dd, J=16.8, 10.4 Hz, 1H), 1.27 (t, J=6.4 Hz, 3H); MS (DCI) m/z 385 (M+H)$^+$.

Example 125

N-{2-methoxy-4-[4-(methylsulfonyl)piperazin-1-yl]phenyl}-6,6-dimethyl-4-oxo-4,5,6,7-tetrahydrofuro[3,2-c]pyridine-3-carboxamide The titled compound was prepared using the procedure described for Example 18 substituting Example 120 for Example 6, and substituting methanesulfonyl chloride for acetyl chloride. $^1$H NMR (300 MHz, DMSO-d$_6$) δ ppm 11.97 (s, 1H), 8.33-8.20 (m, 1H), 8.11 (s, 1H), 7.97 (t, J=8.8 Hz, 1H), 6.67 (d, J=2.5 Hz, 1H), 6.59-6.46 (m, 1H), 3.82 (d, J=8.8 Hz, 3H), 3.25 (s, 8H), 2.96 (d, J=12.8 Hz, 2H), 2.93 (s, 3H), 1.31 (s, 6H); MS (DCI) m/z 477 (M+H)$^+$.

Example 126

N-[4-(4-acetylpiperazin-1-yl)-2-methoxyphenyl]-6,6-dimethyl-4-oxo-4,5,6,7-tetrahydrofuro[3,2-c]pyridine-3-carboxamide The titled compound was prepared using the procedure described for Example 18 substituting Example 120 for Example 6. $^1$H NMR (300 MHz, CDCl$_3$) δ ppm 11.68 (s, 1H), 8.29 (d, J=8.8 Hz, 1H), 8.10 (d, J=4.2 Hz, 1H), 6.53 (d, J=7.4 Hz, 2H), 5.50 (s, 1H), 3.92 (s, 3H), 3.79 (s, 2H), 3.63 (s, 2H), 3.23-3.07 (m, 4H), 2.95 (s, 2H), 2.14 (s, 3H), 1.44 (s, 6H); MS (DCI) m/z 458 (M+NH$_4$)$^+$.

Example 127

N-[2-ethoxy-6-(piperazin-1-yl)pyridin-3-yl]-6,6-dimethyl-4-oxo-4,5,6,7-tetrahydrofuro[3,2-c]pyridine-3-carboxamide

Example 127A tert-butyl 4-(4-{[(6,6-dimethyl-4-oxo-4,5,6,7-tetrahydrofuro[3,2-c]pyridin-3-yl)carbonyl]amino}-3-ethoxyphenyl)piperazine-1-carboxylate The titled compound was prepared using the procedure described for Example 5 substituting Example 120A for Example 1E and substituting Example 92C for tert-butyl 4-(4-amino-3-methoxyphenyl)piperazine-1-carboxylate.

Example 127B

N-[2-ethoxy-6-(piperazin-1-yl)pyridin-3-yl]-6,6-dimethyl-4-oxo-4,5,6,7-tetrahydrofuro[3,2-c]pyridine-3-carboxamide The titled compound was prepared using the procedure described for Example 6 substituting Example 127D for Example 5. $^1$H NMR (300 MHz, CDCl$_3$) δ ppm 11.79-11.54 (s, 1H), 8.49 (d, J=8.6 Hz, 1H), 8.09 (s, 1H), 6.17 (d, J=8.6 Hz, 1H), 5.39 (s, 1H), 4.43 (q, J=7.0 Hz, 2H), 3.56-3.38 (m, 4H), 3.12-3.01 (m, 4H), 2.94 (s, 3H), 1.55-1.30 (m, 9H); MS (DCI) m/z 414 (M+H)$^+$.

Example 128

N-[6-(4-acetylpiperazin-1-yl)-2-ethoxypyridin-3-yl]-6,6-dimethyl-4-oxo-4,5,6,7-tetrahydrofuro[3,2-c]pyridine-3-carboxamide The titled compound was prepared using the procedure described for Example 18 substituting Example 127 for Example 6. $^1$H NMR (300 MHz, CDCl$_3$) δ ppm 11.68 (s, 1H), 8.50 (d, J=8.6 Hz, 1H), 8.09 (s, 1H), 6.18 (d, J=8.6 Hz, 1H), 5.39 (s, 1H), 4.43 (d, J=7.1 Hz, 2H), 3.74 (s, 2H), 3.63-3.54 (m, 2H), 3.53-3.39 (m, 4H), 2.94 (s, 2H), 2.14 (s, 3H), 1.43 (s, 9H); MS (ESI) m/z 456 (M+H)$^+$.

Example 129

N-{6-[(3 aR,6aR)-hexahydropyrrolo[3,4-b]pyrrol-5(1H)-yl]-2-isopropoxypyridin-3-yl}-6,6-dimethyl-4-oxo-4,5,6,7-tetrahydrofuro[3,2-c]pyridine-3-carboxamide

Example 129A 6-chloro-2-isopropoxy-3-nitropyridine

The titled compound was prepared using the procedure described for Example 121A substituting isopropyl alcohol for methanol.

Example 129B tert-butyl(3aR,6aR)-5-(6-isopropoxy-5-nitropyridin-2-yl)hexahydropyrrolo[3,4-b]pyrrole-1(2H)-carboxylate The titled compound was prepared using the procedure described for Example 121B substituting Example 129A for Example 121A and substituting (3aR,6aR)-tert-butyl hexahydropyrrolo[3,4-b]pyrrole-1(2H)-carboxylate (MFCD12198661, CAS#370880-09-4) for tert-butyl piperazine-1-carboxylate.

Example 129C tert-butyl(3aR,6aR)-5-(5-amino-6-isopropoxypyridin-2-yl)hexahydropyrrolo[3,4-b]pyrrole-1(2H)-carboxylate The titled compound was prepared using the procedure described for Example 121C substituting Example 129B for Example 121B.

Example 129D tert-butyl(3aR,6aR)-5-(5-{[(6,6-dimethyl-4-oxo-4,5,6,7-tetrahydrofuro[3,2-c]pyridin-3-yl)carbonyl]amino}-6-isopropoxypyridin-2-yl)hexahydropyrrolo[3,4-b]pyrrole-1(2H)-carboxylate The titled compound was prepared using the procedure described for Example 5 substituting Example 120A for Example 1E, and substituting Example 129C for tert-butyl 4-(4-amino-3-methoxyphenyl)piperazine-1-carboxylate.

Example 129E

N-{6-[(3 aR,6aR)-hexahydropyrrolo[3,4-b]pyrrol-5 (1H)-yl]-2-isopropoxypyridin-3-yl}-6,6-dimethyl-4-oxo-4,5,6,7-tetrahydrofuro[3,2-c]pyridine-3-carboxamide The titled compound was prepared using the procedure described for Example 6 substituting Example 129D for Example 5. $^1$H NMR (300 MHz, CDCl$_3$) δ ppm 11.56 (s, 1H), 8.42 (d, J=8.5 Hz, 1H), 8.09 (s, 1H), 5.90 (d, J=8.5 Hz, 1H), 5.37 (s, 1H), 5.41-5.23 (m, 1H), 4.10 (t, J=5.9 Hz, 1H), 3.57 (ddd, J=15.2, 10.6, 8.5 Hz, 1H), 3.32 (dd, J=10.6, 4.5 Hz, 1H), 3.14 (dtd, J=16.5, 11.1, 5.5 Hz, 1H), 3.03-2.83 (m, 1H), 2.14 (dt, J=20.5, 7.7 Hz, 1H), 1.81 (dt, J=12.4, 5.9 Hz, 1H), 1.43 (s, 1H), 1.39 (dd, J=6.2, 2.1 Hz, 1H); MS (DCI) m/z 454 (M+H)$^+$.

Example 130

N-{2-methoxy-6-[(3aR,6aR)-5-methylhexahydropyrrolo[3,4-b]pyrrol-1 (2H)-yl]pyridin-3-yl}-6,6-dimethyl-4-oxo-4,5,6,7-tetrahydrofuro[3,2-c]pyridine-3-carboxamide

Example 130A tert-butyl(3aR,6aR)-1-(6-methoxy-5-nitropyridin-2-yl)hexahydropyrrolo[3,4-b]pyrrole-5(1H)-carboxylate The titled compound was prepared using the procedure described for Example 121B substituting tert-butyl(3aR,6aR)-hexahydropyrrolo[3,4-b]pyrrole-5(1H)-carboxylate (CAS#370882-39-6, which can be prepared according U.S. Patent Application Publication Number 2005101602A1) for tert-butyl piperazine-1-carboxylate.

Example 130B tert-butyl(3aR,6aR)-1-(5-amino-6-methoxypyridin-2-yl)hexahydropyrrolo[3,4-b]pyrrole-5(1H)-carboxylate The titled compound was prepared using the procedure described for Example 121C substituting Example 130A for Example 121B.

Example 130C tert-butyl(3aR,6aR)-1-(5-{[(6,6-dimethyl-4-oxo-4,5,6,7-tetrahydrofuro[3,2-c]pyridin-3-yl)carbonyl]amino}-6-methoxypyridin-2-yl)hexahydropyrrolo[3,4-b]pyrrole-5(1H)-carboxylate The titled compound was prepared using the procedure described for Example 121D substituting Example 130B for Example 121C.

Example 130D

N-{6-[(3aR,6aR)-hexahydropyrrolo[3,4-b]pyrrol-1 (2H)-yl]-2-methoxypyridin-3-yl}-6,6-dimethyl-4-oxo-4,5,6,7-tetrahydrofuro[3,2-c]pyridine-3-carboxamide The titled compound was prepared using the procedure described for Example 6 substituting Example 130C for Example 5.

Example 130E

N-{2-methoxy-6-[(3aR,6aR)-5-methylhexahydropyrrolo[3,4-b]pyrrol-1(2H)-yl]pyridin-3-yl}6,6-dimethyl-4-oxo-4,5,6,7-tetrahydrofuro[3,2-c]pyridine-3-carboxamide To a solution of Example 130D, N-{6-[(3aR,6aR)-hexahydropyrrolo[3,4-b]pyrrol-1(2H)-yl]-2-methoxypyridin-3-yl}-6,6-dimethyl-4-oxo-4,5,6,7-tetrahydrofuro[3,2-c]pyridine-3-carboxamide (70 mg, 0.165 mmol) in methanol (5 mL) was added formaldehyde (24 μL, 0.329 mmol) and a few drops of acetic acid. The resultant mixture was stirred for 5 minutes. Then sodium triacetoxyhydroborate (69.7 mg, 0.329 mmol) was added, and the mixture was stirred at room temperature for 2 hours. The mixture was diluted with ethyl acetate (10 mL) and washed with H$_2$O and brine. The organic layer was dried (MgSO$_4$), filtered and concentrated under reduced pressure. The residue was chromatographed on silica gel eluting with NH$_4$OH (29%)/methanol/CH$_2$Cl$_2$ (0.3/3/97) to provide the titled compound. $^1$H NMR (300 MHz, CDCl$_3$) δ ppm 11.67-11.52 (m, 1H), 8.39 (d, J=8.5 Hz, 1H), 8.08 (s, 1H), 5.94 (d, J=8.5 Hz, 1H), 5.35 (s, 1H), 4.60-4.35 (m, 1H), 3.97 (s, 3H), 3.64-3.51 (m, 1H), 3.51-3.36 (m, 1H), 3.19-3.01 (m, 1H), 2.94 (s, 2H), 2.74-2.32 (m, 5H), 2.27-2.08 (m, 2H), 2.07-1.86 (m, 2H), 1.43 (s, 6H); MS (DCI) m/z 440 (M+H)$^+$.

Example 131

N-{6-[(3aS,6aS)-1-(2-hydroxyethyl)hexahydropyrrolo[3,4-b]pyrrol-5(1H)-yl]-2-isopropoxypyridin-3-yl}-6,6-dimethyl-4-oxo-4,5,6,7-tetrahydrofuro[3,2-c]pyridine-3-carboxamide

Example 131A tert-butyl(3aS,6aS)-5-(6-isopropoxy-5-nitropyridin-2-yl)hexahydropyrrolo[3,4-b]pyrrole-1(2H)-carboxylate The titled compound was prepared using the procedure described for Example 121B substituting Example 129A for Example 121A, and substituting tert-butyl(3aS,6aS)-hexahydropyrrolo[3,4-b]pyrrole-1(2H)-carboxylate (CAS#: 185693-02-1) for tert-butyl piperazine-1-carboxylate.

Example 131B tert-butyl(3aS,6aS)-5-(5-amino-6-isopropoxypyridin-2-yl)hexahydropyrrolo[3,4-b]pyrrole-1(2H)-carboxylate The titled compound was prepared using the procedure described for Example 121C substituting Example 131A for Example 121B.

Example 131C tert-butyl(3aS,6aS)-5-(5-{[(6,6-dimethyl-4-oxo-4,5,6,7-tetrahydrofuro[3,2-c]pyridin-3-yl)carbonyl]amino}-6-isopropoxypyridin-2-yl)hexahydropyrrolo[3,4-b]pyrrole-1(2H)-carboxylate The titled compound was prepared using the procedure described for Example 5 substituting Example 120A for Example 1E and substituting Example 131B for tert-butyl 4-(4-amino-3-methoxyphenyl)piperazine-1-carboxylate.

Example 131D

N-{6-[(3aS,6aS)-hexahydropyrrolo[3,4-b]pyrrol-5(1H)-yl]-2-isopropoxypyridin-3-yl}-6,6-dimethyl-4-oxo-4,5,6,7-tetrahydrofuro[3,2-c]pyridine-3-carboxamide The titled compound was prepared using the procedure described for Example 6 substituting Example 131C for Example 5.

Example 131E

N-{6-[(3aS,6aS)-1-(2-hydroxyethyl)hexahydropyrrolo[3,4-b]pyrrol-5(1H)-yl]-2-isopropoxypyridin-3-yl}-6,6-dimethyl-4-oxo-4,5,6,7-tetrahydrofuro[3,2-c]pyridine-3-carboxamide To a solution of Example 131D, N-{6-[(3aS,6aS)-hexahydropyrrolo[3,4-b]pyrrol-5(1H)-yl]-2-isopropoxypyridin-3-yl}-6,6-dimethyl-4-oxo-4,5,6,7-tetrahydrofuro[3,2-c]pyridine-3-carboxamide (25 mg, 0.055 mmol) in N,N-dimethylformamide (5 mL) was added 2-bromoethanol (13.8 mg, 0.11 mmol) and triethylamine (0.032 mL, 0.22 mmol) at room temperature, and the mixture was stirred for 16 hours. The mixture was diluted with ethyl acetate (10 mL) and washed with H$_2$O and brine. The organic layer was dried (MgSO$_4$), filtered and concentrated under reduced pressure. The residue was chromatographed on silica gel eluting with NH$_4$OH (29%)/methanol/CH$_2$Cl$_2$ (0.4/4/96) to provide the titled compound. $^1$H NMR (300 MHz, CDCl$_3$) δ ppm 11.61 (s, 1H), 8.48 (d, J=11.9 Hz, 1H), 8.06 (s, 1H), 5.98 (d, J=4.1 Hz, 1H), 5.28 (m, 2H), 3.94 (d, J=40.7 Hz, 3H), 3.49 (d, J=34.1 Hz, 4H), 3.20 (d, J=48.3 Hz, 4H), 2.94 (s, 2H), 2.45 (m, 1H), 2.06 (m, 2H), 1.47-1.35 (m, 12H); MS (DCI) m/z 498 (M+H)$^+$.

Example 132

N-{2-isopropoxy-6-[(3aR,6aR)-1-[(4-methylpiperazin-1-yl)carbonyl]hexahydropyrrolo[3,4-b]pyrrol-5(1H)-yl]pyridin-3-yl}-6,6-dimethyl-4-oxo-4,5,6,7-tetrahydrofuro[3,2-c]pyridine-3-carboxamide The titled compound was prepared using the procedure described for Example 18 substituting Example 129 for Example 6, and substituting 4-methylpiperazine-1-carbonyl chloride for acetyl chloride. $^1$H NMR (300 MHz, CDCl$_3$) δ ppm 11.53 (s, 1H), 8.40 (d, J=17.2 Hz, 1H), 8.07 (s, 1H), 5.91 (d, J=8.5 Hz, 1H), 5.30 (m, 2H), 3.98 (m, 1H), 3.51 (m, 3H), 3.24 (m, 1H), 3.09 (m, 1H), 2.97 (m, 2H), 2.93 (s, 2H), 2.02 (m, 1H), 1.73 (m, 6H), 1.41 (m, 12H); MS (ESI) m/z 580 (M+H)$^+$.

Example 133

N-{6-[(3S)-4-acetyl-3-(hydroxymethyl)piperazin-1-yl]-2-isopropoxypyridin-3-yl}-6,6-dimethyl-4-oxo-4,5,6,7-tetrahydrofuro[3,2-c]pyridine-3-carboxamide

Example 133A 1-tert-butyl 2-methyl(2S)-4-(6-isopropoxy-5-nitropyridin-2-yl)piperazine-1,2-dicarboxylate The titled compound was prepared using the procedure described for Example 121B substituting Example 129A for Example 121A, and substituting (S)-1-tert-butyl 2-methyl piperazine-1,2-dicarboxylate (CAS#: 796096-64-5) for tert-butyl piperazine-1-carboxylate.

Example 133B 1-tert-butyl 2-methyl(2S)-4-(5-amino-6-isopropoxypyridin-2-yl)piperazine-1,2-dicarboxylate The titled compound was prepared using the procedure described for Example 121C substituting Example 133A for Example 121B.

Example 133C 1-tert-butyl 2-methyl(2S)-4-(5-{[(6,6-dimethyl-4-oxo-4,5,6,7-tetrahydrofuro[3,2-c]pyridin-3-yl)carbonyl]amino}-6-isopropoxypyridin-2-yl)piperazine-1,2-dicarboxylate The titled compound was prepared using the procedure described for Example 5 substituting Example 120A for Example 1E and substituting Example 133B for tert-butyl 4-(4-amino-3-methoxyphenyl)piperazine-1-carboxylate.

Example 133D tert-butyl(2S)-4-(5-{[(6,6-dimethyl-4-oxo-4,5,6,7-tetrahydrofuro[3,2-c]pyridin-3-yl)carbonyl]amino}-6-isopropoxypyridin-2-yl)-2-(hydroxymethyl)piperazine-1-carboxylate A solution of Example 133C (370 mg, 0.632 mmol) in anhydrous tetrahydrofuran (20 mL) was chilled with an ice bath. Lithium aluminum hydride (0.95 mL, 1 M in tetrahydrofuran) was added, and the mixture was stirred for 16 hours. The mixture was quenched with H$_2$O/1 N NaOH/H$_2$O (0.04 mL/0.04 mL/0.12 mL), sequentially. The mixture was stirred for 10 minutes, and then it was filtered and washed with additional ethyl acetate. The filtrate was concentrated under reduced pressure. The resulting residue was chromatographed on silica gel eluting with (0-10%) methanol/ethyl acetate to provide the titled compound.

Example 133E

N-{6-[(3S)-3-(hydroxymethyl)piperazin-1-yl]-2-isopropoxypyridin-3-yl}-6,6-dimethyl-4-oxo-4,5,6,7-tetrahydrofuro[3,2-c]pyridine-3-carboxamide The titled compound was prepared using the procedure described for Example 6 substituting Example 133D for Example 5.

Example 133F

N-{6-[(3S)-4-acetyl-3-(hydroxymethyl)piperazin-1-yl]-2-isopropoxypyridin-3-yl}-6,6-dimethyl-4-oxo-4,5,6,7-tetrahydrofuro[3,2-c]pyridine-3-carboxamide The titled compound was prepared using the procedure described for Example 18 substituting Example 133E for Example 6. $^1$H NMR (300 MHz, CDCl$_3$) δ ppm 11.53 (s, 1H), 8.50 (d, J=8.5 Hz, 1H), 8.08 (s, 1H), 6.13 (d, J=8.5 Hz, 1H), 5.25 (d, J=30.0 Hz, 2H), 4.77 (d, J=26.1 Hz, 1H), 4.58-4.37 (m, 1H), 4.32-4.16 (m, 1H), 4.07-3.93 (m, 2H), 3.89-3.62 (m, 3H), 3.63-3.45 (m, 1H), 2.94 (s, 2H), 3.13-2.88 (m, 3H), 2.17 (s, 3H), 1.44 (s, 12H); MS (ESI) m/z 500 (M+H)$^+$.

Example 134

N-{6-[(2S)-4-acetyl-2-(hydroxymethyl)piperazin-1-yl]-2-isopropoxypyridin-3-yl}-6,6-dimethyl-4-oxo-4,5,6,7-tetrahydrofuro[3,2-c]pyridine-3-carboxamide The titled compound was prepared using the procedure described for Example 133 substituting (S)-1-tert-butyl 3-methyl piperazine-1,3-dicarboxylate (CAS#: 314741-39-4) for (S)-1-tert-butyl 2-methyl piperazine-1,2-dicarboxylate (CAS#: 796096-64-5) in Example 133A. $^1$H NMR (300 MHz, CDCl$_3$) δ ppm 11.64 (s, 1H), 8.49 (d, J=13.4 Hz, 1H), 8.06 (s, 1H), 6.12 (d, J=13.4 Hz, 1H), 5.37-5.12 (m, 2H), 4.73-4.33 (m, 1H), 3.94-3.55 (m, 3H), 3.55-3.38 (m, 2H), 3.22-2.97 (m, 2H), 2.94 (s, 2H), 2.19 (s, 3H), 1.45-1.36 (m, 12H); MS (ESI) m/z 500 (M+H)$^+$.

Example 135

N-{6-[(2S)-2-(hydroxymethyl)-4-(morpholin-4-ylcarbonyl)piperazin-1-yl]-2-isopropoxypyridin-3-yl}-6,6-dimethyl-4-oxo-4,5,6,7-tetrahydrofuro[3,2-c]pyridine-3-carboxamide

Example 135A

N-{6-[(2S)-2-(hydroxymethyl)piperazin-1-yl]-2-isopropoxypyridin-3-yl}-6,6-dimethyl-4-oxo-4,5,6,7-tetrahydrofuro[3,2-c]pyridine-3-carboxamide The titled compound was prepared using the procedure described for Example 133A through 133E substituting (S)-1-tert-butyl 3-methyl piperazine-1,3-dicarboxylate (CAS#: 314741-39-4) for (S)-1-tert-butyl 2-methyl piperazine-1,2-dicarboxylate (CAS#:) in Example 133A.

Example 135B

N-{6-[(2S)-2-(hydroxymethyl)-4-(morpholin-4-ylcarbonyl)piperazin-1-yl]-2-isopropoxypyridin-3-yl}-6,6-dimethyl-4-oxo-4,5,6,7-tetrahydrofuro[3,2-c]pyridine-3-carboxamide The titled compound was prepared using the procedure described for Example 18 substituting Example 135A for Example 6 and substituting 1-morphorline-1-carbonyl chloride for acetyl chloride. $^1$H NMR (300 MHz, CDCl$_3$) δ ppm 11.62 (s, 1H), 8.48 (d, J=8.6 Hz, 1H), 8.06 (s, 1H), 6.11 (d, J=8.7 Hz, 1H), 5.26 (m, 2H), 4.51-4.38 (m, 1H), 4.21-4.08 (m, 1H), 3.85-3.57 (m, 8H), 3.44-3.05 (m, 8H), 2.93 (s, 2H), 1.43 (s, 6H), 1.40 (dd, J=6.2, 2.0 Hz, 6H); MS (ESI) m/z 571 (M+H)$^+$.

Example 136

N-{6-[(3S)-3-(dimethylamino)pyrrolidin-1-yl]-2-isopropoxypyridin-3-yl}-6,6-dimethyl-4-oxo-4,5,6,7-tetrahydrofuro[3,2-c]pyridine-3-carboxamide

Example 136A 6-chloro-2-isopropoxypyridin-3-amine

The titled compound was prepared according the procedure described for Example 121C substituting Example 129A for Example 121B.

Example 136B

N-(6-chloro-2-isopropoxypyridin-3-yl)-6,6-dimethyl-4-oxo-4,5,6,7-tetrahydrofuro[3,2-c]pyridine-3-carboxamide The titled compound was prepared using the procedure described for Example 5 substituting Example 120A for Example 1E, and substituting Example 136A for tert-butyl 4-(4-amino-3-methoxyphenyl)piperazine-1-carboxylate.

Example 136C

N-{6-[(3S)-3-(dimethylamino)pyrrolidin-1-yl]-2-isopropoxypyridin-3-yl}-6,6-dimethyl-4-oxo-4,5,6,7-tetrahydrofuro[3,2-c]pyridine-3-carboxamide A mixture of Example 136B (80 mg, 0.212 mmol), (S)—N,N-dimethylpyrrolidin-3-amine (48.4 mg, 0.423 mmol), 2'-(dicyclohexylphosphino)-N,N-dimethylbiphenyl-2-amine (8.3 mg, 0.021 mmol), tris(dibenzylideneacetone)dipalladium(0) (10 mg, 0.011 mmol) and potassium tert-butoxide (36 mg, 0.32 mmol) in anhydrous toluene (3 mL) was sparged with nitrogen, sealed in a microwave reactor vessel, and heated under microwave irradiation (CEM Discover S™, maximum 300 W) to 150° C. for 20 minutes. The mixture was cooled to ambient temperature, filtered through a layer of filtering aid, and washed with ethyl acetate. The filtrate was concentrated under reduced pressure. The residue was chromatographed on silica gel eluting with NH$_4$OH (29%)/methanol/CH$_2$Cl$_2$ (0.3/3/97) to provide the titled compound. $^1$H NMR (300 MHz, CDCl$_3$) δ ppm 11.49 (s, 1H), 8.42 (d, J=8.5 Hz, 1H), 8.07 (s, 1H), 5.85 (d, J=8.5 Hz, 1H), 5.40-5.23 (m, 2H), 3.82-3.55 (m, 2H), 3.38 (td, J=10.1, 6.9 Hz, 1H), 3.22 (d, J=8.8 Hz, 1H), 2.93 (s, 2H), 2.89-2.75 (m, 1H), 2.32 (s, 6H), 2.25-2.09 (m, 1H), 1.97-1.80 (m, 1H), 1.43 (s, 6H), 1.40 (d, J=6.3 Hz, 6H); MS (ESI) m/z 456 (M+H)$^+$.

Example 137

N-{6-[(3S)-3-(hydroxymethyl)piperidin-1-yl]-2-isopropoxypyridin-3-yl}-6,6-dimethyl-4-oxo-4,5,6,7-tetrahydrofuro[3,2-c]pyridine-3-carboxamide

Example 137A (S)-ethyl 1-(6-isopropoxy-5-nitropyridin-2-yl)piperidine-3-carboxylate The titled compound was prepared using the procedure described for Example 121B substituting Example 129A for Example 121A, and substituting ethyl(3S)-piperidine-3-carboxylate (CAS#: 37675-18-6) for tert-butyl piperazine-1-carboxylate.

Example 137B (5)-ethyl 1-(5-amino-6-isopropoxypyridin-2-yl)piperidine-3-carboxylate The titled compound was prepared using the procedure described for Example 121C substituting Example 137A for Example 121B.

Example 137C ethyl(3S)-1-(5-{[(6,6-dimethyl-4-oxo-4,5,6,7-tetrahydrofuro[3,2-c]pyridine-3-yl)carbonyl]amino}-6-isopropoxypyridin-2-yl)piperidine-3-carboxylate The titled compound was prepared using the procedure described for Example 5 substituting Example 120A for Example 1E, and substituting Example 137B for tert-butyl 4-(4-amino-3-methoxyphenyl)piperazine-1-carboxylate.

Example 137D

N-{6-[(3S)-3-(hydroxymethyl)piperidin-1-yl]-2-isopropoxypyridin-3-yl}-6,6-dimethyl-4-oxo-4,5,6,7-tetrahydrofuro[3,2-c]pyridine-3-carboxamide The titled compound was prepared using the procedure described for Example 133D substituting Example 137C for Example 133C. $^1$H NMR (300 MHz, CDCl$_3$) δ ppm 11.57 (s, 1H), 8.46 (d, J=8.6 Hz, 1H), 8.07 (s, 1H), 6.18 (d, J=8.7 Hz, 1H), 5.29 (p, J=6.2 Hz, 1H), 5.29 (s, 1H), 3.98 (dd, J=27.4, 12.1 Hz, 2H), 3.58 (d, J=6.4 Hz, 2H), 3.07-2.85 (m, 3H), 2.95 (s, 2H), 1.80 (dd, J=22.8, 18.5 Hz, 4H), 1.43 (s, 6H), 1.40 (dd, J=6.2, 2.7 Hz, 6H); MS (ESI) m/z 457 (M+H)$^+$.

Example 138

N-{6-[(3R)-4-acetyl-3-(hydroxymethyl)piperazin-1-yl]-2-isopropoxypyridin-3-yl}-6,6-dimethyl-4-oxo-4,5,6,7-tetrahydrofuro[3,2-c]pyridine-3-carboxamide The titled compound was prepared using the procedure described for Example 133 substituting (R)-1-tert-butyl 2-methyl piperazine-1,2-dicarboxylate (CAS#: 252990-05-9) for (5)-1-tert-butyl 2-methyl piperazine-1,2-dicarboxylate in Example 133A. $^1$H NMR (300 MHz, CDCl$_3$) δ ppm 11.65 (s, 1H), 8.51 (d, J=8.6 Hz, 1H), 8.08 (s, 1H), 6.15 (d, J=8.6 Hz, 1H), 5.37-5.16 (m, 2H), 4.58-4.37 (m, 1H), 4.27-3.95 (m, 2H), 3.84-3.67 (m, 3H), 3.63-3.47 (m, 1H), 3.16-2.95 (m, 2H), 2.94 (s, 2H), 2.18 (s, 2H), 1.44 (s, 6H), 1.41 (d, J=6.2 Hz, 6H); MS (ESI) m/z 500 (M+H)$^+$.

Example 139

N-{6-[(2R)-4-acetyl-2-(hydroxymethyl)piperazin-1-yl]-2-isopropoxypyridin-3-yl}-6,6-dimethyl-4-oxo-4,5,6,7-tetrahydrofuro[3,2-c]pyridine-3-carboxamide The titled compound was prepared using the procedure described for Example 133 substituting (R)-1-tert-butyl 3-methyl piperazine-1,3-dicarboxylate (CAS#: 438631-77-7) for (S)-1-tert-butyl 2-methyl piperazine-1,2-dicarboxy-late in Example 133A. $^1$H NMR (300 MHz, CDCl$_3$) δ ppm 11.65 (s, 1H), 8.50 (d, J=12.8 Hz, 1H), 8.08 (s, 1H), 6.13 (d, J=12.6 Hz, 1H), 5.37-5.12 (m, 2H), 4.76-4.30 (m, 2H), 3.95-3.56 (m, 3H), 3.55-3.36 (m, 2H), 3.21-2.97 (m, 2H), 2.94 (s, 2H), 2.19 (s, 3H), 1.43 (s, 26), 1.40 (dd, J=6.1, 2.5 Hz, 6H); MS (ESI) m/z 500 (M+H)$^+$.

Example 140

N-{6-[bis(2-hydroxyethyl)amino]-2-isopropoxypyridin-3-yl}-6,6-dimethyl-4-oxo-4,5,6,7-tetrahydrofuro[3,2-c]pyridine-3-carboxamide Example 140A 2,2'-((6-isopropoxy-5-nitropyridin-2-yl)azanediyl)diethanol The titled compound was prepared using the procedure described for Example 121B substituting Example 129A for Example 121A, and substituting diethanolamine for tert-butyl piperazine-1-carboxylate.

Example 140B 2,2'-((5-amino-6-isopropoxypyridin-2-yl)azanediyl)diethanol

The titled compound was prepared using the procedure described for Example 121C substituting Example 140A for Example 121B.

Example 140C

N-{6-[bis(2-hydroxyethyl)amino]-2-isopropoxypyridin-3-yl}-6,6-dimethyl-4-oxo-4,5,6,7-tetrahydrofuro[3,2-c]pyridine-3-carboxamide The titled compound was prepared using the procedure described for Example 5 substituting Example 120A for Example 1E, and substituting Example 140B for tert-butyl 4-(4-amino-3-methoxyphenyl)piperazine-1-carboxylate. $^1$H NMR (300 MHz, CDCl$_3$) δ ppm 11.58 (s, 1H), 8.42 (d, J=8.7 Hz, 1H), 8.08 (s, 1H), 6.06 (d, J=8.7 Hz, 1H), 5.31 (s, 1H), 5.26-5.07 (m, 1H), 3.90 (t, J=5.0 Hz, 4H), 3.68 (t, J=5.0 Hz, 4H), 2.93 (s, 2H), 1.43 (s, 6H), 1.39 (d, J=6.1 Hz, 6H); MS (ESI) m/z 447 (M+H)$^+$.

Example 141

N-[2,6-bis(2-methoxyethoxy)pyridin-3-yl]-6,6-dimethyl-4-oxo-4,5,6,7-tetrahydrofuro[3,2-c]pyridine-3-carboxamide Example 141A 6-(2-methoxyethoxy)-N-(2-methoxyethyl)-5-nitropyridin-2-amine To a solution of 2-methoxyethanol (0.165 mL, 2.1 mmol) in tetrahydrofuran (20 mL) was added NaH (0.103 g, 60% dispersed in mineral oil, 2.57 mmol) at 0° C., and the mixture was stirred at 0° C. for 25 minutes. Then a solution of 2,6-dichloro-3-nitropyridine (200 mg, 0.95 mmol) in tetrahydrofuran (10 mL) was added slowly, and the mixture was stirred overnight at room temperature. The mixture was then diluted with ether (50 mL) and quenched with H$_2$O, and the organic layer was separated. The aqueous layer was extracted with additional ether. The combined organic layers were washed with brine, dried with MgSO$_4$, filtered and concentrated under reduced pressure to provide the titled compound.

Example 141B 2,6-bis(2-methoxyethoxy)pyridin-3-amine

The titled compound was prepared using the procedure described for Example 121C substituting Example 141A for Example 121B.

Example 141C

N-[2,6-bis(2-methoxyethoxy)pyridin-3-yl]-6,6-dimethyl-4-oxo-4,5,6,7-tetrahydrofuro[3,2-c]pyridine-3-carboxamide The titled compound was prepared using the procedure described for Example 5 substituting Example 120A for Example 1E, and substituting Example 141B for tert-butyl 4-(4-amino-3-methoxyphenyl)piperazine-1-carboxylate. $^1$H NMR (300 MHz, CDCl$_3$) δ ppm 11.73 (s, 1H), 8.58 (d, J=12.9 Hz, 1H), 8.07 (s, 1H), 6.37 (d, J=8.5 Hz, 1H), 5.35 (s, 1H), 4.60-4.49 (m, 2H), 4.45-4.35 (m, 2H), 3.93-3.80 (m, 2H), 3.77-3.68 (m, 2H), 3.43 (s, 6H), 2.94 (s, 2H), 1.43 (s, 6H); MS (ESI) m/z 434 (M+H)$^+$.

Example 142

N-{6-[(3S)-4-acetyl-3-(methoxymethyl)piperazin-1-yl]-2-(2-hydroxy-2-methylpropoxy)pyridin-3-yl}-6,6-dimethyl-4-oxo-4,5,6,7-tetrahydrofuro[3,2-c]pyridine-3-carboxamide

Example 142A 2-(2-(benzyloxy)-2-methylpropoxy)-6-chloro-3-nitropyridine

The titled compound was prepared using the procedure described for Example 121A substituting 2-(benzyloxy)-2-methylpropan-1-ol (CAS#: 91968-71-7) for methanol.

Example 142B (S)-1-tert-butyl 3-methyl 4-acetylpiperazine-1,3-dicarboxylate

To a solution of (S)-1-tert-butyl 3-methyl piperazine-1,3-dicarboxylate (500 mg, 2.05 mmol) in anhydrous dichloromethane (20 mL) at 0° C. was added triethylamine (311 mg 3.1 mmol) and acetyl chloride (0.16 mL, 2.25 mmol). The mixture was stirred for 30 minutes, and then the mixture was diluted with dichloromethane. The organic layer was washed with H$_2$O, dried with MgSO$_4$, filtered and concentrated under reduced pressure to provide the titled compound.

Example 142C (S)-tert-butyl 4-acetyl-3-(hydroxymethyl)piperazine-1-carboxylate To a solution of Example 142B, (S)-1-tert-butyl 3-methyl 4-acetylpiperazine-1,3-dicarboxylate (625 mg, 2.18 mmol), in methanol (30 mL) was added lithium tetrahydroborate (143 mg, 6.55 mmol). The mixture was heated to reflux for 16 hours. The mixture was concentrated under reduce pressure to a smaller volume and diluted with ethyl acetate. It was washed with saturated NaHCO$_3$ and brine, dried with MgSO$_4$ and concentrated under reduced pressure. The resulting residue was chromatographed on silica gel eluting with 30-80% ethyl acetate/heptanes to provide the titled compound.

Example 142D (S)-tert-butyl 4-acetyl-3-(methoxymethyl)piperazine-1-carboxylate To a solution of Example 142C (310 mg, 1.2 mmol) in anhydrous N,N-dimethylformamide (10 mL) was added sodium hydride (60% dispersed in oil, 68 mg, 1.7 mmol), and the mixture was stirred at the temperature for 30 minutes. Iodomethane (0.113 mL, 1.8 mmol) was added, and the resultant mixture was stirred at ambient temperature for 1 hour. The mixture was diluted with ether, quenched with water, and the organic layer was separated. The organic layer was further washed with brine, dried (MgSO$_4$), filtered and concentrated under reduced pressure. The residue was chromatographed on silica gel eluting with 3-70% ethyl acetate/heptanes to provide the titled compound.

Example 142E (5)-1-(2-(methoxymethyl)piperazin-1-yl)ethanone, trifluoroacetic acid salt The product of Example 142D (310 mg, 1.14 mmol) was treated with trifluoroacetic acid (about 2 mL) and stirred for 10 minutes. The mixture was concentrated under reduced pressure. The residue was diluted with ether and concentrated again under reduced pressure. The operation was repeated a few times. Finally, the residue was dissolve in toluene and concentrated under reduced pressure and dried under vacuum to provide the crude titled compound.

Example 142F (5)-1-(4-(6-(2-(benzyloxy)-2-methylpropoxy)-5-nitropyridin-2-yl)-2-(methoxymethyl)piperazin-1-yl)ethanone The titled compound was prepared using the procedure described for Example 121B substituting Example 142A for Example 121A, and substituting Example 142E for tert-butyl piperazine-1-carboxylate.

Example 142G (5)-1-(4-(5-amino-6-(2-hydroxy-2-methylpropoxy)pyridin-2-yl)-2-(methoxymethyl)piperazin-1-yl)ethanone The titled compound was prepared using the procedure described for Example 121C substituting Example 142F for Example 121B.

Example 142H

N-{6-[(3S)-4-acetyl-3-(methoxymethyl)piperazin-1-yl]-2-(2-hydroxy-2-methylpropoxy)pyridin-3-yl}-6,6-dimethyl-4-oxo-4,5,6,7-tetrahydrofuro[3,2-c]pyridine-3-carboxamide The titled compound was prepared using the procedure described for Example 5 substituting Example 120A for Example 1E, and substituting Example 142G for tert-butyl 4-(4-amino-3-methoxyphenyl)piperazine-1-carboxylate. $^1$H NMR (300 MHz, CDCl$_3$) δ ppm 11.90 (s, 1H), 8.71 (d, J=8.6 Hz, 1H), 8.10 (s, 1H), 6.21 (d, J=8.7 Hz, 1H), 5.62 (s, 1H), 5.31 (s, 1H), 4.31-4.01 (m, 3H), 4.19 (s, 2H), 3.77-3.36 (m, 3H), 3.33 (s, 3H), 2.96 (s, 2H), 2.82 (dd, J=27.8, 12.5 Hz, 2H), 2.18 (s, 3H), 1.42 (s, 6H), 1.33 (s, 6H); MS (ESI) m/z 544 (M+H)$^+$.

Example 143

N-[2-ethoxy-6-(2-hydroxyethyl)pyridin-3-yl]-6,6-dimethyl-4-oxo-4,5,6,7-tetrahydrofuro[3,2-c]pyridine-3-carboxamide

Example 143A 6-chloro-2-ethoxy-3-nitropyridine

The titled compound was prepared using the procedure described for Example 121A substituting ethanol for methanol.

Example 143B 1-tert-butyl 3-methyl 2-(6-ethoxy-5-nitropyridin-2-yl)malonate

To a solution of Example 143A, 6-chloro-2-ethoxy-3-nitropyridine (3 g, 14.81 mmol), in N,N-dimethylformamide (30 mL) at 0° C. was added sodium hydride (1.185 g, 29.6 mmol), and the mixture was stirred for 20 minutes. Then, tert-butyl methyl malonate (3.16 mL, 17.77 mmol) was added dropwise, and the mixture was stirred at ambient temperature for 2 hours. The mixture was diluted with ether and quenched with H$_2$O. The mixture was partitioned. The organic layer was washed with brine, dried (MgSO$_4$), filtered and concentrated under reduced pressure. The resulting residue was chromatographed on silica gel eluting with 0-20% ethyl acetate/heptanes to provide the titled compound.

Example 143C methyl 2-(6-ethoxy-5-nitropyridin-2-yl)acetate

The titled compound was prepared using the procedure described for Example 142E substituting Example 143B for Example 142D.

Example 143D methyl 2-(5-amino-6-ethoxypyridin-2-yl)acetate

The titled compound was prepared using the procedure described for Example 121C substituting Example 143C for Example 121B.

Example 143E methyl(5-{[(6,6-dimethyl-4-oxo-4,5,6,7-tetrahydrofuro[3,2-c]pyridin-3-yl)carbonyl]amino}-6-ethoxypyridin-2-yl)acetate The titled compound was prepared using the procedure described for Example 5 substituting Example 120A for Example 1E, and substituting Example 143D for tert-butyl 4-(4-amino-3-methoxyphenyl)piperazine-1-carboxylate.

Example 143F

N-[2-ethoxy-6-(2-hydroxyethyl)pyridin-3-yl]-6,6-dimethyl-4-oxo-4,5,6,7-tetrahydrofuro[3,2-c]pyridine-3-carboxamide The titled compound was prepared using the procedure described for Example 133D substituting Example 143E for Example 133C. $^1$H NMR (300 MHz, CDCl$_3$) δ ppm 11.90 (s, 1H), 8.64 (d, J=7.9 Hz, 1H), 8.11 (s, 1H), 6.73 (d, J=8.0 Hz, 1H), 5.34 (s, 1H), 4.43 (q, J=7.1 Hz, 2H), 4.02-3.94 (m, 2H), 2.95 (s, 2H), 2.93-2.87 (m, 2H), 1.50 (t, J=7.1 Hz, 3H), 1.44 (s, 6H); MS (DCI) m/z 374 (M+H)$^+$.

Example 144

N-[2-ethoxy-6-(hydroxymethyl)pyridin-3-yl]-6,6-dimethyl-4-oxo-4,5,6,7-tetrahydrofuro[3,2-c]pyridine-3-carboxamide

Example 144A 6-hydroxy-5-nitropicolinic acid

A mixture of Example 143B, 1-tert-butyl 3-methyl 2-(6-ethoxy-5-nitropyridin-2-yl)malonate (2.32 g, 6.82 mmol) and 70% nitric acid (60 mL) was heated to reflux for 10 hours. It was cooled to room temperature and concentrated under reduced pressure. The resulting solid was washed with CHCl$_3$, filtered and dried under vacuum to provide the titled compound.

Example 144B ethyl 6-ethoxy-5-nitropicolinate

To a solution of Example 144A, 6-hydroxy-5-nitropicolinic acid (210 mg, 1.141 mmol), in N,N-dimethylformamide (10 mL) was added triethylamine (0.477 mL, 3.42 mmol) and iodoethane (0.277 mL, 3.42 mmol), and the mixture was heated to 50° C. for 16 hours. The mixture was concentrated under reduced pressure and passed through a short silica gel pad to provide the crude titled compound.

Example 144C ethyl 5-amino-6-ethoxypicolinate

The titled compound was prepared using the procedure described for Example 121C substituting Example 144B for Example 121B.

Example 144D ethyl 5-{[(6,6-dimethyl-4-oxo-4,5,6,7-tetrahydrofuro[3,2-c]pyridin-3-yl)carbonyl]amino}-6-ethoxypyridine-2-carboxylate The titled compound was prepared using the procedure described for Example 5 substituting Example 120A for Example 1E and substituting Example 144C for tert-butyl 4-(4-amino-3-methoxyphenyl)piperazine-1-carboxylate.

Example 144E

N-[2-ethoxy-6-(hydroxymethyl)pyridin-3-yl]-6,6-dimethyl-4-oxo-4,5,6,7-tetrahydrofuro[3,2-c]pyridine-3-carboxamide The titled compound was prepared using the procedure described for Example 133D substituting Example 144D for Example 133C. $^1$H NMR (300 MHz, CDCl$_3$) δ ppm 11.93 (s, 1H), 8.72 (d, J=8.0 Hz, 1H), 8.10 (s, 1H), 6.80 (d, J=7.9 Hz, 1H), 5.36 (s, 1H), 4.63 (s, 2H), 4.52 (q, J=7.1 Hz, 2H), 2.96 (s, 2H), 1.50 (t, J=7.1 Hz, 3H), 1.44 (s, 6H); MS (DCI) m/z 360 (M+H)$^+$.

Example 145

6-ethoxy-5-({[5-(2-methoxyethyl)-6,6-dimethyl-4-oxo-4,5,6,7-tetrahydrofuro[3,2-c]pyridin-3-yl]carbonyl}amino)pyridine-2-carboxylic acid

Example 145A 5-(2-methoxyethyl)-6,6-dimethyl-4-oxo-4,5,6,7-tetrahydrofuro[3,2-c]pyridine-3-carboxylic acid To a solution of Example 120A, 6,6-dimethyl-4-oxo-4,5,6,7-tetrahydrofuro[3,2-c]pyridine-3-carboxylic acid (2 g, 9.56 mmol), in N,N-dimethylformamide (30 mL) was added sodium hydride (0.803 g, 60% in mineral oil, 33.5 mmol) at 0° C., and the mixture was stirred for 30 minutes. Then 1-bromo-2-methoxyethane (2.66 g, 19.12 mmol) was added and the mixture was stirred at ambient temperature for 5 hours. The mixture was acidified with HCl (1 N) to pH about 1 and diluted with ethyl acetate. The organic layer was separated. The aqueous layer was extracted with ethyl acetate thrice. The combined organic layers were washed with brine, dried (MgSO$_4$), filtered and concentrated under reduced pressure. The resulting residue was purified by silica gel chromatography eluting with (0-10%) methanol/ethyl acetate to provide the titled compound. $^1$H NMR (300 MHz, CDCl$_3$) δ ppm 14.68 (s, 1H), 8.04 (s, 1H), 3.72-3.64 (m, 2H), 3.61-3.53 (m, 2H), 3.36 (s, 3H), 3.01 (s, 2H), 1.48 (s, 6H); MS (ESI) m/z 268 (M+H)$^+$.

Example 145B ethyl 6-ethoxy-5-({[5-(2-methoxyethyl)-6,6-dimethyl-4-oxo-4,5,6,7-tetrahydrofuro[3,2-c]pyridin-3-yl]carbonyl}amino)pyridine-2-carboxylate The titled compound was prepared using the procedure described for Example 5 substituting Example 145A for Example 1E, and substituting Example 144C for tert-butyl 4-(4-amino-3-methoxyphenyl)piperazine-1-carboxylate.

Example 145C 6-ethoxy-5-({[5-(2-methoxyethyl)-6,6-dimethyl-4-oxo-4,5,6,7-tetrahydrofuro[3,2-c]pyridin-3-yl]carbonyl}amino)pyridine-2-carboxylic acid To a solution of Example 145B, ethyl 6-ethoxy-5-({[5-(2-methoxyethyl)-6,6-dimethyl-4-oxo-4,5,6,7-tetrahydrofuro[3,2-c]pyridin-3-yl]carbonyl}amino)pyridine-2-carboxylate (80 mg, 0.174 mmol), in a mixture of methanol (10 mL), tetrahydrofuran (10 mL) and water (5 mL) was added lithium hydroxide hydrate (14.61 mg, 0.348 mmol). The mixture was stirred at ambient temperature for 5 hours. The mixture was then acidified with HCl (1 N) to pH=2-3. It was diluted with ethyl acetate (30 mL) and partitioned. The aqueous layer was extracted with ethyl acetate twice. The combined organic layers were washed with brine, dried (MgSO$_4$), filtered and concentrated under reduced pressure. The resulting residue was purified by silica gel chromatography eluting with (0-10%) methanol/ethyl acetate to provide the titled compound. $^1$H NMR (300 MHz, CDCl$_3$) δ ppm 12.73 (s, 1H), 9.04 (d, J=8.1 Hz, 1H), 8.13 (s, 1H), 7.86 (d, J=8.1 Hz, 2H), 4.51 (q, J=7.1 Hz, 2H), 3.69 (t, J=5.6 Hz, 2H), 3.59 (t, J=6.2 Hz, 2H), 3.38 (s, 3H), 2.99 (s, 2H), 1.61 (t, J=7.1 Hz, 3H), 1.47 (s, 6H); MS (ESI) m/z 432 (M+H)$^+$.

Example 146

6,6-dimethyl-N-(1-methyl-1H-indazol-5-yl)-4-oxo-4,5,6,7-tetrahydro-1-benzofuran-3-carboxamide To a solution of 6,6-dimethyl-4-oxo-4,5,6,7-tetrahydrobenzofuran-3-carboxylic acid (CAS#121625-78-3) (0.1 g, 0.48 mmol) in N,N-dimethylformamide (4 mL) was added 2-(7-azabenzotriazol-1-yl)-N,N,N',N'-tetramethyluronium hexafluorophosphate (0.192 g, 0.504 mmol) and triethylamine (0.070 mL, 0.504 mmol). After mixing, 1-methyl-1H-indazol-5-amine (0.071 g, 0.480 mmol) was added, and the vial was shaken overnight. The mixture was concentrated, re-dissolved in CHCl$_3$ and methanol, passed through solid-phase extraction cartridge containing silica-supported carbonate (SiliCycle®, Part # SPE-R66030B) eluted with CHCl$_3$ and concentrated. The residue was purified by flash chromatography 0-100% ethyl acetate/hexanes to provide the titled compound. $^1$H NMR (400 MHz, CDCl$_3$) δ ppm 11.75 (s, 1H), 8.36 (d, J=1.6 Hz, 1H), 8.16 (s, 1H), 7.96 (s, 1H), 7.68 (dd, J=8.9, 1.9 Hz, 1H), 7.37 (d, J=8.9 Hz, 1H), 4.08 (s, 1H), 2.87 (s, 1H), 2.57 (s, 1H), 1.22 (s, 1H); MS (APCI) m/z 338 (M+H)$^+$.

Example 147

6,6-dimethyl-N-(2-methyl-2H-indazol-5-yl)-4-oxo-4,5,6,7-tetrahydro-1-benzofuran-3-carboxamide The titled compound was prepared using the procedure described for Example 146 substituting 2-methyl-2H-indazol-5-amine for 1-methyl-1H-indazol-5-amine $^1$H NMR (400 MHz, CDCl$_3$) δ ppm 11.70 (bs, 1H), 8.45 (d, J=1.9 Hz, 1H), 8.15 (s, 1H), 7.86 (s, 1H), 7.67 (d, J=9.1 Hz, 1H), 7.43 (dd, J=9.1, 2.0 Hz, 1H), 4.21 (s, 3H), 2.86 (s, 2H), 2.56 (s, 2H), 1.22 (s, 6H); MS (APCI) m/z 338 (M+H)$^+$.

Example 148

N-[4-(4-acetylpiperazin-1-yl)phenyl]-6,6-dimethyl-4-oxo-4,5,6,7-tetrahydro-1-benzofuran-3-carboxamide To a solution of 6,6-dimethyl-4-oxo-4,5,6,7-tetrahydrobenzofuran-3-carboxylic acid (0.1 g, 0.480 mmol) in N,N- dimethylformamide (4 mL) was added 2-(7-azabenzotriazol-1-yl)-N,N,N',N'-tetramethyluronium hexafluorophosphate (0.192 g, 0.504 mmol) and triethylamine (0.070 mL, 0.504 mmol). After mixing, 1-(4-(4-aminophenyl)piperazin-1-yl)ethanone (0.111 g, 0.504 mmol) was added, and the vial was shaken for 4 hours. The mixture was concentrated and triturated with methanol to provide the titled compound. $^1$H NMR (400 MHz, DMSO-$d_6$) δ ppm 11.54 (s, 1H), 8.37 (s, 1H), 7.56 (d, J=9.0 Hz, 2H), 6.98 (d, J=9.1 Hz, 2H), 3.56 (dd, J=8.3, 4.9 Hz, 4H), 3.13-3.09 (m, 2H), 3.07-3.03 (m, 2H), 2.90 (s, 2H), 2.57 (s, 2H), 2.03 (s, 3H), 1.10 (s, 6H); MS (APCI) m/z 410 (M+H)$^+$.

Example 149

6,6-dimethyl-4-oxo-N-[6-(piperazin-1-yl)pyridin-3-yl]-4,5,6,7-tetrahydro-1-benzofuran-3-carboxamide Example 149A tert-butyl 4-(5-{[(6,6-dimethyl-4-oxo-4,5,6,7-tetrahydro-1-benzofuran-3-yl)carbonyl]amino}pyridin-2-yl)piperazine-1-carboxylate The titled compound was prepared using the procedure described for Example 146 substituting tert-butyl 4-(5-aminopyridin-2-yl)piperazine-1-carboxylate (CAS#119285-07-3) for 1-methyl-1H-indazol-5-amine $^1$H NMR (400 MHz, DMSO-$d_6$) δ ppm 11.52 (s, 1H), 8.43 (d, J=2.0 Hz, 1H), 8.40 (s, 1H), 7.89 (dd, J=9.0, 2.6 Hz, 1H), 6.90 (d, J=9.1 Hz, 1H), 3.47-3.41 (m, 8H), 2.92 (bs, 2H), 2.58 (bs, 2H), 1.42 (s, 9H), 1.13-1.09 (m, 6H); MS (APCI) m/z 569.5 (M+H)$^+$.

Example 149B 6,6-dimethyl-4-oxo-N-[6-(piperazin-1-yl)pyridin-3-yl]-4,5,6,7-tetrahydro-1-benzofuran-3-carboxamide To a solution of the product from Example 149A (24.56 g, 52.4 mmol) in dioxane (100 mL) was added a solution of 4 M hydrochloric acid (100 mL, 400 mmol) in dioxane. The mixture was stirred for 4 hours and a white precipitate formed. The product was concentrated, triturated from ether, and collected by filtration. This solid was mixed with water and potassium carbonate (21.73 g, 157 mmol) and extracted with ethyl acetate (2×250 mL). The combined organic extracts were dried (Na$_2$SO$_4$), filtered and concentrated to provide the titled compound. $^1$H NMR (400 MHz, CDCl$_3$) δ ppm 11.52 (bs, 1H), 8.53 (d, J=2.7 Hz, 1H), 8.12 (s, 1H), 8.05 (dd, J=9.1, 2.7 Hz, 1H), 6.67 (d, J=9.1 Hz, 1H), 3.52-3.45 (m, 4H), 3.04-2.98 (m, 4H), 2.85 (s, 2H), 2.54 (s, 2H), 1.21 (s, 6H).

Example 150

N-(2-methyl-2H-indazol-5-yl)-4-oxo-4,7-dihydro-5H-spiro[1-benzofuran-6,1'-cyclobutane]-3-carboxamide Example 150A 4-oxo-4,7-dihydro-5H-spiro[1-benzofuran-6,1'-cyclobutane]-3-carboxylic acid To a solution of spiro[3.5]nonane-6,8-dione (CAS#221342-48-9) (9.36 g, 61.5 mmol) in water (50 mL) was added potassium hydroxide (4.49 g, 80 mmol). The reaction was cooled in an ice bath, and then a solution of 3-bromo-2-oxopropanoic acid (10.27 g, 61.5 mmol) in methanol (50 mL) was added dropwise over 30 minutes. The mixture was concentrated under reduced pressure, and the residue was acidified with 37% HCl and heated to reflux overnight. The mixture was cooled and then extracted with CH$_2$Cl$_2$ (3×200 mL). The combined CH$_2$Cl$_2$ layers were concentrated and purified by chromatography on silica gel eluting with CH$_2$Cl$_2$. Precipitation from methanol provided the titled compound. $^1$H NMR (400 MHz, CDCl$_3$) δ ppm 13.12 (s, 1H), 8.08 (s, 1H), 3.08 (s, 2H), 2.80 (s, 2H), 2.06-1.94 (m, 6H).

Example 150B

N-(2-methyl-2H-indazol-5-yl)-4-oxo-4,7-dihydro-5H-spiro[1-benzofuran-6,1'-cyclobutane]-3-carboxamide The titled compound was prepared using the procedure described for Example 1F substituting the product from Example 150A for the product from Example 1E. $^1$H NMR (400 MHz, DMSO-$d_6$) δ ppm 11.70 (s, 1H), 8.42 (s, 1H), 8.30 (s, 1H), 8.27 (d, J=1.9 Hz, 1H), 7.62 (d, J=9.1 Hz, 1H), 7.31 (dd, J=9.1, 2.0 Hz, 1H), 4.15 (s, 3H), 3.17 (s, 2H), 2.85 (s, 2H), 1.98-1.86 (m, 6H); MS (APCI) m/z 350 (M+H)$^+$.

Example 151

6,6-dimethyl-4-oxo-N-[5-(piperazin-1-yl)pyridin-2-yl]-4,5,6,7-tetrahydro-1-benzofuran-3-carboxamide Example 151A tert-butyl 4-(6-{[(6,6-dimethyl-4-oxo-4,5,6,7-tetrahydro-1-benzofuran-3-yl)carbonyl]amino}pyridin-3-yl)piperazine-1-carboxylate To a solution of 6,6-dimethyl-4-oxo-4,5,6,7-tetrahydrobenzofuran-3-carboxylic acid (0.987 g, 4.74 mmol) in tetrahydrofuran (40 mL) cooled to 0° C. was added triethylamine (1.322 mL, 9.48 mmol) and ethyl chloroformate (0.455 mL, 4.74 mmol). After stirring for 1 hour, tert-butyl 4-(6-aminopyridin-3-yl)piperazine-1-carboxylate (CAS#571188-59-5) (1.2 g, 4.31 mmol) was added, and the mixture stirred at room temperature for 2 hours. The mixture was partitioned between brine and CHCl$_3$. The layers were separated and the aqueous layer was extracted with CHCl$_3$. The organic layers were combined, dried over Na$_2$SO$_4$, concentrated and purified by chromatography on silica gel eluting with a gradient of 0-100% ethyl acetate in hexane to provide the titled compound. $^1$H NMR (400 MHz, CDCl$_3$) δ ppm 12.74 and 12.15 (s and s, 1H), 8.41-7.38 (m, 4H), 3.75-3.68 (m, 2H), 3.62-3.55 (m, 2H), 3.30-3.24 (m, 2H), 3.02-2.95 (m, 2H), 2.78 and 2.77 (s and s, 2H), 2.52 and 2.48 (s and s, 2H), 1.43 and 1.42 (s and s, 9H), 1.13 and 1.12 (s and s, 6H); MS (APCI) m/z 469 (M+H)$^+$.

Example 151B 6,6-dimethyl-4-oxo-N-[5-(piperazin-1-yl)pyridin-2-yl]-4,5,6,7-tetrahydro-1-benzofuran-3-carboxamide A mixture of Example 151A (0.57 g, 1.217 mmol) in 4 M HCl in dioxane (10 mL, 40 mmol) was stirred for 4 hours and blown dry under warm nitrogen. The product was dissolved in water (~15 mL), neutralized with potassium carbonate (0.673 g, 4.87 mmol), and extracted into $CHCl_3$. The organic phase was passed through a 20 mL Biotage® ISOLUTE® phase separator cartridge and concentrated to provide the titled compound (0.388 g, 1.053 mmol, 87% yield. $^1$H NMR (400 MHz, DMSO-$d_6$) δ ppm 11.97 (s, 1H), 8.99 (bs, 2H), 8.46 (s, 1H), 8.15-8.12 (m, 2H), 7.52 (dd, J=9.1, 3.0 Hz, 1H), 3.42-3.35 (m, 4H), 3.28-3.21 (m, 4H), 2.92 (s, 2H), 2.57 (s, 2H), 1.11 (s, 6H); MS (APCI) m/z 369 $(M+H)^+$.

Example 152

6,6-dimethyl-N-{4-[4-(methylsulfonyl)piperazin-1-yl]phenyl}-4-oxo-4,5,6,7-tetrahydro-1-benzofuran-3-carboxamide Example 152A tert-butyl 4-(4-{[(6,6-dimethyl-4-oxo-4,5,6,7-tetrahydro-1-benzofuran-3-yl)carbonyl]amino}phenyl)piperazine-1-carboxylate The titled compound was prepared using the procedure described in Example 148 substituting tert-butyl 4-(4-aminophenyl)piperazine-1-carboxylate (CAS#170911-92-9) for 1-(4-(4-aminophenyl)piperazin-1-yl)ethanone. $^1$H NMR (400 MHz, DMSO-$d_6$) δ ppm 11.55 (s, 1H), 8.38 (s, 1H), 7.57 (d, J=9.0 Hz, 2H), 6.98 (d, J=9.0 Hz, 2H), 3.49-3.43 (m, 4H), 3.09-3.03 (m, 4H), 2.91 (s, 2H), 2.58 (s, 2H), 1.42 (s, 9H), 1.11 (s, 6H).

Example 152B 6,6-dimethyl-4-oxo-N-[4-(piperazin-1-yl)phenyl]-4,5,6,7-tetrahydro-1-benzofuran-3-carboxamide The titled compound was prepared using the procedure described in Example 151B substituting the product from Example 152A for the product from Example 151A. $^1$H NMR (400 MHz, DMSO-$d_6$) δ ppm 11.57 (s, 1H), 9.17 (bs, 2H), 8.38 (s, 1H), 7.59 (d, J=8.8 Hz, 2H), 7.02 (d, J=8.8 Hz, 2H), 3.36-3.30 (m, 4H), 3.25-3.17 (m, 4H), 2.91 (s, 2H), 2.57 (s, 2H), 1.10 (s, 6H); MS (APCI) m/z 368 $(M+H)^+$.

Example 152C 6,6-dimethyl-N-{4-[4-(methylsulfonyl)piperazin-1-yl]phenyl}-4-oxo-4,5,6,7-tetrahydro-1-benzofuran-3-carboxamide The titled compound was prepared using the procedure described in Example 18 substituting methanesulfonyl chloride for acetyl chloride, and substituting the product from Example 152B for the product from Example 6. $^1$H NMR (400 MHz, DMSO-$d_6$) δ ppm 11.56 (s, 1H), 8.38 (s, 1H), 7.58 (d, J=9.0 Hz, 2H), 7.01 (d, J=9.0 Hz, 2H), 3.27-3.19 (m, 8H), 2.93 (s, 3H), 2.92 (s, 2H), 2.58 (s, 2H), 1.11 (s, 6H); MS (APCI) m/z 446 $(M+H)^+$.

Example 153

N-[2-(2-hydroxyethyl)-2H-indazol-5-yl]-6,6-dimethyl-4-oxo-4,5,6,7-tetrahydro-1-benzofuran-3-carboxamide Example 153A 2-(2-((tert-butyldimethylsilyl)oxy)ethyl)-5-nitro-2H-indazole A mixture of 5-nitro-1H-indazole (1.098 g, 6.731 mmol), $Cs_2CO_3$ (2.70 g, 8.29 mmol), (2-bromoethoxy)-tert-butyldimethylsilane (1.530 mL, 7.13 mmol) and N,N-dimethylformamide (15 mL) was heated at 120° C. for 30 minutes in a microwave (Biotage® Initiator, maximum 300 W). After cooling, the insoluble material was removed by filtration and rinsed with $CHCl_3$. The combined filtrates were concentrated and purified by chromatography on silica gel eluting with a gradient of 0-100% ethyl acetate in hexane providing 1-(2-(tert-butyldimethylsilyloxy)ethyl)-5-nitro-1H-indazole as the first isomer to elute and the titled compound as the second isomer to elute. $^1$H NMR (400 MHz, $CDCl_3$) δ ppm 8.77 (d, J=2.1 Hz, 1H), 8.32 (s, 1H), 8.16 (dd, J=9.4, 2.1 Hz, 1H), 7.78 (d, J=9.4 Hz, 1H), 4.61 (t, J=5.0 Hz, 2H), 4.12 (t, J=5.0 Hz, 2H), 0.81 (s, 9H), −0.10 (s, 6H).

Example 153B 2-(2-((tert-butyldimethylsilyl)oxy)ethyl)-2H-indazol-5-amine

A solution of the product from Example 153A (0.75 g, 2.333 mmol) in tetrahydrofuran (20 mL) was added to 5% Pd/C (0.150 g, 1.410 mmol) in a 50 mL pressure bottle and stirred at room temperature for 1 hour under $H_2$ (30 psi). The mixture was filtered, and the filtrate was concentrated and purified by chromatography on silica gel eluting with a gradient of 0-100% ethyl acetate in hexanes to provide the titled compound. $^1$H NMR (400 MHz, DMSO-$d_6$) δ ppm 7.83 (s, 1H), 7.31 (d, J=9.0 Hz, 1H), 6.71 (dd, J=9.0, 2.1 Hz, 1H), 6.54 (d, J=2.0 Hz, 1H), 4.73 (bs, 2H), 4.34 (t, J=5.4 Hz, 2H), 3.98 (t, J=5.4 Hz, 2H), 0.76 (s, 9H), −0.14 (s, 6H).

Example 153C

N-[2-(2-{[tert-butyl(dimethyl)silyl]oxy}ethyl)-2H-indazol-5-yl]-6,6-dimethyl-4-oxo-4,5,6,7-tetrahydro-1-benzofuran-3-carboxamide The titled compound was prepared using the procedure described in Example 148 substituting the product from Example 153B for 1-(4-(4-aminophenyl)piperazin-1-yl)ethanone. The crude product was purified by chromatography on silica gel eluting with a gradient of 0-100% ethyl acetate in hexane. $^1$H NMR (400 MHz, DMSO-$d_6$) δ ppm 11.69 (s, 1H), 8.41 (s, 1H), 8.29 (s, 1H), 8.26 (d, J=1.9 Hz, 1H), 7.62 (d, J=9.1 Hz, 1H), 7.31 (dd, J=9.1, 2.0 Hz, 1H), 4.46 (t, J=5.2 Hz, 2H), 4.03 (t, J=5.2 Hz, 2H), 2.92 (s, 2H), 2.59 (s, 2H), 1.11 (s, 6H), 0.75 (s, 9H), −0.15 (s, 6H); MS (APCI) m/z 482 $(M+H)^+$.

Example 153D

N-[2-(2-hydroxyethyl)-2H-indazol-5-yl]-6,6-dimethyl-4-oxo-4,5,6,7-tetrahydro-1-benzofuran-3-carboxamide To a solution of the product from Example 153C (0.21 g, 0.436 mmol) in $CHCl_3$ (5 mL) was added a solution of 1 M tetrabutylammonium fluoride in tetrahydrofuran (1 mL, 1.0 mmol). After stirring for 4 hours, the mixture was partitioned with brine, and the organic layer was dried (MgSO$_4$), filtered, concentrated and purified chromatographically on silica gel eluted with a gradient of 0% to 10% methanol in ethyl acetate to provide the titled compound. $^1$H NMR (400 MHz, DMSO-d$_6$) δ ppm 11.69 (s, 1H), 8.41 (s, 1H), 8.31 (s, 1H), 8.27 (d, J=1.9 Hz, 1H), 7.62 (d, J=9.1 Hz, 1H), 7.31 (dd, J=9.1, 2.0 Hz, 1H), 4.99-4.92 (m, 1H), 4.42 (t, J=5.5 Hz, 2H), 3.88-3.82 (m, 2H), 2.92 (s, 2H), 2.59 (s, 2H), 1.11 (s, 6H); MS (APCI) m/z 368 (M+H)$^+$.

Example 154

N-[2-(hydroxymethyl)-1H-benzimidazol-5-yl]-6,6-dimethyl-4-oxo-4,5,6,7-tetrahydro-1-benzofuran-3-carboxamide The titled compound was prepared using the procedure described for Example 148 substituting (5-amino-1H-benzimidazol-2-yl)methanol dihydrochloride for 1-(4-(4-aminophenyl)piperazin-1-yl)ethanone, and using four equivalents of triethylamine. $^1$H NMR (400 MHz, DMSO-d$_6$) δ ppm 12.31 (bs, 1H), 11.73 (s, 1H), 8.40 (s, 1H), 8.11 (d, J=1.9 Hz, 1H), 7.48 (d, J=8.5 Hz, 1H), 7.26 (dd, J=8.5, 1.2 Hz, 1H), 5.67 (t, J=5.7 Hz, 1H), 4.66 (d, J=5.5 Hz, 2H), 2.91 (s, 2H), 2.59 (s, 2H), 1.21-1.02 (m, 6H); MS (APCI) m/z 354 (M+H)$^+$.

Example 155

6,6-dimethyl-N-{5-[4-(methylsulfonyl)piperazin-1-yl]pyridin-2-yl}-4-oxo-4,5,6,7-tetrahydro-1-benzofuran-3-carboxamide The titled compound was prepared using the procedure described in Example 18 substituting methanesulfonyl chloride for acetyl chloride, and substituting the product from Example 151B for the product from Example 6. $^1$H NMR (400 MHz, DMSO-d$_6$) δ ppm 11.92 (s, 1H), 8.43 (s, 1H), 8.12-8.09 (m, 2H), 7.48 (dd, J=9.1, 3.0 Hz, 1H), 3.26 (s, 8H), 2.92 (s, 3H), 2.91 (s, 2H), 2.56 (s, 2H), 1.10 (s, 6H); MS (APCI) m/z 447 (M+H)$^+$.

Example 156

N-[5-(4-acetylpiperazin-1-yl)pyridin-2-yl]-6,6-dimethyl-4-oxo-4,5,6,7-tetrahydro-1-benzofuran-3-carboxamide The titled compound was prepared using the procedure described in Example 18 substituting the product from Example 151B for the product from Example 6. $^1$H NMR (400 MHz, DMSO-d$_6$) δ ppm 11.91 (s, 1H), 8.13-8.06 (m, 2H), 7.46 (dd, J=9.0, 3.1 Hz, 1H), 3.61-3.54 (m, 4H), 3.19-3.15 (m, 2H), 3.12-3.08 (m, 2H), 2.90 (s, 2H), 2.56 (s, 2H), 2.03 (s, 3H), 1.10 (s, 6H); MS (APCI) m/z 411 (M+H)$^+$.

Example 157

N-[2-methoxy-4-(piperazin-1-yl)phenyl]-6,6-dimethyl-4-oxo-4,5,6,7-tetrahydro-1-benzofuran-3-carboxamide Example 157A tert-butyl 4-(4-{[(6,6-dimethyl-4-oxo-4,5,6,7-tetrahydro-1-benzofuran-3-yl)carbonyl]amino}-3-methoxyphenyl)piperazine-1-carboxylate The titled compound was prepared using the procedure described in Example 148 substituting tert-butyl 4-(4-amino-3-methoxyphenyl)piperazine-1-carboxylate (CAS#1246532-96-6) for 1-(4-(4-aminophenyl)piperazin-1-yl)ethanone. The crude product was purified by chromatography on silica gel eluting with a gradient of 0-100% ethyl acetate in hexane. $^1$H NMR (400 MHz, DMSO-d$_6$) δ ppm 11.24 (s, 1H), 8.36 (s, 1H), 8.06 (d, J=8.8 Hz, 1H), 6.68 (d, J=2.5 Hz, 1H), 6.50 (dd, J=8.9, 2.5 Hz, 1H), 3.87 (s, 3H), 3.52-3.39 (m, 4H), 3.16-3.07 (m, 4H), 2.90 (s, 2H), 2.55 (s, 2H), 1.42 (s, 9H), 1.11 (s, 6H); MS (ESI) m/z 498 (M+H)$^+$.

Example 157B

N-[2-methoxy-4-(piperazin-1-yl)phenyl]-6,6-dimethyl-4-oxo-4,5,6,7-tetrahydro-1-benzofuran-3-carboxamide To a solution of the product from Example 157A (2.38 g, 4.78 mmol) in CH$_2$Cl$_2$ (100 mL) and ethyl acetate (100 mL) at 0° C. was added a stream of HCl gas for 10 minutes. The mixture was placed in a warm (~50° C.) water bath and treated with a stream of N$_2$ until the total volume was ~50 mL. The mixture was diluted with ethyl acetate (50 mL), and the solid was collected by filtration and dried under vacuum to provide the titled compound as the di-HCl salt. $^1$H NMR (300 MHz, DMSO-d$_6$) δ ppm 11.26 (s, 1H), 9.14 (bs, 2H), 8.36 (s, 1H), 8.10 (d, J=8.8 Hz, 1H), 6.72 (d, J=2.5 Hz, 1H), 6.54 (dd, J=8.9, 2.5 Hz, 1H), 3.88 (s, 3H), 3.42-3.33 (m, 4H), 3.22 (s, 4H), 2.90 (s, 2H), 2.55 (s, 2H), 1.11 (s, 6H); MS (ESI) m/z 398 (M+H)$^+$.

Example 158

N-[4-(4-acetylpiperazin-1-yl)-2-methoxyphenyl]-6,6-dimethyl-4-oxo-4,5,6,7-tetrahydro-1-benzofuran-3-carboxamide The titled compound was prepared using the procedure described in Example 18 substituting the product from Example 157B for the product from Example 6. $^1$H NMR (400 MHz, DMSO-d$_6$) δ ppm 11.30 (s, 1H), 8.42 (s, 1H), 8.13 (d, J=8.8 Hz, 1H), 6.75 (d, J=2.5 Hz, 1H), 6.57 (dd, J=8.9, 2.5 Hz, 1H), 3.94 (s, 3H), 3.68-3.61 (m, 4H), 3.26-3.13 (m, 4H), 2.96 (s, 2H), 2.61 (s, 2H), 2.11 (s, 3H), 1.17 (s, 6H); MS (ESI) m/z 440 (M+H)$^+$.

Example 159

N-(2-methyl-2H-indazol-5-yl)-4-oxo-4,7-dihydro-5H-spiro[1-benzofuran-6,1'-cyclopropane]-3-carboxamide Example 159A 4-oxo-5,7-dihydro-4H-spiro[benzofuran-6,1'-cyclopropane]-3-carboxylic acid To a solution of spiro[2.5]octane-5,7-dione (CAS#893411-52-4) (1.6 g, 11.58 mmol) in water (8 mL)

was added KOH (0.845 g, 15.05 mmol). The mixture was cooled to about 0° C. in an ice bath, and a solution of 3-bromo-2-oxopropanoic acid (2.320 g, 13.90 mmol) in methanol (15 mL) was added dropwise over 30 minutes. The methanol was removed under reduced pressure and water (8 mL) was added. The mixture was acidified with concentrated HCl and heated to 100° C. for 2 hours. The mixture was cooled with stirring, and the product precipitated. The solid was collected by filtration, washed with water (3×15 mL) and dried under vacuum to provide the titled compound. $^1$H NMR (400 MHz, CDCl$_3$) δ ppm 13.19 (bs, 1H), 8.10 (s, 1H), 2.86 (s, 2H), 2.55 (s, 2H), 0.63 (s, 4H).

Example 159B

N-(2-methyl-2H-indazol-5-yl)-4-oxo-4,7-dihydro-5H-spiro[1-benzofuran-6,1'-cyclopropane]-3-carboxamide A solution of the product from the Example from 159A (70.4 mg, 0.341 mmol) in tetrahydrofuran (7 mL) under N$_2$ was cooled to 0° C., treated with triethylamine (119 μL, 0.854 mmol), treated with ethyl chloroformate (32.8 μL, 0.341 mmol), stirred at 0° C. for 1 hour, treated with 2-methyl-2H-indazol-5-amine (41.9 mg, 0.285 mmol), stirred at room temperature overnight and partitioned between 1 M NaOH (5 mL) and CH$_2$Cl$_2$ (25 mL). The layers were separated, and the aqueous layer was extracted with CH$_2$Cl$_2$ (25 mL). The combined CH$_2$Cl$_2$ layers were dried (MgSO$_4$), filtered, concentrated and purified by chromatography on silica gel eluting with a gradient of 50-100% ethyl acetate in hexane to provide the titled compound. $^1$H NMR (300 MHz, CDCl$_3$) δ ppm 11.75 (s, 1H), 8.45 (d, J=1.3 Hz, 1H), 8.14 (s, 1H), 7.86 (s, 1H), 7.67 (d, J=9.1 Hz, 1H), 7.42 (dd, J=9.2, 2.0 Hz, 1H), 4.21 (s, 3H), 2.85 (s, 2H), 2.54 (s, 2H), 0.62 (s, 4H); MS (ESI) m/z 336 (M+H)$^+$.

Example 160

N-(2-methyl-2H-indazol-5-yl)-4-oxo-4,5,6,7-tetrahydrofuro[2,3-c]pyridine-3-carboxamide Example 160A potassium 1-(tert-butoxycarbonyl)-5-oxo-1,2,5,6-tetrahydropyridin-3-olate A solution of ethyl 2-(tert-butoxycarbonyl(2-oxopropyl)amino)acetate (CAS#873190-14-8) (13.26 g, 51.1 mmol) in anhydrous ether (250 mL) was added over 1 hour to a stirred 0° C. suspension of potassium tert-butoxide (6.31 g, 56.3 mmol) in anhydrous ether (250 mL). The mixture was stirred overnight at room temperature. The solid was collected by filtration, washed with ether and dried under vacuum to provide the titled compound. $^1$H NMR (300 MHz, DMSO-d$_6$) δ ppm 4.48 (s, 0.5H), 3.55 (s, 4H), 1.39 (s, 9H).

Example 160B 6-(tert-butoxycarbonyl)-4-oxo-4,5,6,7-tetrahydrofuro[2,3-c]pyridine-3-carboxylic acid A mixture of the product from Example 160A (9.33 g, 37.1 mmol) and potassium tert-butoxide (0.833 g, 7.42 mmol) in water (37 mL) was treated over 30 minutes with a solution of 3-bromopyruvic acid (7.44 g, 44.5 mmol) in methanol (37 mL), stirred overnight and concentrated to dryness. To this residue was added acetic acid (190 mL, 3319 mmol) and acetic anhydride (95 mL, 1007 mmol), and this mixture was stirred at 100° C. for 30 minutes and concentrated to an oil. This residue was dissolved in ethyl acetate (~50 mL), silica gel (~15 g) was added and the mixture was concentrated. The crude product as a silica gel suspension was purified by chromatography on silica gel eluting with a gradient of 33-100% [200:1:1 ethyl acetate/formic acid/water] in hexane. The residue was dried overnight under vacuum with heating to provide the titled compound. $^1$H NMR (300 MHz, CDCl$_3$) δ ppm 8.17 (s, 1H), 4.84 (s, 2H), 4.40 (s, 2H), 1.50 (d, J=4.8 Hz, 9H); MS (ESI) m/z 280 (M–H)$^-$.

Example 160C tert-butyl 3-[(2-methyl-2H-indazol-5-yl)carbamoyl]-4-oxo-4,7-dihydrofuro[2,3-c]pyridine-6(5H)-carboxylate The titled compound was prepared using the procedure described in Example 159B substituting the product from Example 160C for the product from Example 159A. $^1$H NMR (300 MHz, CDCl$_3$) δ ppm 11.32 (s, 1H), 8.41 (s, 1H), 8.20 (s, 1H), 7.86 (s, 1H), 7.67 (d, J=9.1 Hz, 1H), 7.39 (dd, J=9.1, 1.6 Hz, 1H), 4.82 (s, 2H), 4.37 (s, 2H), 4.21 (s, 3H), 1.52 (s, 9H); MS (ESI) m/z 411 (M+H)$^+$.

Example 160D

N-(2-methyl-2H-indazol-5-yl)-4-oxo-4,5,6,7-tetrahydrofuro[2,3-c]pyridine-3-carboxamide A solution of the product from 160 C (98.6 mg, 0.240 mmol) in ethyl acetate (5 mL) and CH$_2$Cl$_2$ (5 mL) was cooled to 0° C. and treated with a stream of HCl for 5 minutes. After stirring at 0° C. for 30 minutes, the mixture was allowed to warm to room temperature, and the solvent was removed with a stream of nitrogen. The residue was dried under vacuum to provide the titled compound as a dihydrochloride salt. $^1$H NMR (300 MHz, DMSO-d$_6$) δ ppm 11.04 (s, 1H), 10.67 (bs, 3H), 8.66 (s, 1H), 8.33 (s, 1H), 8.27 (s, 1H), 7.64 (d, J=9.2 Hz, 1H), 7.32 (dd, J=9.2, 1.7 Hz, 1H), 4.73 (s, 2H), 4.18-4.15 (m, 5H); MS (ESI) m/z 311 (M+H)$^+$.

Example 161

N-(2-methyl-2H-indazol-5-yl)-6-(methylsulfonyl)-4-oxo-4,5,6,7-tetrahydrofuro[2,3-c]pyridine-3-carboxamide To a mixture of the product from Example 160D (56.8 mg, 0.148 mmol) and triethylamine (0.10 mL, 0.74 mmol) in CH$_2$Cl$_2$ (0.5 mL) was added methanesulfonyl chloride (17.32 μL, 0.222 mmol), and the reaction was stirred at room temperature overnight and then partitioned between 1 M NaOH (5 mL) and CH$_2$Cl$_2$ (25 mL). The layers were separated and the aqueous layer was extracted with CH$_2$Cl$_2$ (25 mL). The combined CH$_2$Cl$_2$ layers were dried (MgSO$_4$), filtered, concentrated and purified by chromatography on silica gel eluting with a gradient of 0-100% ethyl acetate in [9:1 CH$_2$Cl$_2$:ethyl acetate] to provide the titled compound. $^1$H NMR (300 MHz, DMSO-d$_6$) δ ppm 11.13 (s, 1H), 8.57 (s, 1H), 8.31 (s, 1H), 8.28-8.26 (m, 1H), 7.65-7.61 (m, 1H), 7.31 (dd, J=9.2, 2.0 Hz, 1H), 4.82 (s, 2H), 4.26 (s, 2H), 4.15 (s, 3H), 3.11 (s, 3H); MS (ESI) m/z 389 (M+H)$^+$.

Example 162

6-methyl-N³-(2-methyl-2H-indazol-5-yl)-4-oxo-4,5,6,7-tetrahydro-1-benzofuran-3,6-dicarboxamide

Example 162A 1-methyl-3,5-dioxocyclohexanecarboxamide

To a solution of 3,5-dimethoxy-1-methylcyclohexa-2,5-dienecarboxamide (CAS#97294-69-4) (131 mg, 0.664 mmol) in tetrahydrofuran (10 mL) was added 1 M HCl (10 mL), and the mixture was stirred overnight at room temperature and then concentrated to dryness. The residue was dissolved in $CH_2Cl_2$/methanol, silica gel (~1 gram) was added, and the mixture was concentrated to dryness. The crude product as a silica gel suspension was purified by chromatography on silica gel eluting with a gradient of 0-100% [22:1:1 ethyl acetate/formic acid/water] in [200:1:1 ethyl acetate/formic acid/water] to provide the titled compound. ¹H NMR (300 MHz, DMSO-d₆) δ ppm 11.03 (s, 1H), 7.23 (s, 1H), 6.89 (s, 1H), 5.11 (s, 1H), 2.66 (d, J=16.6 Hz, 2H), 2.21 (d, J=16.7 Hz, 2H), 1.17 (s, 3H).

Example 162B 6-carbamoyl-6-methyl-4-oxo-4,5,6,7-tetrahydro-1-benzofuran-3-carboxylic acid To a solution of the product from Example 162A (64 mg, 0.378 mmol) in 1 M KOH (492 µL, 0.492 mmol) was added dropwise a solution of 3-bromopyruvic acid (76 mg, 0.454 mmol) in methanol (0.5 mL). After stirring at room temperature for overnight, the mixture was concentrated to dryness. A mixture of this residue in acetic acid (1 mL) and acetic anhydride (0.5 mL) was heated to 100° C. for 30 minutes, cooled and concentrated to dryness. This crude product was suspended on silica gel and purified by chromatography on silica gel eluting with a gradient of 0-100% [22:1:1 ethyl acetate/formic acid/water] in [200:1:1 ethyl acetate/formic acid/water] to provide the titled compound. ¹H NMR (300 MHz, CDCl₃) δ ppm 8.09 (s, 1H), 6.00 (s, 2H), 3.59 (dd, J=17.6, 1.1 Hz, 1H), 3.08 (dd, J=17.0, 1.2 Hz, 1H), 2.94 (d, J=17.6 Hz, 1H), 2.71 (d, J=17.0 Hz, 1H), 1.52 (s, 3H); MS (ESI) m/z 238 (M+H)⁺.

Example 162C 6-methyl-N³-(2-methyl-2H-indazol-5-yl)-4-oxo-4,5,6,7-tetrahydro-1-benzofuran-3,6-dicarboxamide The titled compound was prepared using the procedure described in Example 159B substituting the product from Example 162B for the product from Example 159A, except that the product was isolated directly as a solid after the reaction was partitioned between 1 M NaOH and $CH_2Cl_2$. ¹H NMR (300 MHz, DMSO-d₆) δ ppm 11.75 (s, 1H), 8.39 (s, 1H), 8.30 (s, 1H), 8.27 (d, J=1.3 Hz, 1H), 7.62 (d, J=9.1 Hz, 1H), 7.54 (s, 1H), 7.32 (dd, J=9.2, 2.0 Hz, 1H), 7.09 (s, 1H), 4.15 (s, 3H), 3.46 (d, J=17.4 Hz, 1H), 3.05 (d, J=17.2 Hz, 1H), 3.00 (d, J=16.1 Hz, 1H), 2.73 (d, J=16.4 Hz, 1H), 1.36 (s, 3H); MS (ESI) m/z 367 (M+H)⁺.

Example 163 methyl 6-methyl-3-[(2-methyl-2H-indazol-5-yl)carbamoyl]-4-oxo-4,5,6,7-tetrahydro-1-benzofuran-6-carboxylate

Example 163A 6-(methoxycarbonyl)-6-methyl-4-oxo-4,5,6,7-tetrahydro-1-benzofuran-3-carboxylic acid To a mixture of methyl 3-hydroxy-1-methyl-5-oxocyclohex-3-enecarboxylate (CAS#126395-85-5) (1.41 g, 7.66 mmol) and sodium bicarbonate (0.836 g, 9.95 mmol) in $H_2O$ (10 mL) was added over 30 minutes in portions a solution of 3-bromopyruvic acid (1.534 g, 9.19 mmol) in methanol (10 mL). The mixture was stirred overnight and concentrated to dryness. The residue was taken up in a mixture of acetic acid (24 mL) and acetic anhydride (12 mL), heated to 100° C. for 30 minutes, concentrated to an oil, re-dissolve in $CH_2Cl_2$, treated with 10 grams of silica gel and concentrated to dryness. The crude product as a silica gel suspension was purified by chromatography on silica gel eluting with a gradient of 33-100% [200:1:1 ethyl acetate/HCOOH/$H_2O$] in hexane to provide the titled compound. ¹H NMR (300 MHz, CDCl₃) δ ppm 12.95 (s, 1H), 8.09 (s, 1H), 3.71 (s, 3H), 3.57 (dd, J=17.6, 0.7 Hz, 1H), 3.16 (dd, J=17.0, 0.9 Hz, 1H), 2.94 (d, J=17.6 Hz, 1H), 2.65 (d, J=17.0 Hz, 1H), 1.50 (s, 3H); MS (ESI) m/z 253 (M+H)⁺.

Example 163B methyl 6-methyl-3-[(2-methyl-2H-indazol-5-yl)carbamoyl]-4-oxo-4,5,6,7-tetrahydro-1-benzofuran-6-carboxylate The titled compound was prepared using the procedure described in Example 159B substituting the product from Example 162A for the product from Example 159A, except that during the workup, sodium bicarbonate solution was used in place of 1 M NaOH and the chromatography on silica gel was eluted with 0-100% (10 minutes) ethyl acetate in [9:1 $CH_2Cl_2$:ethyl acetate]. ¹H NMR (300 MHz, CDCl₃) δ ppm 11.59 (s, 1H), 8.43 (d, J=1.4 Hz, 1H), 8.13 (s, 1H), 7.85 (s, 1H), 7.67 (d, J=9.2 Hz, 1H), 7.42 (dd, J=9.2, 2.0 Hz, 1H), 4.21 (s, 3H), 3.71 (s, 3H), 3.56 (dd, J=17.4, 1.1 Hz, 1H), 3.14 (dd, J=16.6, 1.2 Hz, 1H), 2.93 (d, J=17.4 Hz, 1H), 2.65 (d, J=16.6 Hz, 1H), 1.49 (s, 3H); MS (ESI) m/z 382 (M+H)⁺.

Example 164

6-(hydroxymethyl)-6-methyl-N-(2-methyl-2H-indazol-5-yl)-4-oxo-4,5,6,7-tetrahydro-1-benzofuran-3-carboxamide

Example 164A 6-(hydroxymethyl)-6-methyl-4-oxo-4,5,6,7-tetrahydro-1-benzofuran-3-carboxylic acid A mixture of (3,5-dimethoxy-1-methylcyclohexa-2,5-dienyl)methanol (CAS#73696-80-7) (0.98 g, 5.32 mmol) in tetrahydrofuran (25 mL) and 1 M HCl (25 mL) was stirred at room temperature for 2 hours and concentrated to dryness. The residue was dissolved in a mixture of water (10 mL) and NaHCO$_3$ (1.8 g, 21 mmol), a solution of 3-bromopyruvic acid (1.066 g, 6.38 mmol) in methanol (5 mL) was then added in portions over 30 minutes, stirred overnight at room temperature, and concentrated to dryness. The residue was taken up in acetic acid (20 mL) and acetic anhydride (10 mL), heated to 100° C. for 30 minutes, cooled and concentrated to dryness. A solution of this residue in methanol (50 mL) and 1 M HCl (50 mL) was stirred at 80° C. for 3 hours, stirred at room temperature overnight, and concentrated to dryness. The residue was dissolved in a mixture of CH$_2$Cl$_2$ and methanol and silica gel (~6 g) was added. This mixture was concentrated to dryness. The crude product as a silica gel suspension was purified by chromatography on silica gel eluting with a gradient of 50-100% [200:1:1 ethyl acetate/formic acid/water] in hexane. This residue was treated with diethyl ether and the resulting yellow solid was collected by filtration and dried under vacuum to provide the titled compound. $^1$H NMR (300 MHz, CDCl$_3$) δ ppm 13.06 (bs, 1H), 8.10 (s, 1H), 3.56 (s, 2H), 3.23 (d, J=17.9 Hz, 1H), 2.85 (d, J=17.1 Hz, 1H), 2.71 (d, J=17.9 Hz, 1H), 2.46 (dd, J=17.1, 0.8 Hz, 1H), 1.18 (d, J=17.5 Hz, 3H); MS (ESI) m/z 225 (M+H)$^+$.

Example 164B 6-(hydroxymethyl)-6-methyl-N-(2-methyl-2H-indazol-5-yl)-4-oxo-4,5,6,7-tetrahydro-1-benzofuran-3-carboxamide The titled compound was prepared using the procedure described in Example 159B substituting the product from Example 164A for the product from Example 159A, except that the product was purified by precipitation from ethyl acetate and hexane. $^1$H NMR (300 MHz, DMSO-d$_6$) δ ppm 11.72 (s, 1H), 8.41 (s, 1H), 8.30 (s, 1H), 8.27 (d, J=1.5 Hz, 1H), 7.62 (d, J=9.1 Hz, 1H), 7.32 (dd, J=9.2, 2.0 Hz, 1H), 5.01 (t, J=5.4 Hz, 1H), 4.15 (s, 3H), 3.34-3.28 (m, 2H), 3.09 (d, J=17.7 Hz, 1H), 2.79-2.71 (m, 2H), 2.50-2.41 (m, 1H), 1.03 (s, 3H); MS (ESI) m/z 354 (M+H)$^+$.

Example 165 tert-butyl 4-[4-({[6-(hydroxymethyl)-6-methyl-4-oxo-4,5,6,7-tetrahydro-1-benzofuran-3-yl]carbonyl}amino)-3-methoxyphenyl]piperazine-1-carboxylate The titled compound was prepared using the procedure described in Example 159B substituting the product from Example 164A for the product from Example 159A, and substituting tert-butyl 4-(4-amino-3-methoxyphenyl)piperazine-1-carboxylate (CAS#1246532-96-6) for 2-methyl-2H-indazol-5-amine. $^1$H NMR (300 MHz, CDCl$_3$) δ ppm 11.28 (s, 1H), 8.29 (d, J=8.7 Hz, 1H), 8.12 (s, 1H), 6.58-6.49 (m, 2H), 3.96 (s, 3H), 3.62-3.56 (m, 4H), 3.54 (dd, J=5.1, 1.4 Hz, 2H), 3.20-3.08 (m, 5H), 2.76 (d, J=16.5 Hz, 1H), 2.69 (d, J=17.7 Hz, 1H), 2.43 (dd, J=16.3, 0.5 Hz, 1H), 1.69 (t, J=5.1 Hz, 1H), 1.49 (s, 9H), 1.15 (s, 3H); MS (ESI) m/z 514 (M+H)$^+$.

Example 166

6-(methoxymethyl)-N-[2-methoxy-4-(piperazin-1-yl)phenyl]-6-methyl-4-oxo-4,5,6,7-tetrahydro-1-benzofuran-3-carboxamide Example 166A 6-(methoxymethyl)-6-methyl-4-oxo-4,5,6,7-tetrahydro-1-benzofuran-3-carboxylic acid A solution of 1,5-dimethoxy-3-(methoxymethyl)-3-methylcyclohexa-1,4-diene (CAS#73696-81-8) (397 mg, 2 mmol) in tetrahydrofuran (10 mL) and 1 M HCl (10 mL) was stirred at room temperature for 4 hours and concentrated to dryness. This residue was dissolved in a mixture of water (5 mL) and sodium bicarbonate (670 mg, 8 mmol), treated portion-wise with a solution of 3-bromopyruvic acid (434 mg, 2.60 mmol) in methanol (5 mL) over 30 minutes, stirred at room temperature overnight, and concentrated to dryness. The residue was taken up in acetic acid (12 mL) and acetic anhydride (6 mL), heated to 100° C. for 30 minutes, concentrated to dryness, dissolved in CH$_2$Cl$_2$ (~30 mL), treated with silica gel (6 grams) and concentrated to dryness. The crude product as a silica gel suspension was purified by chromatography on silica gel eluting with 33-80% (10 minutes) [200:1:1 ethyl acetate/formic acid/water] in hexane to provide the titled compound. $^1$H NMR (300 MHz, CDCl$_3$) δ ppm 12.95 (s, 1H), 8.09 (s, 1H), 3.71 (s, 3H), 3.57 (dd, J=17.6, 0.7 Hz, 1H), 3.16 (dd, J=17.0, 0.9 Hz, 1H), 2.94 (d, J=17.6 Hz, 1H), 2.65 (d, J=17.0 Hz, 1H), 1.50 (s, 3H); MS (ESI) m/z 253 (M+H)$^+$.

Example 166B tert-butyl 4-[3-methoxy-4-({[6-(methoxymethyl)-6-methyl-4-oxo-4,5,6,7-tetrahydro-1-benzofuran-3-yl]carbonyl}amino)phenyl]piperazine-1-carboxylate The titled compound was prepared using the procedure described in Example 159B substituting the product from Example 166A for the product from Example 159A, and substituting tert-butyl 4-(4-amino-3-methoxyphenyl)piperazine-1-carboxylate (CAS#1246532-96-6) for 2-methyl-2H-indazol-5-amine. $^1$H NMR (300 MHz, CDCl$_3$) δ ppm 11.30 (s, 1H), 8.29 (d, J=8.7 Hz, 1H), 8.12 (s, 1H), 6.58-6.49 (m, 2H), 3.97 (s, 3H), 3.65-3.54 (m, 4H), 3.36 (s, 3H), 3.26 (d, J=9.2 Hz, 1H), 3.22 (d, J=9.2 Hz, 1H), 3.16 (d, J=17.6 Hz, 1H), 3.15-3.08 (m, 4H), 2.78 (d, J=16.6 Hz, 1H), 2.66 (d, J=17.6 Hz, 1H), 2.40 (d, J=16.6 Hz, 1H), 1.49 (s, 9H), 1.13 (s, 3H); MS (ESI) m/z 528 (M+H)$^+$.

Example 166C 6-(methoxymethyl)-N-[2-methoxy-4-(piperazin-1-yl)phenyl]-6-methyl-4-oxo-4,5,6,7-tetrahydro-1-benzofuran-3-carboxamide The product from Example 166B (107.7 mg, 0.204 mmol) was dissolved in trifluoroacetic acid (5 mL), heated to 60° C. for 2 minutes and concentrated. This residue was diluted with CH$_2$Cl$_2$ (50 mL) and washed with 1 M NaOH (5 mL). The aqueous layer was extracted with CH$_2$Cl$_2$ (25 mL). The combined CH$_2$Cl$_2$ layers were dried (MgSO$_4$), filtered and concentrated to provide the titled compound. $^1$H NMR (300 MHz, DMSO-d$_6$) δ ppm 11.18 (s, 1H), 8.34 (s, 1H), 8.03 (d, J=8.9 Hz, 1H), 6.62 (d, J=2.5 Hz, 1H), 6.46 (dd, J=8.9, 2.5

Hz, 1H), 3.86 (s, 3H), 3.27 (s, 3H), 3.24 (s, 2H), 3.09-3.02 (m, 5H), 2.81 (dd, J=13.7, 9.0 Hz, 5H), 2.69 (d, J=16.4 Hz, 1H), 2.50-2.43 (m, 1H), 1.06 (s, 3H); MS (ESI) m/z 428 (M+H)$^+$.

Example 167

5-(hydroxymethyl)-5-methyl-N-(2-methyl-2H-indazol-5-yl)-4-oxo-4,5,6,7-tetrahydro-1-benzofuran-3-carboxamide Example 167A 5-(acetoxymethyl)-5-methyl-4-oxo-4,5,6,7-tetrahydro-1-benzofuran-3-carboxylic acid The titled compound was prepared using the procedure described in Example 166A substituting 3-hydroxy-6-(hydroxymethyl)-6-methylcyclohex-2-enone (CAS#1167996-92-0) for 1,5-dimethoxy-3-(methoxymethyl)-3-methylcyclohexa-1,4-diene, and was isolated as the second isomer to elute from the chromatography column. $^1$H NMR (300 MHz, CDCl$_3$) δ ppm 8.11 (s, 1H), 4.46 (d, J=11.1 Hz, 1H), 4.09 (d, J=11.1 Hz, 1H), 3.05 (dd, J=7.8, 5.0 Hz, 2H), 2.43 (dt, J=13.9, 7.8 Hz, 1H), 2.05 (s, 3H), 2.10-2.00 (m, 1H), 1.27 (s, 3H); MS (ESI) m/z 267 (M+H)$^+$. The first isomer to elute from the chromatography column was 7-(acetoxymethyl)-7-methyl-4-oxo-4,5,6,7-tetrahydro-1-benzofuran-3-carboxylic acid.

Example 167B

{5-methyl-3-[(2-methyl-2H-indazol-5-yl)carbamoyl]-4-oxo-4,5,6,7-tetrahydro-1-benzofuran-5-yl}methyl acetate The titled compound was prepared using the procedure described in Example 159B substituting the product from Example 167A for the product from Example 159A. $^1$H NMR (300 MHz, CDCl$_3$) δ ppm 11.74 (bs, 1H), 8.44 (d, J=1.9 Hz, 1H), 8.16 (s, 1H), 7.87 (s, 1H), 7.69 (d, J=9.1 Hz, 1H), 7.46 (dd, J=9.1, 2.0 Hz, 1H), 4.50 (d, J=11.0 Hz, 1H), 4.22 (s, 3H), 4.12 (d, J=11.0 Hz, 1H), 3.05 (dd, J=7.9, 4.9 Hz, 2H), 2.41 (dt, J=13.9, 7.9 Hz, 1H), 2.06 (s, 3H), 2.07-2.02 (m, 1H), 1.28 (s, 3H); MS (ESI) m/z 396 (M+H)$^+$.

Example 167C 5-(hydroxymethyl)-5-methyl-N-(2-methyl-2H-indazol-5-yl)-4-oxo-4,5,6,7-tetrahydro-1-benzofuran-3-carboxamide To a solution of the product from Example 167B (69 mg, 0.175 mmol) in tetrahydrofuran (4 mL) and methanol (4 mL) was added 1 M NaOH (2 mL), and the mixture was stirred for 1 hour at room temperature and partitioned between 1 M NaOH (5 mL) and CH$_2$Cl$_2$ (25 mL). The layers were separated and the aqueous layer was extracted with CH$_2$Cl$_2$ (25 mL). The combined CH$_2$Cl$_2$ layers were dried (MgSO$_4$), filtered, and concentrated to provide the titled compound. $^1$H NMR (300 MHz, CDCl$_3$) δ ppm 11.70 (bs, 1H), 8.43 (d, J=1.9 Hz, 1H), 8.14 (s, 1H), 7.86 (s, 1H), 7.68 (d, J=9.1 Hz, 1H), 7.41 (dd, J=9.1, 2.0 Hz, 1H), 4.21 (s, 3H), 3.97 (d, J=11.2 Hz, 1H), 3.61 (d, J=11.2 Hz, 1H), 3.10-3.01 (m, 2H), 2.48 (ddd, J=13.8, 9.1, 7.4 Hz, 1H), 1.96-1.87 (m, 1H), 1.25 (s, 3H); MS (ESI) m/z 354 (M+H)$^+$.

Example 168

5,5-dimethyl-N-(2-methyl-2H-indazol-5-yl)-4-oxo-4,5,6,7-tetrahydro-1-benzofuran-3-carboxamide Example 168A ethyl 5,5-dimethyl-4-oxo-4,5,6,7-tetrahydro-1-benzofuran-3-carboxylate To a solution of 4,4-dimethylcyclohexane-1,3-dione (5 g, 35.7 mmol) and KOH (2.60 g, 46.4 mmol) in water (25.5 mL) was added a solution of 3-bromo-2-oxopropanoic acid (7.15 g, 42.8 mmol) in methanol (51.0 mL). After stirring for 2 hours, the methanol was removed by concentration under reduced pressure. Water (25.5 mL) was added, and the mixture was heated to reflux for 2 hours. Upon cooling, a mixture of 5,5-dimethyl-4-oxo-4,5,6,7-tetrahydro-1-benzofuran-3-carboxylic acid and 7,7-dimethyl-4-oxo-4,5,6,7-tetrahydro-1-benzofuran-3-carboxylic acid precipitated and was collected by filtration and dried in a vacuum oven. This solid was taken up in ethanol (100 mL), treated with concentrated sulfuric acid (0.1 mL), heated to 80° C. for 1 hour, cooled, treated with NaHCO$_3$ (5 g), stirred for 15 minutes and concentrated to approximately 20 mL total volume. The residue was partitioned between ethyl acetate and water. The ethyl acetate layer was dried (MgSO$_4$), filtered and concentrated. The residue was purified by chromatography on silica gel eluting with a gradient of 5-100% ethyl acetate in hexane to provide the titled compound as the first isomer to elute from the column. The second isomer to elute from the chromatography column was ethyl 7,7-dimethyl-4-oxo-4,5,6,7-tetrahydro-1-benzofuran-3-carboxylate.

Example 168B 5,5-dimethyl-4-oxo-4,5,6,7-tetrahydrobenzofuran-3-carboxylic acid

To a solution of the product from Example 168A (108 mg, 0.457 mmol) in tetrahydrofuran (3 mL) and methanol (3 mL) was added 1 M NaOH (1 mL), and the mixture was stirred for 30 minutes. Ether (10 mL) and water (10 mL) were added. The resulting mixture was stirred vigorously as 1 M HCl was added until the aqueous layer was acidic. The mixture was extracted with ethyl acetate (50 mL). The organic layer was isolated, dried (MgSO$_4$), filtered and concentrated to provide the titled compound. $^1$H NMR (300 MHz, CDCl$_3$) δ ppm 13.43 (s, 1H), 8.09 (s, 1H), 2.99 (t, J=6.3 Hz, 2H), 2.11 (t, J=6.3 Hz, 2H), 1.28 (s, 6H); MS (ESI) m/z 209 (M+H)$^+$.

Example 168C 5,5-dimethyl-N-(2-methyl-2H-indazol-5-yl)-4-oxo-4,5,6,7-tetrahydro-1-benzofuran-3-carboxamide The titled compound was prepared using the procedure described in Example 159B substituting the product from Example 168B for the product from Example 159A. $^1$H NMR (300 MHz, CDCl$_3$) δ ppm 11.91 (bs, 1H), 8.45 (dd, J=2.0, 0.8 Hz, 1H), 8.14 (s, 1H), 7.85 (s, 1H), 7.68 (dt, J=9.1, 0.9 Hz, 1H), 7.46 (dd, J=9.1, 2.0 Hz, 1H), 4.21 (s, 3H), 2.99 (t, J=6.3 Hz, 2H), 2.13-2.02 (m, 2H), 1.28 (s, 6H); MS (ESI) m/z 338 (M+H)$^+$.

Example 169

N-[4-(4-acetylpiperazin-1-yl)-2-methoxyphenyl]-5-(aminomethyl)-5-methyl-4-oxo-4,5,6,7-tetrahydro-1-benzofuran-3-carboxamide

Example 169A ethyl 2-cyano-2-methyl-5-oxohexanoate

To a solution of 2-cyanopropionic acid ethyl ester (10 g, 79 mmol) in acetonitrile (240 mL) was added sodium tetramethoxyborate (1.242 g, 7.87 mmol) followed by methyl vinyl ketone (6.49 mL, 79 mmol). After stirring at room temperature for 5 days, the mixture was concentrated. The residue was purified by chromatography on silica gel eluting with a gradient of 10-50% ethyl acetate in hexane to provide the titled compound. $^1$H NMR (300 MHz, CDCl$_3$) δ ppm 4.27 (q, J=7.1 Hz, 2H), 2.78-2.52 (m, 2H), 2.24 (ddd, J=14.3, 10.0, 5.6 Hz, 1H), 2.19 (s, 3H), 2.05 (ddd, J=14.3, 10.1, 5.6 Hz, 1H), 1.61 (s, 3H), 1.34 (t, J=7.1 Hz, 3H); MS (ESI) m/z 215 (M+NH$_4$)$^+$.

Example 169B 1-methyl-2,4-dioxocyclohexanecarbonitrile

To a solution of ethanol (80 mL, 1366 mmol) in tetrahydrofuran (450 mL) under nitrogen was added potassium tert-butoxide (16.86 g, 150 mmol). The mixture was cooled to 0° C., and a solution of the product from Example 169A (13.47 g, 68.3 mmol) in tetrahydrofuran (50 mL) was added over 15 minutes. The mixture was concentrated to remove most of the solvent, diluted with cold water (100 mL), acidified dropwise with concentrated HCl to pH ~5, and treated with ethyl acetate (100 mL). The aqueous layer of this mixture was neutral, so concentrated HCl was further added until the aqueous remained acidic. The layers were separated, and the aqueous layer was extracted with ethyl acetate (2×100 mL). The combined organic layers were washed with brine, dried (MgSO$_4$), filtered and concentrated to provide the titled compound. $^1$H NMR (300 MHz, DMSO-d$_6$) δ ppm 11.78 (s, 1H), 5.25 (s, 1H), 2.55-2.46 (m, 2H), 2.36-2.24 (m, 1H), 2.12-2.01 (m, 1H), 1.43 (s, 3H); MS (ESI) m/z 150 (M−H)$^−$.

Example 169C ethyl 5-cyano-5-methyl-4-oxo-4,5,6,7-tetrahydro-1-benzofuran-3-carboxylate To a mixture of the product from Example 169B (6 g, 39.7 mmol) and NaHCO$_3$ (13.34 g, 159 mmol) in ethanol (100 mL) was added ethyl bromopyruvate (6.47 mL, 51.6 mmol). The reaction was stirred overnight at room temperature, filtered to remove the solids, and the filtrate was concentrated to dryness. The residue was treated with acetic acid (200 mL) and acetic anhydride (100 mL), heated to 110° C. overnight, concentrated to an oil, diluted with ethyl acetate (300 mL) and washed with saturated NaHCO$_3$ solution. The aqueous solution was extracted with ethyl acetate, and the combined ethyl acetate layers were washed with brine, dried (MgSO$_4$), filtered and concentrated. The residue was purified by chromatography on silica gel eluting with a gradient of 15-50% ethyl acetate in hexane to provide the titled compound as the first isomer to elute from the column. $^1$H NMR (300 MHz, CDCl$_3$) δ ppm 7.95 (s, 1H), 4.34 (q, J=7.1 Hz, 2H), 3.28 (ddd, J=18.1, 10.0, 5.3 Hz, 1H), 3.03 (ddd, J=18.1, 5.3, 4.1 Hz, 1H), 2.54 (ddd, J=13.7, 5.3, 4.0 Hz, 1H), 2.28-2.16 (m, 1H), 1.64 (s, 3H), 1.37 (t, J=7.1 Hz, 3H); MS (ESI) m/z 248 (M+H)$^+$. The second isomer to elute from the chromatography column was ethyl 7-cyano-7-methyl-4-oxo-4,5,6,7-tetrahydro-1-benzofuran-3-carboxylate.

Example 169D ethyl 5-{[(tert-butoxycarbonyl)amino]methyl}-5-methyl-4-oxo-4,5,6,7-tetrahydro-1-benzofuran-3-carboxylate The product from Example 169C (3.19 g, 12.90 mmol) in ethanol (155 mL) was added to a mixture of Raney®-nickel 2800 (water slurry) (15 g) and di-tert-butyl dicarbonate (7.49 mL, 32.3 mmol). The mixture was shaken under 30 psi of hydrogen at room temperature for 2 hours and filtered. The filtrate was concentrated to dryness, and the residue was purified by chromatography on silica gel eluting with a gradient of 10-50% ethyl acetate in hexane to provide the titled compound. $^1$H NMR (300 MHz, CDCl$_3$) δ ppm 7.89 (s, 1H), 5.19 (t, J=5.9 Hz, 1H), 4.33 (q, J=7.1 Hz, 2H), 3.44 (dd, J=13.8, 6.3 Hz, 1H), 3.22 (dd, J=13.8, 6.9 Hz, 1H), 3.01-2.94 (m, 2H), 2.29-2.14 (m, 1H), 1.90 (dt, J=13.8, 4.6 Hz, 1H), 1.41 (s, 9H), 1.35 (t, J=7.1 Hz, 3H), 1.16 (s, 3H); MS (ESI) m/z 352 (M+H)$^+$.

Example 169E

5-{[(tert-butoxycarbonyl)amino]methyl}-5-methyl-4-oxo-4,5,6,7-tetrahydro-1-benzofuran-3-carboxylic acid The titled compound was prepared using the procedure described in Example 168B substituting the product from Example 169D for the product from Example 168A. $^1$H NMR (300 MHz, CDCl$_3$) δ ppm 13.14 (s, 1H), 8.10 (s, 1H), 4.90 (bt, 1H), 3.46 (dd, J=14.1, 6.2 Hz, 1H), 3.34 (dd, J=14.2, 7.4 Hz, 1H), 3.23-2.95 (m, 2H), 2.37-2.24 (m, 1H), 2.10-1.98 (m, 1H), 1.43 (s, 9H), 1.23 (s, 3H); MS (ESI) m/z 324 (M+H)$^+$.

Example 169F tert-butyl[(3-{[4-(4-acetylpiperazin-1-yl)-2-methoxyphenyl]carbamoyl}-5-methyl-4-oxo-4,5,6,7-tetrahydro-1-benzofuran-5-yl)methyl]carbamate The titled compound was prepared using the procedure described in Example 159B substituting the product from Example 169E for the product from Example 159A, and substituting 1-(4-(4-amino-3-methoxyphenyl)piperazin-1-yl)ethanone for 2-methyl-2H-indazol-5-amine. A gradient of 25-100% [20% ethanol in ethyl acetate] in ethyl acetate was used in place of 50-100% ethyl acetate in hexane as the eluent in the chromatography. $^1$H NMR (300 MHz, CDCl$_3$) δ ppm 11.32 (s, 1H), 8.27 (d, J=8.6 Hz, 1H), 8.11 (d, J=4.5 Hz, 1H), 6.58-6.49 (m, 2H), 5.05-4.97 (m, 1H), 3.96 (s, 3H), 3.82-3.76 (m, 2H), 3.68-3.59 (m, 2H), 3.50 (dd, J=13.9, 6.2 Hz, 1H), 3.31 (dd, J=13.9, 7.1 Hz, 1H), 3.22-3.09 (m, 4H), 3.03 (dd, J=8.0, 4.7 Hz, 2H), 2.33-2.20 (m, 1H), 2.14 (s, 3H), 1.97 (dt, J=13.4, 4.4 Hz, 1H), 1.43 (s, 9H), 1.22 (s, 3H); MS (ESI) m/z 555 (M+H)$^+$

Example 169G

N-[4-(4-acetylpiperazin-1-yl)-2-methoxyphenyl]-5-(aminomethyl)-5-methyl-4-oxo-4,5,6,7-tetrahydro-1-benzofuran-3-carboxamide A solution of the product from Example 169F (1.42 g, 2.56 mmol) in 4 M HCl in dioxane (4 mL) and water (2 mL) was warmed to 60° C. for 2 minutes and concentrated with a stream of $N_2$. The residue was partitioned between 1 M NaOH (25 mL) and $CH_2Cl_2$ (50 mL). The layers were separated and the aqueous layer was extracted with $CH_2Cl_2$ (2×25 mL). The combined $CH_2Cl_2$ layers were dried ($MgSO_4$), filtered, concentrated and chromatographed on silica gel eluting with a gradient of 2-10% (9:1 methanol: 29% aqueous ammonium hydroxide solution) in $CH_2Cl_2$ to provide the free base of the titled compound. A solution of this free base in $CH_2Cl_2$ (20 mL) was cooled to 0° C. and HCl gas was bubbled into the solution for 1 minute. The solvent was removed with a stream of nitrogen, and ethyl acetate was added to the residue. The solid was collected by filtration, washed with ethyl acetate and dried under vacuum to provide the di-hydrochloric acid salt of the titled compound. $^1$H NMR (300 MHz, DMSO-$d_6$) δ ppm 11.18 (s, 1H), 8.40 (s, 1H), 8.11 (s, 3H), 8.07 (d, J=8.9 Hz, 1H), 6.82 (s, 1H), 6.64 (d, J=8.0 Hz, 1H), 3.91 (s, 3H), 3.68-3.59 (m, 4H), 3.32-3.07 (m, 7H), 2.98 (dd, J=13.1, 6.0 Hz, 1H), 2.27 (dt, J=15.9, 8.0 Hz, 1H), 2.06 (s, 3H), 2.09-1.96 (m, 1H), 1.25 (s, 3H); MS (ESI) m/z 455 (M+H)$^+$

Example 170

N-[4-(4-acetylpiperazin-1-yl)-2-methoxyphenyl]-4-oxo-4,7-dihydrospiro[furo[2,3-c]pyran-5,4'-piperidine]-3-carboxamide

Example 170A benzyl 4-(2-ethoxy-2-oxoethoxy)-4-ethynylpiperidine-1-carboxylate To a solution of benzyl 4-ethynyl-4-hydroxypiperidine-1-carboxylate (CAS#495415-65-1)(5.4 g, 20.8 mmol) in tetrahydrofuran (100 mL) was added a 60% dispersion of NaH in mineral oil (0.83 g, 20.8 mmol). After stirring at room temperature for 30 minutes, ethyl bromoacetate (2.55 mL, 22.91 mmol) was added, and the reaction was stirred at room temperature overnight and then treated with saturated NH$_4$Cl (50 mL). After stirring for 10 minutes, the mixture was concentrated under reduced pressure to remove a significant amount of the tetrahydrofuran. The residue was extracted with ethyl acetate (100 mL). The layers were separated and the aqueous layer was treated with water (10 mL) and extracted with ethyl acetate (50 mL). The combined organic layers were washed with brine, dried (MgSO$_4$), filtered, concentrated and purified by chromatography on silica gel eluting with a gradient of 16-50% ethyl acetate in hexane to provide the titled compound. $^1$H NMR (300 MHz, CDCl$_3$) δ ppm 7.41-7.27 (m, 5H), 5.13 (s, 2H), 3.92-3.78 (m, 2H), 3.44-3.31 (m, 2H), 2.54 (s, 1H), 2.05 (bs, 1H), 1.92 (d, J=12.6 Hz, 2H), 1.80-1.67 (m, 2H); MS (ESI) m/z 346 (M+H)$^+$.

Example 170B benzyl 3,5-dioxo-1-oxa-9-azaspiro[5.5]undecane-9-carboxylate

To a solution of the product Example 170A (3.66 g, 10.60 mmol) in methanol (300 mL) was added mercury(II) acetate (0.338 g, 1.060 mmol) followed by sulfuric acid (10 drops). The reaction was heated to 60° C. for 30 minutes and then concentrated under reduced pressure to approximately 100 mL total volume. 1 M HCl (200 mL) was added, and the resulting mixture was stirred for 5 minutes and partitioned between ethyl acetate (100 mL) and water (300 mL). The layers were separated, and the aqueous layer was extracted with ethyl acetate (2×50 mL). The combined organic layers were washed with brine, dried (MgSO$_4$), filtered and concentrated to provide a mixture of benzyl 4-acetyl-4-(2-methoxy-2-oxoethoxy)piperidine-1-carboxylate and benzyl 4-acetyl-4-(2-ethoxy-2-oxoethoxy)piperidine-1-carboxylate. In a separate flask, potassium tert-butoxide (2.62 g, 23.32 mmol) was added to a solution of ethanol (12.38 mL, 212 mmol) in tetrahydrofuran (80 mL) under N$_2$, and the resulting mixture was cooled to 0° C. To this mixture was added a solution of benzyl 4-acetyl-4-(2-methoxy-2-oxoethoxy)piperidine-1-carboxylate and benzyl 4-acetyl-4-(2-ethoxy-2-oxoethoxy)piperidine-1-carboxylate in tetrahydrofuran (10 mL) dropwise over 15 minutes. The reaction was stirred at 0° C. for 30 minutes, concentrated to ~25 mL total volume, diluted with water (100 mL) and neutralized with concentrated HCl. The mixture was treated with ethyl acetate (100 mL) and further acidified to pH ~1. The mixture was transferred to a separatory funnel, and the layers were separated. The aqueous layer was extracted with ethyl acetate (2×50 mL). The combined organic layers were washed with brine, dried (MgSO$_4$), filtered and concentrated to provide the titled compound. MS (ESI) m/z 335 (M+NH$_4$)$^+$.

Example 170C

1'-[(benzyloxy)carbonyl]-4-oxo-4,7-dihydrospiro[furo[2,3-c]pyran-5,4'-piperidine]-3-carboxylic acid To a solution of the product from Example 170B (3.36 g, 10.6 mmol) and NaHCO$_3$ (3.56 g, 42.4 mmol) in water (15 mL) was added a solution of 3-bromopyruvic acid (2.301 g, 13.78 mmol) in methanol (15 mL) in portions over 1 hour. The resultant mixture was stirred overnight at room temperature, concentrated to dryness, treated with acetic acid (150 mL) and acetic anhydride (75 mL), and heated to 100° C. for 30 minutes. The mixture was then concentrated to dryness. The residue was partitioned between 1 M HCl (100 mL) and CH$_2$Cl$_2$ (100 mL). The layers were separated, and the aqueous layer was extracted with CH$_2$Cl$_2$ (2 times, 50 mL and 25 mL). The combined CH$_2$Cl$_2$ layers were dried (MgSO$_4$), filtered, treated with silica gel (8 scupulas) and concentrated to dryness. The crude product as a silica gel suspension was purified by chromatography on silica gel eluting with a gradient of 40-100% [200:1:1 ethyl acetate/formic acid/water] in hexane to provide the titled compound as the second isomer to elute from the column. $^1$H NMR (300 MHz, CDCl$_3$) δ ppm 8.17 (s, 1H), 7.41-7.29 (m, 5H), 5.15 (s, 2H), 4.95 (s, 2H), 4.25-4.04 (m, 2H), 3.32-3.06 (m, 2H), 2.11-1.95 (m, 2H), 1.94-1.79 (m, 2H); MS (ESI) m/z 403 (M+NH$_4$)$^+$. The first isomer to elute from the chromatography column was 1'-[(benzyloxy)carbonyl]-4-oxo-4,5-dihydrospiro[furo[2,3-c]pyran-7,4'-piperidine]-3-carboxylic acid.

Example 170D benzyl 3-{[4-(4-acetylpiperazin-1-yl)-2-methoxyphenyl]carbamoyl}-4-oxo-4,7-dihydro-1'H-spiro[furo[2,3-c]pyran-5,4'-piperidine]-1'-carboxylate The titled compound was prepared using the procedure described in Example 159B substituting the product from Example 170C for the product from Example 159A, and substituting 1-(4-(4-amino-3-methoxyphenyl)piperazin-1-yl)ethanone for 2-methyl-2H-indazol-5-amine. A gradient of 25-100% [20% ethanol in ethyl acetate] in ethyl acetate was used in place of 50-100% ethyl acetate in hexane as the eluent in the chromatography. $^1$H NMR (300 MHz, CDCl$_3$) δ ppm 11.00 (bs, 1H), 8.29 (d, J=8.8 Hz, 1H), 8.18 (s, 1H), 7.40-7.28 (m, 5H), 6.62-6.51 (m, 2H), 5.16 (s, 2H), 4.92 (s, 2H), 4.25-4.05 (m, 2H), 3.96 (s, 3H), 3.80 (s, 2H), 3.70-3.60 (m, 2H), 3.28-3.07 (m, 7H), 2.15 (s, 3H), 2.13-2.02 (m, 2H), 1.94-1.81 (m, 1H); MS (ESI) m/z 617 (M+H)$^+$.

Example 170E

N-[4-(4-acetylpiperazin-1-yl)-2-methoxyphenyl]-4-oxo-4,7-dihydrospiro[furo[2,3-c]pyran-5,4'-piperidine]-3-carboxamide A mixture of the product from Example 170D (0.34 g, 0.551 mmol), methanol (20 mL), and 20% Pd(OH)$_2$/C, wet, (0.068 g, 0.484 mmol) was stirred under a hydrogen atmosphere at 30 psi for 2 hours. The mixture was filtered to remove the solids, and the filtrate was concentrated. The residue was purified by chromatography on silica gel eluting with a gradient of 4-20% (9:1 methanol:29% ammonium hydroxide) in CH$_2$Cl$_2$ to provide the free base of the titled compound. A solution of this free base in CH$_2$Cl$_2$ (20 mL) was cooled to 0° C. and HCl gas was bubbled into the solution for 1 minute. The solvent was removed with a stream of nitrogen, and ethyl acetate was added to the residue. The solid was collected by filtration, washed with ethyl acetate and dried under vacuum to provide the dihydrochloric acid salt of the titled compound. $^1$H NMR (300 MHz, DMSO-d$_6$) δ ppm 10.88 (s, 1H), 9.17 (d, J=9.3 Hz, 1H), 9.04-8.84 (m, 1H), 8.55 (s, 1H), 8.12 (d, J=8.8 Hz, 1H), 6.90 (bs, 1H), 6.72 (d, J=7.4 Hz, 1H), 5.13 (s, 2H), 3.90 (s, 3H), 3.74-3.59 (m, 4H), 3.34-3.13 (m, 6H), 3.13-2.94 (m, 2H), 2.20-2.09 (m, 4H), 2.06 (s, 3H); MS (ESI) m/z 483 (M+H)$^+$.

Example 171

N-[6-(4-acetylpiperazin-1-yl)-2-methoxypyridin-3-yl]-5,5-dimethyl-4-oxo-4,7-dihydro-5H-furo[2,3-c]pyran-3-carboxamide Example 171A ethyl 3-hydroxy-5,5-dimethyl-4-oxo-3,4,5,7-tetrahydro-2H-furo[2,3-c]pyran-3-carboxylate To a mixture of 2,2-dimethyl-2H-pyran-3,5(4H,6H)-dione (CAS#98272-63-0) (1.9 g, 13.37 mmol) and NaHCO$_3$ (4.49 g, 53.5 mmol) in ethanol (40 mL) was added ethyl bromopyruvate (3.39 g, 17.38 mmol), and the reaction was stirred overnight at room temperature, diluted with ethanol, and filtered to remove the solids. The filtrate was concentrated to dryness, and the residue was purified by chromatography on silica gel eluting with 50% diethyl ether in hexane to provide the titled compound as the isomer first to elute from the column. $^1$H NMR (300 MHz, CDCl$_3$) δ ppm 4.82 (d, J=10.5 Hz, 1H), 4.61 (d, J=10.5 Hz, 1H), 4.54 (s, 2H), 4.42-4.20 (m, 2H), 1.71 (bs, 1H), 1.38 (s, 3H), 1.34 (s, 3H), 1.28 (t, J=7.1 Hz, 3H); MS (ESI) m/z 257 (M+H)$^+$. The second isomer to elute from the chromatography column was ethyl 3-hydroxy-7,7-dimethyl-4-oxo-3,4,5,7-tetrahydro-2H-furo[2,3-c]pyran-3-carboxylate.

Example 171B ethyl 5,5-dimethyl-4-oxo-4,7-dihydro-5H-furo[2,3-c]pyran-3-carboxylate To a solution of the product from Example 171A (0.16 g, 0.624 mmol) and triethylamine (0.348 mL, 2.498 mmol) in CH$_2$Cl$_2$ (20 mL) was added methanesulfonyl chloride (0.097 mL, 1.249 mmol). After stirring at room temperature for 1 hour, the mixture was partitioned between saturated NaHCO$_3$ solution (10 mL) and CH$_2$Cl$_2$ (25 mL). The layers were separated, and the aqueous layer was extracted with CH$_2$Cl$_2$ (25 mL). The combined CH$_2$Cl$_2$ layers were dried (MgSO$_4$), filtered and concentrated. The residue was purified by chromatography on silica gel eluting with a gradient of 10-33% ethyl acetate in hexane to provide the titled compound. $^1$H NMR (300 MHz, CDCl$_3$) δ ppm 7.98 (s, 1H), 4.87 (s, 2H), 4.35 (q, J=7.1 Hz, 2H), 1.44 (s, 6H), 1.38 (t, J=7.1 Hz, 3H); MS (ESI) m/z 239 (M+H)$^+$.

Example 171C 5,5-dimethyl-4-oxo-4,7-dihydro-5H-furo[2,3-c]pyran-3-carboxylic acid The titled compound was prepared using the procedure described in Example 168B substituting the product from Example 171B for the product from Example 168A. $^1$H NMR (300 MHz, CDCl$_3$) δ ppm 12.60 (s, 1H), 8.16 (s, 1H), 4.94 (s, 2H), 1.51 (s, 6H); MS (ESI) m/z 211 (M+H)$^+$.

Example 171D

N-[6-(4-acetylpiperazin-1-yl)-2-methoxypyridin-3-yl]-5,5-dimethyl-4-oxo-4,7-dihydro-5H-furo[2,3-c]pyran-3-carboxamide The titled compound was prepared using the procedure described in Example 159B substituting the product from Example 171C for the product from Example 159A, and substituting 1-(4-(4-amino-3-methoxyphenyl)piperazin-1-yl)ethanone for 2-methyl-2H-indazol-5-amine. A gradient of 0-100% [10% ethanol in ethyl acetate] in ethyl acetate was used in place of 50-100% ethyl acetate in hexane as the eluent in the chromatography. $^1$H NMR (300 MHz, CDCl$_3$) δ ppm 10.99 (s, 1H), 8.44 (d, J=8.6 Hz, 1H), 8.15 (s, 1H), 6.20 (d, J=8.6 Hz, 1H), 4.91 (s, 2H), 4.03 (s, 3H), 3.78-3.71 (m, 2H), 3.64-3.52 (m, 4H), 3.51-3.45 (m, 2H), 2.15 (s, 3H), 1.51 (s, 6H); MS (ESI) m/z 443 (M+H)$^+$.

Example 172

N-[4-(4-acetylpiperazin-1-yl)-2-methoxyphenyl]-4-oxo-4,7-dihydrospiro[furo[2,3-c]pyran-5,3'-oxetane]-3-carboxamide Example 172A 2-((3-ethynyloxetan-3-yl)oxy)acetic acid To a suspension of 60% dispersion of sodium hydride in mineral oil (0.912 g, 22.80 mmol) in tetrahydrofuran (20 mL) under nitrogen was added a solution of 3-ethynyloxetan-3-ol (CAS#1352492-38-6) (0.559 g, 5.7 mmol) in tetrahydrofuran (5 mL). The mixture was stirred at room temperature for 30 minutes, and then a solution of bromoacetic acid (1.584 g, 11.40 mmol) in tetrahydrofuran (5 mL) was added dropwise. The mixture was diluted with tetrahydrofuran (7 mL), stirred overnight, cooled to 0° C., treated with water (30 mL, dropwise at first), and concentrated to remove the tetrahydrofuran. This basic aqueous layer was washed with diethyl ether (2×50 mL, discarded), acidified with concentrated HCl and extracted with ethyl acetate (3×75 mL). The combined ethyl acetate layers were washed with brine, dried (MgSO$_4$), filtered and concentrated to provide the desired product which was carried onto the next step without further purification.

Example 172B methyl 2-((3-acetyloxetan-3-yl)oxy)acetate

To a solution of the product from Example 172A (890 mg, 5.7 mmol) in methanol (130 mL) was added mercury(II) acetate (182 mg, 0.570 mmol) followed by concentrated H$_2$SO$_4$ (~0.1 mL). The reaction was heated to 60° C. for 1 hour and cooled. NaHCO$_3$ (5 g) was added, and the mixture was stirred at room temperature for 10 minutes and concentrated to dryness. The residue was partitioned between ethyl acetate and water. The ethyl acetate layer was washed with brine, dried (MgSO$_4$), filtered, concentrated and purified by chromatographed on silica gel eluting with a gradient of 15% to 50% ethyl acetate in hexane to provide the titled compound.

Example 172C 2,5-dioxaspiro[3.5]nonane-7,9-dione

To a solution of 1 M potassium tert-butoxide in tert-butanol (1.9 mL, 1.9 mmol) in tetrahydrofuran (10 mL) under N$_2$ cooled to 0° C. was added a solution of the product from Example 172B (181 mg, 0.962 mmol) in tetrahydrofuran (5 mL) dropwise over 5 minutes. The reaction was stirred at 0° C. for 30 minutes and concentrated to dryness. The residue was treated with 1 M HCl (5 mL) and extracted with ethyl acetate (100 mL). The ethyl acetate layer was washed with brine, dried (MgSO$_4$), filtered, and concentrated to provide the titled compound.

Example 172D 4-oxo-4,7-dihydrospiro[furo[2,3-c]pyran-5,3'-oxetane]-3-carboxylic acid The titled compound was prepared using the procedure described in Example 163A substituting the product from Example 172C for methyl 3-hydroxy-1-methyl-5-oxocyclohex-3-enecarboxylate to provide the titled compound as the second isomer to elute form the column. $^1$H NMR (300 MHz, CDCl$_3$) δ ppm 8.19 (s, 1H), 5.05 (s, 2H), 4.97 (dd, J=7.1, 1.0 Hz, 2H), 4.80 (dd, J=7.0, 0.9 Hz, 2H); MS (ESI) m/z 225 (M+H)$^+$. The first isomer to elute from the chromatography column was 4-oxo-4,5-dihydrospiro[furo[2,3-c]pyran-7,3'-oxetane]-3-carboxylic acid.

Example 172E

N-[4-(4-acetylpiperazin-1-yl)-2-methoxyphenyl]-4-oxo-4,7-dihydrospiro[furo[2,3-c]pyran-5,3'-oxetane]-3-carboxamide The titled compound was prepared using the procedure described in Example 159B substituting the product from Example 172D for the product from Example 159A, and substituting 1-(4-(4-amino-3-methoxyphenyl)piperazin-1-yl)ethanone for 2-methyl-2H-indazol-5-amine. A gradient of 0-100% [10% ethanol in ethyl acetate] in ethyl acetate was used in place of 50-100% ethyl acetate in hexane as the eluent in the chromatography. $^1$H NMR (300 MHz, CDCl$_3$) δ ppm 10.92 (s, 1H), 8.28 (d, J=8.6 Hz, 1H), 8.19 (s, 1H), 6.58-6.48 (m, 2H), 5.05-4.98 (m, 4H), 4.78 (d, J=6.8 Hz, 2H), 4.00 (s, 3H), 3.81-3.75 (m, 2H), 3.66-3.60 (m, 2H), 3.22-3.11 (m, 4H), 2.15 (s, 3H); MS (ESI) m/z 456 (M+H)$^+$.

Example 173

N-[6-(4-acetylpiperazin-1-yl)-2-ethoxypyridin-3-yl]-5,6,6-trimethyl-4-oxo-4,5,6,7-tetrahydrofuro[3,2-c]pyridine-3-carboxamide

Example 173A methyl 5,6,6-trimethyl-4-oxo-4,5,6,7-tetrahydrofuro[3,2-c]pyridine-3-carboxylate To a solution of the product from Example 120A (100 mg, 0.478 mmol) in N,N-dimethylformamide (2.5 mL) under N$_2$ at 0° C. was added a 60% dispersion of sodium hydride in mineral oil (42.1 mg, 1.052 mmol). After stirring at 0° C. for 5 minutes, iodomethane (74.7 μL, 1.195 mmol) was added, and the reaction mixture was stirred at room temperature overnight. The mixture was diluted with diethyl ether (30 mL) and washed with water (twice, 20 mL and 20 mL), washed with brine, dried (MgSO$_4$), filtered and concentrated. The residue was purified by chromatography on silica gel eluting with a gradient of 50-100% (over 5 minutes) ethyl acetate in hexane to provide the titled compound. $^1$H NMR (300 MHz, CDCl$_3$) δ ppm 7.86 (s, 1H), 3.88 (s, 3H), 3.00 (s, 3H), 2.89 (s, 2H), 1.37 (s, 6H); MS (ESI) m/z 238 (M+H)$^+$.

Example 173B 5,6,6-trimethyl-4-oxo-4,5,6,7-tetrahydrofuro[3,2-c]pyridine-3-carboxylic acid The titled compound was prepared using the procedure described in Example 168B substituting the product from Example 173A for the product from Example 168A. $^1$H NMR (300 MHz, CDCl$_3$) δ ppm 14.81 (s, 1H), 8.04 (s, 1H), 3.05 (s, 3H), 3.01 (s, 2H), 1.45 (s, 6H); MS (ESI) m/z 224 (M+H)$^+$.

Example 173C

N-[6-(4-acetylpiperazin-1-yl)-2-ethoxypyridin-3-yl]-5,6,6-trimethyl-4-oxo-4,5,6,7-tetrahydrofuro[3,2-c]pyridine-3-carboxamide The titled compound was prepared using the procedure described in Example 159B substituting the product from Example 173B for the product from Example 159A, and substituting 1-(4-(5-amino-6-ethoxypyridin-2-yl)piperazin-1-yl)ethanone for 2-methyl-2H-indazol-5-amine. A gradient of 0-100% [10% ethanol in ethyl acetate] in ethyl acetate was used in place of 50-100% ethyl acetate in hexane as the eluent in the chromatography. $^1$H NMR (300 MHz, CDCl$_3$) δ ppm 12.18 (s, 1H), 8.59 (d, J=8.5 Hz, 1H), 8.07 (s, 1H), 6.18 (d, J=8.6 Hz, 1H), 4.43 (q, J=7.1 Hz, 2H), 3.77-3.71 (m, 2H), 3.61-3.55 (m, 2H), 3.54-3.48 (m, 2H), 3.47-3.42 (m, 2H), 3.05 (s, 3H), 2.96 (s, 2H), 2.14 (s, 3H), 1.52 (t, J=7.1 Hz, 3H), 1.41 (s, 6H); MS (ESI) m/z 470 (M+H)+.

Example 174

N-[6-(4-acetylpiperazin-1-yl)-2-ethoxypyridin-3-yl]-5-(2-hydroxyethyl)-6,6-dimethyl-4-oxo-4,5,6,7-tetrahydrofuro[3,2-c]pyridine-3-carboxamide Example 174A 5-[2-(benzyloxy)ethyl]-6,6-dimethyl-4-oxo-4,5,6,7-tetrahydrofuro[3,2-c]pyridine-3-carboxylic acid To a solution of the product from Example 120A (5 g, 23.90 mmol) in N,N-dimethylformamide (80 mL) under $N_2$ was added a 60% dispersion of sodium hydride in mineral oil (2.87 g, 71.7 mmol). After stirring at room temperature for 10 minutes, ((2-bromoethoxy)methyl)benzene (15.42 g, 71.7 mmol) in N,N-dimethylformamide (20 mL) was added, and the reaction mixture was stirred at room temperature for 10 minutes, heated to 50° C. overnight, cooled, diluted with 50 mL of 1 M NaOH, diluted further with 50 mL of water, stirred for 15 minutes, diluted with water (400 mL) and washed with diethyl ether (2×100 mL). These diethyl ether washes were discarded. The aqueous layer was acidified with concentrated HCl and extracted with diethyl ether (3×100 mL). The combined diethyl ether extractions were washed with 0.1 M HCl (100 mL), washed with brine, dried ($MgSO_4$), filtered and concentrated. The residue was purified by chromatography on silica gel eluting with a gradient of 50-100% [9:1 $CH_2Cl_2$:ethyl acetate] in $CH_2Cl_2$ to provide the titled compound. $^1$H NMR (300 MHz, $CDCl_3$) δ ppm 14.68 (s, 1H), 8.04 (s, 1H), 7.37-7.27 (m, 5H), 4.53 (s, 2H), 3.79-3.61 (m, 4H), 2.98 (s, 2H), 1.47 (s, 6H); MS (ESI) m/z 344 (M+H)+.

Example 174B

N-[6-(4-acetylpiperazin-1-yl)-2-ethoxypyridin-3-yl]-5-[2-(benzyloxy)ethyl]-6,6-dimethyl-4-oxo-4,5,6,7-tetrahydrofuro[3,2-c]pyridine-3-carboxamide The titled compound was prepared using the procedure described in Example 159B substituting the product from Example 174A for the product from Example 159A, and substituting 1-(4-(5-amino-6-ethoxypyridin-2-yl)piperazin-1-yl)ethanone for 2-methyl-2H-indazol-5-amine. A gradient of 0-100% [10% ethanol in ethyl acetate] in ethyl acetate was used in place of 50-100% ethyl acetate in hexane as the eluent in the chromatography. $^1$H NMR (500 MHz, $CDCl_3$) δ ppm 12.10 (s, 1H), 8.59 (d, J=8.5 Hz, 1H), 8.06 (s, 1H), 7.37-7.27 (m, 5H), 6.18 (d, J=8.5 Hz, 1H), 4.54 (s, 2H), 4.40 (q, J=7.0 Hz, 2H), 3.77-3.68 (m, 6H), 3.60-3.56 (m, 2H), 3.54-3.48 (m, 2H), 3.46-3.42 (m, 2H), 2.94 (s, 2H), 2.14 (s, 3H), 1.49 (t, J=7.1 Hz, 3H), 1.44 (s, 6H); MS (ESI) m/z 590 (M+H)+.

Example 174C

N-[6-(4-acetylpiperazin-1-yl)-2-ethoxypyridin-3-yl]-5-(2-hydroxyethyl)-6,6-dimethyl-4-oxo-4,5,6,7-tetrahydrofuro[3,2-c]pyridine-3-carboxamide The titled compound was prepared using the procedure described in Example 9 substituting the product from Example 174B for the product from Example 8B. $^1$H NMR (300 MHz, $CDCl_3$) δ ppm 11.82 (s, 1H), 8.57 (d, J=8.5 Hz, 1H), 8.09 (s, 1H), 6.18 (d, J=8.6 Hz, 1H), 4.42 (q, J=7.1 Hz, 2H), 3.90-3.82 (m, 2H), 3.77-3.70 (m, 4H), 3.61-3.41 (m, 6H), 3.30 (t, J=4.6 Hz, 1H), 3.01 (s, 2H), 2.14 (s, 3H), 1.51-1.44 (m, 9H); MS (ESI) m/z 500 (M+H)+.

Example 175

N-[6-(4-acetylpiperazin-1-yl)-2-ethoxypyridin-3-yl]-5-(2-methoxyethyl)-6,6-dimethyl-4-oxo-4,5,6,7-tetrahydrofuro[3,2-c]pyridine-3-carboxamide The titled compound was prepared using the procedure described in Example 159B substituting the product from Example 145A for the product from Example 159A, and substituting 1-(4-(5-amino-6-ethoxypyridin-2-yl)piperazin-1-yl)ethanone for 2-methyl-2H-indazol-5-amine. A gradient of 0-100% [10% ethanol in ethyl acetate] in ethyl acetate was used in place of 50-100% ethyl acetate in hexane as the eluent in the chromatography. $^1$H NMR (300 MHz, $CDCl_3$) δ ppm 12.09 (s, 1H), 8.59 (d, J=8.5 Hz, 1H), 8.06 (s, 1H), 6.18 (d, J=8.6 Hz, 1H), 4.41 (q, J=7.1 Hz, 2H), 3.77-3.41 (m, 12H), 3.37 (s, 3H), 2.96 (s, 2H), 2.14 (s, 3H), 1.51 (t, J=7.1 Hz, 3H), 1.45 (s, 6H); MS (ESI) m/z 514 (M+H)+.

Example 176

N-[6-(4-acetylpiperazin-1-yl)-2-ethoxypyridin-3-yl]-5-[2-(2-hydroxyethoxyl)ethyl]-6,6-dimethyl-4-oxo-4,5,6,7-tetrahydrofuro[3,2-c]pyridine-3-carboxamide Example 176A 5-{2-[2-(benzyloxy)ethoxy]ethyl}-6,6-dimethyl-4-oxo-4,5,6,7-tetrahydrofuro[3,2-c]pyridine-3-carboxylic acid The titled compound was prepared using the procedure described in Example 8A substituting ((2-(2-bromoethoxyl)ethoxy)methyl)benzene (CAS#125562-32-5) for benzyl 2-bromoethyl ether, and substituting the product from Example 120A for the product from Example 1E. MS (ESI) m/z 388 (M+H)+.

Example 176B

N-[6-(4-acetylpiperazin-1-yl)-2-ethoxypyridin-3-yl]-5-{2-[2-(benzyloxy)ethoxy]ethyl}-6,6-dimethyl-4-oxo-4,5,6,7-tetrahydrofuro[3,2-c]pyridine-3-carboxamide The procedure for Example 8B substituting the product from Example 176A for the product from Example 8A, provided the titled compound. $^1$H NMR (300 MHz, $CDCl_3$) δ ppm 12.08 (s, 1H), 8.58 (d, J=8.5 Hz, 1H), 8.06 (s, 1H), 7.35-7.27 (m, 5H), 6.18 (d, J=8.6 Hz, 1H), 4.56 (s, 2H), 4.39 (q, J=7.1 Hz, 2H), 3.82-3.36 (m, 16H), 2.92 (s, 2H), 2.14 (s, 3H), 1.48 (t, J=7.1 Hz, 3H), 1.44 (s, 6H); MS (ESI) m/z 634 (M+H)+.

Example 176C

N-[6-(4-acetylpiperazin-1-yl)-2-ethoxypyridin-3-yl]-5-[2-(2-hydroxyethoxyl)ethyl]-6,6-dimethyl-4-oxo-4,5,6,7-tetrahydrofuro[3,2-c]pyridine-3-carboxamide The procedure for Example 9 substituting the product from Example 176B for the product from Example 8B, provided the titled compound. ¹H NMR (300 MHz, CDCl₃) δ ppm 12.03 (s, 1H), 8.58 (d, J=8.5 Hz, 1H), 8.07 (s, 1H), 6.18 (d, J=8.6 Hz, 1H), 4.41 (q, J=7.1 Hz, 2H), 3.78-3.69 (m, 8H), 3.54 (dddd, J=28.9, 19.3, 7.0, 3.3 Hz, 8H), 2.97 (s, 2H), 2.14 (s, 3H), 1.98 (t, J=6.0 Hz, 1H), 1.50 (t, J=7.1 Hz, 3H), 1.46 (s, 6H); MS (ESI) m/z 544 (M+H)⁺.

Example 177

N-[6-(4-acetylpiperazin-1-yl)-2-(2-methoxyethoxyl)pyridin-3-yl]-6,6-dimethyl-4-oxo-4,5,6,7-tetrahydrofuro[3,2-c]pyridine-3-carboxamide The titled compound was prepared using the procedure described for Example 19 substituting the product from Example 20C for 1-(4-(5-amino-6-ethoxypyridin-2-yl)piperazin-1-yl)ethanone, and substituting the product from Example 120A for the product from Example 1E. ¹H NMR (300 MHz, CDCl₃) δ ppm 11.71 (s, 1H), 8.53 (d, J=8.6 Hz, 1H), 8.08 (s, 1H), 6.20 (d, J=8.6 Hz, 1H), 5.37 (bs, 1H), 4.51 (t, J=5.3 Hz, 2H), 3.87 (t, J=5.3 Hz, 2H), 3.77-3.70 (m, 2H), 3.60-3.42 (m, 6H), 3.44 (s, 3H), 2.94 (s, 2H), 2.14 (s, 3H), 1.43 (s, 6H); MS (ESI) m/z 486 (M+H)⁺.

Example 178

N-[6-(4-acetylpiperazin-1-yl)-2-(2,2,2-trifluoroethoxyl)pyridin-3-yl]-6,6-dimethyl-4-oxo-4,5,6,7-tetrahydrofuro[3,2-c]pyridine-3-carboxamide

Example 178A 1-(4-(5-amino-6-(2,2,2-trifluoroethoxyl)pyridin-2-yl)piperazin-1-yl)ethanone The titled compound was prepared by sequentially using the procedures described for Example 20A, Example 20B, and Example 20C substituting 2,2,2-trifluoroethanol for 2-methoxyethanol in Example 20A. ¹H NMR (300 MHz, CDCl₃) δ ppm 6.97 (d, J=8.2 Hz, 1H), 6.20 (d, J=8.2 Hz, 1H), 4.74 (q, J=8.6 Hz, 2H), 3.78-3.71 (m, 2H), 3.63-3.56 (m, 2H), 3.42 (bs, 2H), 3.40-3.34 (m, 2H), 3.31-3.26 (m, 2H), 2.14 (s, 3H); MS (ESI) m/z 319 (M+H)⁺.

Example 178B

N-[6-(4-acetylpiperazin-1-yl)-2-(2,2,2-trifluoroethoxyl)pyridin-3-yl]-6,6-dimethyl-4-oxo-4,5,6,7-tetrahydrofuro[3,2-c]pyridine-3-carboxamide The titled compound was prepared using the procedure described for Example 19 substituting the product from Example 178A for 1-(4-(5-amino-6-ethoxypyridin-2-yl)piperazin-1-yl)ethanone, and substituting the product from Example 120A for the product from Example 1E. ¹H NMR (300 MHz, CDCl₃) δ ppm 11.82 (bs, 1H), 8.49 (d, J=8.6 Hz, 1H), 8.09 (s, 1H), 6.31 (d, J=8.6 Hz, 1H), 5.36 (bs, 1H), 4.80 (q, J=8.6 Hz, 2H), 3.78-3.71 (m, 2H), 3.67-3.36 (m, 6H), 2.95 (s, 2H), 2.15 (s, 3H), 1.44 (s, 6H); MS (ESI) m/z 510 (M+H)⁺.

Example 179

N-[6-(4-acetylpiperazin-1-yl)-2-(oxetan-3-yloxy)pyridin-3-yl]-6,6-dimethyl-4-oxo-4,5,6,7-tetrahydrofuro[3,2-c]pyridine-3-carboxamide The titled compound was prepared using the procedure described for Example 19 substituting the product from Example 21C for 1-(4-(5-amino-6-ethoxypyridin-2-yl)piperazin-1-yl)ethanone, and substituting the product from Example 120A for the product from Example 1E. ¹H NMR (300 MHz, CDCl₃) δ ppm 11.88 (s, 1H), 8.59 (d, J=8.6 Hz, 1H), 8.10 (s, 1H), 6.24 (d, J=8.6 Hz, 1H), 5.64 (p, J=5.8 Hz, 1H), 5.41 (bs, 1H), 5.04-4.87 (m, 4H), 3.76-3.69 (m, 2H), 3.61-3.54 (m, 2H), 3.51-3.31 (m, 4H), 2.96 (s, 2H), 2.14 (s, 3H), 1.45 (s, 6H); MS (ESI) m/z 484 (M+H)⁺.

Example 180

N-[6-(4-acetylpiperazin-1-yl)-2-(tetrahydro-2H-pyran-4-yloxy)pyridin-3-yl]-6,6-dimethyl-4-oxo-4,5,6,7-tetrahydrofuro[3,2-c]pyridine-3-carboxamide The titled compound was prepared by sequentially using the procedures described for Example 20A, Example 20B, Example 20C and Example 19 substituting tetrahydro-2H-pyran-4-ol for 2-methoxyethanol in Example 20A and substituting the product from Example 120A for the product from Example 1E in Example 19. ¹H NMR (300 MHz, CDCl₃) δ ppm 11.73 (s, 1H), 8.48 (d, J=8.6 Hz, 1H), 8.09 (s, 1H), 6.21 (d, J=8.6 Hz, 1H), 5.36 (bs, 1H), 5.33-5.24 (m, 1H), 4.17-3.99 (m, 2H), 3.77-3.70 (m, 2H), 3.67-3.55 (m, 4H), 3.52-3.39 (m, 4H), 2.95 (s, 2H), 2.14 (s, 3H), 2.11-1.88 (m, 4H), 1.44 (s, 6H); MS (ESI) m/z 512 (M+H)⁺.

Example 181

N-{6-(4-acetylpiperazin-1-yl)-2-[(3S)-tetrahydrofuran-3-yloxy]pyridin-3-yl}-6,6-dimethyl-4-oxo-4,5,6,7-tetrahydrofuro[3,2-c]pyridine-3-carboxamide The titled compound was prepared by sequentially using the procedures described for Example 20A, Example 20B, Example 20C and Example 19 substituting (S)-(+)-3-hydroxytetrahydrofuran for 2-methoxyethanol in Example 20A and substituting the product from Example 120A for the product from Example 1E in Example 19. ¹H NMR (300 MHz, CDCl₃) δ ppm 11.76 (bs, 1H), 8.58 (d, J=8.6 Hz, 1H), 8.08 (d, J=3.2 Hz, 1H), 6.22 (d, J=8.6 Hz, 1H), 5.56-5.46 (m, 1H), 5.37 (bs, 1H), 4.17-3.98 (m, 3H), 3.90 (td, J=8.1, 4.3 Hz, 1H), 3.78-3.70 (m, 2H), 3.62-3.55 (m, 2H), 3.55-3.35 (m, 4H), 2.94 (s, 2H), 2.45-2.32 (m, 1H), 2.32-2.16 (m, 1H), 2.15 (s, 3H), 1.43 (s, 6H); MS (ESI) m/z 498 (M+H)⁺.

Example 182

N-[6-(4-formylpiperazin-1-yl)-2-(2-methoxyethoxyl)pyridin-3-yl]-6,6-dimethyl-4-oxo-4,5,6,7-tetrahydrofuro[3,2-c]pyridine-3-carboxamide

Example 182A tert-butyl 4-[5-{[(6,6-dimethyl-4-oxo-4,5,6,7-tetrahydrofuro[3,2-c]pyridin-3-yl)carbonyl]amino}-6-(2-methoxyethoxyl)pyridin-2-yl]piperazine-1-carboxylate The titled compound was prepared by sequentially using the procedures described for Example 20A, Example 20B, Example 20C and Example 19 substituting tert-butyl piperazine-1-carboxylate (CAS#57260-71-6) for 1-acetylpiperazine in Example 20B, substituting the product from Example 120A for the product from Example 1E in Example 19, and washing the CH₂Cl₂ layers with 0° C. 0.1 M HCl in place of 1 M HCl in Example 19. ¹H NMR (300 MHz, CDCl$_3$) δ ppm 11.68 (bs, 1H), 8.51 (d, J=8.5 Hz, 1H), 8.08 (s, 1H), 6.19 (d, J=8.6 Hz, 1H), 5.30 (bs, 1H), 4.51 (t, J=5.3 Hz, 2H), 3.86 (t, J=5.3 Hz, 2H), 3.56-3.51 (m, 4H), 3.44-3.44 (m, 4H), 3.44 (s, 3H), 2.94 (s, 2H), 1.48 (s, 9H), 1.43 (s, 6H); MS (ESI) m/z 544 (M+H)$^+$.

Example 182B

N-[2-(2-methoxyethoxy)-6-(piperazin-1-yl)pyridin-3-yl]-6,6-dimethyl-4-oxo-4,5,6,7-tetrahydrofuro[3,2-c]pyridine-3-carboxamide dihydrochloride A solution of the product from Example 182A (0.5 g, 0.920 mmol) in CH$_2$Cl$_2$ (30 mL) at 0° C. was treated with a stream of HCl gas for 3 minutes until saturated. The mixture was warmed and allowed to stand at room temperature for 15 minutes. The mixture was concentrated with a stream of N$_2$. The residue was treated with ethyl acetate (50 mL), and the sides of the vessel were scraped with a spatula to free the solid. The solid was collected by filtration, washed with ethyl acetate and dried under vacuum with heating to provide the titled compound. $^1$H NMR (300 MHz, DMSO-d$_6$) δ ppm 12.05 (s, 1H), 9.13 (bs, 2H), 8.31 (d, J=8.6 Hz, 1H), 8.28 (s, 1H), 8.04 (s, 1H), 6.44 (d, J=8.6 Hz, 1H), 4.41 (t, J=5.0 Hz, 2H), 3.76-3.71 (m, 2H), 3.70-3.63 (m, 4H), 3.29 (s, 3H), 3.18 (bs, 4H), 2.99 (s, 2H), 1.32 (s, 6H); MS (ESI) m/z 444 (M+H)$^+$.

Example 182C

N-[6-(4-formylpiperazin-1-yl)-2-(2-methoxyethoxyl)pyridin-3-yl]-6,6-dimethyl-4-oxo-4,5,6,7-tetrahydrofuro[3,2-c]pyridine-3-carboxamide To a mixture of the product from Example 182B (53 mg, 0.103 mmol) in ethanol (1 mL) was added triethylamine (143 μL, 1.026 mmol) and ethyl formate (167 μL, 2.053 mmol). The reaction was heated to 80° C. for 24 hours, cooled, and partitioned between 1 M NaOH (20 mL) and CH$_2$Cl$_2$ (25 mL). The layers were separated, and the aqueous layer was extracted with CH$_2$Cl$_2$ (25 mL). The combined CH$_2$Cl$_2$ layers were dried (MgSO$_4$), filtered, concentrated and purified by chromatography on silica gel eluting with a gradient of 0-100% [20% ethanol in ethyl acetate] in ethyl acetate to provide the titled compound. $^1$H NMR (500 MHz, CDCl$_3$) δ ppm 11.77 (s, 1H), 8.53 (d, J=8.5 Hz, 1H), 8.12 (s, 1H), 8.09 (s, 1H), 6.23 (d, J=8.6 Hz, 1H), 5.61 (bs, 1H), 4.51 (t, J=5.2 Hz, 2H), 3.87 (t, J=5.2 Hz, 2H), 3.70-3.63 (m, 2H), 3.57-3.44 (m, 6H), 3.44 (s, 3H), 2.94 (s, 2H), 1.42 (s, 6H); MS (ESI) m/z 472 (M+H)$^+$.

Example 183

N-{6-(4-acetylpiperazin-1-yl)-2-[(1-oxidothietan-3-yl)oxy]pyridin-3-yl}-6,6-dimethyl-4-oxo-4,5,6,7-tetrahydrofuro[3,2-c]pyridine-3-carboxamide

Example 183A 1-(4-(5-nitro-6-(thietan-3-yloxy)pyridin-2-yl)piperazin-1-yl)ethanone The titled compound was prepared by sequentially using the procedures described for Example 20A and Example 20B substituting thietan-3-ol (CAS#10304-16-2) for 2-methoxyethanol in Example 20A. The residue was purified by chromatography on silica gel eluting with a gradient of 25-100% [20% ethanol in ethyl acetate] in ethyl acetate to provide the titled compound. $^1$H NMR (300 MHz, CDCl$_3$) δ ppm 8.30 (d, J=9.1 Hz, 1H), 6.21 (d, J=9.1 Hz, 1H), 5.97-5.85 (m, 1H), 3.88-3.57 (m, 10H), 3.41 (dd, J=9.7, 7.7 Hz, 2H), 2.16 (s, 3H).

Example 183B 1-(4-(5-nitro-6-((1-oxidothietan-3-yl)oxy)pyridin-2-yl)piperazin-1-yl)ethanone A solution of 1-(4-(5-nitro-6-(thietan-3-yloxy)pyridin-2-yl)piperazin-1-yl)ethanone (72 mg, 0.213 mmol, Example 183A) in CH$_2$Cl$_2$ (2 mL) was treated with a solution of 3-chloroperoxybenzoic acid (52.5 mg, 0.213 mmol) in CH$_2$Cl$_2$ stirred at room temperature overnight and partitioned between NaHCO$_3$ solution and CH$_2$Cl$_2$. The layers were separated, and the aqueous layer was extracted with CH$_2$Cl$_2$ (25 mL). The combined CH$_2$Cl$_2$ layers were dried (MgSO$_4$), filtered and concentrated. The residue was purified by chromatography on silica gel eluting with a gradient of 10-100% [10% methanol in CH$_2$Cl$_2$] in CH$_2$Cl$_2$ to provide the titled compound.

Example 183C 1-(4-(5-amino-6-((1-oxidothietan-3-yl)oxy)pyridin-2-yl)piperazin-1-yl)ethanone A solution of the product from Example 183B (50 mg, 0.141 mmol) and tetrahydrofuran (10 mL) was added to 5% Pd/C, wet, (10 mg) in a 50 mL pressure bottle and stirred for 16 hours under H$_2$ (30 psi). The mixture was filtered and concentrated to provide the titled compound. MS (APCI) m/z 325 (M+H)$^+$.

Example 183D

N-{6-(4-acetylpiperazin-1-yl)-2-[(1-oxidothietan-3-yl)oxy]pyridin-3-yl}-6,6-dimethyl-4-oxo-4,5,6,7-tetrahydrofuro[3,2-c]pyridine-3-carboxamide The titled compound was prepared using the procedure described for Example 19 substituting the product from Example 183C for 1-(4-(5-amino-6-ethoxypyridin-2-yl)piperazin-1-yl)ethanone, and substituting the product from Example 120A for the product from Example 1E. The residue was chromatographed on silica gel eluted with a gradient of 0% to 100% [50% ethanol in ethyl acetate] in ethyl acetate to provide the titled compound. $^1$H NMR (300 MHz, CDCl$_3$) δ ppm 11.85 (s, 1H), 8.66 (d, J=8.7 Hz, 1H), 8.10 (s, 1H), 6.38 (d, J=8.7 Hz, 1H), 6.19-6.06 (m, 1H), 3.99-3.90 (m, 2H), 3.77 (s, 2H), 3.66-3.55 (m, 4H), 3.45 (d, J=25.8 Hz, 4H), 2.97 (s, 2H), 2.15 (s, 3H), 1.46 (s, 6H); MS (ESI) m/z 516 (M+H)$^+$.

Example 184

N-[6-(1-acetylpiperidin-4-yl)-2-ethoxypyridin-3-yl]-6,6-dimethyl-4-oxo-4,5,6,7-tetrahydrofuro[3,2-c]pyridine-3-carboxamide

Example 184A tert-butyl 6-ethoxy-5-nitro-5',6'-dihydro-[2,4'-bipyridine]-1'(2'H)-carboxylate A mixture of 6-chloro-2-ethoxy-3-nitropyridine (CAS#1094323-19-9) (370 mg, 1.826 mmol), tert-butyl 4-(4,4,5,5-tetramethyl-1,3,2-dioxaborolan-2-yl)-5,6-dihydropyridine-1(2H)-carboxylate (CAS#286961-14-6) (490 mg, 1.585 mmol), tetrakis(triphenylphosphine)palladium(0) (92 mg, 0.079 mmol), 1.5 M sodium carbonate (2.64 mL, 3.96 mmol) and dioxane (6 mL) under nitrogen was heated to 80° C. for 24 hours and then allowed to cool to room temperature. The mixture was partitioned between ethyl acetate (75 mL) and water (25 mL). The layers were separated, and the organic layer was washed with brine, dried (MgSO$_4$), filtered, concentrated and purified by chromatography on silica gel eluting with a gradient of 15 to 50% ethyl acetate in heptane to provide the titled compound. $^1$H NMR (300 MHz, CDCl$_3$) δ ppm 8.27 (d, J=8.3 Hz, 1H), 7.04 (d, J=8.3 Hz, 1H), 6.84 (bs, 1H), 4.59 (q, J=7.0 Hz, 2H), 4.18 (q, J=3.0 Hz, 2H), 3.65 (t, J=5.7 Hz, 2H), 2.67-2.56 (m, 2H), 1.50-1.44 (m, 12H); MS (ESI) m/z 249 (M+H)$^+$.

Example 184B tert-butyl 4-(5-amino-6-ethoxypyridin-2-yl)piperidine-1-carboxylate The titled compound was prepared using the procedure described for Example 20C substituting the product from Example 184A for the product from Example 20B. $^1$H NMR (300 MHz, CDCl$_3$) δ ppm 6.98 (d, J=7.6 Hz, 1H), 6.55 (d, J=7.6 Hz, 1H), 4.44 (q, J=7.1 Hz, 2H), 4.23-4.09 (m, 2H), 2.82 (t, J=12.0 Hz, 2H), 2.67 (tt, J=11.6, 3.5 Hz, 1H), 1.90-1.80 (m, 2H), 1.66 (qd, J=12.7, 4.4 Hz, 2H), 1.48 (s, 9H), 1.40 (t, J=7.0 Hz, 3H); MS (ESI) m/z 322 (M+H)$^+$.

Example 184C tert-butyl 4-(5-{[(6,6-dimethyl-4-oxo-4,5,6,7-tetrahydrofuro[3,2-c]pyridin-3-yl)carbonyl]amino}-6-ethoxypyridin-2-yl)piperidine-1-carboxylate To a solution of the product from Example 120A (100 mg, 0.479 mmol) in tetrahydrofuran (30 mL) under N$_2$ was added triethylamine (200 μL, 1.437 mmol) followed by ethyl chloroformate (46.0 μL, 0.479 mmol). After stirring at room temperature for 1 hour, The product of Example 184B, tert-butyl 4-(5-amino-6-ethoxypyridin-2-yl)piperidine-1-carboxylate (154 mg, 0.479 mmol), was added, and the reaction was stirred over the weekend, concentrated to dryness, suspended with ethyl acetate (75 mL), cooled to 0° C., washed with 0° C. 0.1 M HCl (25 mL), washed with saturated NaHCO$_3$ solution, washed with brine, dried (MgSO$_4$), filtered, concentrated and purified by chromatography on silica gel eluting with a gradient of 0-100% ethyl acetate in [9:1 CH$_2$Cl$_2$:ethyl acetate] to provide the titled compound. $^1$H NMR (300 MHz, CDCl$_3$) δ ppm 11.86 (s, 1H), 8.60 (d, J=7.9 Hz, 1H), 8.11 (s, 1H), 6.71 (d, J=8.0 Hz, 1H), 5.36 (s, 1H), 4.52 (q, J=7.0 Hz, 2H), 4.33-4.07 (m, 2H), 2.95 (s, 2H), 2.92-2.65 (m, 3H), 1.94-1.84 (m, 2H), 1.82-1.61 (m, 2H), 1.50-1.46 (m, 12H), 1.44 (s, 6H); MS (ESI) m/z 513 (M+H)$^+$.

Example 184D

N-[2-ethoxy-6-(piperidin-4-yl)pyridin-3-yl]-6,6-dimethyl-4-oxo-4,5,6,7-tetrahydrofuro[3,2-c]pyridine-3-carboxamide dihydrochloride The titled compound was prepared using the procedure described for Example 182B substituting the product from Example 184C for the product from Example 182A. $^1$H NMR (400 MHz, DMSO-d$_6$) δ ppm 12.30 (s, 1H), 9.15 (d, J=9.1 Hz, 1H), 8.81 (d, J=9.5 Hz, 1H), 8.49 (d, J=7.9 Hz, 1H), 8.34 (s, 1H), 8.10 (s, 1H), 6.85 (d, J=8.0 Hz, 1H), 4.41 (q, J=7.0 Hz, 2H), 3.38-3.30 (m, 2H), 3.00 (s, 2H), 3.09-2.82 (m, 3H), 2.10-1.82 (m, 4H), 1.39 (t, J=7.0 Hz, 3H), 1.33 (s, 6H); MS (ESI) m/z 413 (M+H)$^+$.

Example 184E

N-[6-(1-acetylpiperidin-4-yl)-2-ethoxypyridin-3-yl]-6,6-dimethyl-4-oxo-4,5,6,7-tetrahydrofuro[3,2-c]pyridine-3-carboxamide To a mixture of the product from Example 184D (68 mg, 0.140 mmol) and triethylamine (58.6 μL, 0.420 mmol) in CH$_2$Cl$_2$ (5 mL) was added acetic anhydride (26.4 μL, 0.280 mmol). The reaction was stirred at room temperature for 2 hours and concentrated to dryness. The residue was dissolved in tetrahydrofuran (2 mL) and methanol (2 mL). The solution was treated with 1 M NaOH (1 mL), stirred at room temperature for 15 minutes, and partitioned between 1 M HCl (15 mL) and ethyl acetate (50 mL). The layers were separated and the ethyl acetate layer was washed with saturated NaHCO$_3$ solution, washed with brine, dried (MgSO$_4$), filtered and concentrated to provide the titled compound. $^1$H NMR (300 MHz, CDCl$_3$) δ ppm 11.90 (s, 1H), 8.63 (d, J=7.9 Hz, 1H), 8.11 (s, 1H), 6.72 (d, J=7.9 Hz, 1H), 5.35 (bs, 1H), 4.79-4.63 (m, 1H), 4.59-4.47 (m, 2H), 3.30-3.06 (m, 1H), 2.95 (s, 2H), 3.03-2.59 (m, 3H), 2.14 (s, 3H), 1.99-1.90 (m, 2H), 1.81-1.66 (m, 2H), 1.51-1.42 (m, 9H); MS (ESI) m/z 455 (M+H)$^+$.

Example 185

N-[6-(4-acetylpiperazin-1-yl)-2-ethoxypyridin-3-yl]-5-(2,5-difluorophenyl)-4-oxo-4,5,6,7-tetrahydro-1-benzofuran-3-carboxamide Example 185A 6-(2,5-difluorophenyl)-7-oxaspiro[bicyclo[4.1.0]heptane-3,2'-[1,3]dioxolane]

To a solution of 8-(2,5-difluorophenyl)-1,4-dioxaspiro[4.5]dec-7-ene (CAS#1187537-71-8) (1.44 g, 5.71 mmol) (10436912-0842) in CH$_2$Cl$_2$ (30 mL) was added 3-chloroperoxybenzoic acid (1.92 g, 8.56 mmol), and the reaction was stirred at room temperature overnight. The mixture was diluted with CH$_2$Cl$_2$, washed with water, washed with saturated NaHCO$_3$ solution, washed with brine, dried (Na$_2$SO$_4$), filtered, and concentrated. The residue was purified by chromatography on silica gel eluting with 10% ethyl acetate in heptane to provide the titled compound.

Example 185B 8-(2,5-difluorophenyl)-1,4-dioxaspiro[4.5]decan-7-ol

A mixture of 10% Pd/C (3.5 g, 3.29 mmol) and the product from Example 185A (10 g, 37.3 mmol) in methanol (150 mL) was stirred at room temperature under H$_2$ (50 psi) for 12 hours, filtered and concentrated. The residue was purified by chromatography on silica gel eluting with 10% ethyl acetate in heptane to provide the titled compound.

Example 185C 8-(2,5-difluorophenyl)-1,4-dioxaspiro[4.5]decan-7-one

A mixture of Dess-Martin periodinane (CAS#87413-09-0) (17.26 g, 40.7 mmol) and the product from Example 185B (10 g, 37.0 mmol) in $CH_2Cl_2$ (50 mL) was stirred at room temperature for 12 hours and concentrated. The residue was purified by chromatography on silica gel eluting with 10% ethyl acetate in heptane to provide the titled compound.

Example 185D 4-(2,5-difluorophenyl)cyclohexane-1,3-dione

To a solution of the product from Example 185C (4 g, 14.91 mmol) in acetone (20 mL) was added 37% HCl (20 mL), and the mixture was stirred at 80° C. for 2 hours and cooled to room temperature. The reaction mixture was diluted with saturated $K_2CO_3$ and extracted with ethyl acetate (2×100 mL). The combined organic layers were washed with brine, dried over $Na_2SO_4$, filtered, and concentrated under reduced pressure to provide the titled compound.

Example 185E methyl 5-(2,5-difluorophenyl)-4-oxo-4,5,6,7-tetrahydro-1-benzofuran-3-carboxylate To a solution of the product from Example 185D (4.05 g, 18.06 mmol) in ethanol (60 mL) at 0° C. was added sodium ethoxide (1.598 g, 23.48 mmol) portionwise, and the mixture was stirred for 30 minutes at 0° C. Ethyl bromopyruvate (2.95 mL, 23.48 mmol) was added dropwise, and the reaction mixture was stirred at 0° C. for 30 minutes, stirred at room temperature for 3 hours, and concentrated. The residue was taken up in 1,4-dioxane (80 mL) and 4 M HCl (80 mL) was added. The resulting mixture was stirred at 100° C. for 3 hours and concentrated to dryness and suspended in ethyl ether (100 mL). The solid was collected and dried to afford a mixture of 5-(2,5-difluorophenyl)-4-oxo-4,5,6,7-tetrahydro-1-benzofuran-3-carboxylic acid and 7-(2,5-difluorophenyl)-4-oxo-4,5,6,7-tetrahydro-1-benzofuran-3-carboxylic acid. This solid was dissolved in methanol (50 mL) and concentrated $H_2SO_4$ (2 mL) was added. The mixture was heated to 80° C. for 16 hours, cooled and concentrated. The residue was purified by chromatography on silica gel eluting with 30:1 petroleum ether/ethyl acetate to provide the titled compound as the first isomer to elute from the column. $^1$H NMR (400 MHz, CDCl$_3$) δ ppm 7.95 (s, 1H), 7.03 (td, J=9.1, 4.6 Hz, 1H), 6.98-6.91 (m, 1H), 6.87 (ddd, J=8.7, 5.6, 3.1 Hz, 1H), 3.97 (dd, J=12.4, 4.5 Hz, 1H), 3.85 (s, 3H), 3.16-3.00 (m, 2H), 2.56-2.43 (m, 1H), 2.42-2.34 (m, 1H); MS (ESI) m/z 307 (M+H)$^+$. The second isomer to elute from the chromatography column was methyl 7-(2,5-difluorophenyl)-4-oxo-4,5,6,7-tetrahydro-1-benzofuran-3-carboxylate.

Example 185F 5-(2,5-difluorophenyl)-4-oxo-4,5,6,7-tetrahydro-1-benzofuran-3-carboxylic acid The titled compound was prepared using the procedure described for Example 168B substituting the product from Example 185E for the product from Example 168A. $^1$H NMR (400 MHz, DMSO-D$_2$O) δ ppm 9.92-9.84 (m, 1H), 8.44 (s, 1H), 7.37 (td, J=9.4, 4.6 Hz, 1H), 7.26 (tdd, J=9.0, 6.6, 3.3 Hz, 2H), 4.79 (dd, J=9.7, 5.3 Hz, 1H), 2.85 (ddd, J=16.7, 11.7, 4.8 Hz, 1H), 2.66 (dt, J=17.0, 4.5 Hz, 1H), 2.47 (dq, J=13.2, 5.0 Hz, 1H), 2.41-2.29 (m, 1H); MS (ESI) m/z 293 (M+H)$^+$.

Example 185G

N-[6-(4-acetylpiperazin-1-yl)-2-ethoxypyridin-3-yl]-5-(2,5-difluorophenyl)-4-oxo-4,5,6,7-tetrahydro-1-benzofuran-3-carboxamide The procedure for Example 8B substituting the product from Example 185F for the product from Example 8A, provided the titled compound. $^1$H NMR (300 MHz, CDCl$_3$) δ ppm 11.37 (s, 1H), 8.55 (d, J=8.5 Hz, 1H), 8.15 (s, 1H), 7.15-6.87 (m, 3H), 6.29 (d, J=8.5 Hz, 1H), 4.34-4.20 (m, 2H), 4.04 (dd, J=12.6, 4.7 Hz, 1H), 3.80-3.73 (m, 2H), 3.66-3.57 (m, 2H), 3.53-3.39 (m, 4H), 3.19-3.10 (m, 2H), 2.66-2.34 (m, 2H), 2.13 (s, 3H), 1.22 (t, J=7.1 Hz, 3H); MS (ESI) m/z 539 (M+H)$^+$.

Determination of Biological Activity

Abbreviations: ahx for 2-aminohexanoic acid; ATP for adenosine triphosphate; BSA for bovine serum albumin; EDTA for ethylenediaminetetraacetic acid; HEPES for HEPES for 2-(4-(2-hydroxyethyl)piperazin-1-yl)ethanesulfonic acid; LCK for leukocyte specific protein tyrosine kinase; Tween® 20 for polyethylene glycol sorbitan monolaurate.

Determination of Inhibitory Potency at TrkA Kinase, TrkB Kinase, and TrkC Kinase TrkA enzyme was obtained from Invitrogen (as catalog numbers PV3144, PV3616, and PV3617, respectively). Enzyme activity was measured in an HTRF® (homogeneous time resolved fluorescence) assay, which detects enzymatic phosphorylation of a biotinylated synthetic peptide substrate (an LCK peptide analog, biotin-ahx-GAEEEIYAAFFA, from Genemed Synthesis). Phosphorylation is assessed by HTRF® in the presence of an anti-phosphotyrosine antibody conjugated to Eu$^{3+}$ cryptate (Cisbio) as donor fluorophore, and streptavidin conjugated to allophycocyanin (ProZyme) as acceptor fluorophore. The HTRF® signal was detected at two different wavelengths (620 nm and 665 nm) which were used to calculate the fluorescence ratio.

TrkA enzyme was titrated to a concentration optimized to ensure accurate measurement of the initial reaction rate. To allow the TrkA enzyme to undergo activation and autophosphorylation, a 20 minute pre-incubation with ATP was carried out (at twice the final targeted enzyme and ATP concentration) prior to addition of test compound and the peptide substrate.

TrkA in vitro assays were performed by pre-incubating TrkA (2-10 nM) with ATP (200 µM) for 20 minutes at ambient temperature in 50 mM HEPES pH 7.4, 10 mM MgCl$_2$, 2 mM MnCl$_2$, 100 µM Na$_3$VO$_4$, 1 mM dithiothreitol, 0.01% BSA (bovine serum albumin). Then, to the activated Trk enzyme mixture was added the test compound in 2% dimethyl sulfoxide. After 10 minutes, the peptide substrate (125 nM) was added. After 1 hour, enzyme reactions were terminated by addition of equal reaction volumes of detection/stop reagent (containing 0.2 µg/mL anti-phosphotyrosine monoclonal antibody labeled with europium from Cisbio (catalog#PT66-K), and 4 µg/mL PhycoLink®

Streptavidin-Allophycocyanin conjugate from ProZyme (catalog#PJ25S) in 60 mM EDTA in 40 mM HEPES pH 7.4, 480 mM KF, 0.01% Tween® 20 and 0.1% BSA bovine serum albumin) Reaction plates were stored at 4° C. overnight before reading the fluorescence ratio signal on a PerkinElmer EnVision™ fluorescence detector. Individual reaction wells were stopped at time points to obtain reaction rates. The test inhibitor compounds were assayed in duplicate, at half-log serial dilutions over a range of concentrations (e.g. starting at 50 µM or 5 µM as the high compound concentration). The percent Trk enzyme inhibition was calculated from the initial rates of the inhibited reactions relative to the uninhibited control. $IC_{50}$ values were calculated by fitting the inhibition percent to the concentration of inhibitor [I] in the assay in equation 1 below, to solve for the $IC_{50}$.

$$\text{Inhibition \%} = 100[I]/([I]+[IC_{50}]) \quad \text{equation 1}$$

| Example | $IC_{50}$ TrkA [µM] |
|---|---|
| 1 | 0.0442 |
| 2 | 0.0602 |
| 3 | 0.1730 |
| 4 | 0.3750 |
| 5 | 0.0544 |
| 6 | 0.0467 |
| 7 | 0.2120 |
| 8 | 0.0695 |
| 9 | 0.0051 |
| 10 | 0.0559 |
| 11 | 0.0640 |
| 12 | 0.0996 |
| 13 | 0.1660 |
| 14 | 0.1108 |
| 15 | 0.0693 |
| 16 | 0.2790 |
| 17 | 0.0814 |
| 18 | 0.0598 |
| 19 | 0.0163 |
| 20 | 0.0259 |
| 21 | 0.0216 |
| 22 | 0.2000 |
| 23 | 0.2568 |
| 24 | 0.1890 |
| 25 | 0.1120 |
| 26 | 0.2020 |
| 27 | 0.4280 |
| 28 | 0.1100 |
| 29 | 0.1690 |
| 30 | 0.5210 |
| 31 | 0.3900 |
| 32 | 0.5540 |
| 33 | 0.1110 |
| 34 | 0.9100 |
| 35 | 0.1170 |
| 36 | 8.0100 |
| 37 | 3.2100 |
| 38 | 1.7200 |
| 39 | 0.4300 |
| 40 | 3.2400 |
| 41 | 1.3900 |
| 42 | 0.9180 |
| 43 | 5.6400 |
| 44 | 4.4700 |
| 45 | 3.4800 |
| 46 | 0.8550 |
| 47 | 1.2200 |
| 48 | 0.5060 |
| 49 | 0.6310 |
| 50 | 0.0907 |
| 51 | 0.0189 |
| 52 | 0.0184 |
| 53 | 0.0675 |
| 54 | 0.1080 |
| 55 | 0.0208 |
| 56 | 0.0485 |
| 57 | 0.0346 |
| 58 | 0.1050 |
| 59 | 0.9840 |
| 60 | 2.1100 |
| 61 | 0.1950 |
| 62 | 0.8270 |
| 63 | 0.3190 |
| 64 | 0.1340 |
| 65 | 0.1460 |
| 66 | 5.0800 |
| 67 | 1.0800 |
| 68 | 5.8200 |
| 69 | 4.3400 |
| 70 | 2.4900 |
| 71 | 3.6700 |
| 72 | 2.4800 |
| 73 | 1.0800 |
| 74 | 2.5900 |
| 75 | 2.0500 |
| 76 | 1.5300 |
| 77 | 0.3670 |
| 78 | 0.2360 |
| 79 | 0.0447 |
| 80 | 0.0677 |
| 81 | 0.0658 |
| 82 | 0.6820 |
| 83 | 0.4960 |
| 84 | 0.0053 |
| 85 | 0.2660 |
| 86 | 1.3200 |
| 87 | 0.2240 |
| 88 | 0.0950 |
| 89 | 0.0047 |
| 90 | 0.0047 |
| 91 | 0.0070 |
| 92 | 0.0182 |
| 93 | 0.0163 |
| 94 | 0.0015 |
| 95 | 0.0043 |
| 96 | 0.0067 |
| 97 | 0.0048 |
| 98 | 0.0015 |
| 99 | 0.0033 |
| 100 | 0.0235 |
| 101 | 0.0195 |
| 102 | 0.0127 |
| 103 | 0.0169 |
| 104 | 0.0060 |
| 105 | 0.0235 |
| 106 | 0.0286 |
| 107 | 0.0069 |
| 108 | 0.2260 |
| 109 | 0.2250 |
| 110 | 0.0392 |
| 111 | 0.0039 |
| 112 | 0.0273 |
| 113 | 0.0654 |
| 114 | 0.0072 |
| 115 | 0.0085 |
| 116 | 0.0031 |
| 117 | 0.0053 |
| 118 | 0.0030 |
| 119 | 0.0068 |
| 120 | 0.0280 |
| 121 | 0.0181 |
| 122 | 0.0141 |
| 123 | 0.0119 |
| 124 | 0.0737 |
| 125 | 0.0359 |
| 126 | 0.0250 |
| 127 | 0.0132 |
| 128 | 0.0054 |
| 129 | 0.0108 |
| 130 | 0.0383 |
| 131 | 0.0981 |
| 132 | 0.0069 |

-continued

| Example | IC$_{50}$ TrkA [μM] |
|---|---|
| 133 | 0.0033 |
| 134 | 0.0039 |
| 135 | 0.0023 |
| 136 | 0.0102 |
| 137 | 0.0133 |
| 138 | 0.0063 |
| 139 | 0.0024 |
| 140 | 0.0105 |
| 141 | 0.0601 |
| 142 | 0.0018 |
| 143 | 0.0246 |
| 144 | 0.0492 |
| 145 | 0.0079 |
| 146 | 0.0341 |
| 147 | 0.0161 |
| 148 | 0.0324 |
| 149 | 0.1350 |
| 150 | 0.0432 |
| 151 | 0.0634 |
| 152 | 0.0358 |
| 153 | 0.0456 |
| 154 | 0.0740 |
| 155 | 0.0548 |
| 156 | 0.0467 |
| 157 | 0.0064 |
| 158 | 0.0042 |
| 159 | 0.0103 |
| 160 | 0.2580 |
| 161 | 0.8720 |
| 162 | 0.0580 |
| 163 | 0.1560 |
| 164 | 0.0219 |
| 165 | 0.0133 |
| 166 | 0.1040 |
| 167 | 0.0353 |
| 168 | 0.0059 |
| 169 | 0.0596 |
| 170 | 0.0565 |
| 171 | 0.0029 |
| 172 | 0.0600 |
| 173 | 0.0035 |
| 174 | 0.0052 |
| 175 | 0.0047 |
| 176 | 0.0021 |
| 177 | 0.0122 |
| 178 | 0.0052 |
| 179 | 0.0049 |
| 180 | 0.0110 |
| 181 | 0.0102 |
| 182 | 0.0178 |
| 183 | 0.0048 |
| 184 | 0.0035 |
| 185 | 0.0066 |

Determination of the Efficacy of Compounds to Reduce Osteoarthritis Pain

Members of the TrkA inhibitors described above were tested and found effective in reducing osteoarthritis pain. The compounds tested were assessed in an in vivo model well known to those skilled in the art, the rat model of mono-iodoacetic acid induced osteoarthritis pain. A general review of various models of pain can be found in Joshi and Honore, Expert Opinion in Drug Discovery (2004) 1, pp. 323-334, and in the book 'Drug Discovery and Evaluation, 2$^{nd}$ edition (H. Gerhard Vogel, editor; Springer-Verlag, New York, 2002; pp. 702-706).

Activity in an Osteoarthritis Model

Pain behavior was assessed by measurement of hind limb grip force (GF) in adult osteoarthritic rats. Male Sprague Dawley rats, generally weighing 125-150 g, were injected in the unilateral knee join with a single intra-articular injection of sodium monoiodoacetate (MIA). Rats were tested at 21-28 days following MIA injection. A behavioral measure of activity-induced pain was carried out. Measurements of the peak hind limb grip force were conducted by recording the maximum compressive force ($CF_{max}$), in grams of force, exerted on a hind limb strain gauge setup, in a commercially available grip force measurement system (Columbus Instruments, Columbus, Ohio).

During testing, each rat was gently restrained by grasping it around its rib cage and then allowed to grasp the wire mesh frame attached to the strain gauge. The experimenter then moved the animal in a rostral-to-caudal direction until the grip was broken. Each rat was sequentially tested twice at an approximately 2-3 minute interval to obtain a raw mean grip force ($CF_{max}$). This raw mean grip force data was in turn converted to a maximum hindlimb cumulative compressive force ($CF_{max}$), as the grams of force/kg of body weight, for each animal.

For evaluating the compound effects, the hind limb grip force testing in the MIA-treated rats was conducted generally 30-60 minutes after dosing with the test compound. A group of age-matched naïve (not injected with MIA) animals was added as a comparator to the drug-dosed groups. The vehicle control response for each group of MIA-treated animals was defined as the 0% response (0% effect), whereas the naïve control group was defined as the normal response and as 100% effect. The % effect=(Treatment $CF_{max}$–Vehicle $CF_{max}$)/Vehicle $CF_{max}$]×100). Higher % effect numbers indicate increased relief from the pain in the model, with 100% indicating a return to the level of response seen in normal (non-osteoarthritic) animals. All experiments evaluating drug effects in this model were conducted in a randomized blinded fashion.

Animals, Compounds, and Dosing.

Male Sprague Dawley rats (generally 250-300 g body weight at the time of testing) obtained from Charles River Laboratories (Wilmington, Mass.) were used for all experiments, unless indicated otherwise. The animals were housed in Association for Assessment and Accreditation of Laboratory Animal Care (AAALAC) approved facilities at AbbVie in a temperature-regulated environment under a controlled 12-hour light-dark cycle, with lights on at 6:00 a.m. Food and water were available ad libitum at all times except during testing. All testing was done following procedures outlined in protocols approved by AbbVie Institutional Animal Care and Use Committee.

The following table illustrates that compounds of the invention are effective in reducing osteoarthritis pain, with efficacy in the MIA model after oral dosing:

| Compound Name (Example number) | dose (mg/kg, p.o.) | % Effect[1] |
|---|---|---|
| N-[6-(4-acetylpiperazin-1-yl)-2-ethoxy-pyridin-3-yl]-5-(2-hydroxyethyl)-4-oxo-4,5,6,7-tetrahydrofuro[3,2-c]pyridine-3-carboxamide (Example 9) | 30 | 69% ** |
| N-{2-methoxy-6-[4-(morpholin-4-ylcarbonyl)piperazin-1-yl]pyridin-3-yl}-6,6-dimethyl-4-oxo-4,5,6,7-tetrahydrofuro[3,2-c]pyridine-3-carboxamide (Example 121) | 30 | 74% *** |
| N-[4-(4-acetylpiperazin-1-yl)-2-methoxy-phenyl]-6,6-dimethyl-4-oxo-4,5,6,7-tetrahydrofuro[3,2-c]pyridine-3-carboxamide (Example 126) | 100 | 47% ** (tested 3 hours post dose) |
| N-[6-(4-acetylpiperazin-1-yl)-2-ethoxy-pyridin-3-yl]-6,6-dimethyl-4-oxo-4,5,6,7-tetrahydrofuro[3,2-c]pyridine-3-carboxamide (Example 128) | 30 | 55% *** (tested 3 hours post dose) |

-continued

| Compound Name (Example number) | dose (mg/kg, p.o.) | % Effect[1] |
|---|---|---|
| 6,6-dimethyl-N-(2-methyl-2H-indazol-5-yl)-4-oxo-4,5,6,7-tetrahydro-1-benzofuran-3-carboxamide (Example 147) | 300 | 69% *** (tested 3 hours post dose) |
| N-[6-(4-acetylpiperazin-1-yl)-2-(2-methoxyethoxy)pyridin-3-yl]-6,6-dimethyl-4-oxo-4,5,6,7-tetrahydrofuro[3,2-c]pyridine-3-carboxamide (Example 177) | 30 | 68% *** |

[1]Data represent mean percent effect.
Statistical significance
* $p < 0.05$,
** $p < 0.01$,
*** $p < 0.001$ as compared to vehicle-treated animals.
Abbreviations: SEM = standard error of the mean; p.o. = per os = oral dosed. Unless otherwise noted, testing was conducted 30-60 minutes postdosing of compound.

Representative compounds of the invention are active in this model, with preferred compounds of the invention active in the model at doses of ranging about 0.1 to 100 mg/kg of body weight.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:

1. A compound of formula (I):

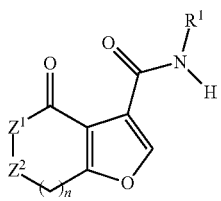

(I)

or a pharmaceutically acceptable salt thereof, wherein:
n is 1 or 2;
$R^1$ is phenyl or monocyclic heteroaryl, wherein the monocyclic heteroaryl contains one or two ring nitrogens and optionally one ring oxygen or one ring sulfur, wherein the phenyl or monocyclic heteroaryl is optionally substituted with 1, 2, or 3 substituents selected from the group consisting of $C_1$-$C_6$-alkyl; $C_1$-$C_6$-alkylcarbonylamino; hydroxy$C_1$-$C_6$-alkylcarbonylamino; $C_1$-$C_6$-alkoxy$C_1$-$C_6$alkylcarbonylamino; $C_1$-$C_6$-alkoxy; $C_1$-$C_6$-alkoxy$C_1$-$C_6$-alkoxy; $C_1$-$C_6$-alkoxy$C_1$-$C_6$-alkyl; $C_1$-$C_6$-alkoxycarbonyl; $C_1$-$C_6$-alkoxycarbonyl$C_1$-$C_6$-alkyl; aminocarbonyl; $C_1$-$C_6$-alkylaminocarbonyl; hydroxy$C_1$-$C_6$-alkylaminocarbonyl; $C_1$-$C_6$-alkoxy$C_1$-$C_6$-alkylaminocarbonyl; cyano; carboxy; hydroxy; hydroxy$C_1$-$C_6$-alkoxy; hydroxy$C_1$-$C_6$-alkyl; di(hydroxy)$C_1$-$C_6$-alkyl; di($C_1$-$C_6$alkyl)amino; di(hydroxy$C_1$-$C_6$-alkyl)amino; di($C_1$-$C_6$-alkoxy$C_1$-$C_6$alkyl)amino; ($C_1$-$C_6$-alkoxy$C_1$-$C_6$-alkyl)(hydroxy$C_1$-$C_6$-alkyl)amino; halo$C_1$-$C_6$-alkyl; and halogen; wherein only 1 substituent can be present on the two atoms adjacent to the atom connected to the amide nitrogen pendant on the furan ring; or
$R^1$ is fused-bicyclic heteroaryl, wherein the fused-bicyclic heteroaryl contains 1, 2, 3 or 4 ring nitrogens and optionally one ring oxygen or one ring sulfur, wherein the fused-bicyclic heteroaryl is optionally substituted with 1, 2, 3, or 4 substituents selected from the group consisting of $C_1$-$C_6$-alkyl; $C_1$-$C_6$-alkylcarbonylamino; hydroxy$C_1$-$C_6$-alkylcarbonylamino; $C_1$-$C_6$-alkoxy$C_1$-$C_6$-alkylcarbonylamino; $C_1$-$C_6$-alkoxy; $C_1$-$C_6$-alkoxy$C_1$-$C_6$-alkoxy; $C_1$-$C_6$alkoxy-$C_1$-$C_6$alkyl; $C_1$-$C_6$-alkoxycarbonyl; $C_1$-$C_6$-alkoxycarbonyl$C_1$-$C_6$-alkyl; $C_3$-$C_7$cycloalkyloxy; heterocycleoxy, wherein the heterocycle of heterocycleoxy wherein the heterocycle of heterocycleoxy is a 4-7 membered monocyclic ring containing 0-3 double bonds and 1-3 heteroatoms selected from the group consisting of O, N, and, S, optionally substituted with $C_1$-$C_6$-alkyl; aminocarbonyl; $C_1$-$C_6$-alkylaminocarbonyl; hydroxy$C_1$-$C_6$-alkylaminocarbonyl; $C_1$-$C_6$-alkoxy$C_1$-$C_6$-alkylamincarbonyl; cyano; hydroxy; hydroxy$C_1$-$C_6$-alkoxy; hydroxy$C_1$-$C_6$-alkyl; di($C_1$-$C_6$alkyl)amino; di(hydroxy$C_1$-$C_6$-alkyl)amino; di($C_1$-$C_6$-alkoxy$C_1$-$C_6$-alkyl)amino; ($C_1$-$C_6$-alkoxy$C_1$-$C_6$-alkyl)(hydroxy$C_1$-$C_6$-alkyl)amino; halo$C_1$-$C_6$-alkyl; halogen; $C_1$-$C_6$-alkylsulfonylamino$C_2$-$C_6$-alkyl; and (i),

(i)

wherein $R^a$ is selected from the group consisting of a bond, $CH_2$, $CHR^b$, O, S, and N—$R^c$; wherein only 1 substituent can be present on the two atoms adjacent to the atom connected to the amide nitrogen pendant on the furan ring;
m is 2, 3 or 4 when (i) is attached to a ring nitrogen atom of the bicyclic heteroaryl; or
m is 0, 1, 2, 3 or 4 when (i) is attached to a ring carbon atom of the bicyclic heteroaryl;
$R^b$, at each occurrence, is independently selected from the group consisting of hydrogen, $C_1$-$C_6$-alkyl, halo$C_1$-$C_6$-alkyl, $C_1$-$C_6$-alkoxy$C_1$-$C_6$-alkyl, and hydroxy$C_1$-$C_6$-alkyl;
$R^c$ is selected from the group consisting of hydrogen, $C_1$-$C_6$-alkyl, $C_1$-$C_6$-alkoxycarbonyl, $C_1$-$C_6$-alkycarbonyl, $C_1$-$C_6$-alkysulfonyl, di($C_1$-$C_6$-alkyl)aminosulfonyl, heterocyclecarbonyl, $C_3$-$C_7$-cycloalkylcarbonyl, —C(O)NH$_2$, —C(O)NH(alkyl), —C(O)N(alkyl)$_2$ and —C(=NCN)NHCH$_3$; or
$R^1$ is (ii), (iii), or (iv);

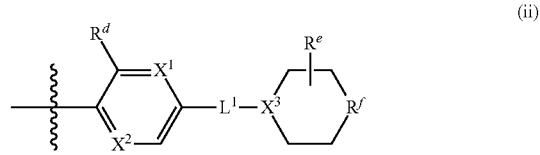

(ii)

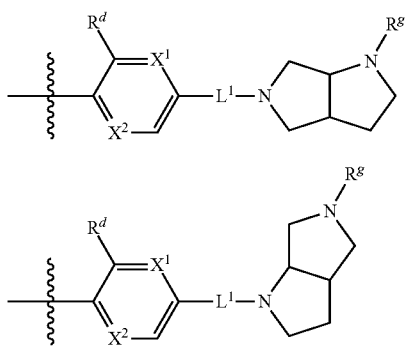

wherein both X¹ and X² are CH, or one of X¹ and X² is N and the other is CH;

X³ is CH or N;

L¹ is a bond, C(O), or —NHC(O)—;

R$^d$ is selected from the group consisting of hydrogen; $C_1$-$C_6$alkoxy; fluoro$C_1$-$C_6$-alkoxy; $C_1$-$C_6$-alkoxy$C_1$-$C_6$-alkoxy; $C_3$-$C_7$-cycloalkyloxy; $C_3$-$C_7$-cycloalkyl$C_1$-$C_6$-alkoxy; hydroxy$C_1$-$C_6$-alkoxy; phenyl$C_1$-$C_6$-alkoxy$C_1$-$C_6$-alkoxy; heterocycleoxy,—wherein the heterocycle of heterocycleoxy is a 4-7 membered monocyclic ring containing 0-3 double bonds and 1-3 heteroatoms selected from the group consisting of O, N, and, S, optionally substituted with $C_1$-$C_6$-alkyl or oxo; and phenoxy, wherein the phenyl of phenoxy is optionally substituted with hydroxy$C_1$-$C_6$-alkyl, $C_1$-$C_6$-alkoxy, $C_1$-$C_6$-alkoxy$C_1$-$C_6$-alkoxy, or $C_1$-$C_6$-alkoxycarbonyl;

R$^e$ at each occurrence is independently selected from the group consisting of hydrogen, $C_1$-$C_6$-alkyl, di($C_1$-$C_6$-alkyl)amino, halo$C_1$-$C_6$-alkyl, $C_1$-$C_6$-alkoxy$C_1$-$C_6$alkyl, and hydroxy$C_1$-$C_6$-alkyl;

R$^f$ is selected from the group consisting of a bond, CH₂, CHR$^e$, CH₂CH₂, O, NR$^g$, and CH₂NR$^g$;

R$^g$ is selected from the group consisting of hydrogen; $C_1$-$C_6$-alkyl; $C_1$-$C_6$-alkoxycarbonyl; $C_1$-$C_6$-alkycarbonyl; $C_1$-$C_6$-alkysulfonyl; di($C_1$-$C_6$-alkyl)aminosulfonyl; $C_3$-$C_7$cycloalkylcarbonyl; $C_1$-$C_6$-alkoxy$C_1$-$C_6$-alkylcarbony; hydroxy$C_2$-$C_6$-alkyl; hydroxy$C_1$-$C_6$-alkylcarbonyl; formyl; —C(O)NH₂; —C(O)NH(alkyl); —C(O)N(alkyl)₂; —C(=NCN)NHCH₃; and heterocyclecarbonyl, wherein the heterocycle of heterocyclecarbonyl is a 4-7 membered monocyclic ring containing 0-3 double bonds and 1-3 heteroatoms selected from the group consisting of O, N, and, S, optionally substituted with $C_1$-$C_6$-alkyl;

Z¹ is NR² or CR³R⁴;

R² is selected from the group consisting of hydrogen, $C_1$-$C_6$-alkyl, hydroxy$C_2$-$C_6$-alkyl, di(hydroxy)$C_2$-$C_6$-alkyl, $C_1$-$C_6$-alkoxy$C_2$-$C_6$alkyl, hydroxy$C_2$-$C_6$-alkoxy$C_2$-$C_6$-alkyl, $C_1$-$C_6$-alkylcarbonyloxy$C_2$-$C_6$-alkyl, $C_1$-$C_6$-alkoxycarbonyl$C_1$-$C_6$-alkyl, $C_1$-$C_6$-alkylcarbonyl$C_1$-$C_6$-alkyl and phenyl$C_1$-$C_6$-alkoxy$C_2$-$C_6$alkyl;

R³ and R⁴ are each independently selected from the group consisting of hydrogen, $C_1$-$C_6$-alkyl, hydroxy$C_1$-$C_6$-alkyl, amino$C_1$-$C_6$-alkyl, and phenyl, wherein phenyl is optionally substituted with 1, 2, 3 or 4 substituents selected from halogen, $C_1$-$C_6$-alkyl, and cyano; or R³ and R⁴ taken together with the carbon atom to which they are attached form a a 4-7 membered heterocycle monocyclic ring containing 0-3 double bonds and 1-3 heteroatoms selected from the group consisting of O, N, and, S, optionally substituted with 1, 2 or 3 halogen, $C_1$-$C_6$-alkyl, cyano or oxo;

Z² is O, NR⁵, or CR⁶R⁷;

R⁵ is selected from the group consisting of hydrogen, $C_1$-$C_6$-alkyl, $C_1$-$C_6$-alkylsulfonyl, $C_1$-$C_6$-alkylcarbonyl, and $C_1$-$C_6$-alkoxycarbonyl; and R⁶ and R⁷ are each independently selected from the group consisting of hydrogen, $C_1$-$C_6$-alkyl, $C_1$-$C_6$-alkoxy$C_1$-$C_6$-alkyl, hydroxy$C_1$-$C_6$-alkyl, amino$C_1$-$C_6$-alkyl, aminocarbonyl, and $C_1$-$C_6$-alkoxycarbonyl;

wherein one or more of R³, R⁴, R⁶ and R⁷ is other than hydrogen; or

R⁶ and R⁷ taken together with the carbon atom to which they are attached form a $C_3$-$C_6$-cycloalkyl or a 4-7 membered heterocycle monocyclic ring containing 0-3 double bonds and 1-3 heteroatoms selected from the group consisting of O, N, and, S, wherein the $C_3$-$C_6$-cycloalkyl or the 4-7 membered heterocycle monocyclic ring containing 0-3 double bonds and 1-3 heteroatoms selected from the group consisting of O, N, and, S, are optionally substituted with 1, 2, or 3 substituents selected from $C_1$-$C_6$-alkyl, cyano, aminocarbonyl, halogen, oxo and $C_1$-$C_6$-alkylcarbonyl;

provided that when Z¹ is CR³R⁴, Z² cannot be CR⁶R⁷.

2. The compound of claim 1, wherein

Z¹ is NR²; and

Z² is CR⁶R⁷.

3. The compound of claim 2, wherein R¹ is phenyl or monocyclic heteroaryl, wherein the monocyclic heteroaryl contains one or two ring nitrogens and optionally one ring oxygen or one ring sulfur, wherein the phenyl or monocyclic heteroaryl is optionally substituted with 1, 2, or 3 substituents selected from the group consisting of $C_1$-$C_6$-alkyl; $C_1$-$C_6$-alkylcarbonylamino; hydroxy$C_1$-$C_6$-alkylcarbonylamino; $C_1$-$C_6$-alkoxy$C_1$-$C_6$alkylcarbonylamino; $C_1$-$C_6$-alkoxy; $C_1$-$C_6$-alkoxy$C_1$-$C_6$-alkoxy; $C_1$-$C_6$-alkoxy$C_1$-$C_6$-alkyl; $C_1$-$C_6$-alkoxycarbonyl; $C_1$-$C_6$-alkoxycarbonyl$C_1$-$C_6$-alkyl; aminocarbonyl; $C_1$-$C_6$-alkylaminocarbonyl; hydroxy$C_1$-$C_6$-alkylaminocarbonyl; $C_1$-$C_6$-alkoxy$C_1$-$C_6$-alkylaminocarbonyl; cyano; carboxy; hydroxy; hydroxy$C_1$-$C_6$-alkoxy; hydroxy$C_1$-$C_6$-alkyl; di(hydroxy)$C_1$-$C_6$-alkyl; di($C_1$-$C_6$alkyl)amino; di(hydroxy$C_1$-$C_6$-alkyl)amino; di($C_1$-$C_6$-alkoxy$C_1$-$C_6$alkyl)amino; ($C_1$-$C_6$-alkoxy$C_1$-$C_6$-alkyl)(hydroxy$C_1$-$C_6$-alkyl)amino; halo$C_1$-$C_6$-alkyl; and halogen; wherein only 1 substituent can be present on the two atoms adjacent to the atom connected to the amide nitrogen pendant on the furan ring.

4. The compound of claim 3, wherein n is 1;

R¹ is phenyl optionally substituted with 1 or 2 substituents selected from the group consisting of $C_1$-$C_6$-alkyl; $C_1$-$C_6$-alkylcarbonylamino; aminocarbonyl; cyano; hydroxy; and di($C_1$-$C_6$alkyl)amino; wherein only 1 substituent can be present on the two atoms adjacent to the atom connected to the amide nitrogen pendant on the furan ring; or R¹ is monocyclic heteroaryl, wherein the monocyclic heteroaryl is pyridyl, pyrazinyl or isoxazolyl, wherein the monocyclic heteroaryl is optionally substituted with 1, 2, or 3 substituents selected from the group consisting of $C_1$-$C_6$-alkyl; $C_1$-$C_6$-alkoxy; $C_1$-$C_6$-alkoxycarbonyl$C_1$-$C_6$-alkyl; hydroxy$C_1$-$C_6$-alkyl; halo$C_1$-$C_6$-alkyl; and halogen; wherein only 1 substituent can be present on the two atoms adjacent to the atom connected to the amide nitrogen pendant on the furan ring;

$R^2$ is hydrogen or $C_1$-$C_6$-alkyl; and
$R^6$ and $R^7$ are each hydrogen.
5. The compound of claim 3, wherein
n is 1;
$R^1$ is monocyclic heteroaryl, wherein the monocyclic heteroaryl is pyridyl, wherein the monocyclic heteroaryl is optionally substituted with 1, 2, or 3 substituents selected from the group consisting of $C_1$-$C_6$-alkoxy; $C_1$-$C_6$-alkoxy$C_1$-$C_6$-alkoxy; carboxy; hydroxy$C_1$-$C_6$-alkyl; and di(hydroxy$C_1$-$C_6$-alkyl) amino; wherein only 1 substituent can be present on the two atoms adjacent to the atom connected to the amide nitrogen pendant on the furan ring;
$R^2$ is hydrogen or $C_1$-$C_6$-alkoxy$C_2$-$C_6$alkyl; and
$R^6$ and $R^7$ are each independently $C_1$-$C_6$-alkyl.
6. The compound of claim 2, wherein $R^1$ is fused-bicyclic heteroaryl, wherein the fused-bicyclic heteroaryl contains 1, 2, 3 or 4 ring nitrogens and optionally one ring oxygen or one ring sulfur, wherein the fused-bicyclic heteroaryl is optionally substituted with 1, 2, 3, or 4 substituents selected from the group consisting of $C_1$-$C_6$-alkyl; $C_1$-$C_6$-alkylcarbonylamino; hydroxy$C_1$-$C_6$-alkylcarbonylamino; $C_1$-$C_6$-alkoxy$C_1$-$C_6$-alkylcarbonylamino; $C_1$-$C_6$-alkoxy; alkoxy$C_1$-$C_6$-alkoxy; $C_1$-$C_6$alkoxy-$C_1$-$C_6$alkyl; $C_1$-$C_6$-alkoxycarbonyl; $C_1$-$C_6$-alkoxycarbonyl$C_1$-$C_6$-alkyl; $C_3$-$C_7$cycloalkyloxy; heterocycleoxy, wherein the heterocycle of heterocycleoxy is a 4-7 membered monocyclic ring containing 0-3 double bonds and 1-3 heteroatoms selected from the group consisting of O, N, and, S, optionally substituted with $C_1$-$C_6$-alkyl; aminocarbonyl; $C_1$-$C_6$-alkylaminocarbonyl; hydroxy$C_1$-$C_6$-alkylaminocarbonyl; $C_1$-$C_6$-alkoxy$C_1$-$C_6$-alkylamincarbonyl; cyano; hydroxy; hydroxy$C_1$-$C_6$-alkoxy; hydroxy$C_1$-$C_6$-alkyl; di($C_1$-$C_6$alkyl) amino; di(hydroxy$C_1$-$C_6$-alkyl)amino; di($C_1$-$C_6$-alkoxy$C_1$-$C_6$-alkyl)amino; ($C_1$-$C_6$-alkoxy$C_1$-$C_6$-alkyl)(hydroxy$C_1$-$C_6$-alkyl)amino; halo$C_1$-$C_6$-alkyl; halogen; $C_1$-$C_6$-alkylsulfonylamino$C_2$-$C_6$-alkyl; and (i),

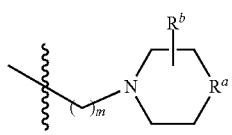

(i)

wherein $R^a$ is selected from the group consisting of a bond, $CH_2$, $CHR^b$, O, S, and N—$R^c$; wherein only 1 substituent can be present on the two atoms adjacent to the atom connected to the amide nitrogen pendant on the furan ring;
m is 2, 3 or 4 when (i) is attached to a ring nitrogen atom of the bicyclic heteroaryl; or
m is 0, 1, 2, 3 or 4 when (i) is attached to a ring carbon atom of the bicyclic heteroaryl;
$R^b$, at each occurrence, is independently selected from the group consisting of hydrogen, $C_1$-$C_6$-alkyl, halo$C_1$-$C_6$-alkyl, $C_1$-$C_6$-alkoxy$C_1$-$C_6$-alkyl, and hydroxy$C_1$-$C_6$-alkyl; and
$R^c$ is selected from the group consisting of hydrogen, $C_1$-$C_6$-alkyl, $C_1$-$C_6$-alkoxycarbonyl, $C_1$-$C_6$-alkycarbonyl, $C_1$-$C_6$-alkysulfonyl, di($C_1$-$C_6$-alkyl)aminosulfonyl, heterocyclecarbonyl, $C_3$-$C_7$-cycloalkylcarbonyl, —C(O)NH$_2$, —C(O)NH(alkyl), —C(O)N(alkyl)$_2$ and —C(=NCN)NHCH$_3$.
7. The compound of claim 6, wherein
n is 1;
$R^1$ is fused-bicyclic heteroaryl, wherein the fused-bicyclic heteroaryl is 2H-indazol-5-yl, 1H-indazol-5-yl, 1H-benzimidazol-5-yl, 1,3-benzothiazol-6-yl, quinolin-6-yl, 1H-indazol-6-yl, 1,3-benzothiazol-2-yl, wherein the fused-bicyclic heteroaryl is optionally substituted with 1, 2, or 3, substituents selected from the group consisting of $C_1$-$C_6$-alkyl; $C_1$-$C_6$-alkoxycarbonyl; hydroxy$C_1$-$C_6$-alkyl; halogen; $C_1$-$C_6$-alkylsulfonylamino$C_2$-$C_6$-alkyl; and (i),

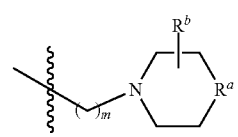

(i)

wherein $R^a$ is selected from the group consisting of a bond, O, and N—$R^c$; wherein only 1 substituent can be present on the two atoms adjacent to the atom connected to the amide nitrogen pendant on the furan ring;
m is 2;
$R^b$ is hydrogen;
$R^c$ is $C_1$-$C_6$-alkyl;
$R^2$ is hydrogen or $C_1$-$C_6$-alkyl; and
$R^6$ and $R^7$ are each hydrogen.
8. The compound of claim 2, wherein $R^1$ is (ii), (iii), or (iv);

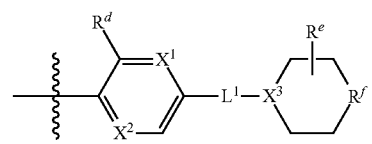

(ii)

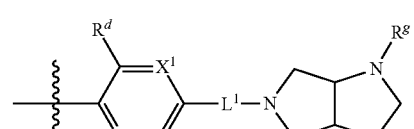

(iii)

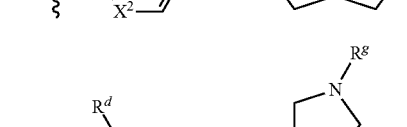

(iv)

wherein both $X^1$ and $X^2$ are CH, or one of $X^1$ and $X^2$ is N and the other is CH;
$X^3$ is CH or N;
$L^1$ is a bond; C(O), or NHC(O)—;
$R^d$ is selected from the group consisting of hydrogen; $C_1$-$C_6$-alkoxy; fluoro$C_1$-$C_6$-alkoxy; $C_1$-$C_6$-alkoxy$C_1$-$C_6$-alkoxy; $C_3$-$C_7$-cycloalkyloxy; $C_3$-$C_7$-cycloalkyl$C_1$-$C_6$-alkoxy; hydroxy$C_1$-$C_6$-alkoxy; phenyl$C_1$-$C_6$-alkoxy$C_1$-$C_6$-alkoxy; heterocycleoxy, wherein the heterocycle of heterocycleoxy 4-7 membered monocyclic ring containing 0-3 double bonds and 1-3 heteroatoms selected from the group consisting of O, N, and, S, is optionally substituted with $C_1$-$C_6$-alkyl or oxo; and phenoxy, wherein the phenyl of phenoxy is optionally substituted with hydroxy$C_1$-$C_6$-alkyl, $C_1$-$C_6$-alkoxy, $C_1$-$C_6$-alkoxy$C_1$-$C_6$-alkoxy, or $C_1$-$C_6$-alkoxycarbonyl;
$R^e$ at each occurrence is independently selected from the group consisting of hydrogen, $C_1$-$C_6$-alkyl, di($C_1$-$C_6$- alkyl)amino, haloC$_1$-C$_6$-alkyl, C$_1$-C$_6$-alkoxyC$_1$-C$_6$alkyl, and hydroxyC$_1$-C$_6$-alkyl;

R$^f$ is selected from the group consisting of a bond, CH$_2$, CHR$^e$, CH$_2$CH$_2$, O, NR$^g$, and CH$_2$NR$^g$; and R$^g$ is selected from the group consisting of hydrogen; C$_1$-C$_6$-alkyl; C$_1$-C$_6$-alkoxycarbonyl; C$_1$-C$_6$-alkycarbonyl; C$_1$-C$_6$-alkysulfonyl; di(C$_1$-C$_6$-alkyl)aminosulfonyl; C$_3$-C$_7$-cycloalkylcarbonyl; C$_1$-C$_6$-alkoxyC$_1$-C$_6$-alkylcarbonyl; hydroxyC$_2$-C$_6$-alkyl; hydroxyC$_1$-C$_6$-alkylcarbonyl; formyl; —C(O)NH$_2$; —C(O)NH(alkyl); —C(O)N(alkyl)$_2$; —C(=NCN)NHCH$_3$; and heterocyclecarbonyl, wherein the heterocycle of heterocyclecarbonyl is a 4-7 membered monocyclic ring containing 0-3 double bonds and 1-3 heteroatoms selected from the group consisting of O, N, and, S, optionally substituted with C$_1$-C$_6$-alkyl.

9. The compound of claim 8, wherein n is 1 or 2;

R$^1$ is (ii);

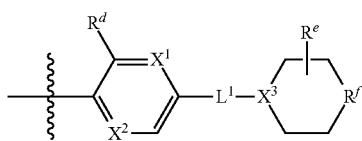

(ii)

wherein both X$^1$ and X$^2$ are CH, or one of X$^1$ and X$^2$ is N and the other is CH;

X$^3$ is N;

L$^1$ is a bond;

R$^d$ is selected from the group consisting of hydrogen; C$_1$-C$_6$alkoxy; C$_1$-C$_6$-alkoxyC$_1$-C$_6$-alkoxy; hydroxyC$_1$-C$_6$-alkoxy; phenylC$_1$-C$_6$-alkoxyC$_1$-C$_6$-alkoxy; heterocycleoxy, wherein the heterocycle of heterocycleoxy is a 4-7 membered monocyclic ring containing 0-3 double bonds and 1-3 heteroatoms selected from the group consisting of O, N, and, S, optionally substituted with C$_1$-C$_6$-alkyl or oxo; and phenoxy, wherein the phenyl of phenoxy is optionally substituted with hydroxyC$_1$-C$_6$-alkyl or C$_1$-C$_6$-alkoxycarbonyl;

R$^e$ at each occurrence is hydrogen;

R$^f$ is selected from the group consisting of a CH$_2$, O, and NR$^g$;

R$^g$ is selected from the group consisting of hydrogen; C$_1$-C$_6$-alkyl; C$_1$-C$_6$-alkoxycarbonyl; C$_1$-C$_6$-alkycarbonyl; di(C$_1$-C$_6$-alkyl)aminosulfonyl; —C(=NCN)NHCH$_3$; and heterocyclecarbonyl, wherein the heterocycle of heterocyclecarbonyl is a 4-7 membered monocyclic ring containing 0-3 double bonds and 1-3 heteroatoms selected from the group consisting of O, N, and, S, optionally substituted with C$_1$-C$_6$-alkyl;

R$^2$ is hydrogen, C$_1$-C$_6$-alkyl, hydroxyC$_2$-C$_6$-alkyl, C$_1$-C$_6$-alkoxyC$_2$-C$_6$alkyl, hydroxyC$_2$-C$_6$-alkoxyC$_2$-C$_6$-alkyl, C$_1$-C$_6$-alkylcarbonyloxyC$_2$-C$_6$-alkyl, or phenylC$_1$-C$_6$-alkoxyC$_2$-C$_6$alkyl; and R$^6$ and R$^7$ are each hydrogen.

10. The compound of claim 8 wherein n is 1;

R$^1$ is (ii), (iii), or (iv);

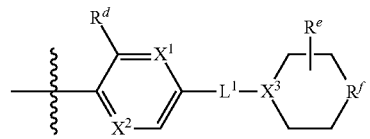

(ii)

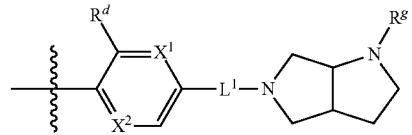

(iii)

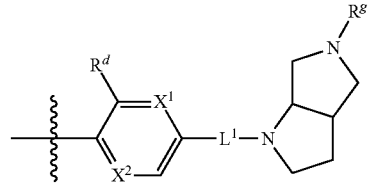

(iv)

wherein both X$^1$ and X$^2$ are CH, or one of X$^1$ and X$^2$ is N and the other is CH;

X$^3$ is CH or N;

L$^1$ is a bond;

R$^d$ is selected from the group consisting of C$_1$-C$_6$alkoxy; fluoroC$_1$-C$_6$-alkoxy; C$_1$-C$_6$-alkoxyC$_1$-C$_6$-alkoxy; and heterocycleoxy, wherein the heterocycle of heterocycleoxy is a 4-7 membered monocyclic ring containing 0-3 double bonds and 1-3 heteroatoms selected from the group consisting of O, N, and, S, optionally substituted with oxo;

R$^e$ at each occurrence is independently selected from the group consisting of hydrogen, di(C$_1$-C$_6$-alkyl)amino, C$_1$-C$_6$-alkoxyC$_1$-C$_6$alkyl, and hydroxyC$_1$-C$_6$-alkyl;

R$^f$ is selected from the group consisting of a bond, CH$_2$, and NR$^g$;

R$^g$ is selected from the group consisting of hydrogen; C$_1$-C$_6$-alkyl; C$_1$-C$_6$-alkycarbonyl; C$_1$-C$_6$-alkysulfonyl; hydroxyC$_2$-C$_6$-alkyl; formyl; —C(=NCN)NHCH$_3$; and heterocyclecarbonyl, wherein the heterocycle of heterocyclecarbonyl is a 4-7 membered monocyclic ring containing 0-3 double bonds and 1-3 heteroatoms selected from the group consisting of O, N, and, S, optionally substituted with C$_1$-C$_6$-alkyl;

R$^2$ is selected from the group consisting of hydrogen, C$_1$-C$_6$-alkyl, hydroxyC$_2$-C$_6$-alkyl, di(hydroxy)C$_2$-C$_6$-alkyl, C$_1$-C$_6$-alkoxyC$_2$-C$_6$alkyl, and hydroxyC$_2$-C$_6$-alkoxyC$_2$-C$_6$-alkyl;

R$^6$ is selected from the group consisting of hydrogen and C$_1$-C$_6$-alkyl; and R$^7$ is selected from the group consisting of C$_1$-C$_6$-alkyl and hydroxyC$_1$-C$_6$-alkyl; or R$^6$ and R$^7$ taken together with the carbon atom to which they are attached form a C$_3$-C$_6$-cycloalkyl or heterocycle, wherein the heterocycle is a 4-7 membered monocyclic ring containing 0-3 double bonds and 1-3 heteroatoms selected from the group consisting of O, N, and, S, optionally substituted with 1 or 2 substituents selected from C$_1$-C$_6$-alkyl, oxo and C$_1$-C$_6$-alkylcarbonyl.

11. The compound of claim 1, wherein

Z$^1$ is CR$^3$R$^4$; and

Z$^2$ is NR$^5$.

12. The compound of claim 11, wherein $R^1$ is phenyl or monocyclic heteroaryl, wherein the monocyclic heteroaryl contains one or two ring nitrogens and optionally one ring oxygen or one ring sulfur, wherein the phenyl or monocyclic heteroaryl is optionally substituted with 1, 2, or 3 substituents selected from the group consisting of $C_1$-$C_6$-alkyl; $C_1$-$C_6$-alkylcarbonylamino; hydroxy$C_1$-$C_6$-alkylcarbonylamino; $C_1$-$C_6$-alkoxy$C_1$-$C_6$alkylcarbonylamino; $C_1$-$C_6$-alkoxy; $C_1$-$C_6$-alkoxy$C_1$-$C_6$-alkoxy; $C_1$-$C_6$-alkoxy$C_1$-$C_6$-alkyl; $C_1$-$C_6$-alkoxycarbonyl; $C_1$-$C_6$-alkoxycarbonyl$C_1$-$C_6$-alkyl; aminocarbonyl; $C_1$-$C_6$-alkylaminocarbonyl; hydroxy$C_1$-$C_6$-alkylaminocarbonyl; $C_1$-$C_6$-alkoxy$C_1$-$C_6$-alkylaminocarbonyl; cyano; carboxy; hydroxy; hydroxy$C_1$-$C_6$-alkoxy; hydroxy$C_1$-$C_6$-alkyl; di(hydroxy)$C_1$-$C_6$-alkyl; di($C_1$-$C_6$alkyl)amino; di(hydroxy$C_1$-$C_6$-alkyl)amino; di($C_1$-$C_6$-alkoxy$C_1$-$C_6$-alkyl)amino; ($C_1$-$C_6$-alkoxy$C_1$-$C_6$-alkyl)(hydroxy$C_1$-$C_6$-alkyl)amino; halo$C_1$-$C_6$-alkyl; and halogen; wherein only 1 substituent can be present on the two atoms adjacent to the atom connected to the amide nitrogen pendant on the furan ring.

13. The compound of claim 11, wherein $R^1$ is fused-bicyclic heteroaryl, wherein the fused-bicyclic heteroaryl contains 1, 2, 3 or 4 ring nitrogens and optionally one ring oxygen or one ring sulfur, wherein the fused-bicyclic heteroaryl is optionally substituted with 1, 2, 3, or 4 substituents selected from the group consisting of $C_1$-$C_6$-alkyl; $C_1$-$C_6$-alkylcarbonylamino; hydroxy$C_1$-$C_6$-alkylcarbonylamino; $C_1$-$C_6$-alkoxy$C_1$-$C_6$-alkylcarbonylamino; $C_1$-$C_6$-alkoxy; $C_1$-$C_6$-alkoxy$C_1$-$C_6$-alkoxy; $C_1$-$C_6$alkoxy-$C_1$-$C_6$alkyl; $C_1$-$C_6$-alkoxycarbonyl; $C_1$-$C_6$-alkoxycarbonyl$C_1$-$C_6$-alkyl; $C_3$-$C_7$-cycloalkyloxy; heterocycleoxy, wherein the heterocycle of heterocycleoxy is a 4-7 membered monocyclic ring containing 0-3 double bonds and 1-3 heteroatoms selected from the group consisting of O, N, and, S, optionally substituted with $C_1$-$C_6$-alkyl; aminocarbonyl; $C_1$-$C_6$-alkylaminocarbonyl; hydroxy$C_1$-$C_6$-alkylaminocarbonyl; $C_1$-$C_6$-alkoxy$C_1$-$C_6$-alkylamincarbonyl; cyano; hydroxy; hydroxy$C_1$-$C_6$-alkoxy; hydroxy$C_1$-$C_6$-alkyl; di($C_1$-$C_6$alkyl)amino; di(hydroxy$C_1$-$C_6$-alkyl)amino; di($C_1$-$C_6$-alkoxy$C_1$-$C_6$-alkyl)amino; ($C_1$-$C_6$-alkoxy$C_1$-$C_6$-alkyl)(hydroxy$C_1$-$C_6$-alkyl)amino; halo$C_1$-$C_6$-alkyl; halogen; $C_1$-$C_6$-alkylsulfonylamino$C_2$-$C_6$-alkyl; and (i),

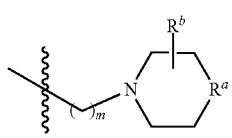

(i)

wherein $R^a$ is selected from the group consisting of a bond, $CH_2$, $CHR^b$, O, S, and N—$R^c$;
wherein only 1 substituent can be present on the two atoms adjacent to the atom connected to the amide nitrogen pendant on the furan ring;
m is 2, 3 or 4 when (i) is attached to a ring nitrogen atom of the bicyclic heteroaryl; or
m is 0, 1, 2, 3 or 4 when (i) is attached to a ring carbon atom of the bicyclic heteroaryl;
$R^b$, at each occurrence, is independently selected from the group consisting of hydrogen, $C_1$-$C_6$-alkyl, halo$C_1$-$C_6$-alkyl, $C_1$-$C_6$-alkoxy$C_1$-$C_6$-alkyl, and hydroxy$C_1$-$C_6$-alkyl; and
$R^c$ is selected from the group consisting of hydrogen, $C_1$-$C_6$-alkyl, $C_1$-$C_6$-alkoxycarbonyl, $C_1$-$C_6$-alkycarbonyl, $C_1$-$C_6$-alkysulfonyl, di($C_1$-$C_6$-alkyl)aminosulfonyl, heterocyclecarbonyl, $C_3$-$C_7$-cycloalkylcarbonyl, —C(O)NH$_2$, —C(O)NH(alkyl), —C(O)N(alkyl)$_2$ and —C(=NCN)NHCH$_3$.

14. The compound of claim 13, wherein
n is 1;
$R^1$ is fused-bicyclic heteroaryl, wherein the fused-bicyclic heteroaryl is 2H-indazol-5-yl, wherein the fused-bicyclic heteroaryl is optionally substituted with 1 or 2 $C_1$-$C_6$-alkyl; wherein only 1 substituent can be present on the two atoms adjacent to the atom connected to the amide nitrogen pendant on the furan ring;
$R^3$ and $R^4$ are both hydrogen; and
$R^5$ is hydrogen or $C_1$-$C_6$-alkylsulfonyl.

15. The compounds of claim 11, wherein $R^1$ is (ii), (iii), or (iv);

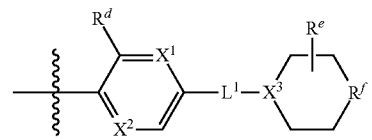

(ii)

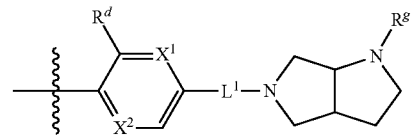

(iii)

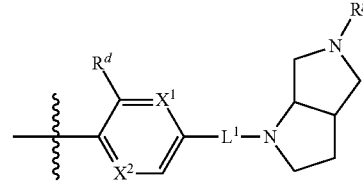

(iv)

wherein both $X^1$ and $X^2$ are CH, or one of $X^1$ and $X^2$ is N and the other is CH;
$X^3$ is CH or N;
$L^1$ is a bond, C(O), or —NHC(O)—;
$R^d$ is selected from the group consisting of hydrogen; $C_1$-$C_6$alkoxy; fluoro$C_1$-$C_6$-alkoxy; $C_1$-$C_6$-alkoxy$C_1$-$C_6$-alkoxy; $C_3$-$C_7$-cycloalkyloxy; $C_3$-$C_7$-cycloalkyl$C_1$-$C_6$-alkoxy; hydroxy$C_1$-$C_6$-alkoxy; phenyl$C_1$-$C_6$-alkoxy$C_1$-$C_6$-alkoxy; heterocycleoxy, wherein the heterocycle of heterocycleoxy is a 4-7 membered monocyclic ring containing 0-3 double bonds and 1-3 heteroatoms selected from the group consisting of O, N, and, S, optionally substituted with $C_1$-$C_6$-alkyl or oxo; and phenoxy, wherein the phenyl of phenoxy is optionally substituted with hydroxy$C_1$-$C_6$-alkyl, $C_1$-$C_6$-alkoxy, $C_1$-$C_6$-alkoxy$C_1$-$C_6$-alkoxy, or $C_1$-$C_6$-alkoxycarbonyl;
$R^e$ at each occurrence is independently selected from the group consisting of hydrogen, $C_1$-$C_6$-alkyl, di($C_1$-$C_6$-alkyl)amino, halo$C_1$-$C_6$-alkyl, $C_1$-$C_6$-alkoxy$C_1$-$C_6$alkyl, and hydroxy$C_1$-$C_6$-alkyl;
$R^f$ is selected from the group consisting of a bond, $CH_2$, $CHR^e$, $CH_2CH_2$, O, NR$^g$, and $CH_2NR^g$; and
$R^g$ is selected from the group consisting of hydrogen; $C_1$-$C_6$-alkyl; $C_1$-$C_6$-alkoxycarbonyl; $C_1$-$C_6$-alkycarbonyl; $C_1$-$C_6$-alkysulfonyl; di($C_1$-$C_6$-alkyl)aminosulfonyl; $C_3$-$C_7$-cycloalkylcarbonyl; $C_1$-$C_6$-alkoxy$C_1$-$C_6$-alkylcarbonyl; hydroxy$C_2$-$C_6$-alkyl; hydroxy$C_1$-$C_6$-alkylcarbonyl; formyl; —C(O)NH$_2$; —C(O)NH(alkyl);

—C(O)N(alkyl)$_2$; —C(=NCN)NHCH$_3$; and heterocyclecarbonyl, wherein the heterocycle of heterocyclecarbonyl is a 4-7 membered monocyclic ring containing 0-3 double bonds and 1-3 heteroatoms selected from the group consisting of O, N, and S optionally substituted with C$_1$-C$_6$-alkyl.

16. The compound of claim 1, wherein
Z$^1$ is CR$^3$R$^4$; and
Z$^2$ is O.

17. The compound of claim 16, wherein R$^1$ is phenyl or monocyclic heteroaryl, wherein the monocyclic heteroaryl contains one or two ring nitrogens and optionally one ring oxygen or one ring sulfur, wherein the phenyl or monocyclic heteroaryl is optionally substituted with 1, 2, or 3 substituents selected from the group consisting of C$_1$-C$_6$-alkyl; C$_1$-C$_6$-alkylcarbonylamino; hydroxyC$_1$-C$_6$-alkylcarbonylamino; C$_1$-C$_6$-alkoxyC$_1$-C$_6$alkylcarbonylamino; C$_1$-C$_6$-alkoxy; C$_1$-C$_6$-alkoxyC$_1$-C$_6$-alkoxy; C$_1$-C$_6$-alkoxyC$_1$-C$_6$-alkyl; C$_1$-C$_6$-alkoxycarbonyl; C$_1$-C$_6$-alkoxycarbonylC$_1$-C$_6$-alkyl; aminocarbonyl; C$_1$-C$_6$-alkylaminocarbonyl; hydroxyC$_1$-C$_6$-alkylaminocarbonyl; C$_1$-C$_6$-alkoxyC$_1$-C$_6$-alkylaminocarbonyl; cyano; carboxy; hydroxy; hydroxyC$_1$-C$_6$-alkoxy; hydroxyC$_1$-C$_6$-alkyl; di(hydroxy)C$_1$-C$_6$-alkyl; di(C$_1$-C$_6$alkyl)amino; di(hydroxyC$_1$-C$_6$alkyl)amino; di(C$_1$-C$_6$-alkoxyC$_1$-C$_6$alkyl)amino; (C$_1$-C$_6$-alkoxyC$_1$-C$_6$-alkyl)(hydroxyC$_1$-C$_6$-alkyl)amino; haloC$_1$-C$_6$-alkyl; and halogen; wherein only 1 substituent can be present on the two atoms adjacent to the atom connected to the amide nitrogen pendant on the furan ring.

18. The compound of claim 16, wherein R$^1$ is fused-bicyclic heteroaryl, wherein the fused-bicyclic heteroaryl contains 1, 2, 3 or 4 ring nitrogens and optionally one ring oxygen or one ring sulfur, wherein the fused-bicyclic heteroaryl is optionally substituted with 1, 2, 3, or 4 substituents selected from the group consisting of C$_1$-C$_6$-alkyl; C$_1$-C$_6$-alkylcarbonylamino; hydroxyC$_1$-C$_6$-alkylcarbonylamino; C$_1$-C$_6$-alkoxyC$_1$-C$_6$-alkylcarbonylamino; C$_1$-C$_6$-alkoxy; C$_1$-C$_6$-alkoxyC$_1$-C$_6$-alkoxy; C$_1$-C$_6$alkoxy-C$_1$-C$_6$alkyl; C$_1$-C$_6$-alkoxycarbonyl; C$_1$-C$_6$-alkoxycarbonylC$_1$-C$_6$-alkyl; C$_3$-C$_7$-cycloalkyloxy; heterocycleoxy, wherein the heterocycle of heterocycleoxy is a 4-7 membered monocyclic ring containing 0-3 double bonds and 1-3 heteroatoms selected from the group consisting of O, N, and, S, optionally substituted with C$_1$-C$_6$-alkyl; aminocarbonyl; C$_1$-C$_6$-alkylaminocarbonyl; hydroxyC$_1$-C$_6$-alkylaminocarbonyl; C$_1$-C$_6$-alkoxyC$_1$-C$_6$-alkylamincarbonyl; cyano; hydroxy; hydroxyC$_1$-C$_6$-alkoxy; hydroxyC$_1$-C$_6$-alkyl; di(C$_1$-C$_6$alkyl)amino; di(hydroxyC$_1$-C$_6$-alkyl)amino; di(C$_1$-C$_6$-alkoxyC$_1$-C$_6$-alkyl)amino; (C$_1$-C$_6$-alkoxyC$_1$-C$_6$-alkyl)(hydroxyC$_1$-C$_6$-alkyl)amino; haloC$_1$-C$_6$-alkyl; halogen; C$_1$-C$_6$-alkylsulfonylaminoC$_2$-C$_6$-alkyl; and (i),

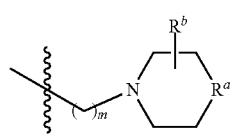

(i)

wherein R$^a$ is selected from the group consisting of a bond, CH$_2$, CHR$^b$, O, S, and N—R$^c$; wherein only 1 substituent can be present on the two atoms adjacent to the atom connected to the amide nitrogen pendant on the furan ring;
m is 2, 3 or 4 when (i) is attached to a ring nitrogen atom of the bicyclic heteroaryl; or m is 0, 1, 2, 3 or 4 when (i) is attached to a ring carbon atom of the bicyclic heteroaryl;
R$^b$, at each occurrence, is independently selected from the group consisting of hydrogen, C$_1$-C$_6$-alkyl, haloC$_1$-C$_6$-alkyl, C$_1$-C$_6$-alkoxyC$_1$-C$_6$-alkyl, and hydroxyC$_1$-C$_6$-alkyl; and
R$^c$ is selected from the group consisting of hydrogen, C$_1$-C$_6$-alkyl, C$_1$-C$_6$-alkoxycarbonyl, C$_1$-C$_6$-alkycarbonyl, C$_1$-C$_6$-alkysulfonyl, di(C$_1$-C$_6$-alkyl)aminosulfonyl, heterocyclecarbonyl, C$_3$-C$_7$-cycloalkylcarbonyl, —C(O)NH$_2$, —C(O)NH(alkyl), —C(O)N(alkyl)$_2$ and —C(=NCN)NHCH$_3$.

19. The compound of claim 16, wherein R$^1$ is (ii), (iii), or (iv);

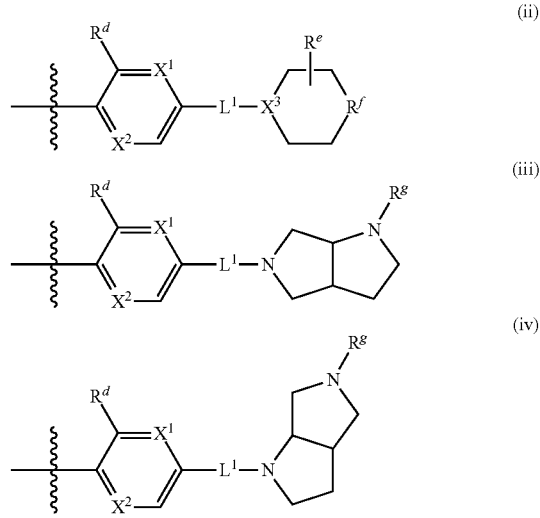

wherein both X$^1$ and X$^2$ are CH, or one of X$^1$ and X$^2$ is N and the other is CH;
X$^3$ is CH or N;
L$^1$ is a bond, C(O), or —NHC(O)—;
R$^d$ is selected from the group consisting of hydrogen; C$_1$-C$_6$alkoxy; fluoroC$_1$-C$_6$-alkoxy; C$_1$-C$_6$-alkoxyC$_1$-C$_6$-alkoxy; C$_3$-C$_7$-cycloalkyloxy; C$_3$-C$_7$-cycloalkylC$_1$-C$_6$-alkoxy; hydroxyC$_1$-C$_6$-alkoxy; phenylC$_1$-C$_6$-alkoxyC$_1$-C$_6$-alkoxy; heterocycleoxy, wherein the heterocycle of heterocycleoxy is a 4-7 membered monocyclic ring containing 0-3 double bonds and 1-3 heteroatoms selected from the group consisting of O, N, and, S, optionally substituted with C$_1$-C$_6$-alkyl or oxo; and phenoxy, wherein the phenyl of phenoxy is optionally substituted with hydroxyC$_1$-C$_6$-alkyl, C$_1$-C$_6$-alkoxy, C$_1$-C$_6$-alkoxyC$_1$-C$_6$-alkoxy, or C$_1$-C$_6$-alkoxycarbonyl;
R$^e$ at each occurrence is independently selected from the group consisting of hydrogen, C$_1$-C$_6$-alkyl, di(C$_1$-C$_6$-alkyl)amino, haloC$_1$-C$_6$-alkyl, C$_1$-C$_6$-alkoxyC$_1$-C$_6$alkyl, and hydroxyC$_1$-C$_6$-alkyl;
R$^f$ is selected from the group consisting of a bond, CH$_2$, CHR$^e$, CH$_2$CH$_2$, O, NR$^g$, and CH$_2$NR$^g$; and
R$^g$ is selected from the group consisting of hydrogen; C$_1$-C$_6$-alkyl; C$_1$-C$_6$-alkoxycarbonyl; C$_1$-C$_6$-alkycarbonyl; C$_1$-C$_6$-alkysulfonyl; di(C$_1$-C$_6$-alkyl)aminosulfonyl; C$_3$-C$_7$-cycloalkylcarbonyl; C$_1$-C$_6$-alkoxyC$_1$-C$_6$-alkylcarbonyl; hydroxyC$_2$-C$_6$-alkyl; hydroxyC$_1$-C$_6$-alkylcarbonyl; formyl; —C(O)NH$_2$; —C(O)NH(alkyl); —C(O)N(alkyl)$_2$; —C(=NCN)NHCH$_3$; and heterocyclecarbonyl, wherein the heterocycle of heterocyclecarbonyl is a 4-7 membered monocyclic ring containing 0-3 double bonds and 1-3 heteroatoms selected from the group consisting of O, N, and, S, optionally substituted with $C_1$-$C_6$-alkyl.

20. The compound of claim 19, wherein
n is 1;
$R^1$ is (ii);

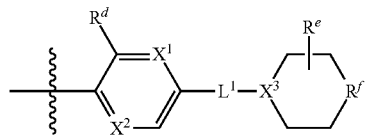

wherein both $X^1$ and $X^2$ are CH, or one of $X^1$ and $X^2$ is N and the other is CH;
$X^3$ is N;
$L^1$ is a bond;
$R^d$ is $C_1$-$C_6$alkoxy;
$R^e$ at each occurrence is hydrogen;
$R^f$ is $NR^g$
$R^g$ is $C_1$-$C_6$-alkycarbonyl; and
$R^3$ and $R^4$ are each independently $C_1$-$C_6$-alkyl; or
$R^3$ and $R^4$ taken together with the carbon atom to which they are attached form a heterocycle wherein heterocycle is a 4-7 membered monocyclic ring containing 0-3 double bonds and 1-3 heteroatoms selected from the group consisting of O, N, and, S.

21. The compound of claim 1, selected from the group consisting of:
- N-(2-methyl-2H-indazol-5-yl)-4-oxo-4,5,6,7-tetrahydrofuro[3,2-c]pyridine-3-carboxamide;
- 5-methyl-N-(2-methyl-2H-indazol-5-yl)-4-oxo-4,5,6,7-tetrahydrofuro[3,2-c]pyridine-3-carboxamide;
- N-[4-(morpholin-4-yl)phenyl]-4-oxo-4,5,6,7-tetrahydrofuro[3,2-c]pyridine-3-carboxamide;
- 5-methyl-N-(4-methylphenyl)-4-oxo-4,5,6,7-tetrahydrofuro[3,2-c]pyridine-3-carboxamide;
- tert-butyl 4-(3-methoxy-4-{[(4-oxo-4,5,6,7-tetrahydrofuro[3,2-c]pyridin-3-yl)carbonyl]amino}phenyl)piperazine-1-carboxylate;
- N-[2-methoxy-4-(piperazin-1-yl)phenyl]-4-oxo-4,5,6,7-tetrahydrofuro[3,2-c]pyridine-3-carboxamide;
- N-[2-methoxy-6-(4-methylpiperazin-1-yl)pyridin-3-yl]-4-oxo-5,6,7, 8-tetrahydro-4H-furo[3,2-c]azepine-3-carboxamide;
- N-[6-(4-acetylpiperazin-1-yl)-2-ethoxypyridin-3-yl]-5-[2-(benzyloxy)ethyl]-4-oxo-4,5,6,7-tetrahydrofuro[3,2-c]pyridine-3-carboxamide;
- N-[6-(4-acetylpiperazin-1-yl)-2-ethoxypyridin-3-yl]-5-(2-hydroxyethyl)-4-oxo-4,5,6,7-tetrahydrofuro[3,2-c]pyridine-3-carboxamide;
- N-[4-(4-acetylpiperazin-1-yl)phenyl]-4-oxo-4,5,6,7-tetrahydrofuro[3,2-c]pyridine-3-carboxamide;
- N-(1-methyl-1H-indazol-5-yl)-4-oxo-4,5,6,7-tetrahydrofuro[3,2-c]pyridine-3-carboxamide;
- N-(1H-benzimidazol-5-yl)-4-oxo-4,5,6,7-tetrahydrofuro[3,2-c]pyridine-3-carboxamide;
- N-(4-carbamoylphenyl)-4-oxo-4,5,6,7-tetrahydrofuro[3,2-c]pyridine-3-carboxamide;
- N-(1H-indazol-5-yl)-4-oxo-4,5,6,7-tetrahydrofuro[3,2-c]pyridine-3-carboxamide;
- N-(2-methyl-1,3-benzothiazol-6-yl)-4-oxo-4,5,6,7-tetrahydrofuro[3,2-c]pyridine-3-carboxamide;
- N-[5-(4-methylpiperazin-1-yl)pyridin-2-yl]-4-oxo-4,5,6, 7-tetrahydrofuro[3,2-c]pyridine-3-carboxamide;
- N-[4-(4-methylpiperazin-1-yl)phenyl]-4-oxo-4,5,6,7-tetrahydrofuro[3,2-c]pyridine-3-carboxamide;
- N-[4-(4-acetylpiperazin-1-yl)-2-methoxyphenyl]-4-oxo-4,5,6,7-tetrahydrofuro[3,2-c]pyridine-3-carboxamide;
- N-[6-(4-acetylpiperazin-1-yl)-2-ethoxypyridin-3-yl]-4-oxo-4,5,6,7-tetrahydrofuro[3,2-c]pyridine-3-carboxamide;
- N-[6-(4-acetylpiperazin-1-yl)-2-(2-methoxyethoxy)pyridin-3-yl]-4-oxo-4,5,6,7-tetrahydrofuro[3,2-c]pyridine-3-carboxamide;
- N-[6-(4-acetylpiperazin-1-yl)-2-(oxetan-3-yloxy)pyridin-3-yl]-4-oxo-4,5,6,7-tetrahydrofuro[3,2-c]pyridine-3-carboxamide;
- 5-methyl-N-[4-(4-methylpiperazin-1-yl)phenyl]-4-oxo-4,5,6,7-tetrahydrofuro[3,2-c]pyridine-3-carboxamide;
- N-(1H-indazol-5-yl)-5-methyl-4-oxo-4,5,6,7-tetrahydrofuro[3,2-c]pyridine-3-carboxamide;
- 5-methyl-N-(1-methyl-1H-indazol-5-yl)-4-oxo-4,5,6,7-tetrahydrofuro[3,2-c]pyridine-3-carboxamide;
- 5-methyl-N-[4-(morpholin-4-yl)phenyl]-4-oxo-4,5,6,7-tetrahydrofuro[3,2-c]pyridine-3-carboxamide;
- N-(4-carbamoylphenyl)-5-methyl-4-oxo-4,5,6,7-tetrahydrofuro[3,2-c]pyridine-3-carboxamide;
- N-(1H-benzimidazol-5-yl)-5-methyl-4-oxo-4,5,6,7-tetrahydrofuro[3,2-c]pyridine-3-carboxamide;
- N-[4-(4-acetylpiperazin-1-yl)phenyl]-5-methyl-4-oxo-4,5,6,7-tetrahydrofuro[3,2-c]pyridine-3-carboxamide;
- 5-methyl-N-(2-methyl-1,3-benzothiazol-6-yl)-4-oxo-4,5,6,7-tetrahydrofuro[3,2-c]pyridine-3-carboxamide;
- N-(4-methylphenyl)-4-oxo-4,5,6,7-tetrahydrofuro[3,2-c]pyridine-3-carboxamide;
- N-(4-hydroxyphenyl)-4-oxo-4,5,6,7-tetrahydrofuro[3,2-c]pyridine-3-carboxamide;
- N-(4-acetamidophenyl)-4-oxo-4,5,6,7-tetrahydrofuro[3,2-c]pyridine-3-carboxamide;
- 4-oxo-N-(quinolin-6-yl)-4,5,6,7-tetrahydrofuro[3,2-c]pyridine-3-carboxamide;
- N-(1H-indazol-6-yl)-4-oxo-4,5,6,7-tetrahydrofuro[3,2-c]pyridine-3-carboxamide;
- N-(2,6-dimethoxypyridin-3-yl)-4-oxo-4,5,6,7-tetrahydrofuro[3,2-c]pyridine-3-carboxamide;
- N-(1,2-oxazol-3-yl)-4-oxo-4,5,6,7-tetrahydrofuro[3,2-c]pyridine-3-carboxamide;
- 4-oxo-N-(pyrazin-2-yl)-4,5,6,7-tetrahydrofuro[3,2-c]pyridine-3-carboxamide;
- N-(5-methyl-1,2-oxazol-3-yl)-4-oxo-4,5,6,7-tetrahydrofuro[3,2-c]pyridine-3-carboxamide;
- N-(4-cyanophenyl)-4-oxo-4,5,6,7-tetrahydrofuro[3,2-c]pyridine-3-carboxamide;
- N-(5-fluoropyridin-2-yl)-4-oxo-4,5,6,7-tetrahydrofuro[3,2-c]pyridine-3-carboxamide;
- N-(6-methoxypyridin-3-yl)-4-oxo-4,5,6,7-tetrahydrofuro[3,2-c]pyridine-3-carboxamide;
- N-(5-chloropyridin-2-yl)-4-oxo-4,5,6,7-tetrahydrofuro[3,2-c]pyridine-3-carboxamide;
- N-(3-cyanophenyl)-4-oxo-4,5,6,7-tetrahydrofuro[3,2-c]pyridine-3-carboxamide;
- N-(6-ethoxypyridin-3-yl)-4-oxo-4,5,6,7-tetrahydrofuro[3,2-c]pyridine-3-carboxamide;
- N-(3-methyl-1H-indazol-5-yl)-4-oxo-4,5,6,7-tetrahydrofuro[3,2-c]pyridine-3-carboxamide;
- N-(6-methyl-1H-indazol-5-yl)-4-oxo-4,5,6,7-tetrahydrofuro[3,2-c]pyridine-3-carboxamide;

N-(1,3-benzothiazol-2-yl)-4-oxo-4,5,6,7-tetrahydrofuro[3,2-c]pyridine-3-carboxamide;
methyl 5-{[(4-oxo-4,5,6,7-tetrahydrofuro[3,2-c]pyridin-3-yl)carbonyl]amino}-1H-indazole-3-carboxylate;
N-[4-(diethylamino)phenyl]-4-oxo-4,5,6,7-tetrahydrofuro[3,2-c]pyridine-3-carboxamide;
N-[1-(2-hydroxypropyl)-1H-indazol-5-yl]-4-oxo-4,5,6,7-tetrahydrofuro[3,2-c]pyridine-3-carboxamide;
N-(2-{2-[(methylsulfonyl)amino]ethyl}-2H-indazol-5-yl)-4-oxo-4,5,6,7-tetrahydrofuro[3,2-c]pyridine-3-carboxamide;
N-{2-[2-(4-methylpiperazin-1-yl)ethyl]-2H-indazol-5-yl}-4-oxo-4,5,6,7-tetrahydrofuro[3,2-c]pyridine-3-carboxamide;
N-[1-(2-hydroxyethyl)-1H-indazol-5-yl]-4-oxo-4,5,6,7-tetrahydrofuro[3,2-c]pyridine-3-carboxamide;
4-oxo-N-{1-[2-(pyrrolidin-1-yl)ethyl]-1H-indazol-5-yl}-4,5,6,7-tetrahydrofuro[3,2-c]pyridine-3-carboxamide;
N-[2-(2-hydroxypropyl)-2H-indazol-5-yl]-4-oxo-4,5,6,7-tetrahydrofuro[3,2-c]pyridine-3-carboxamide;
N-{1-[2-(morpholin-4-yl)ethyl]-1H-indazol-5-yl}-4-oxo-4,5,6,7-tetrahydrofuro[3,2-c]pyridine-3-carboxamide;
N-{1-[2-(4-methylpiperazin-1-yl)ethyl]-1H-indazol-5-yl}-4-oxo-4,5,6,7-tetrahydrofuro[3,2-c]pyridine-3-carboxamide;
N-(1-{2-[(methylsulfonyl)amino]ethyl}-1H-indazol-5-yl)-4-oxo-4,5,6,7-tetrahydrofuro[3,2-c]pyridine-3-carboxamide;
N-(4-hydroxyphenyl)-5-methyl-4-oxo-4,5,6,7-tetrahydrofuro[3,2-c]pyridine-3-carboxamide;
N-(4-acetamidophenyl)-5-methyl-4-oxo-4,5,6,7-tetrahydrofuro[3,2-c]pyridine-3-carboxamide;
5-methyl-4-oxo-N-[4-(piperidin-1-yl)phenyl]-4,5,6,7-tetrahydrofuro[3,2-c]pyridine-3-carboxamide;
5-methyl-4-oxo-N-(quinolin-3-yl)-4,5,6,7-tetrahydrofuro[3,2-c]pyridine-3-carboxamide;
5-methyl-4-oxo-N-(quinolin-6-yl)-4,5,6,7-tetrahydrofuro[3,2-c]pyridine-3-carboxamide;
N-(1H-indazol-6-yl)-5-methyl-4-oxo-4,5,6,7-tetrahydrofuro[3,2-c]pyridine-3-carboxamide;
N-(2,6-dimethoxypyridin-3-yl)-5-methyl-4-oxo-4,5,6,7-tetrahydrofuro[3,2-c]pyridine-3-carboxamide;
5-methyl-N-(5-methyl-1,2-oxazol-3-yl)-4-oxo-4,5,6,7-tetrahydrofuro[3,2-c]pyridine-3-carboxamide;
N-(4-cyanophenyl)-5-methyl-4-oxo-4,5,6,7-tetrahydrofuro[3,2-c]pyridine-3-carboxamide;
N-(5-fluoropyridin-2-yl)-5-methyl-4-oxo-4,5,6,7-tetrahydrofuro[3,2-c]pyridine-3-carboxamide;
N-(6-methoxypyridin-3-yl)-5-methyl-4-oxo-4,5,6,7-tetrahydrofuro[3,2-c]pyridine-3-carboxamide;
N-(5-chloropyridin-2-yl)-5-methyl-4-oxo-4,5,6,7-tetrahydrofuro[3,2-c]pyridine-3-carboxamide;
N-(3-cyanophenyl)-5-methyl-4-oxo-4,5,6,7-tetrahydrofuro[3,2-c]pyridine-3-carboxamide;
N-(6-ethoxypyridin-3-yl)-5-methyl-4-oxo-4,5,6,7-tetrahydrofuro[3,2-c]pyridine-3-carboxamide;
5-methyl-N-(3-methyl-1H-indazol-5-yl)-4-oxo-4,5,6,7-tetrahydrofuro[3,2-c]pyridine-3-carboxamide;
5-methyl-N-(6-methyl-1H-indazol-5-yl)-4-oxo-4,5,6,7-tetrahydrofuro[3,2-c]pyridine-3-carboxamide;
N-(1,3-benzothiazol-2-yl)-5-methyl-4-oxo-4,5,6,7-tetrahydrofuro[3,2-c]pyridine-3-carboxamide;
5-methyl-4-oxo-N-[5-(trifluoromethyl)pyridin-2-yl]-4,5,6,7-tetrahydrofuro[3,2-c]pyridine-3-carboxamide;
N-(6-chloro-1H-indazol-5-yl)-5-methyl-4-oxo-4,5,6,7-tetrahydrofuro[3,2-c]pyridine-3-carboxamide;
5-methyl-N-(2-methyl-1H-benzimidazol-5-yl)-4-oxo-4,5,6,7-tetrahydrofuro[3,2-c]pyridine-3-carboxamide;
N-{4-[4-(3,3-dimethylbutanoyl)piperazin-1-yl]-2-methoxyphenyl}-4-oxo-4,5,6,7-tetrahydrofuro[3,2-c]pyridine-3-carboxamide;
N-{2-methoxy-4-[4-(pyrrolidin-1-ylcarbonyl)piperazin-1-yl]phenyl}-4-oxo-4,5,6,7-tetrahydrofuro[3,2-c]pyridine-3-carboxamide;
N-{4-[4-(dimethylsulfamoyl)piperazin-1-yl]-2-methoxyphenyl}-4-oxo-4,5,6,7-tetrahydrofuro[3,2-c]pyridine-3-carboxamide;
methyl 4-{[6-(4-methylpiperazin-1-yl)-3-{[(4-oxo-5,6,7,8-tetrahydro-4H-furo[3,2-c]azepin-3-yl)carbonyl]amino}pyridin-2-yl]oxy}benzoate;
N-{2-[4-(hydroxymethyl)phenoxy]-6-(4-methylpiperazin-1-yl)pyridin-3-yl}-4-oxo-5,6,7,8-tetrahydro-4H-furo[3,2-c]azepine-3-carboxamide;
N-[6-(4-acetylpiperazin-1-yl)-2-ethoxypyridin-3-yl]-5-(2-methoxy ethyl)-4-oxo-4,5,6,7-tetrahydrofuro[3,2-c]pyridine-3-carboxamide;
N-[6-(4-acetylpiperazin-1-yl)-2-(2-methoxyethoxy)pyridin-3-yl]-5-[2-(benzyloxy)ethyl]-4-oxo-4,5,6,7-tetrahydrofuro[3,2-c]pyridine-3-carboxamide;
N-{6-(4-acetylpiperazin-1-yl)-2-[2-(benzyloxy)ethoxy]pyridin-3-yl}-5-[2-(benzyloxy)ethyl]-4-oxo-4,5,6,7-tetrahydrofuro[3,2-c]pyridine-3-carboxamide;
N-[6-(4-acetylpiperazin-1-yl)-2-(2-methoxyethoxy)pyridin-3-yl]-5-(2-hydroxyethyl)-4-oxo-4,5,6,7-tetrahydrofuro[3,2-c]pyridine-3-carboxamide;
N-[6-(4-acetylpiperazin-1-yl)-2-(2-hydroxyethoxy)pyridin-3-yl]-5-(2-hydroxy ethyl)-4-oxo-4,5,6,7-tetrahydrofuro[3,2-c]pyridine-3-carboxamide;
N-[6-(4-acetylpiperazin-1-yl)-2-ethoxypyridin-3-yl]-5-(3-hydroxypropyl)-4-oxo-4,5,6,7-tetrahydrofuro[3,2-c]pyridine-3-carboxamide;
N-[6-(4-acetylpiperazin-1-yl)-2-ethoxypyridin-3-yl]-5-(4-hydroxybutyl)-4-oxo-4,5,6,7-tetrahydrofuro[3,2-c]pyridine-3-carboxamide;
N-[6-(4-acetylpiperazin-1-yl)-2-ethoxypyridin-3-yl]-5-[2-(2-hydroxy ethoxy)ethyl]-4-oxo-4,5,6,7-tetrahydrofuro[3,2-c]pyridine-3-carboxamide;
tert-butyl 4-(6-ethoxy-5-{[(4-oxo-4,5,6,7-tetrahydrofuro[3,2-c]pyridin-3-yl)carbonyl]amino}pyridin-2-yl)piperazine-1-carboxylate;
N-{6-[4-(N-cyano-N-methylcarbamimidoyl)piperazin-1-yl]-2-ethoxypyridin-3-yl}-4-oxo-4,5,6,7-tetrahydrofuro[3,2-c]pyridine-3-carboxamide;
(2R)-1-[3-{[6-(4-acetylpiperazin-1-yl)-2-ethoxypyridin-3-yl]carbamoyl}-4-oxo-6,7-dihydrofuro[3,2-c]pyridin-5(4H)-yl]propan-2-yl acetate;
N-[6-(4-acetylpiperazin-1-yl)-2-ethoxypyridin-3-yl]-5-[(2R)-2-hydroxypropyl]-4-oxo-4,5,6,7-tetrahydrofuro[3,2-c]pyridine-3-carboxamide;
(2S)-1-[3-{[6-(4-acetylpiperazin-1-yl)-2-ethoxypyridin-3-yl]carbamoyl}-4-oxo-6,7-dihydrofuro[3,2-c]pyridin-5(4H)-yl]propan-2-yl acetate;
N-[6-(4-acetylpiperazin-1-yl)-2-ethoxypyridin-3-yl]-5-[(2S)-2-hydroxypropyl]-4-oxo-4,5,6,7-tetrahydrofuro[3,2-c]pyridine-3-carboxamide;
(2R)-2-[3-{[6-(4-acetylpiperazin-1-yl)-2-ethoxypyridin-3-yl]carbamoyl}-4-oxo-6,7-dihydrofuro[3,2-c]pyridin-5(4H)-yl]propyl acetate;
N-[6-(4-acetylpiperazin-1-yl)-2-ethoxypyridin-3-yl]-5-[(2R)-1-hydroxypropan-2-yl]-4-oxo-4,5,6,7-tetrahydrofuro[3,2-c]pyridine-3-carboxamide;

(2S)-2-[3-{[6-(4-acetylpiperazin-1-yl)-2-ethoxypyridin-3-yl]carbamoyl}-4-oxo-6,7-dihydrofuro[3,2-c]pyridin-5 (4H)-yl]propyl acetate;

N-[6-(4-acetylpiperazin-1-yl)-2-ethoxypyridin-3-yl]-5-[(2S)-1-hydroxypropan-2-yl]-4-oxo-4,5,6,7-tetrahydrofuro[3,2-c]pyridine-3-carboxamide;

N-[6-(4-acetylpiperazin-1-yl)-2-ethoxypyridin-3-yl]-5-(1-hydroxy-2-methylpropan-2-yl)-4-oxo-4,5,6,7-tetrahydrofuro[3,2-c]pyridine-3-carboxamide;

1-[3-{[6-(4-acetylpiperazin-1-yl)-2-ethoxypyridin-3-yl]carbamoyl}-4-oxo-6,7-dihydrofuro[3,2-c]pyridin-5 (4H)-yl]-2-methylpropan-2-yl acetate;

N-[6-(4-acetylpiperazin-1-yl)-2-ethoxypyridin-3-yl]-5-(2-hydroxy-2-methylpropyl)-4-oxo-4,5,6,7-tetrahydrofuro[3,2-c]pyridine-3-carboxamide;

N-{6-(4-acetylpiperazin-1-yl)-2-[(3 S)-tetrahydrofuran-3-yloxy]pyridin-3-yl}-4-oxo-4,5,6,7-tetrahydrofuro[3,2-c]pyridine-3-carboxamide;

N-[2-ethoxy-6-(morpholin-4-yl)pyridin-3-yl]-4-oxo-4,5,6,7-tetrahydrofuro[3,2-c]pyridine-3-carboxamide;

N-[2-(2-hydroxy-2-methylpropoxy)-6-(morpholin-4-yl)pyridin-3-yl]-4-oxo-4,5,6,7-tetrahydrofuro[3,2-c]pyridine-3-carboxamide;

methyl (6-ethoxy-5-{[(4-oxo-4,5,6,7-tetrahydrofuro[3,2-c]pyridin-3-yl)carbonyl]amino}pyridin-2-yl)acetate;

N-[2-ethoxy-6-(2-hydroxyethyl)pyridin-3-yl]-4-oxo-4,5,6,7-tetrahydrofuro[3,2-c]pyridine-3-carboxamide;

N-[6-(4-acetylpiperazin-1-yl)-2-ethoxypyridin-3-yl]-4'-oxo-4',7'-dihydro-5'H-spiro[cyclobutane-1,6'-furo[3,2-c]pyridine]-3'-carboxamide;

N-[6-(4-acetylpiperazin-1-yl)-2-ethoxypyridin-3-yl]-4'-oxo-4',7'-dihydro-5'H-spiro[cyclohexane-1,6'-furo[3,2-c]pyridine]-3'-carboxamide;

1-acetyl-N-[6-(4-acetylpiperazin-1-yl)-2-ethoxypyridin-3-yl]-4'-oxo-4', 7'-dihydro-5'H-spiro[azetidine-3,6'-furo[3,2-c]pyridine]-3'-carboxamide;

N-[6-(4-acetylpiperazin-1-yl)-2-ethoxypyridin-3-yl]-4-oxo-4,7-dihydro-5H-spiro[furo[3,2-c]pyridine-6,3'-oxetane]-3-carboxamide;

(6R)—N-[6-(4-acetylpiperazin-1-yl)-2-ethoxypyridin-3-yl]-6-[(1R)-1-hydroxyethyl]-4-oxo-4,5,6,7-tetrahydrofuro[3,2-c]pyridine-3-carboxamide;

N-[6-(4-acetylpiperazin-1-yl)-2-ethoxypyridin-3-yl]-5'-(2-hydroxyethyl)-4'-oxo-4',7'-dihydro-5'H-spiro[cyclobutane-1,6'-furo[3,2-c]pyridine]-3'-carboxamide;

N-[6-(4-acetylpiperazin-1-yl)-2-ethoxypyridin-3-yl]-4'-oxo-4',7'-dihydro-5'H-spiro[cyclopropane-1,6'-furo[3,2-c]pyridine]-3'-carboxamide;

N-{6-[4-(N-cyano-N-methylcarbamimidoyl)piperazin-1-yl]-2-ethoxypyridin-3-yl}-4'-oxo-4',7'-dihydro-5'H-spiro[cyclobutane-1,6'-furo[3,2-c]pyridine]-3'-carboxamide;

N-[6-(4-acetylpiperazin-1-yl)-2-ethoxypyridin-3-yl]-5-(2,3-dihydroxypropyl)-6,6-dimethyl-4-oxo-4,5,6,7-tetrahydrofuro[3,2-c]pyridine-3-carboxamide;

N-[2-methoxy-4-(piperazin-1-yl)phenyl]-6,6-dimethyl-4-oxo-4,5,6,7-tetrahydrofuro[3,2-c]pyridine-3-carboxamide;

N-{2-methoxy-6-[4-(morpholin-4-ylcarbonyl)piperazin-1-yl]pyridin-3-yl}-6,6-dimethyl-4-oxo-4,5,6,7-tetrahydrofuro[3,2-c]pyridine-3-carboxamide;

N-[6-(4-acetylpiperazin-1-yl)-2-methoxypyridin-3-yl]-6,6-dimethyl-4-oxo-4,5,6,7-tetrahydrofuro[3,2-c]pyridine-3-carboxamide;

N-{2-methoxy-6-[4-(pyrrolidin-1-ylcarbonyl)piperazin-1-yl]pyridin-3-yl}-6,6-dimethyl-4-oxo-4,5,6,7-tetrahydrofuro[3,2-c]pyridine-3-carboxamide;

N-[2-methoxy-4-(piperazin-1-yl)phenyl]-6-methyl-4-oxo-4,5,6,7-tetrahydrofuro[3,2-c]pyridine-3-carboxamide;

N-{2-methoxy-4-[4-(methylsulfonyl)piperazin-1-yl]phenyl}-6,6-dimethyl-4-oxo-4,5,6,7-tetrahydrofuro[3,2-c]pyridine-3-carboxamide;

N-[4-(4-acetylpiperazin-1-yl)-2-methoxyphenyl]-6,6-dimethyl-4-oxo-4,5,6,7-tetrahydrofuro[3,2-c]pyridine-3-carboxamide;

N-[2-ethoxy-6-(piperazin-1-yl)pyridin-3-yl]-6,6-dimethyl-4-oxo-4,5,6,7-tetrahydrofuro[3,2-c]pyridine-3-carboxamide;

N-[6-(4-acetylpiperazin-1-yl)-2-ethoxypyridin-3-yl]-6,6-dimethyl-4-oxo-4,5,6,7-tetrahydrofuro[3,2-c]pyridine-3-carboxamide;

N-{6-[(3aR,6aR)-hexahydropyrrolo[3,4-b]pyrrol-5 (1H)-yl]-2-isopropoxypyridin-3-yl}-6,6-dimethyl-4-oxo-4,5,6,7-tetrahydrofuro[3,2-c]pyridine-3-carboxamide;

N-{2-methoxy-6-[(3 aR,6aR)-5-methylhexahydropyrrolo[3,4-b]pyrrol-1 (2H)-yl]pyridin-3-yl}-6,6-dimethyl-4-oxo-4,5,6,7-tetrahydrofuro[3,2-c]pyridine-3-carboxamide;

N-{6-[(3aS,6aS)-1-(2-hydroxyethyl)phexahydropyrrolo[3,4-b]pyrrol-5 (1H)-yl]-2-isopropoxypyridin-3-yl}-6,6-dimethyl-4-oxo-4,5,6,7-tetrahydrofuro[3,2-c]pyridine-3-carboxamide;

N-{2-isopropoxy-6-[(3 aR,6aR)-1-[(4-methylpiperazin-1-yl)carbonyl]hexahydropyrrolo[3,4-b]pyrrol-5 (1H)-yl]pyridin-3-yl}-6,6-dimethyl-4-oxo-4,5,6,7-tetrahydrofuro[3,2-c]pyridine-3-carboxamide;

N-{6-[(3S)-4-acetyl-3-(hydroxy methyl)piperazin-1-yl]-2-isopropoxypyridin-3-yl}-6,6-dimethyl-4-oxo-4,5,6,7-tetrahydrofuro[3,2-c]pyridine-3-carboxamide;

N-{6-[(2S)-4-acetyl-2-(hydroxy methyl)piperazin-1-yl]-2-isopropoxy pyridin-3-yl}-6,6-dimethyl-4-oxo-4,5,6,7-tetrahydrofuro[3,2-c]pyridine-3-carboxamide;

N-{6-[(2S)-2-(hydroxymethyl)-4-(morpholin-4-ylcarbonyl)piperazin-1-yl]-2-isopropoxypyridin-3-yl}-6,6-dimethyl-4-oxo-4,5,6,7-tetrahydrofuro[3,2-c]pyridine-3-carboxamide;

N-{6-[(3S)-3-(dimethylamino)pyrrolidin-1-yl]-2-isopropoxypyridin-3-yl}-6,6-dimethyl-4-oxo-4,5,6,7-tetrahydrofuro[3,2-c]pyridine-3-carboxamide;

N-{6-[(3S)-3-(hydroxymethyl)piperidin-1-yl]-2-isopropoxypyridin-3-yl}-6,6-dimethyl-4-oxo-4,5,6,7-tetrahydrofuro[3,2-c]pyridine-3-carboxamide;

N-{6-[(3R)-4-acetyl-3-(hydroxymethyl)piperazin-1-yl]-2-isopropoxypyridin-3-yl}-6,6-dimethyl-4-oxo-4,5,6,7-tetrahydrofuro[3,2-c]pyridine-3-carboxamide;

N-{6-[(2R)-4-acetyl-2-(hydroxy methyl)piperazin-1-yl]-2-isopropoxypyridin-3-yl}-6,6-dimethyl-4-oxo-4,5,6,7-tetrahydrofuro[3,2-c]pyridine-3-carboxamide;

N-{6-[bis(2-hydroxyethyl)amino]-2-isopropoxypyridin-3-yl}-6,6-dimethyl-4-oxo-4,5,6,7-tetrahydrofuro[3,2-c]pyridine-3-carboxamide;

N-[2,6-bis(2-methoxyethoxy)pyridin-3-yl]-6,6-dimethyl-4-oxo-4,5,6,7-tetrahydrofuro[3,2-c]pyridine-3-carboxamide;

N-{6-[(3S)-4-acetyl-3-(methoxymethyl)piperazin-1-yl]-2-(2-hydroxy-2-methylpropoxy)pyridin-3-yl}-6,6-dimethyl-4-oxo-4,5,6,7-tetrahydrofuro[3,2-c]pyridine-3-carboxamide;

N-[2-ethoxy-6-(2-hydroxy ethyl)pyridin-3-yl]-6,6-dimethyl-4-oxo-4,5,6,7-tetrahydrofuro[3,2-c]pyridine-3-carboxamide;

N-[2-ethoxy-6-(hydroxy methyl)pyridin-3-yl]-6,6-dimethyl-4-oxo-4,5,6,7-tetrahydrofuro[3,2-c]pyridine-3-carboxamide;

6-ethoxy-5-({[5-(2-methoxyethyl)-6,6-dimethyl-4-oxo-4,5,6,7-tetrahydrofuro[3,2-c]pyridin-3-yl]carbonyl}amino)pyridine-2-carboxylic acid;

N-(2-methyl-2H-indazol-5-yl)-4-oxo-4,5,6,7-tetrahydrofuro[2,3-c]pyridine-3-carboxamide;

N-(2-methyl-2H-indazol-5-yl)-6-(methylsulfonyl)-4-oxo-4,5,6,7-tetrahydrofuro[2,3-c]pyridine-3-carboxamide;

N-[4-(4-acetylpiperazin-1-yl)-2-methoxyphenyl]-4-oxo-4,7-dihydrospiro[furo[2,3-c]pyran-5,4'-piperidine]-3-carboxamide;

N-[6-(4-acetylpiperazin-1-yl)-2-methoxypyridin-3-yl]-5,5-dimethyl-4-oxo-4,7-dihydro-5H-furo[2,3-c]pyran-3-carboxamide;

N-[4-(4-acetylpiperazin-1-yl)-2-methoxyphenyl]-4-oxo-4,7-dihydrospiro[furo[2,3-c]pyran-5,3'-oxetane]-3-carboxamide;

N-[6-(4-acetylpiperazin-1-yl)-2-ethoxypyridin-3-yl]-5,6,6-trimethyl-4-oxo-4,5,6,7-tetrahydrofuro[3,2-c]pyridine-3-carboxamide;

N-[6-(4-acetylpiperazin-1-yl)-2-ethoxypyridin-3-yl]-5-(2-hydroxy ethyl)-6, 6-dimethyl-4-oxo-4,5,6,7-tetrahydrofuro[3,2-c]pyridine-3-carboxamide;

N-[6-(4-acetylpiperazin-1-yl)-2-ethoxypyridin-3-yl]-5-(2-methoxyethyl)-6,6-dimethyl-4-oxo-4,5,6,7-tetrahydrofuro[3,2-c]pyridine-3-carboxamide;

N-[6-(4-acetylpiperazin-1-yl)-2-ethoxypyridin-3-yl]-5-[2-(2-hydroxy ethoxy)ethyl]-6,6-dimethyl-4-oxo-4,5,6,7-tetrahydrofuro[3,2-c]pyridine-3-carboxamide;

N-[6-(4-acetylpiperazin-1-yl)-2-(2-methoxyethoxy)pyridin-3-yl]-6,6-dimethyl-4-oxo-4,5,6,7-tetrahydrofuro[3,2-c]pyridine-3-carboxamide;

N-[6-(4-acetylpiperazin-1-yl)-2-(2,2,2-trifluoroethoxy)pyridin-3-yl]-6,6-dimethyl-4-oxo-4,5,6,7-tetrahydrofuro[3,2-c]pyridine-3-carboxamide;

N-[6-(4-acetylpiperazin-1-yl)-2-(oxetan-3-yloxy)pyridin-3-yl]-6,6-dimethyl-4-oxo-4,5,6,7-tetrahydrofuro[3,2-c]pyridine-3-carboxamide;

N-[6-(4-acetylpiperazin-1-yl)-2-(tetrahydro-2H-pyran-4-yloxy)pyridin-3-yl]-6,6-dimethyl-4-oxo-4,5,6,7-tetrahydrofuro[3,2-c]pyridine-3-carboxamide;

N-{6-(4-acetylpiperazin-1-yl)-2-[(3S)-tetrahydrofuran-3-yloxy]pyridin-3-yl}-6,6-dimethyl-4-oxo-4,5,6,7-tetrahydrofuro[3,2-c]pyridine-3-carboxamide;

N-[6-(4-formylpiperazin-1-yl)-2-(2-methoxyethoxy)pyridin-3-yl]-6,6-dimethyl-4-oxo-4,5,6,7-tetrahydrofuro[3,2-c]pyridine-3-carboxamide;

N-{6-(4-acetylpiperazin-1-yl)-2-[(1-oxidothietan-3-yl)oxy]pyridin-3-yl}-6,6-dimethyl-4-oxo-4,5,6,7-tetrahydrofuro[3,2-c]pyridine-3-carboxamide; and N-[6-(1-acetylpiperidin-4-yl)-2-ethoxypyridin-3-yl]-6,6-dimethyl-4-oxo-4,5,6,7-tetrahydrofuro[3,2-c]pyridine-3-carboxamide.

22. A pharmaceutical composition comprising a therapeutically effective amount of a compound of claim 1 in combination with a pharmaceutically acceptable carrier.

23. A method of treating pain modulated by TrkA (Tropomyosin receptor kinase isoform A) in a mammal comprising administering an inhibitory effective amount of a compound of claim 1, wherein the pain is selected from the group consisting of osteoarthritis pain, joint pain, neuropathic pain, post-surgical pain, low back pain, diabetic neuropathy, pain during surgery, cancer pain, chemotherapy induced pain, cluster headache, tension headache, migraine pain, trigeminal neuralgia, shingles pain, post-herpetic neuralgia, carpal tunnel syndrome, inflammatory pain, pain from rheumatoid arthritis; pain of interstitial cystitis, visceral pain, pain from kidney stone, pain from gallstone, angina, fibromyalgia, chronic pain syndrome, thalamic pain syndrome, pain from stroke, phantom limb pain, sunburn, radiculopathy, complex regional pain syndrome, HIV sensory neuropathy, central neuropathic pain syndromes, multiple sclerosis pain, Parkinson disease pain, spinal cord injury pain, menstrual pain, toothache, pain from bone metastasis, pain from endometriosis, pain from uterine fibroids, nociceptive pain, hyperalgesia, and temporomandibular joint pain.

* * * * *